US006989367B2

(12) United States Patent
Fruebis et al.

(10) Patent No.: US 6,989,367 B2
(45) Date of Patent: Jan. 24, 2006

(54) OBG3 GLOBULAR HEAD AND USES THEREOF

(75) Inventors: Joachim Fruebis, Redmond, WA (US); Mary Ruth Erickson, San Diego, CA (US); Frances Yen-Potin, San Diego, CA (US); Bernard Bihain, Cancale (FR)

(73) Assignee: Genset S.A. (FR)

( * ) Notice: Subject to any disclaimer, the term of this patent is extended or adjusted under 35 U.S.C. 154(b) by 85 days.

(21) Appl. No.: 10/285,833

(22) Filed: Nov. 1, 2002

(65) Prior Publication Data

US 2004/0067881 A1 Apr. 8, 2004

(Under 37 CFR 1.47)

Related U.S. Application Data

(63) Continuation-in-part of application No. 09/909,547, filed on Jul. 19, 2001, now Pat. No. 6,579,852, which is a continuation-in-part of application No. 09/776,976, filed on Feb. 5, 2001, now Pat. No. 6,566,332, which is a continuation-in-part of application No. 09/758,055, filed on Jan. 10, 2001, now abandoned, and a continuation-in-part of application No. 10/231,814, filed on Aug. 29, 2002, which is a continuation of application No. 09/758,055, filed on Jan. 10, 2001, now abandoned.

(60) Provisional application No. 60/176,228, filed on Jan. 14, 2000, provisional application No. 60/198,087, filed on Apr. 13, 2000, provisional application No. 60/229,881, filed on Sep. 1, 2000, provisional application No. 60/313,696, filed on Aug. 20, 2001, provisional application No. 60/340,077, filed on Nov. 1, 2001, provisional application No. 60/355,478, filed on Feb. 6, 2002, and provisional application No. 60/355,563, filed on Feb. 6, 2002.

(30) Foreign Application Priority Data

Jan. 10, 2001 (WO) ................................ PCT/IB01/00084

(51) Int. Cl.

| | |
|---|---|
| ***A61K 38/17*** | (2006.01) |
| ***A61K 38/18*** | (2006.01) |
| ***C07K 14/47*** | (2006.01) |
| ***C07K 14/475*** | (2006.01) |

(52) U.S. Cl. ......................... 514/12; 514/909; 530/399; 530/350; 930/10

(58) Field of Classification Search ................. 530/399, 530/350; 514/12, 909

See application file for complete search history.

(56) References Cited

U.S. PATENT DOCUMENTS

| | | | |
|---|---|---|---|
| 5,270,170 | A | 12/1993 | Schatz et al. |
| 5,635,373 | A | 6/1997 | Wozney et al. |
| 5,869,330 | A | 2/1999 | Scherrer et al. |
| 6,126,939 | A | 10/2000 | Eisenbach-Schwartz et al. |
| 6,197,930 | B1 | 3/2001 | Sheppard et al. |
| 6,344,441 | B1 | 2/2002 | Bihain et al. |
| 6,635,431 | B1 | 10/2003 | Bihain et al. |
| 2002/0165154 | A1 | 11/2002 | Bihain et al. |

FOREIGN PATENT DOCUMENTS

| | | | |
|---|---|---|---|
| EP | 1 033 134 | A1 | 9/2000 |
| EP | 1033134 | A1 | 9/2000 |
| WO | WO 96/30400 | A1 | 10/1996 |
| WO | WO 96/34981 | A2 | 11/1996 |
| WO | WO 96/39429 | A2 | 12/1996 |
| WO | WO 97/27285 | A1 | 7/1997 |
| WO | WO 97/27286 | A1 | 7/1997 |
| WO | WO 98/01257 | | 1/1998 |
| WO | WO 98/20165 | A2 | 5/1998 |
| WO | WO 98/54311 | A1 | 12/1998 |
| WO | WO 99/07736 | A2 | 2/1999 |
| WO | WO 99/07737 | A2 | 2/1999 |
| WO | WO 99/10492 | A1 | 3/1999 |
| WO | WO 99/21577 | A1 | 5/1999 |
| WO | WO 99/21577 | | 5/1999 |
| WO | WO 99/21577 | | 6/1999 |

OTHER PUBLICATIONS

U.S. Appl. No. 10/650,507, Bihain et al., filed Aug. 27, 2003.

U.S. Appl. No. 10/072,159, Bihain et al., filed Feb. 25, 2002.

Groenen, P. et al. "Structure, Sequence and Chromosome 19 Localization of Human USF2 and Its Rearrangement in a Patient with Multicystic Renal Adysplasia", *Genomics*, 1995, pp. 141–148, vol. 38, XP002067467.

Bihain, B. et al. "The Lypolysis–Stimulated Receptor; A Gene At Last",*Current Opinion in Liodology*, 1998, pp. 221–224, vol. 9, No. 3.

Das, K. et al. "Chromosomal Localizations, Expression Pattern, and Promoter Analysis of the Mouse Gene Encoding Adipocye–Specific Secretory Protein ACRP30", *Biochem. and Biophys. Res. Comm.*, 2001, pp. 1120–1129, vol. 280, Academic Press.

Dietrich, J. et al. "CD3y Contains a Phosphoserine–Dependent Di–Leucine Motif Involved in Down–Regulation of the T Cell Receptor," *EMBO Journal*, 1994, pp. 2156–2166, vol. 13.

Van Den Berg, R.H., et al. "Intracellular Localization of the Human Receptor for the Globular Domains of C1q," *Journal of Immunology*, 1997, pp. 3909–3916, vol. 158.

Lamerdin, J. E. "Homo Sapiens DNA From Chromosome 19–Cosmid R30879 Containing USF2, Genomic Sequence", *EMBL Sequence Database*, 1997, XP002096567.

(Continued)

*Primary Examiner*—Christine J. Saoud

(74) *Attorney, Agent, or Firm*—Saliwanchik, Lloyd & Saliwanchik

(57) ABSTRACT

The present invention relates to the field of obesity research. Obesity is a public health problem that is serious and widespread. A compound, globular OBG3, has been identified that reduces weight gain in animals. This compound should be effective for reducing body mass and for treating obesity-related diseases and disorders. These obesity-related diseases and disorders include hyperlipidemias, atherosclerosis, diabetes, and hypertension.

26 Claims, 27 Drawing Sheets

OTHER PUBLICATIONS

Alexeev and Yoon, "Stable and Inheritable Changes in Genotype and Phenotype of Albino Melanocytes Induced by an RNA–DNA Oligonucleotide": Nature Biotech. 16:1343–1346, 1998.

Arita, et al., "Paradoxical Decrease of an Adipose–Specific Protein, Adiponectin, in Obesity", Biochem. and Biophys. Research Comm. 257:79–83, 1999 (Academic Press).

Austin, et al., "Hypertriglyceridemia as a Cardiovascular Risk Factor", Am. J. Cardiol. 81(4A):7B–12B, 1998 (Excerpta Medica, Inc.).

Baldo, et al., "The Adipsin–Acylation Stimulating Protein System and Regulation of Intracellular Triglyceride Synthesis", J. Clin. Invest., 92:1543–1547; Sep. 1993 (The American Society for Clinical Investigation, Inc.).

Bartles, J.R. et al., "Biogenesis of the Rat Hepatocyte Plasma Membrane", Methods Enzymol., 191:825–0841, 1990 (Academic Press).

Bihain, B.E., et al., "Characterization and Purification of the Lipolysis–Stimulated Receptor", Elsevier Science B.V., pp. 465–470, 1995.

Bihane, B.E., et al., "Free Fatty Acids Activate a High–Affinity Saturable Pathway for Degradation of Low–Density Lipoproteins in Fibroblasts from a Subject Homozygous for Familial Hypercholesterolemia", Biochemistry, 31:4628–4636, 1992 (American Chemical Society).

Brendel, V., et al., "Methods and Algorithms for Statistical Analysis of Protein Sequences", Proc. Natl. Acad. Sci. USA, vol. 89:2002–2006, Mar. 1992.

Chen, W.J., et al., "NPXY, A Sequence Often Found in Cytoplasmic Tails, Is Required for Coated Pit–Mediated Internalization of the Low Density Lipoprotein Receptor", J. Biol. Chem. 265:3116–3123, Feb. 25, 1990 (The American Society for Biochemistry and Molecular Biology, Inc.).

Cole–Strauss, et al., "Correction of the Mutation Responsible for Sickle Cell Anemia by an RNA–DNA Oligonucleotide", Science, 273:1386–1389, Sep. 6, 1996.

Costet, P., et al., "Peroxisome Proliferator–Activated Receptor a–Isoform Deficiency Leads to Progressive Dyslipidemia with Sexually Dimorphic Obesity and Steatosis", J. Biol. Chem., vol. 273, No. 45, 29577–29585, Nov. 6, 1998 (The American Society for Biochemistry and Molecular Biology, Inc.).

Davis, C.G., et al., "The J.D. Mutation in Familial Hypercholesterolemia: Amino Acid Substitution in Cytoplasmic Domain Impedes Internalization of LDL Receptors," Cell, 45:15–24, Apr. 11, 1986 (Cell Press).

Everhart, J. E., "Weight Change and Obesity After Liver Transplantation: Incidence and Risk Factors", Liver Transpl. Surg., vol. 4, No. 4:285–296, Jul. 1998.

Feeman, Jr., W.E., "Hypertriglyceridemia and Atherosclerosis", Annals of Internal Medicine, vol. 128, No. 1, pp. 73–74, 1998.

Ghebrehiwet, et al., "Isolation, cDNA Cloning, and Overexpression of a 33–kD Cell Surface Glycoprotein that Binds to the Globular 'Heads' of C1q", J. Exp. Med., 179:1809–1821; Jun. 1994 (The Rockefeller University Press).

Goldstein, J.L., et al., "Familial Hypercholesterolemia," The Metabolic and Molecular Bases of Inherited Disease, vol. II, 7th Edition (Scriver, C.R., et al., ed), McGraw–Hill, New York, pp. 1981–2030, 1995.

Goldstein, et al., "Hyperlipidemia in Coronary Heart Disease", J. Clin. Invest., 52:1533–1543, Jul. 1973.

Gura, et al., "Obesity Sheds its Secrets", Science, 275:751–753, Feb. 7, 1997.

Hayward, et al., "The cDNA Sequenmce of Human Endothelial Cell Multimerin". J. Biol. Chem., vol. 270, No. 31:18246–18251, Aug. 4, 1995 (The American Society for Biochemistry and Molecular Biology, Inc.).

Hennon, et al., "Structure, Sequence, and Chromosomal Location of the Gene for USF2 Transcription Factors in Mouse", Genomics, 25:36–43 (1995) (Academic Press, Inc.).

Herz, J., et al., "Surface Locations and High Affinity for Calcium of a 500–kd Liver Membrane Protein Closely Related to the LDL–Receptor Suggest a Physiological Role as Lipoprotein Receptor", European Molecular Biology Laboratory, 7:4119–4127 (1988) (IRL Press Limited, Oxford, England).

Honore, B., et al., "Cloning and Expression of a cDNA Covering the Complete Coding Region of the P32 Subunit of Human Pre–mRNA Splicing Factor SF2", Gene, 134:283–287 (1993) (Elsevier Science Publishers B.V.).

Hu, et al., "AdipoQ is a Novel Adipose–Specific Gene Dysregulated in Obesity", J. Biol. Chem. vol. 271, No. 18:10697–10703 (May 3, 1996).

Huetlinger M., et al., "Characteristics of Chylomicron Remnant Uptake into Ray Liver", Clin. Biochem. 21:87–92 (1988).

Imagawa, et al., "Structure–Function Studies of Human Leptin", J. Biol. Chem., vol. 273, No. 52:35245–35249, Dec. 25, 1998 (The American Society for Biochemistry and Molecular Biology, Inc.).

Karpe, F., et al., "Clearance of Lipoprotein Remnant Particles in Adipose Tissue and Muscle in Humans", J. Lipid Res. 38:2335–2343 (1997).

Karpe, F. et al., "Magnitude of Alimentary Lipernia is Related to Intima–Media Thickness of the Common Carotid Artery in Middle–Aged Men", Elsevier Science Ireland, 141:307–314, 1998.

Kersten, S., et al., "Peroxisome Proliferator?Activated Receptor aMediates the Adaptive Response to Fasting", J. Clin. Invest., vol. 103, No. 11:1489–1498, Jun. 1999 (The American Society for Clinical Investigations).

Khaliou, et al., "Correction of Delayed Postprandial Plasma Lipid Response in Genetically Obese Mice by Injection of Recombinant Leptin", Abstract from the 69th Scientific Sessions, New Orleans, LA: Supplemental to Circulation, American Heart Assoc. vol. 94:8 (1996).

Krainer, A.R., et al., "Functional Expression of Cloned Human Splicing Factor SF2: Homology to RNA–Binding Proteins, U1 70K, and Drosophila Splicing Regulators", Cell, 66:383–394, Jul. 26, 1991 (Cell Press).

Lee, M.G.–S., et al., "Characterization of a cDNA Encoding a Cysteine–Rich Cell Surface Protein Located in the Flagellar Pocket of the Protozoan Trypanosoma Brucei", Molec. Cell. Biol., 10:4506–4517 (Sep. 1990) (American Society for Microbiology).

Lelourneur, F., et al., "A Novel Di–Leucine Motif and a Tyrosine–Based Motif Independently Mediate Lysosomal Targeting and Endocytosis of CD3 Chains", Cell, 69:1143–1157 (Jun. 26, 1992) (Cell Press).

Lewis, G.F., et al., "Postprandial Lipoprotein Metabolism in Normal and Obesre Subjects: Comparison after the Vitamin A Fat–Loading Test", Jr. of Clinic. Endo., 71:1041–1050 (1990) (The Endorcrine Society).

Lin, et al., "Archaic Structure of the Gene Encoding Transcription Factor USF", Jr. of Bio. Chem. 269:23894–23903 (1994) (The American Society for Biochemistry and Molecular Biology, Inc.).

Liu, O., et al., "Design of Polydactyl Zinc–Finger Proteins for Unique Addressing Within Complex Genomes", Proc. Natl. Acad. Sci. USA, vol. 94, No. 11:5525–5530, May 27, 1997.

Maeda, et al., "cDNA Cloning and Expression of a Novel Adipose Specific Collagen–Like Factor, apM1 (Adipose Most Abundant Gene Transcript 1)", Biochem. and Biophys. Research Comm. 221:286–289, 1996 (Academic Press).

Mahley, R.W., et al., "Type III Hyperlipoproteinemia (Dysbetalipoproteinemia): The Role of Apolipoprotein E in Normal and Abnormal Lipoprotein Metabolism", The Molecular Basis of Inherited Disease. eds. Scriver, et al., McGraw Hill Inc., New York, pp. 1953–1980, 1995 (The Amnerican Chemical Society).

Mann, C. J., et al., "Mechanism of Activation and Fuinctional Significance of the Lipolysis–Stimulated Receptor, Evidence for a Role as Chylomicron Remnant Receptor", Biochemistry, 34:10421–10431 (1995).

Mann, et al., "ApoCIII Inhibits the Binding of Triclyceride–Rich Lipoproteins to the Lipolysis Stimulated Receptor", Abstract (1996).

Massie, et al., "Inducible Overexpression of a Toxic Protein by an Adenovirus Vector with a Tetracycline–Regulatable Expression Cassette", Journal of Virology, 72:2289–2296, Mar. 1998 (American Society for Microbiology).

Montague, et al., "Congenital Leptin Deficiency is Associated with Severe Early–Onset Obesity in Humans", Nature, 387:903–908, 1997.

Parra–Lopez, C.A., et al., "Presentation on Class II MHC Molecules of Endogenous Lysozyme Targeted to the Endocytic Pathway1", J. Immunol., 158:2670–2679, 1997 (The American Association of Immunologists).

Pengue, G., et al., "Repression of Transcriptional Activity at a Distance by the Evolutionarily Conserved KRAB Domain Present is a Subfamily of Zinc Finger Proteins", Nucleic Acids Research, vol. 22, No. 15, 2908–2914 (1994) (Oxford University Press).

Perusse, L., et al., "The Human Obesity Gene Map: The 1998 Update", Obes. Res. 7:111–129, Jan. 1999.

Rajput–Williams, J., et al., "Variation of Apolipoprotein–B Gene is Associated with Obesity, High Blood Cholesterol Levels, and Increased Risk of Coronary Heart Disease", The Lancet, pp. 1442–1446, Dec. 24/31, 1988.

Rutherford, S., et al., "Association of a Low Density Lipoprotein Receptor Micro–Satellite Variant with Obesity", Intl. Jr. of Obesity, 21:1032–1037, 1997 (Stockton Press).

Saito, et al., "Organization of the Gene for Gelatin–Binding Protein (GBP28)", Gene, 229:67–73, Jan. 12, 1999 (Elsevier Science B.V.).

Schaffler, et al., "Identification and Characterization of the Human Adipocyte apM–1 Promoter", Biochem. and Biophys. Res. Comm. 1399:187–197, Jun. 22, 1998 (Elsevier Science B.V.).

Schaffler, et al., "The Human apM–1, an Adipocyte–Specific Gene Linked to the Family of TNF's and to Genes Expressed in Activated T Cells, is Mapped to Chromosone 1q21.3–q23. A Susceptibility Locus Identified for Familia Combined Hyperlipidaemia (FCH)", Biochem. and Biophys. Res. Comm. 260:416–425, May 7, 1999 (Academic Press).

Scharer, et al., "A Novel Serum Protein Similar to C1Q, Produced Exclusively in Adipocytes", J. Biol. Chem., vol. 270, #45, 26746–26749, Nov. 10, 1995 (The American Society for Biochemistry and Molecular Biology, Inc.).

Seliar, et al., "Characterization and Organization of athe Genes Encoding the A–, B– and C–Chains of Human Complement Subcomponent C1q", Biochemical Journal, 274:481–490 (1991).

Shimabukuro, M., et al., "Direct Antidiabetic Effect of Leptin Through Triglyceride Depletion of Tissues", Proc. Natl. Acad. Sci. USA, vol. 94, #9:4637–4641, Apr. 29, 1997.

Shimano, H., et al., "Overproduction of Cholesterol and Fatty Acids Causes Massive–Liver Enlargement in Transgenic Mice Expressing Truncated SREBP–1a", J. Clin. Invest., vol. 98, #7:1575–1584, Oct. 1996 (The American Society for Clinical Investigation, Inc.).

Shimomura, et al., "Leptin Reverses Insulin Resistance and Diabetes Mellitus in Mice with Congenital Lipodystrophy", Nature, 401:73–76, Sep. 2, 1999.

Shin, J., et al., "Phosphorylation–Dependent Down–Modulation of CD4 Requires a Specific Structure Within the Cytoplasmic Domain of CD4", Jr. of Biol. Chem., vol. 265:10658–10665, 1991 (The American Society for Biochemistry and Molecular Biology, Inc.).

Simos, G., et al., "The Lamin B Receptor–Associated Protein p34 Shares Sequence Homology and Antigenic Determinants with the Splicing Factor 2–Associated Protein p32", FEBS Letters 346:225–228, 1994 (Federation of European Biochemical Societies).

Steingrimsson, E., et al., "Murine Chromosomal Location of Five bHLH–ZIP Transcription Factor Genes", Genomics, 28:179–183, 1995 (Academic Press, Inc.).

Troussard, A.A., et al., "Inhibitory Effect on the Lipolysis-Stimulated Receptor of the 39–kDa Receptor–Associated Protein", Jr. of Biol. Chem., vol. 270, #29:17068–71, Jul. 21, 1995 (The American Society for Biochemistry and Molecular Biology, Inc.).

Urade, Y., et al., "Precerebellin is a Cerebellum–Specific Protein with Similarity to the Globular Domain of Complement C1qB Chain", Proc. Natl. Sci. USA, 88:1069–1073, Feb., 1991.

Uotani. S., "Functional Properties of Leptin Receptor Isoforms Internalization and Edgradation of Leptin and Legand–Induced Receptor Downregulation Diabetes", 48:279–286, Feb. 1999.

Vansant, G., et al., "Determinants of Postprandial Lipernia in Obese Women", Intl. Jr. of Obesity, 23:Supp. 1, 14–21, 1999 (Stockton Press).

Verhey, K. J., et al., "A Leu–Leu Sequence is Essential for Cooh–Terminal Targeting Signal of Glut4 Glucose Transporter in Fibroblasts", J. Biol. Chem. 269:2353–2356, 1994 (The American Society for Biochemistry and Molecular Biology, Inc.).

Wang, et al.; "Upstream Stimulatory Factor Binding to the E–Box at –65 is Required for Insulin Regulation of the Fatty Acid Synthase Promoter", J. Biol. Chem., vol. 272, #42:26367–26374, Oct. 17, 1997.

Yen, et al., "Molecular Cloning of a Lipolysis–Stimulated Remnant Receptor Expressed in the Liver", J. Biol. Chem., vol. 274, #19:13390–13398, 1999 (The American Society for Biochemistry and Molecular Biology, Inc.).

Yen, F.T., et al., "Identification of a Lipolysis–Stimulated Receptor that is Distinct From the LDL Receptor and the LDL Receptor–Related Protein", Biochemistry, 33:1172–1180, 1994 (American Chemical Society).

Zhang, M., et al., "Tumor Necrosis Factor", The Cytokine Handbook, Third Ed., pp. 517–548, 1998 (Academic Press Limited).

Zhong, G., et al., "Related Leucine–Based Cytoplasmic Targeting Signals in Invariant Chain and Major Histocompatibility Complex Class II Molecules Control Endocytic Presentation of Distinct Determinants in a Single Protein", J. Exp. Med., vol. 165, #3:429–436, Feb. 3, 1997.

Barsh, G., et al., "Genetics of Body–Weight Regulation", Nature, vol. 404:644–651, Apr. 6, 2000.

Friedmen, J.M., "Obesity in the New Millennium", Nature; vol. 404:632–634; Apr. 6, 2000 (Macmilan Magazines Ltd.).

Oksana, G., et al., "Hormones: Leptin and Diabetes in Lipoatrophic Mice", Nature, vol. 403:850, Feb. 24, 2000 (Macmillan Publishers Ltd.).

Oksana, G., et al., "Lack of Responses to a [[Beta].Sub.3] –Adrenergic Agonist in Lipoatrophic A–Zip Mice", Diabetes, vol. 49, #11:1910, Nov. 2000 (American Diabetes Association).

Hotta, K., et al., "Plasma Concentrations fo a Novel, Adipose–Specific Protein, Adiponectin, in Type 2 Diabetic Patients", Arterioscler Thromb Vasc Biol., 1595–1599, Jun. 2000 (American Heart Association, Inc.).

Kishore, U., et al., "Modular Organization of Proteins Containing Clq–like Globular Domain", Immunopharmacology 42 (1999) 15–21 (1999 Elsevier Science B.V.).

Kishor, U., et al., "Clq: Structure, Function, and Receptors", Immunopharmacology 49 (2000) 159–170 (2000 Elsevier Science B.V.).

Kopelman, P., "Obesity as a Medical Problem", Nature, vol. 404:635–643, Apr. 6, 2000 (Macmillan Magazines Ltd.).

Mann, C., et al., "Inhibitory Effects of Specific Apolipoprotein C–III Isoforms on the Binding of Triglyceride–Rich Lipoproteins to the Lipolysis–Stimulated Receptor", The Journal of Biological Chemistry, vol. 272, #50:31348–31354, 1997 (The American Society for Biochemistry and Molecular Biology, Inc.).

Nakano, Y., et al., "Isolation and Characterization of GBP28, a Novel Gelatin–Binding Protein Purified from Human Plasma", J. Biochem, vol. 120, #4:803–812 (1996).

Okamoto, Y., et al., "An Adipocyte–Derived Plasma Protein, Adiponectin, Adheres to Injured Vascular Walls", Horm Metab Res 2000; 32:47–50 (Georg Thieme Verlag Stuttgart-New York).

Ouchi, N., et al., "Novel Modulator for Endothelial Adhesion Molecules / Adipocyte–Derived Plasma Protein Adiponectin", Circulation, vol. 100:2473–2476, Dec. 21/28, 1999 (American Heart Association).

Montague, C.T., et al., "Congenital Leptin Deficiency is Associated with Severe Early–Onset Obesity in Humans", Nature, vol. 387, pp. 903–908, Jun. 26, 1997.

Saito, K., et al., "Regulation of Gelatin–Binding Protein 28 (GBP28) Gene Expression by C/EBP", Biol. Pharm. Bull. 22(11) 1158–1162 (1999).

Shapiro, L., et al., "The Crystal Structure of a Complement–1q Family Protein Suggests an Evolutionary Link to Tumor Necrosis Factor", Current Biology, vol. 8, No. 6, pp. 335–338.

Takahashi, M., et al., "Genomic Structure and Mutations in Adipose–Specific Gene, Andiponectin", International Journal of Obesity (2000) 24, 861–868 (Macmillan Publishers Ltd.).

Yokota, T., et al., "Adiponectin, a New Member of the Family of Soluble Defense Collagens, Negatively Regulates the Growth of Myelomonocytic Progenitors and the Functions of Macrophages", Blood, Sep. 1, 2000—Vol. 96, No. 5, pp. 1723–1732 (The American Society of Hematology).

Berg, Anders H., et al., "The Adipocyte–Secreted Protein Acrp30 Enhances Hepatic Insulin Action," *Nature Medicine*, Aug. 2001, pp. 947–953, vol. 7, No. 8, Nature Publishing Group, http://medicine.nature.com.

Yamauchi, T., et al., "The Fat–Derived Hormone Adiponectin Reverses Insulin Resistance Associated with Both Lipoatrophy and Obesity," *Nature Medicine*, Aug. 2001, pp. 941–946, vol. 7, No. 8, Nature Publishing Group, http://medicine.nature.com.

Alexeev, V. and Yoon, K. "Stable and Inheritable Changes in Genotype and Phenotype of Albino Melanocytes induced by an RNA–DNA Oligonucleotide" *Nature Biotech,* 1998, pp. 1343–1346, vol. 16.

Arita, Y. et al. "Paradoxical Decrease of an Adipose–Specific Protein, Adiponectin, in Obesity"*Biochem. and Biophys. Research Comm.,* 1999, pp. 79–83, vol. 257 (Academic Press).

Austin, M.A. et al. "Hypertriglyceridemia as a Cardiovascular Risk Factor"*Am. J. Cardiol.,* 1998, pp. 7B–12B, vol. 81, No. 4A (Excerpta Medica, Inc.).

Baldo, A. et al. "The Adipsin–Acylation Stimulating Protein System and Regulation of Intracellular Triglyceride Synthesis"*J. Clin. Invest.,* Sep. 1993, pp. 1543–1547, vol. 92 (The American Society for Clinical Investigation, Inc.).

Bartles, J.R. et al. "Biogenesis of the Rat Hepatocyte Plasma Membrane"*Methods Enzymol,* 1990, pp. 825–841, vol. 191 (Academic Press).

Bihain, B.E. et al. "Characterization and Purification of the Lipolysis–Stimulated Receptor" 1995, pp. 465–470, Elsevier Science B.V.

Bihain, B.E. et al. "Free Fatty Acids Activate a High–Affinity Saturable Pathway for Degradation of Low–Density Lipoproteins in Fibroblasts from a Subject Homozygous for Familial Hypercholesterolemia"*Biochemistry,* 1992, pp. 4628–4636, vol. 31 (American Chemical Society).

Brendel, V. et al. "Methods for Algorithms for Statistical Analysis of Protein Sequences"*Proc. Natl. Sci.* USA, Mar. 1992, pp. 2002–2006, vol. 89.

Chen, W.J. et al. "NPXY, a Sequence often Found in Cytoplasmic Tails, is Required for Coated Pit–Mediated Internalization of the Low Density Lipoprotein Receptor"*J. Biol. Chem,* Feb. 25, 1990, pp. 3116–3123, vol. 265 (The American Society for Biochemistry and Molecular Biology, Inc.).

Cole–Strauss, A. et al. "Correction of the Mutation Responsible for Sickle Cell Anemia by an RNA–DNA Oligonucleotide"*Science,* Sep. 6, 1996, pp. 1386–1389, vol. 273.

Costet, P. et al. "Peroxisome Proliferator–Activated Receptor–αisoform Deficiency Leads to Progressive Dyslipidemia with Sexually Dimorphic Obesity and Steatosis"*J. Biol. Chem.,* Nov. 6, 1998, pp. 29577–29585, vol. 273, No. 45 (The American Society for Biochemistry and Molecular Biology, Inc.).

Davis, C.G. et al. "The J.D. Mutation in Familal Hypercholesterolemia: Amino Acid Substitution in Cytoplasmic Domain Impedes Internalization of LDL Receptors"*Cell,* Apr. 11, 1986, pp. 15–24, vol. 45 (Cell Press).

Everhart, J.E. et al. "Weight Changes and Obesity After Liver Transplantation: Incidence and Risk Factors"*Liver Transpl. Surg.,* Jul. 1998, pp. 285–296, vol. 4, No. 4.

Feeman, Jr., W.E. et al. "Hypertriglyceridemia and Athersclerosis"*Annals of Internal Medicine,* 1998, pp. 73–74, vol. 128, No. 1.

Ghebrehiwet, B. et al. "Isolation, cDNA Cloning, and Overexpression of a 33–kD Cell Surface Glycoprotein that Binds to the Globular 'Heads'of C1q"*J. Exp. Med.,* Jun. 1994, pp. 1809–1821, vol. 179 (The Rockfeller University Press).

Goldstein, J.L. et al. "Famitial Hypercholesterolemia"*The Metabolic and Molecular Bases of Inherited Disease,* 1995, pp. 1981–2030, vol. II, 7th Edition, ed. Scriver, C.R. et al., McGraw–Hill, New York.

Goldstein, J.L. et al. "Hyperlipidemia in Coronary Heart Diseases"*J. Clin. Invest.,* Jul. 1973, pp. 1533–1543, vol. 52.

Gura, T. et al. "Obesity Sheds its Secrets"*Science,* Feb. 7, 1997, pp. 751–753, vol. 275.

Hayward, C.P. et al. "The cDNA Sequence of Human Endothelial Cell Multimerin"*J. Biol. Chem.,* Aug. 4, 1995, pp. 18246–18251, vol. 270, No. 31 (The American Society for Biochemistry and Molecular Biology, Inc.).

Henrion, A.A. et al. "Structure, Sequence, and Chromosmal Location of the Gene for USF2 Transcription Factors In Mouse"*Genomics,* 1995, pp. 36–43, vol. 25 (Academic Press, Inc.).

Herz, J. et al. "Surface Locations and High Affinity for Calcium of a 500–kd Liver Membrane Protein Closely Related to the LDL–Receptor Suggest a Physiological Role as Lipoprotein Receptor"*European Molecular Biology Laboratory,* 1988, pp. 4119–4127, vol. 7 (IRL Press Limited, Oxford, England).

Honore, B. et al., "Cloning and Expression of a cDNA Covering the Complete Coding Region of the P32 Subunit of Human Pre–mRNA Splicing Factor SF2"*Gene,* 1993, pp. 283–287, vol. 134 (Elsevier Science Publishers B.V.).

Hu, E. et al. "AdipoQ is a Novel Adipose–Specific Gene Dysregulated in Obesity"*J. Biol. Chem.* May 3, 1996, pp. 10697–10703, vol. 271, No. 18.

Huettinger, M. et al. "Characterstics of Chylomicron Remnant Uptake into Rat Liver"*Clin. Biochem.,* 1988, pp. 87–92 vol. 21.

Inagawa, K. et al. "Structure–Function Studies of Human Leptin"*J. Biol. Chem.,* Dec. 25, 1998, pp. 35245–35249, vol. 273, No. 52 (The American Society for Biochemistry and Molecular Biology, Inc.).

Karpe, F. et al. "Clearance of Lipoprotein Remnant Particles in Adipose Tissue and Muslce in Humans"*J. Lipid Res.,* 1997, pp. 2335–2343, vol. 38.

Karp, F. et al. "Magnitude of Alimentary Lipemia is Related to Related to Intima–media Thickness of the Common Carotid Artery in Midddle–Aged Men"*Atheroscierosis,* 1998, pp. 307–314, vol. 141.

Kerstein, S. et al. "Peroxisome Proliferator–Activated Receptor αMediates The Adaptive Response to Fasting"*J. Clin. Invest.,* Jun. 1999, pp. 1489–1498, vol. 103, No. 11 (The American Society for Clinical Investigations).

Khallou et al. "Correction of Delayed Postprandial Plasma Lipid Response in Genetically Obese Mice by Injection of Recombinant Leptin" Abstract from the 69th Scientific Sessions, New Orleans, LA; Supplemental to *Circulation,* American Heart Association, 1996, p. 8, vol. 94.

Krainer, A.R. et al. "Functional Expression of Cloned Human Splicing Factor SF2: Homology to RNA–Binding Proteins, U1 70K, and Drosophila Splicing Regulations-"*Cell,* Jul. 26, 1991, pp. 383–394, vol. 66 (Cell Press).

Letourneur, F., et al. "A Novel Di–Leucine Motif and a Tyrosine–Based Motif Independently Mediate Lysosmal Trageting and Endocytosis of CD3 Chains"*Cell,* Jun. 26, 1992, pp. 1143–1157, vol. 69 (Cell Press).

Lewis, G.F. et al. "Postprandial Lipoprotein Metabolism in Normal and Obese Subjects: Comparsion After the Vitamin A Fat–Loading Tect"*Jr. of Clinic. Endo.,* 1990, pp. 1041–1050, vol. 71 (The Endocrine Society).

Lin, Q. et al. "Archaic Structure of the Gene Encoding Transcription Factor USF"*J. of Bio. Chem.,* 1994, pp. 23894–23903, vol. 269 (The American Society for biochemistry and Molecular Biology, Inc.).

Lin, Q. et al. "Design of Polydactyl Zinc–Finger Proteins for Unique Addressing Within Complex Genomes"*Proc. Natl. Acad. Sci.* USA, May 27, 1997, pp. 5525–5530, vol. 94, No. 11.

Maeda, K. et al. "cDNA Cloning and Expression of a Novel Adlpose Specific Collagen–Like Factor, apM1 (Adipose most Abundant Gene Transcript 1)"*Biochem. and Biophys. Research Comm.,* 1996, pp. 286–289, vol. 221 (Academic Press).

Mahley, R.W. et al. "Type III Hyperlipoproteinemia (Dysbetalipoproteinmia): The Role of Apolipoprotein E in Normal and Abnormal Lipoprotein Metabolism "*The Molecular Basis of Inherited Disease,* 1995, pp. 1953–1980, eds Scriver et al., McGraw–Hill, Inc., New York (The American Chemical Society).

Mann, C.J. et al. "Mechanism for Activation and Functional Signifiance of the Lipolysis–Stimulated Receptor, Evidence for a Role as Chylomicron Remnant Receptor"*Biochemistry,* 1995, pp. 10421–10431, vol. 34.

Mann et al. "ApoCIII Inhibits the Binding of Triglyceride–Rich Lipoproteins to the Lipolysis Stimulated Receptor" 1996, abstract only.

Massie, B. et al. "Inducible Overexpression of a Toxic Protein by an Adenovirus Vector with a Tetracycline–Regulatable Expression Cassette"*Journal of Virology,* Mar. 1998, pp. 2289–2296, vol. 72 (American Society for Microbiology).

Montague, C.T. et al. "Congenital Leptin Deficiency is Associated with Severe Early–onset Obesity in Humans"*Nature,* 1997, pp. 903–908, vol. 387.

Parra–Lopez, C.A. et al. "Presentation on Class II MHC Molecules of Endogenous Lysozymes Targeted to the Endocytic Pathway"*J. Immunol.,* 1997, pp. 2670–2679, vol. 158 (The American Association of Immunologist).

Pengue, G. et al. "Repression of Transcriptional Activity at a Distance by the Evolutionarily Conserved KRAB Domain Present in a Subfamily of Zinc Finger Proteins"*Nucleic Acids Research,* 1994, pp. 2908–2914, vol. 22, No. 15 (Oxford University Press).

Perusse, L. et al. "The Human Obsesity Gene Map: The 1998 Update"*Obes. Res.,* Jan. 1999, pp. 111–129, vol. 7.*

Rajput–Williams, J. et al. "Variation of Apolipoprotein–B Gene is Associated with Obesity, High Blood Cholestrol Levels and increased Risk of Coronary Heart Disease"*The Lancet,* Dec. 24–31, 1988, pp. 1442–1446.*

Rutherford, S. et al. "Association of a Low Density Lipoprotein Receptor Micro–Satellite Variant with Obesity"*Intl. Jr. of Obesity,* 1997, pp. 1032–1037, vol. 21 (Stockton Press).*

Saito, K. et al. "Organization of the Gene for Gelatin–Binding Protein (GBP28)"*Gene,* Jan. 12, 1999, pp. 67–73, vol. 229 (Elsevier Science B.V.).*

Schaffler, A. et al. "Identification and Characterization of the Human Adipocyte apM–1 Promoter"*Biochem. and Biophys. Res. Comm,* Jun. 22, 1998, pp. 187–197, vol. 1399 (Elsevier Science B.V.).*

Schaffler, A. et al. "The Human apM–1, an Adipoccyte–Specific Gene Linked to the Family of TNF's and to Genes Expressed in Activated T Cells, is Mapped to Chromosome 1q21.3–q23, a Susceptibility Locus Identified for Familial Combined Hyperlipdaemia (FCH)"*Biochem. and Biophys. Res. Comm.,* May 7, 1999, pp. 416–425, vol. 260 (Academic Press).*

Scherer, P.E. et al. "A Novel Serum Protein Similar to C1Q, Produced Exclusively in Adipocytes"*J. Biol. Chem.,* Nov. 10, 1995, pp. 26746–26749, vol. No. 45 (The American Society for Biochemistry and Molecular Biology, Inc.).*

Sellar, G.C. et al. "Characterization and Organization of the Genes Encoding the A–, B–and C–Chains of Human Complement Subcomponent C1q"*Biochemical Journal,* 1991, pp. 481–490, vol. 274.*

Shimabukuro, M. et al. "Direct Antidiabetic Effect of Leptin Through Triglyceride Depletion of Tissues"*Proc. Natl. Acad. Sci. USA,* Apr. 29, 1997, pp. 4637–4641, vol. 94, No. 9.*

Shimano, H. et al., "Overproduction of Cholesterol and Fatty Acids Causes Massive Liver Enlargement in Transgenic Mice Expressing Truncated SREPB–1A"*J. Clin. Invest.,* Oct. 1996, pp. 1575–1584, vol. 98, No. 7 (The American Society for Clinical Investigation, Inc.).*

Shimomura, I. et al. "Leptin Reverses Insulin Resistance and Diabetes Mellitus in Mice with Congenital Lipodystrophy"*Nature,* Sep. 2, 1999, pp. 73–76, vol. 401.

Shin, J. et al. "Phoshorylation–Dependent Down–Modulation of CD4 Requires a Speccific Structure Within the Cytoplasmic Domain of CD4"*J. Biol. Chem.,* 1991, pp. 10658–10665, vol. 266 (The American Society for Biochemistry and Molecular Biology, Inc.).

Simos, G. et al. "The Lamin B Receptor–Associated Protein p34 Shares Sequence Homology and Antignetic Determinants with the Splicing Factor 2–Associated Protein p32"*FEBS Letters,* 1994, pp. 225–228, vol. 346 (Federation Biochemical Societies).

Steingrimsson, E. et al. "Murine Chromosmal of Five bHLH–ZIP Transcription Factor Genes"*Genomics,* 1995, pp. 179–183, vol. 28 (Academic Press, Inc.).

Troussard, A.A. et al. "Inhibitory Effect on the Lipolysis-Stimulated Receptor of the 39–kDa Receptor–Associated Protein"*J. of Biol. Chem.,* Jul. 21, 1995, pp. 17068–17071, vol. 270, No. 29 (The American Society for Biochemistry and Molecular Biology, Inc.).

Urade, Y. et al. "Precerebellin is a Cerebellum–Specific Protein with Similarity to the Globular Domain of Complement C1qB Chain"*Proc. Natl. Sci. USA,* Feb. 1991, pp. 1069–1073, vol. 88.

Uotani, S. et al. Functional Properties of Leptin Receptor Isoforms Internalization and Edgradation of Leptin and legand–Induced Receptor Downregulation Diabetes, Feb. 1999, pp. 279–286, vol. 48.

Vansant, G. et al. "Determinants of Postpradial Lipemia in Obese Women"*Intl. Jr. of Obesity,* 1999, pp. 14–21, vol. 23, Supp. 1, (Stockton Press).

Verhey, K.J. et al. "A Leu–Leu Sequence is Essential for COOH–Terminal Targeting Signal of GLUT4 Glucose Transporter in Fibroblasts"*J. Biol. Chem.,* 1994, pp. 2353–2356, vol. 269 (The American Society for Biochemistry and Molecular Biology, Inc.).

Wang, D. et al. "Upstream Stimulatory Factor Binding to the E–Box at –65 is Required for Insulin Regulation of the Fatty Acid Synthase Promoter"*J. Biol. Chem.,* Oct. 17, 1997, pp. 26367–26374, vol. 272, No. 42.

Yen, F.T. et al. "Molecular Cloning of a LipolysisStimualted Remnant Receptor Expressed in the Liver"*J. Biol. Chem.,* 1999, pp. 13390–13398, vol. 274, No. 19 (The American Society for Biochemistry and Molecular Biology, Inc.).

Yen, F.T. et al. "Identification of a Lipolysis–Stimulated Receptor that is Distinct from the LDL Recceptor and the LDL Receptor–Related Protein"*Biochemistry,* 1994, pp. 1172–1180, vol. 33 (American Press Society).

Zhang, M. et al. "Tumor Necrosis Factor"*The Cytokine Handbook,* Third Edition, 1988, pp. 517–548, Academic Press Limited.

Zhong, G. et al. "Related Lecine–Based Cytoplasmic Targeting Signals in Invariant Chain and Major Histocompatibility Complex Class II Molecules Control Endocytic Presentation of Distinct Determinants in a Single Protein"*J. Exp. Med.,* Feb. 3, 1997, pp. 429–438, 185, No. 3.

Barsh, G. et al. "Genetics of Body–Weight Regulation"*Nature,* Apr. 6, 2000, pp. 644–651, vol. 404.

Friedman, J.M. "Obesity in the New Millennium"*Nature,* Apr. 3, 2000, pp. 632–634, vol. 404 (MacMillian Magazines Ltd.).

Oksana, G. et al. "Hormones: Leptin and Diabetes in Lipaotrophic Mice"*Nature,* Feb. 24, 2000, p. 850, vol. 403 (MacMillan Publishers ltd.).

Oksana, G. et al. "Lack of Responses to a [[Beta].sub.3] Adrengic Agonist in Lipoatrophic A–ZIP/F–1 Mice"*Diabetes,* Nov. 2000, p. 1910, vol. 49, No. 11 (American Diabetes Association).

Hotta, K. et al. "Plasma Concentrations of a Novel, Adipose–Specific Protein, Adiponectin, in Type 2 Diabetic Patients"*Arterioscler Thromb Vasc Biol,* Jun. 2000, pp. 1595–1599, vol. 20, No. 6 (American Association, Inc.).

Kishore, U. et al. "Molecular Organization of Proteins Containing Clq–like Globular Domain"*Immunopharmacology,* 1999, pp. 15–21, vol. 42 (Elsevier Science B.V.).

Kishore, U. et al. "Ciq: Structure, Function, and Receptors"*Immunopharmacology,* 2000, pp. 159–170, vol. 49 (Elsevier Science B.V.).

Kopelman, P. et al. "Obesity as a Medical Problem"*Nature,* Apr. 6, 2000, pp. 635–643, vol. 404 (MacMillan Magazines Ltd.).

Mann, C. et al. "Inhibitory Effects of Specific Apolipoprotein C–III Isoforms on the Binding of Triglyceride–Rich Lipoproteins to the Lipolysis–Stimulated Receptors"*The Journal of Biological Chemistry,* 1997, pp. 31348–31354, vol. 272, No. 50 (The American Society for Biochemistry and Molecular Biology, Inc.

Nakano, Y. et al. "Isolation and Characterization of GBp28, a Novel Gelatin–Binding Protein Purified From Human Plasma"*J. Biochem.,* 1996, pp. 803–812, vol. 120, No. 4.

Okamoto, Y. et al. "An Adipocyte–Derived Plasma Protein, Adioponectin, Adheres to injured Vascular Walls"*Horm Metab Res.,* pp. 47–50, vol. 32 (Georg Thieme Veriag Stuttgart–New York).

Ouchui, N. et al. "Novel Modulator for Endothlial Adhesion Molecules/Adiopocyte–Derived Plasma Protein Adiponectin"*Circulation,* Dec. 21–28, 1999, pp. 2473–2476, vol. 100 (American Heart Association).

Montague, C.T. et al. "Congenital Leptin Deficiency is Associated with Severe Early–Onset Obesity in Humans"*Nature,* Jun. 26, 1997, pp. 903–908, vol. 387.

Saito, K. et al. "Regulation of Gelatin–Binding Protein 28 (GBP28) Gene Expression by C/EBP"*Biol. Pharma. Bull.,* 1999, pp. 1158–1162, vol. 22, No. 11.

Shapiro, L. et al. "The Crystal Structure of a Complement–1q Family Protein Suggests an Evolutionary Link to Tumor Necrosis Factor"*Current Biology,* 1998, pp. 335–338, vol. 8, No. 6.

Takahashi, M. et al. "Genomic Structure and Mutation in Adipose–Specific Gene, Adiponectin"*International Journal of Obesity,* 2000, pp. 861–868, vol. 24 (MacMillan Publishers Ltd.).

Yokota, T. et al. "Adiponectin, a New Member of the Family of Soluble Defense Collagens, Negatively Regulates the Growth of Myelomonocytic Progenitors and the Functions of Macrophages"*Blood,* Sep. 1, 2000, pp. 1723–1732, vol. 96, No. 5 (The American Society of Hematology).

Berg, A. H. et al. "The Adipocyte–Secreted Protein Acrp30 Enhances Hepatic Insulin Action"*Nature Medicine,* Aug. 2001, pp. 947–953, vol. 7, No. 8 (Nature Publishing Group).

Yamauchi, T. et al. "The Fat–Derived Hormone Adiponectin Reverses Insulin Resistance Associated with Both Lipoatrophy and Obesity"*Nature Medicine,* Aug. 2001, pp. 941–946, vol. 7, No. 8 (Nature Publishing Group).*

* cited by examiner

```
                           10                            20                           30
1     M L L L G A V L L L L A L P G H D Q E - - - T T T Q G P G V      apmlprotein
1     M L L L Q A L L F L L I L P S H A E D D V T T T E E L A P A      adipoQprotein
1     M L L L Q A L L F L L I L P S H A E D D V T T T E E L A P A      acrp30protein2

                           40                            50                           60
28    L L P L P K G A C T G W M A G I P G H P G H N G A P G R D G      apmlprotein
31    L V P P P K G T C A G W M A G I P G H S G H N G T P G R D G      adipoQprotein
31    L V P P P K G T C A G W M A G I P G H P G H N G T P G R D G      acrp30protein2

                           70                            80                           90
58    R D G T P G E K G E K G D P G L L G P K G D I G E T G V P G      apmlprotein
61    R D G T P G E K G E K G D S G L L G P K G E T G D V G M T G      adipoQprotein
61    R D G T P G E K G E K G D A G L L G P K G E T G D V G M T G      acrp30protein2

                           100                           110                          120
88    A E G P R G F P G I Q G R K G E P G E G A Y V Y R S A F S V      apmlprotein
91    A E G P R G F P G T P G R K G E P G E A A Y V Y R S G F S V      adipoQprotein
91    A E G P R G F P G T P G R K G E P G E A A Y M Y R S A F S V      acrp30protein2

                           130                           140                          150
118   G L E T Y V T I P N M P I R F T K I F Y N Q Q N H Y D G S T      apmlprotein
121   G L E T R V T V P N V P I R F T K I F Y N Q Q N H Y D N S T      adipoQprotein
121   G L E T R V T V P N V P I R F T K I F Y N Q Q N H Y D G S T      acrp30protein2

                           160                           170                          180
148   G K F H C N I P G L Y Y F A Y H I T V Y M K D V K V S L F K      apmlprotein
151   G K F Y C N I P G L Y Y F S Y H I T V Y M K D V K V S L F K      adipoQprotein
151   G K F Y C N I P G L Y Y F S Y H I T V Y M K D V K V S L F K      acrp30protein2

                           190                           200                          210
178   K D K A M L F T Y D Q Y Q E N N V D Q A S G S V L L H L E V      apmlprotein
181   K D K A V L F T Y D Q Y Q E K N V D Q A S G S V L L H L E V      adipoQprotein
181   K D K A V L F T Y D Q Y Q E K N V D Q A S G S V L L H L E V      acrp30protain2

                           220                           230                          240
208   G D Q V W L Q V Y G E G E R N G L Y A D N D N D S T F T G F      apmlprotein
211   G D Q V W L Q V Y G D G D H N G L Y A D N V N D S T F T G F      adipoQprotein
211   G D Q V W L Q V Y G D G D H N G L Y A D N V N D S T F T G F      acrp30protein2

238   L L Y H D T N .                                                  apmlprotein
241   L L F H D T - N                                                  adipoQprotein
241   L L Y H D T - N                                                  acrp30protein2
```

FIG. 1

GTTTGACAGCTTATCATCGACTGCACGGTGCACCAATGCTTCTGGCGTCAGGCAGCCATCGGAAGCTGTGGTATGGCTGT
GCAGGTCGTAAATCACTGCATAATTCGTGTCGCTCAAGGCGCACTCCCGTTCTGGATAATGTTTTTTGCGCCGACATCAT
AACGGTTCTGGCAAATATTCTGAAATGAGCTGTTGACAATTAATCATCCGGCTCGTATAATGTGTGGAATTGTGAGCGGA
TAACAATTTCACACAGGAAACAGCGCCGCTGAGAAAAAGCGAAGCGGCACTGCTCTTTAACAATTTATCAGACAATCTGT
GTGGGCACTCGACCGGAATTATCGATTAACTTTATTATTAAAAATTAAAGAGGTATATATTAATGTATCGATTAAATAAG
GAGGAATAAACCATGGGGGGTTCTCATCATCATCATCATCATGGTATGGCTAGCATGACTGGTGGACAGCAAATGGGTCG
GGATCTGTACGACGATGACGATAAGGATCCGAGTCATGCCGAAGATGACGTTACTACAACTGAAGAGCTAGCTCCTGCTT
TGGTCCCTCCACCCAAGGGAACTTGTGCAGGTTGGATGGCAGGCATCCCAGGACATCCTGGCCACAATGGCACACCAGGC
CGTGATGGCAGAGATGGCACTCCTGGAGAGAAGGGAGAGAAAGGAGATGCAGGTCTTCTTGGTCCTAAGGGTGAGACAGG
AGATGTTGGAATGACAGGAGCTGAAGGGCCACGGGGCTTCCCCGGAACCCCTGGCAGGAAAGGAGAGCCTGGAGAAGCCG
CTTATGTGTATCGCTCAGCGTTCAGTGTGGGGCTGGAGACCCGCGTCACTGTTCCCAATGTACCCATTCGCTTTACTAAG
ATCTTCTACAACCAACAGAATCATTATGACGGCAGCACTGGCAAGTTCTACTGCAACATTCCGGGACTCTACTACTTCTC
TTACCACATCACGGTGTACATGAAAGATGTGAAGGTGAGCCTCTTCAAGAAGGACAAGGCCGTTCTCTTCACCTACGACC
AGTATCAGGAAAAGAATGTGGACCAGGCCTCTGGCTCTGTGCTCCTCCATCTGGAGGTGGGAGACCAAGTCTGGCTCCAG
GTGTATGGGGATGGGGACCACAATGGACTCTATGCAGATAACGTCAACGACTCTACATTTACTGGCTTTCTTCTCTACCA
TGATACCAACTGACTCGAGATCTGCAGCTGGTACCATATGGGAATTCGAAGCTTGGCTGTTTTGGCGGATGAGAGAAGAT
TTTCAGCCTGATACAGATTAAATCAGAACGCAGAAGCGGTCTGATAAAACAGAATTTGCCTGGCGGCAGTAGCGCGGTGG
TCCCACCTGACCCCATGCCGAACTCAGAAGTGAAACGCCGTAGCGCCGATGGTAGTGTGGGGTCTCCCCATGCGAGAGTA
GGGAACTGCCAGGCATCAAATAAAACGAAAGGCTCAGTCGAAAGACTGGGCCTTTCGTTTTATCTGTTGTTTGTCGGTGA
ACGCTCTCCTGAGTAGGACAAATCCGCCGGGAGCGGATTTGAACGTTGCGAAGCAACGGCCCGGAGGGTGGCGGGCAGGA
CGCCCGCCATAAACTGCCAGGCATCAAATTAAGCAGAAGGCCATCCTGACGGATGGCCTTTTTGCGTTTCTACAAACTCT
TTTTGTTTATTTTTCTAAATACATTCAAATATGTATCCGCTCATGAGACAATAACCCTGATAAATGCTTCAATAATATTG
AAAAAGGAAGAGTATGAGTATTCAACATTTCCGTGTCGCCCTTATTCCCTTTTTTGCGGCATTTTGCCTTCCTGTTTTTG
CTCACCCAGAAACGCTGGTGAAAGTAAAAGATGCTGAAGATCAGTTGGGTGCACGAGTGGGTTACATCGAACTGGATCTC
AACAGCGGTAAGATCCTTGAGAGTTTTCGCCCCGAAGAACGTTTTCCAATGATGAGCACTTTTAAAGTTCTGCTATGTGG

FIG. 2A

CGCGGTATTATCCCGTGTTGACGCCGGGCAAGAGCAACTCGGTCGCCGCATACACTATTCTCAGAATGACTTGGTTGAGT
ACTCACCAGTCACAGAAAAGCATCTTACGGATGGCATGACAGTAAGAGAATTATGCAGTGCTGCCATAACCATGAGTGAT
AACACTGCGGCCAACTTACTTCTGACAACGATCGGAGGACCGAAGGAGCTAACCGCTTTTTTGCACAACATGGGGGATCA
TGTAACTCGCCTTGATCGTTGGGAACCGGAGCTGAATGAAGCCATACCAAACGACGAGCGTGACACCACGATGCCTGTAG
CAATGGCAACAACGTTGCGCAAACTATTAACTGGCGAACTACTTACTCTAGCTTCCCGGCAACAATTAATAGACTGGATG
GAGGCGGATAAAGTTGCAGGACCACTTCTGCGCTCGGCCCTTCCGGCTGGCTGGTTTATTGCTGATAAATCTGGAGCCGG
TGAGCGTGGGTCTCGCGGTATCATTGCAGCACTGGGGCCAGATGGTAAGCCCTCCCGTATCGTAGTTATCTACACGACGG
GGAGTCAGGCAACTATGGATGAACGAAATAGACAGATCGCTGAGATAGGTGCCTCACTGATTAAGCATTGGTAACTGTCA
GACCAAGTTTACTCATATATACTTTAGATTGATTTAAAACTTCATTTTTAATTTAAAAGGATCTAGGTGAAGATCCTTTT
TGATAATCTCATGACCAAAATCCCTTAACGTGAGTTTTCGTTCCACTGAGCGTCAGACCCCGTAGAAAAGATCAAAGGAT
CTTCTTGAGATCCTTTTTTTCTGCGCGTAATCTGCTGCTTGCAAACAAAAAAACCACCGCTACCAGCGGTGGTTTGTTTG
CCGGATCAAGAGCTACCAACTCTTTTTCCGAAGGTAACTGGCTTCAGCAGAGCGCAGATACCAAATACTGTCCTTCTAGT
GTAGCCGTAGTTAGGCCACCACTTCAAGAACTCTGTAGCACCGCCTACATACCTCGCTCTGCTAATCCTGTTACCAGTGG
CTGCTGCCAGTGGCGATAAGTCGTGTCTTACCGGGTTGGACTCAAGACGATAGTTACCGGATAAGGCGCAGCGGTCGGGC
TGAACGGGGGGTTCGTGCACACAGCCCAGCTTGGAGCGAACGACCTACACCGAACTGAGATACCTACAGCGTGAGCTATG
AGAAAGCGCCACGCTTCCCGAAGGGAGAAAGGCGGACAGGTATCCGGTAAGCGGCAGGGTCGGAACAGGAGAGCGCACGA
GGGAGCTTCCAGGGGGAAACGCCTGGTATCTTTATAGTCCTGTCGGGTTTCGCCACCTCTGACTTGAGCGTCGATTTTTG
TGATGCTCGTCAGGGGGGCGGAGCCTATGGAAAAACGCCAGCAACGCGGCCTTTTTACGGTTCCTGGCCTTTTGCTGGCC
TTTTGCTCACATGTTCTTTCCTGCGTTATCCCCTGATTCTGTGGATAACCGTATTACCGCCTTTGAGTGAGCTGATACCG
CTCGCCGCAGCCGAACGACCGAGCGCAGCGAGTCAGTGAGCGAGGAAGCGGAAGAGCGCCTGATGCGGTATTTTCTCCTT
ACGCATCTGTGCGGTATTTCACACCGCATATGGTGCACTCTCAGTACAATCTGCTCTGATGCCGCATAGTTAAGCCAGTA
TACACTCCGCTATCGCTACGTGACTGGGTCATGGCTGCGCCCCGACACCCGCCAACACCCGCTGACGCGCCCTGACGGGC
TTGTCTGCTCCCGGCATCCGCTTACAGACAAGCTGTGACCGTCTCCGGGAGCTGCATGTGTCAGAGGTTTTCACCGTCAT
CACCGAAACGCGCGAGGCAGCAGATCAATTCGCGCGCGAAGGCGAAGCGGCATGCATTTACGTTGACACCATCGAATGGT
GCAAAACCTTTCGCGGTATGGCATGATAGCGCCCGGAAGAGAGTCAATTCAGGGTGGTGAATGTGAAACCAGTAACGTTA

FIG. 2B

TACGATGTCGCAGAGTATGCCGGTGTCTCTTATCAGACCGTTTCCCGCGTGGTGAACCAGGCCAGCCACGTTTCTGCGAA
AACGCGGGAAAAAGTGGAAGCGGCGATGGCGGAGCTGAATTACATTCCCAACCGCGTGGCACAACAACTGGCGGGCAAAC
AGTCGTTGCTGATTGGCGTTGCCACCTCCAGTCTGGCCCTGCACGCGCCGTCGCAAATTGTCGCGGCGATTAAATCTCGC
GCCGATCAACTGGGTGCCAGCGTGGTGGTGTCGATGGTAGAACGAAGCGGCGTCGAAGCCTGTAAAGCGGCGGTGCACAA
TCTTCTCGCGCAACGCGTCAGTGGGCTGATCATTAACTATCCGCTGGATGACCAGGATGCCATTGCTGTGGAAGCTGCCT
GCACTAATGTTCCGGCGTTATTTCTTGATGTCTCTGACCAGACACCCATCAACAGTATTATTTTCTCCCATGAAGACGGT
ACGCGACTGGGCGTGGAGCATCTGGTCGCATTGGGTCACCAGCAAATCGCGCTGTTAGCGGGCCCATTAAGTTCTGTCTC
GGCGCGTCTGCGTCTGGCTGGCTGGCATAAATATCTCACTCGCAATCAAATTCAGCCGATAGCGGAACGGGAAGGCGACT
GGAGTGCCATGTCCGGTTTTCAACAAACCATGCAAATGCTGAATGAGGGCATCGTTCCCACTGCGATGCTGGTTGCCAAC
GATCAGATGGCGCTGGGCGCAATGCGCGCCATTACCGAGTCCGGGCTGCGCGTTGGTGCGGATATCTCGGTAGTGGGATA
CGACGATACCGAAGACAGCTCATGTTATATCCCGCCGTTAACCACCATCAAACAGGATTTTCGCCTGCTGGGGCAAACCA
GCGTGGACCGCTTGCTGCAACTCTCTCAGGGCCAGGCGGTGAAGGGCAATCAGCTGTTGCCCGTCTCACTGGTGAAAAGA
AAAACCACCCTGGCGCCCAATACGCAAACCGCCTCTCCCCGCGCGTTGGCCGATTCATTAATGCAGCTGGCACGACAGGT
TTCCCGACTGGAAAGCGGGCAGTGAGCGCAACGCAATTAATGTGAGTTAGCGCGAATTGATCTG

FIG. 2C

GTTTGACAGCTTATCATCGACTGCACGGTGCACCAATGCTTCTGGCGTCAGGCAGCCATCGGAAGCTGTGGTATGGCTGT
GCAGGTCGTAAATCACTGCATAATTCGTGTCGCTCAAGGCGCACTCCCGTTCTGGATAATGTTTTTTGCGCCGACATCAT
AACGGTTCTGGCAAATATTCTGAAATGAGCTGTTGACAATTAATCATCCGGCTCGTATAATGTGTGGAATTGTGAGCGGA
TAACAATTTCACACAGGAAACAGCGCCGCTGAGAAAAAGCGAAGCGGCACTGCTCTTTAACAATTTATCAGACAATCTGT
GTGGGCACTCGACCGGAATTATCGATTAACTTTATTATTAAAAATTAAAGAGGTATATATTAATGTATCGATTAAATAAG
GAGGAATAAACCATGGGGGGTTCTCATCATCATCATCATCATGGTATGGCTAGCATGACTGGTGGACAGCAAATGGGTCG
GGATCTGTACGACGATGACGATAAGGATCCCGCTTATGTGTATCGCTCAGCGTTCAGTGTGGGGCTGGAGACCCGCGTCA
CTGTTCCCAATGTACCCATTCGCTTTACTAAGATCTTCTACAACCAACAGAATCATTATGACGGCAGCACTGGCAAGTTC
TACTGCAACATTCCGGGACTCTACTACTTCTCTTACCACATCACGGTGTACATGAAAGATGTGAAGGTGAGCCTCTTCAA
GAAGGACAAGGCCGTTCTCTTCACCTACGACCAGTATCAGGAAAAGAATGTGGACCAGGCCTCTGGCTCTGTGCTCCTCC
ATCTGGAGGTGGGAGACCAAGTCTGGCTCCAGGTGTATGGGGATGGGGACCACAATGGACTCTATGCAGATAACGTCAAC
GACTCTACATTTACTGGCTTTCTTCTCTACCATGATACCAACTGACTCGAGATCTGCAGCTGGTACCATATGGGAATTCG
AAGCTTGGCTGTTTTGGCGGATGAGAGAAGATTTTCAGCCTGATACAGATTAAATCAGAACGCAGAAGCGGTCTGATAAA
ACAGAATTTGCCTGGCGGCAGTAGCGCGGTGGTCCCACCTGACCCCATGCCGAACTCAGAAGTGAAACGCCGTAGCGCCG
ATGGTAGTGTGGGGTCTCCCCATGCGAGAGTAGGGAACTGCCAGGCATCAAATAAAACGAAAGGCTCAGTCGAAAGACTG
GGCCTTTCGTTTTATCTGTTGTTTGTCGGTGAACGCTCTCCTGAGTAGGACAAATCCGCCGGGAGCGGATTTGAACGTTG
CGAAGCAACGGCCCGGAGGGTGGCGGGCAGGACGCCCGCCATAAACTGCCAGGCATCAAATTAAGCAGAAGGCCATCCTG
ACGGATGGCCTTTTTGCGTTTCTACAAACTCTTTTTGTTTATTTTTCTAAATACATTCAAATATGTATCCGCTCATGAGA
CAATAACCCTGATAAATGCTTCAATAATATTGAAAAAGGAAGAGTATGAGTATTCAACATTTCCGTGTCGCCCTTATTCC
CTTTTTTGCGGCATTTTGCCTTCCTGTTTTTGCTCACCCAGAAACGCTGGTGAAAGTAAAAGATGCTGAAGATCAGTTGG
GTGCACGAGTGGGTTACATCGAACTGGATCTCAACAGCGGTAAGATCCTTGAGAGTTTTCGCCCCGAAGAACGTTTTCCA
ATGATGAGCACTTTTAAAGTTCTGCTATGTGGCGCGGTATTATCCCGTGTTGACGCCGGGCAAGAGCAACTCGGTCGCCG
CATACACTATTCTCAGAATGACTTGGTTGAGTACTCACCAGTCACAGAAAAGCATCTTACGGATGGCATGACAGTAAGAG
AATTATGCAGTGCTGCCATAACCATGAGTGATAACACTGCGGCCAACTTACTTCTGACAACGATCGGAGGACCGAAGGAG
CTAACCGCTTTTTTGCACAACATGGGGGATCATGTAACTCGCCTTGATCGTTGGGAACCGGAGCTGAATGAAGCCATACC
AAACGACGAGCGTGACACCACGATGCCTGTAGCAATGGCAACAACGTTGCGCAAACTATTAACTGGCGAACTACTTACTC
TAGCTTCCCGGCAACAATTAATAGACTGGATGGAGGCGGATAAAGTTGCAGGACCACTTCTGCGCTCGGCCCTTCCGGCT
GGCTGGTTTATTGCTGATAAATCTGGAGCCGGTGAGCGTGGGTCTCGCGGTATCATTGCAGCACTGGGGCCAGATGGTAA
GCCCTCCCGTATCGTAGTTATCTACACGACGGGGAGTCAGGCAACTATGGATGAACGAAATAGACAGATCGCTGAGATAG
GTGCCTCACTGATTAAGCATTGGTAACTGTCAGACCAAGTTTACTCATATATACTTTAGATTGATTTAAAACTTCATTTT

FIG. 4A

TAATTTAAAAGGATCTAGGTGAAGATCCTTTTTGATAATCTCATGACCAAAATCCCTTAACGTGAGTTTTCGTTCCACTG
AGCGTCAGACCCCGTAGAAAAGATCAAAGGATCTTCTTGAGATCCTTTTTTTCTGCGCGTAATCTGCTGCTTGCAAACAA
AAAAACCACCGCTACCAGCGGTGGTTTGTTTGCCGGATCAAGAGCTACCAACTCTTTTTCCGAAGGTAACTGGCTTCAGC
AGAGCGCAGATACCAAATACTGTCCTTCTAGTGTAGCCGTAGTTAGGCCACCACTTCAAGAACTCTGTAGCACCGCCTAC
ATACCTCGCTCTGCTAATCCTGTTACCAGTGGCTGCTGCCAGTGGCGATAAGTCGTGTCTTACCGGGTTGGACTCAAGAC
GATAGTTACCGGATAAGGCGCAGCGGTCGGGCTGAACGGGGGGTTCGTGCACACAGCCCAGCTTGGAGCGAACGACCTAC
ACCGAACTGAGATACCTACAGCGTGAGCTATGAGAAAGCGCCACGCTTCCCGAAGGGAGAAAGGCGGACAGGTATCCGGT
AAGCGGCAGGGTCGGAACAGGAGAGCGCACGAGGGAGCTTCCAGGGGGAAACGCCTGGTATCTTTATAGTCCTGTCGGGT
TTCGCCACCTCTGACTTGAGCGTCGATTTTTGTGATGCTCGTCAGGGGGGCGGAGCCTATGGAAAAACGCCAGCAACGCG
GCCTTTTTACGGTTCCTGGCCTTTTGCTGGCCTTTTGCTCACATGTTCTTTCCTGCGTTATCCCCTGATTCTGTGGATAA
CCGTATTACCGCCTTTGAGTGAGCTGATACCGCTCGCCGCAGCCGAACGACCGAGCGCAGCGAGTCAGTGAGCGAGGAAG
CGGAAGAGCGCCTGATGCGGTATTTTCTCCTTACGCATCTGTGCGGTATTTCACACCGCATATGGTGCACTCTCAGTACA
ATCTGCTCTGATGCCGCATAGTTAAGCCAGTATACACTCCGCTATCGCTACGTGACTGGGTCATGGCTGCGCCCCGACAC
CCGCCAACACCCGCTGACGCGCCCTGACGGGCTTGTCTGCTCCCGGCATCCGCTTACAGACAAGCTGTGACCGTCTCCGG
GAGCTGCATGTGTCAGAGGTTTTCACCGTCATCACCGAAACGCGCGAGGCAGCAGATCAATTCGCGCGCGAAGGCGAAGC
GGCATGCATTTACGTTGACACCATCGAATGGTGCAAAACCTTTCGCGGTATGGCATGATAGCGCCCGGAAGAGAGTCAAT
TCAGGGTGGTGAATGTGAAACCAGTAACGTTATACGATGTCGCAGAGTATGCCGGTGTCTCTTATCAGACCGTTTCCCGC
GTGGTGAACCAGGCCAGCCACGTTTCTGCGAAAACGCGGGAAAAAGTGGAAGCGGCGATGGCGGAGCTGAATTACATTCC
CAACCGCGTGGCACAACAACTGGCGGGCAAACAGTCGTTGCTGATTGGCGTTGCCACCTCCAGTCTGGCCCTGCACGCGC
CGTCGCAAATTGTCGCGGCGATTAAATCTCGCGCCGATCAACTGGGTGCCAGCGTGGTGGTGTCGATGGTAGAACGAAGC
GGCGTCGAAGCCTGTAAAGCGGCGGTGCACAATCTTCTCGCGCAACGCGTCAGTGGGCTGATCATTAACTATCCGCTGGA
TGACCAGGATGCCATTGCTGTGGAAGCTGCCTGCACTAATGTTCCGGCGTTATTTCTTGATGTCTCTGACCAGACACCCA
TCAACAGTATTATTTTCTCCCATGAAGACGGTACGCGACTGGGCGTGGAGCATCTGGTCGCATTGGGTCACCAGCAAATC
GCGCTGTTAGCGGGCCCATTAAGTTCTGTCTCGGCGCGTCTGCGTCTGGCTGGCTGGCATAAATATCTCACTCGCAATCA
AATTCAGCCGATAGCGGAACGGGAAGGCGACTGGAGTGCCATGTCCGGTTTTCAACAAACCATGCAAATGCTGAATGAGG
GCATCGTTCCCACTGCGATGCTGGTTGCCAACGATCAGATGGCGCTGGGCGCAATGCGCGCCATTACCGAGTCCGGGCTG
CGCGTTGGTGCGGATATCTCGGTAGTGGGATACGACGATACCGAAGACAGCTCATGTTATATCCCGCCGTTAACCACCAT
CAAACAGGATTTTCGCCTGCTGGGGCAAACCAGCGTGGACCGCTTGCTGCAACTCTCTCAGGGCCAGGCGGTGAAGGGCA
ATCAGCTGTTGCCCGTCTCACTGGTGAAAAGAAAAACCACCCTGGCGCCCAATACGCAAACCGCCTCTCCCCGCGCGTTG
GCCGATTCATTAATGCAGCTGGCACGACAGGTTTCCCGACTGGAAAGCGGGCAGTGAGCGCAACGCAATTAATGTGAGTT
AGCGCGAATTGATCTG

FIG. 4B

```
         10        20        30        40        50        60        70        80        90
--------------SHAEDDVTTTEELAPALVPPPKGTCAGWMAGIPGHPGHNGTPGRDGRDGTPGEKGEKGDAGLLGPKGETGDVGMTG  76   obg3 clone
MLLLQALLFLLILPSHAEDDVTTTEELAPALVPPPKGTCAGWMAGIPGHSGHNGTPGRDGRDGTPGEKGEKGDSGLLGPKGETGDVGMTG  90   adipoQ
MLLLGAVLLLLALPGHDQE---TTTQGPGVLLPLPKGACTGWMAGIPGHPGHNGAPGRDGRDGTPGEKGEKGDPGLIGPKGDIGETGVPG  87   apm1
MLLLQALLFLLILPSHAEDDVTTTEELAPALVPPPKGTCAGWMAGIPGHPGHNGTPGRDGRDGTPGEKGEKGDAGLLGPKGETGDVGMTG  90   acrp30

        100       110       120       130       140       150       160       170       180
AEGPRGFPGTPGRKGEPGEAAYVYRSAFSVGLETRVTVPNVPIRFTKIFYNQQNHYDGSTGKFYCNIPGLYYFSYHITVYMKDVKVSLFK  166  obg3 clone
AEGPRGFPGTPGRKGEPGEAAYVYRSGFSVGLETRVTVPNVPIRFTKIFYNQQNHYDNSTGKFYCNIPGLYYFSYHITVYMKDVKVSLFK  180  adipoQ
AEGPRGFPGIQGRKGEPGEGAYVYRSAFSVGLETYVTIPNMPIRFTKIFYNQQNHYDGSTGKFHCNIPGLYYFAYHITVYMKDVKVSLFK  177  apm1
AEGPRGFPGTPGRKGEPGEAAYMYRSAFSVGLETRVTVPNVPIRFTKIFYNQQNHYDGSTGKFYCNIPGLYYFSYHITVYMKDVKVSLFK  180  acrp30

        190       200       210       220       230       240
KDKAVLFTYDQYQEKNVDQASGSVLLHLEVGDQVWLQVYGDGDHNGLYADNVNDSTFTGFLLYHDTN                233  obg3 clone
KDKAVLFTYDQYQEKNVDQASGSVLLHLEVGDQVWLQVYGDGDHNGLYADNVNDSTFTGFLLFHDTN                247  adipoQ
KDKAMLFTYDQYQENNVDQASGSVLLHLEVGDQVWLQVYGEGERNGLYADNDNDSTFTGFLLYHDTN                244  apm1
KDKAVLFTYDQYQEKNVDQASGSVLLHLEVGDQVWLQVYGDGDHNGLYADNVNDSTFTGFLLYHDTN                247  acrp30
```

FIG. 7 p=0.006

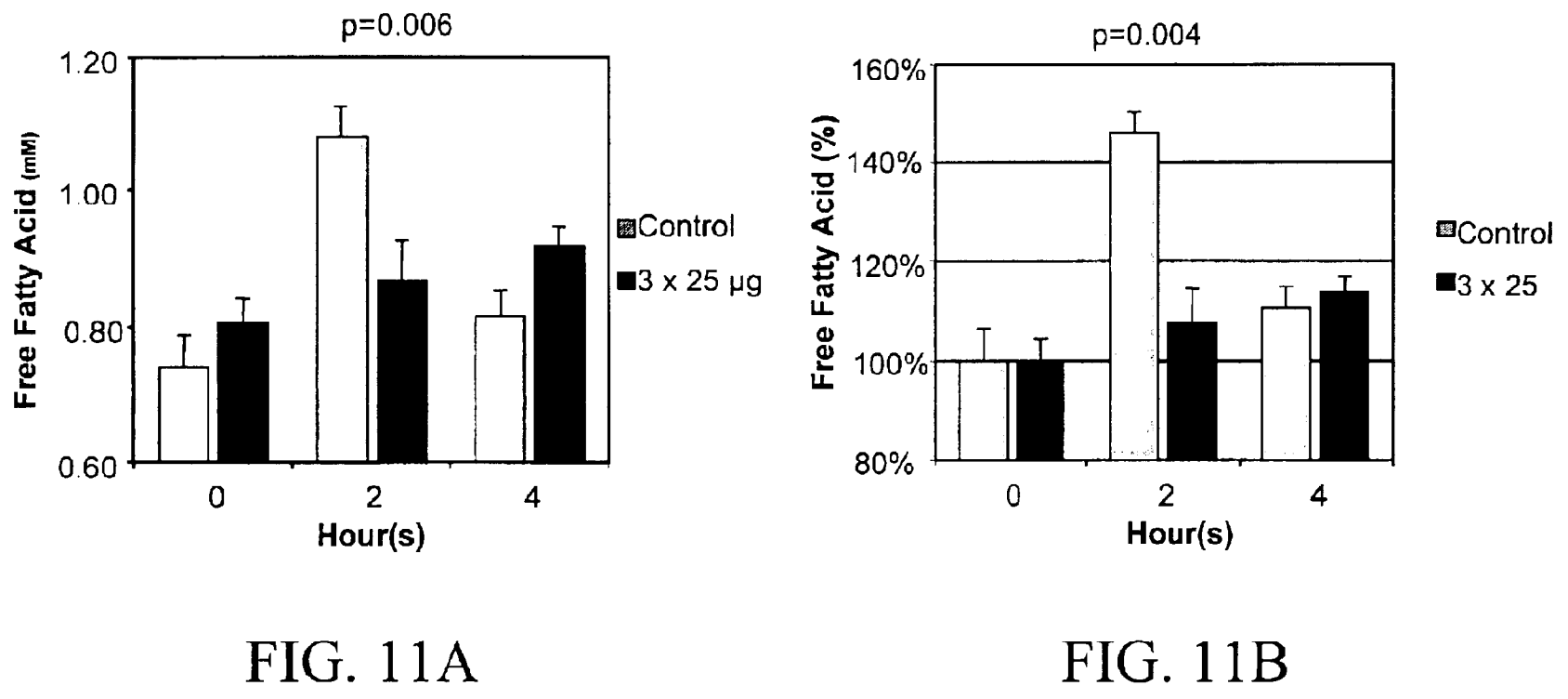

Free Fatty Acid (mM)

1.20
1.00
0.80
0.60

0
2
4
Hour(s)

Control
3 x 25 µg

FIG. 11A p=0.004

Free Fatty Acid (%)

160%
140%
120%
100%
80%

0
2
4
Hour(s)

Control
3 x 25

FIG. 11B

APM1 MARKERS/PRIMER SEQUENCE

| KNOWN BASE CHGS | LOCATION | PRIOR MARKERS | AMPLICON | FORWARD PRIMER (5' - 3') | REVERSE PRIMER (5' - 3') |
|---|---|---|---|---|---|
| 3738 | PROMOTER | | 9-27F/9-27R | TGGACATTAGCAGGAAGC | ATGCCTATTCTGTCTCTTG |
| 3773 | PROMOTER | | 9-27F/9-27R | TGGACATTAGCAGGAAGC | ATGCCTATTCTGTCTCTTG |
| 3787 | PROMOTER | 9_27/261 | | | |
| 5095 | INTRON 0 | | 4798F/5364R | TCCTCCTCACTTCCATTCTGAC | TGTGAACCCAATCCACTGTCTA |
| 5210 | INTRON 0 | | 4798F/5364R | TCCTCCTCACTTCCATTCTGAC | TGTGAACCCAATCCACTGTCTA |
| 11039 | INTRON 0 | | 99-14387F/99-14387R | TCAGAGTCCGTTCTTGGTC | CTTGTCACCTCCACCCTTTC |
| 11118 | INTRON 0 | 99_14387/129 | | | |
| 11188 | INTRON 0 | | 99-14387F/99-14387R | TCAGAGTCCGTTCTTGGTC | CTTGTCACCTCCACCCTTTC |
| 13973 | TGAGACT INSERT | | 13843F/14496R | TAGTCTTTGTCCCCTGGTACTTG | ACGAGAGACACATCATCCCATG |
| 14702 | INTRON 0 | | 13843F/14839R | TAGTCTTTGTCCCCTGGTACTTG | CATGTCTGAGCACAGGACCAA |
| 14757 | INTRON 0 | | 13843F/14839R | TAGTCTTTGTCCCCTGGTACTTG | CATGTCTGAGCACAGGACCAA |
| 14815 | INTRON 0 | | 13843F/14839R | TAGTCTTTGTCCCCTGGTACTTG | CATGTCTGAGCACAGGACCAA |
| 15050 | INTRON 0 | | 14745F/15199R | CTGGTTAGCATTGAATGGAGCA | TGAGTCGTGGTTTCCTGGTCA |
| 15120 | INTRON 0 | 9_12/1948 | | | |
| 15196 | EXON 1 Gly to Gly | 9_12/124 | | | |
| 15427 | INTRON 1 | 9_12/355 | | | |
| 15500 | INTRON 1 | 9_12/428 | | | |
| 15680 | INTRON 1 | | 15831F/15966R | GCCTCTTTCATCACAGACCTCC | CAATTCTACCCCCTCCATCTAG |
| 15790 | INTRON 1 | | 15831F/15966R | GCCTCTTTCATCACAGACCTCC | CAATTCTACCCCCTCCATCTAG |
| 15863 | INTRON 1 | 99_14405/105 | | | |
| 17170 | 3' UTR/A DELETION | 9_16/189 | | | |
| 17829 | 3' UTR | | 17201F/18240R | CAGAGCTGTGGACTTTGTTCAC | ACTCAAGGAGACAATGGCTTCA |
| 18011 | 3' UTR | | 17201F/18240R | CAGAGCTGTGGACTTTGTTCAC | ACTCAAGGAGACAATGGCTTCA |
| 18489 | 3' UTR | | 18141F/19314R | CCACTGAAGTTAGGGATGACTGT | GACTCAGTGATTGGTCAGAAACA |

FIG. 17

| | Mouse # | EDTA Plasma Comments | Alkaline Phosphatase (IU/l) | ALT (SGPT) (IU/l) | AST (SGOT) (IU/l) | Blood Urea Nitrogen (mg/dl) | Cholesterol (mg/dl) | Creatinine (mg/dl) | Direct Bilirubin (mg/dl) | GGT (IU/l) | Total Bilirubin (mg/dl) | Triglycerides (mg/dl) | Uric Acid (mg/dl) |
|---|---|---|---|---|---|---|---|---|---|---|---|---|---|
| Saline | 1 | Slight hemolysis | <20 | 187 | 23 | 34 | 115 | 0.2 | 0.0 | <5 | 0.4 | 128 | <0.5 |
| | 2 | Slight hemolysis | <20 | 116 | 22 | 27 | 165 | 0.3 | 0.0 | <5 | 0.5 | 167 | 0.6 |
| | 3 | Slight hemolysis | <20 | 184 | 18 | 34 | 161 | 0.3 | 0.0 | <5 | 0.5 | 183 | 1.2 |
| | 4 | Slight hemolysis | <20 | 251 | 25 | 35 | 169 | 0.3 | 0.0 | <5 | 0.3 | 122 | 0.7 |
| | 5 | Slight hemolysis | <20 | 85 | 15 | 32 | 146 | 0.3 | 0.0 | <5 | 0.6 | 185 | 2.1 |
| | 6 | low vol. - diluted | <20 | 52 | 146 | 27 | 186 | 0.3 | <0.1 | <5 | 0.5 | 113 | 3.6 |
| | 7 | Slight hemolysis | 79 | 240 | 215 | 26 | 209 | 0.2 | 0.0 | <5 | 0.4 | 120 | 1.6 |
| | 8 | Slight hemolysis | 80 | 160 | 345 | 29 | 202 | 0.2 | 0.0 | <5 | 0.7 | 108 | 3.0 |
| Acrp30 | 9 | Slight hemolysis | <20 | 115 | 19 | 16 | 176 | 0.2 | 0.0 | <5 | 0.4 | 129 | 2.0 |
| | 10 | low vol. - diluted | <20 | 82 | <3 | 12 | 126 | | ND | <5 | 0.5 | 281 | ND |
| | 11 | Slight hemolysis | <20 | 43 | 6 | 18 | 140 | 0.2 | 0.0 | <5 | 0.3 | 148 | 1.5 |
| | 12 | None | <20 | 114 | 20 | 25 | 199 | 0.2 | 0.0 | <5 | 0.3 | 118 | 2.0 |
| | 13 | low vol. - diluted | <20 | 169 | 227 | 27 | 216 | 0.3 | <0.1 | <5 | 0.5 | 137 | 3.6 |
| | 14 | Slight hemolysis | 46 | 99 | 234 | 28 | 166 | 0.2 | 0.0 | <5 | 0.7 | 157 | 4.5 |
| | 15 | low vol. - diluted | <20 | 175 | 173 | 18 | 234 | 0.3 | <0.1 | <5 | 0.5 | 158 | 2.7 |
| | 16 | Moderate hemolysis | 36 | 55 | 171 | 18 | 195 | 0.2 | 0.0 | 5 | 1.4 | 125 | 4.0 |
| gAcrp30 | 17 | None | <20 | 127 | 17 | 24 | 109 | 0.2 | 0.0 | <5 | 0.1 | 147 | 0.8 |
| | 18 | None | <20 | 62 | 16 | 20 | 145 | 0.2 | 0.0 | <5 | 0.2 | 123 | 1.2 |
| | 19 | None | <20 | 163 | 22 | 35 | 160 | 0.5 | 0.0 | <5 | 0.2 | 142 | 0.5 |
| | 20 | Slight hemolysis | <20 | 88 | 33 | 38 | 94 | 0.3 | 0.0 | <5 | 0.5 | 143 | 1.1 |
| | 21 | Marked hemolysis | 66 | 194 | 294 | 21 | 209 | 0.1 | 0.0 | 17 | 2.6 | 127 | 6.1 |
| | 22 | Marked hemolysis | 74 | 289 | 381 | 19 | 227 | 0.1 | 0.0 | 7 | 1.9 | 133 | 6.5 |
| | 23 | Moderate hemolysis | 49 | 100 | 250 | 19 | 179 | 0.1 | 0.0 | 7 | 1.4 | 126 | 4.2 |
| | 24 | None | ND | ND | ND | 18 | 150 | 0.2 | ND | ND | ND | 198 | ND |

| | Mouse # | | Alkaline Phosphatase (IU/l) | ALT (SGPT) (IU/l) | AST (SGOT) (IU/l) | Blood Urea Nitrogen (mg/dl) | Cholesterol (mg/dl) | Creatinine (mg/dl) | Direct Bilirubin (mg/dl) | GGT (IU/l) | Total Bilirubin (mg/dl) | Triglycerides (mg/dl) | Uric Acid (mg/dl) |
|---|---|---|---|---|---|---|---|---|---|---|---|---|---|
| Saline | ave | | | 159 | 101 | 31 | 169 | 0.26 | 0.00 | | 0.49 | 141 | 1.83 |
| Acrp30 | ave | | | 107 | 121 | 20 | 182 | 0.23 | 0.00 | | 0.58 | 157 | 2.90 |
| gAcrp30 | ave | | | 146 | 145 | 24 | 159 | 0.21 | 0.00 | | 0.99 | 142 | 2.91 |

FIG. 22

SEQUENCE LISTING

```
<160> NUMBER OF SEQ ID NOS: 7

<210> SEQ ID NO 1
<211> LENGTH: 1152
<212> TYPE: DNA
<213> ORGANISM: mus musculus

<400> SEQUENCE: 1

gaattcggca cgaggg atg cta ctg ttg caa gct ctc ctg ttc ctc tta atc      52
                  Met Leu Leu Leu Gln Ala Leu Leu Phe Leu Leu Ile
                  1               5                   10

ctg ccc agt cat gcc gaa gat gac gtt act aca act gaa gag cta gct      100
Leu Pro Ser His Ala Glu Asp Asp Val Thr Thr Thr Glu Glu Leu Ala
        15                  20                  25

cct gct ttg gtc cct cca ccc aag gga act tgt gca ggt tgg atg gca      148
Pro Ala Leu Val Pro Pro Pro Lys Gly Thr Cys Ala Gly Trp Met Ala
    30                  35                  40

ggc atc cca gga cat tct ggc cac aat ggc aca cca ggc cgt gat ggc      196
Gly Ile Pro Gly His Ser Gly His Asn Gly Thr Pro Gly Arg Asp Gly
45                  50                  55                  60

aga gat ggc act cct gga gag aag gga gag aaa gga gat tca ggt ctt      244
Arg Asp Gly Thr Pro Gly Glu Lys Gly Glu Lys Gly Asp Ser Gly Leu
                65                  70                  75

ctt ggt cct aag ggt gag aca gga gat gtt gga atg aca gga gct gaa      292
Leu Gly Pro Lys Gly Glu Thr Gly Asp Val Gly Met Thr Gly Ala Glu
            80                  85                  90
```

-continued

```
ggg cct cgg ggc ttc ccc gga acc cct ggc agg aaa gga gag cct gga      340
Gly Pro Arg Gly Phe Pro Gly Thr Pro Gly Arg Lys Gly Glu Pro Gly
        95                  100                 105

gaa gcc gct tat gtg tat cgc tca ggc ttc agt gtg ggg ctg gag acc      388
Glu Ala Ala Tyr Val Tyr Arg Ser Gly Phe Ser Val Gly Leu Glu Thr
    110                 115                 120

cgc gtc act gtt ccc aat gta ccc att cgc ttt act aag atc ttc tac      436
Arg Val Thr Val Pro Asn Val Pro Ile Arg Phe Thr Lys Ile Phe Tyr
125                 130                 135                 140

aac caa cag aat cat tat gac aac agc act ggc aag ttc tac tgc aac      484
Asn Gln Gln Asn His Tyr Asp Asn Ser Thr Gly Lys Phe Tyr Cys Asn
                145                 150                 155

att ccg gga ctc tac tac ttc tct tac cac atc acg gtg tac atg aaa      532
Ile Pro Gly Leu Tyr Tyr Phe Ser Tyr His Ile Thr Val Tyr Met Lys
            160                 165                 170

gat gtg aag gtg agc ctc ttc aag aag gac aag gcc gtt ctc ttc acc      580
Asp Val Lys Val Ser Leu Phe Lys Lys Asp Lys Ala Val Leu Phe Thr
        175                 180                 185

tac gac cag tat cag gaa aag aat gtg gac cag gcc tct ggc tct gtg      628
Tyr Asp Gln Tyr Gln Glu Lys Asn Val Asp Gln Ala Ser Gly Ser Val
    190                 195                 200

ctc ctc cat ctg gag gtg gga gac caa gtc tgg ctc cag gtg tat ggg      676
Leu Leu His Leu Glu Val Gly Asp Gln Val Trp Leu Gln Val Tyr Gly
205                 210                 215                 220

gat ggg gac cac aat gga ctc tat gca gat aac gtc aac gac tct aca      724
Asp Gly Asp His Asn Gly Leu Tyr Ala Asp Asn Val Asn Asp Ser Thr
                225                 230                 235

ttt act ggc ttt ctt ctc ttc cat gat acc aac tga ctgcaactac           770
Phe Thr Gly Phe Leu Leu Phe His Asp Thr Asn  *
            240                 245

tcatagccca tacaccagga gaatcatgga acgtcgacac actttcagct tagtttgaga    830

gattgatttt attgcttagt ttgagagtcc tgagtattat ccacacgtgt actcacttgt    890

tcattaaacg actttataaa aaataatttg tgttcctagt ccagaaaaaa aggcactccc    950

tggtctccac gactcttaca tggtagcaat aacagaatga aaatcacatt tggtatgggg   1010

gcttcacaat attcgcatga ctgtctggaa gtagaccatg ctatttttct gctcactgta   1070

cacaaatatt gttcacataa accctataat gtaaatatga aatacagtga ttatcttctc   1130

aaaaaaaact cgtgccgaat tc                                            1152


<210> SEQ ID NO 2
<211> LENGTH: 247
<212> TYPE: PRT
<213> ORGANISM: mus musculus

<400> SEQUENCE: 2

Met Leu Leu Leu Gln Ala Leu Leu Phe Leu Leu Ile Leu Pro Ser His
1               5                   10                  15

Ala Glu Asp Asp Val Thr Thr Thr Glu Glu Leu Ala Pro Ala Leu Val
            20                  25                  30

Pro Pro Pro Lys Gly Thr Cys Ala Gly Trp Met Ala Gly Ile Pro Gly
        35                  40                  45

His Ser Gly His Asn Gly Thr Pro Gly Arg Asp Gly Arg Asp Gly Thr
    50                  55                  60

Pro Gly Glu Lys Gly Glu Lys Gly Asp Ser Gly Leu Leu Gly Pro Lys
65                  70                  75                  80

Gly Glu Thr Gly Asp Val Gly Met Thr Gly Ala Glu Gly Pro Arg Gly
```

-continued

```
                85                  90                  95

Phe Pro Gly Thr Pro Gly Arg Lys Gly Glu Pro Gly Glu Ala Ala Tyr
            100                 105                 110

Val Tyr Arg Ser Gly Phe Ser Val Gly Leu Glu Thr Arg Val Thr Val
        115                 120                 125

Pro Asn Val Pro Ile Arg Phe Thr Lys Ile Phe Tyr Asn Gln Gln Asn
    130                 135                 140

His Tyr Asp Asn Ser Thr Gly Lys Phe Tyr Cys Asn Ile Pro Gly Leu
145                 150                 155                 160

Tyr Tyr Phe Ser Tyr His Ile Thr Val Tyr Met Lys Asp Val Lys Val
                165                 170                 175

Ser Leu Phe Lys Lys Asp Lys Ala Val Leu Phe Thr Tyr Asp Gln Tyr
            180                 185                 190

Gln Glu Lys Asn Val Asp Gln Ala Ser Gly Ser Val Leu Leu His Leu
        195                 200                 205

Glu Val Gly Asp Gln Val Trp Leu Gln Val Tyr Gly Asp Gly Asp His
    210                 215                 220

Asn Gly Leu Tyr Ala Asp Asn Val Asn Asp Ser Thr Phe Thr Gly Phe
225                 230                 235                 240

Leu Leu Phe His Asp Thr Asn
                245


<210> SEQ ID NO 3
<211> LENGTH: 1276
<212> TYPE: DNA
<213> ORGANISM: mus musculus

<400> SEQUENCE: 3

ctctaaagat tgtcagtgga tctgacgaca ccaaaagggc tcagg atg cta ctg ttg      57
                                                  Met Leu Leu Leu
                                                  1

caa gct ctc ctg ttc ctc tta atc ctg ccc agt cat gcc gaa gat gac      105
Gln Ala Leu Leu Phe Leu Leu Ile Leu Pro Ser His Ala Glu Asp Asp
5                   10                  15                  20

gtt act aca act gaa gag cta gct cct gct ttg gtc cct cca ccc aag      153
Val Thr Thr Thr Glu Glu Leu Ala Pro Ala Leu Val Pro Pro Pro Lys
                25                  30                  35

gga act tgt gca ggt tgg atg gca ggc atc cca gga cat cct ggc cac      201
Gly Thr Cys Ala Gly Trp Met Ala Gly Ile Pro Gly His Pro Gly His
            40                  45                  50

aat ggc aca cca ggc cgt gat ggc aga gat ggc act cct gga gag aag      249
Asn Gly Thr Pro Gly Arg Asp Gly Arg Asp Gly Thr Pro Gly Glu Lys
        55                  60                  65

gga gag aaa gga gat gca ggt ctt ctt ggt cct aag ggt gag aca gga      297
Gly Glu Lys Gly Asp Ala Gly Leu Leu Gly Pro Lys Gly Glu Thr Gly
    70                  75                  80

gat gtt gga atg aca gga gct gaa ggg cca cgg ggc ttc ccc gga acc      345
Asp Val Gly Met Thr Gly Ala Glu Gly Pro Arg Gly Phe Pro Gly Thr
85                  90                  95                  100

cct ggc agg aaa gga gag cct gga gaa gcc gct tat atg tat cgc tca      393
Pro Gly Arg Lys Gly Glu Pro Gly Glu Ala Ala Tyr Met Tyr Arg Ser
                105                 110                 115

gcg ttc agt gtg ggg ctg gag acc cgc gtc act gtt ccc aat gta ccc      441
Ala Phe Ser Val Gly Leu Glu Thr Arg Val Thr Val Pro Asn Val Pro
            120                 125                 130

att cgc ttt act aag atc ttc tac aac caa cag aat cat tat gac ggc      489
Ile Arg Phe Thr Lys Ile Phe Tyr Asn Gln Gln Asn His Tyr Asp Gly
        135                 140                 145
```

-continued

```
agc act ggc aag ttc tac tgc aac att ccg gga ctc tac tac ttc tct      537
Ser Thr Gly Lys Phe Tyr Cys Asn Ile Pro Gly Leu Tyr Tyr Phe Ser
    150                 155                 160

tac cac atc acg gtg tac atg aaa gat gtg aag gtg agc ctc ttc aag      585
Tyr His Ile Thr Val Tyr Met Lys Asp Val Lys Val Ser Leu Phe Lys
165                 170                 175                 180

aag gac aag gcc gtt ctc ttc acc tac gac cag tat cag gaa aag aat      633
Lys Asp Lys Ala Val Leu Phe Thr Tyr Asp Gln Tyr Gln Glu Lys Asn
                185                 190                 195

gtg gac cag gcc tct ggc tct gtg ctc ctc cat ctg gag gtg gga gac      681
Val Asp Gln Ala Ser Gly Ser Val Leu Leu His Leu Glu Val Gly Asp
            200                 205                 210

caa gtc tgg ctc cag gtg tat ggg gat ggg gac cac aat gga ctc tat      729
Gln Val Trp Leu Gln Val Tyr Gly Asp Gly Asp His Asn Gly Leu Tyr
        215                 220                 225

gca gat aac gtc aac gac tct aca ttt act ggc ttt ctt ctc tac cat      777
Ala Asp Asn Val Asn Asp Ser Thr Phe Thr Gly Phe Leu Leu Tyr His
    230                 235                 240

gat acc aac tga ctgcaactac ccatagccca tacaccagga gaatcatgga          829
Asp Thr Asn  *
245

acagtcgaca cactttcagc ttagtttgag agattgattt tattgcttag tttgagagtc    889

ctgagtatta tccacacgtg tactcacttg ttcattaaac gactttataa aaaataattt    949

gtgttcctag tccagaaaaa aaggcactcc ctggtctcca cgactcttac atggtagcaa   1009

taacagaatg aaaatcacat ttggtatggg ggcttcacaa tattcgcatg actgtctgga   1069

agtagaccat gctatttttc tgctcactgt acacaaatat tgttcacata aaccctataa   1129

tgtaaatatg aaatacagtg attactcttc tcacaggctg agtgtatgaa tgtctaaaga   1189

cccataagta ttaaagtggt agggataaat tggaaaaaaa aaaaaaaaaa aagaaaaact   1249

ttagagcaca ctggcggccg ttactag                                       1276


<210> SEQ ID NO 4
<211> LENGTH: 247
<212> TYPE: PRT
<213> ORGANISM: mus musculus

<400> SEQUENCE: 4

Met Leu Leu Leu Gln Ala Leu Leu Phe Leu Leu Ile Leu Pro Ser His
1               5                   10                  15

Ala Glu Asp Asp Val Thr Thr Thr Glu Glu Leu Ala Pro Ala Leu Val
            20                  25                  30

Pro Pro Pro Lys Gly Thr Cys Ala Gly Trp Met Ala Gly Ile Pro Gly
        35                  40                  45

His Pro Gly His Asn Gly Thr Pro Gly Arg Asp Gly Arg Asp Gly Thr
    50                  55                  60

Pro Gly Glu Lys Gly Glu Lys Gly Asp Ala Gly Leu Leu Gly Pro Lys
65                  70                  75                  80

Gly Glu Thr Gly Asp Val Gly Met Thr Gly Ala Glu Gly Pro Arg Gly
                85                  90                  95

Phe Pro Gly Thr Pro Gly Arg Lys Gly Glu Pro Gly Glu Ala Ala Tyr
            100                 105                 110

Met Tyr Arg Ser Ala Phe Ser Val Gly Leu Glu Thr Arg Val Thr Val
        115                 120                 125

Pro Asn Val Pro Ile Arg Phe Thr Lys Ile Phe Tyr Asn Gln Gln Asn
    130                 135                 140
```

-continued

```
His Tyr Asp Gly Ser Thr Gly Lys Phe Tyr Cys Asn Ile Pro Gly Leu
145                 150                 155                 160

Tyr Tyr Phe Ser Tyr His Ile Thr Val Tyr Met Lys Asp Val Lys Val
                165                 170                 175

Ser Leu Phe Lys Lys Asp Lys Ala Val Leu Phe Thr Tyr Asp Gln Tyr
            180                 185                 190

Gln Glu Lys Asn Val Asp Gln Ala Ser Gly Ser Val Leu Leu His Leu
        195                 200                 205

Glu Val Gly Asp Gln Val Trp Leu Gln Val Tyr Gly Asp Gly Asp His
    210                 215                 220

Asn Gly Leu Tyr Ala Asp Asn Val Asn Asp Ser Thr Phe Thr Gly Phe
225                 230                 235                 240

Leu Leu Tyr His Asp Thr Asn
                245


<210> SEQ ID NO 5
<211> LENGTH: 4517
<212> TYPE: DNA
<213> ORGANISM: Homo sapiens

<400> SEQUENCE: 5

ctgattccat accagagggg ctcagg atg ctg ttg ctg gga gct gtt cta ctg      53
                             Met Leu Leu Leu Gly Ala Val Leu Leu
                             1               5

cta tta gct ctg ccc ggg cat gac cag gaa acc acg act caa ggg ccc      101
Leu Leu Ala Leu Pro Gly His Asp Gln Glu Thr Thr Thr Gln Gly Pro
10                  15                  20                  25

gga gtc ctg ctt ccc ctg ccc aag ggg gcc tgc aca ggt tgg atg gcg      149
Gly Val Leu Leu Pro Leu Pro Lys Gly Ala Cys Thr Gly Trp Met Ala
                30                  35                  40

ggc atc cca ggg cat ccg ggc cat aat ggg gcc cca ggc cgt gat ggc      197
Gly Ile Pro Gly His Pro Gly His Asn Gly Ala Pro Gly Arg Asp Gly
            45                  50                  55

aga gat ggc acc cct ggt gag aag ggt gag aaa gga gat cca ggt ctt      245
Arg Asp Gly Thr Pro Gly Glu Lys Gly Glu Lys Gly Asp Pro Gly Leu
        60                  65                  70

att ggt cct aag gga gac atc ggt gaa acc gga gta ccc ggg gct gaa      293
Ile Gly Pro Lys Gly Asp Ile Gly Glu Thr Gly Val Pro Gly Ala Glu
    75                  80                  85

ggt ccc cga ggc ttt ccg gga atc caa ggc agg aaa gga gaa cct gga      341
Gly Pro Arg Gly Phe Pro Gly Ile Gln Gly Arg Lys Gly Glu Pro Gly
90                  95                  100                 105

gaa ggt gcc tat gta tac cgc tca gca ttc agt gtg gga ttg gag act      389
Glu Gly Ala Tyr Val Tyr Arg Ser Ala Phe Ser Val Gly Leu Glu Thr
                110                 115                 120

tac gtt act atc ccc aac atg ccc att cgc ttt acc aag atc ttc tac      437
Tyr Val Thr Ile Pro Asn Met Pro Ile Arg Phe Thr Lys Ile Phe Tyr
            125                 130                 135

aat cag caa aac cac tat gat ggc tcc act ggt aaa ttc cac tgc aac      485
Asn Gln Gln Asn His Tyr Asp Gly Ser Thr Gly Lys Phe His Cys Asn
        140                 145                 150

att cct ggg ctg tac tac ttt gcc tac cac atc aca gtc tat atg aag      533
Ile Pro Gly Leu Tyr Tyr Phe Ala Tyr His Ile Thr Val Tyr Met Lys
    155                 160                 165

gat gtg aag gtc agc ctc ttc aag aag gac aag gct atg ctc ttc acc      581
Asp Val Lys Val Ser Leu Phe Lys Lys Asp Lys Ala Met Leu Phe Thr
170                 175                 180                 185

tat gat cag tac cag gaa aat aat gtg gac cag gcc tcc ggc tct gtg      629
Tyr Asp Gln Tyr Gln Glu Asn Asn Val Asp Gln Ala Ser Gly Ser Val
```

-continued

```
                190                 195                 200

ctc ctg cat ctg gag gtg ggc gac caa gtc tgg ctc cag gtg tat ggg      677
Leu Leu His Leu Glu Val Gly Asp Gln Val Trp Leu Gln Val Tyr Gly
            205                 210                 215

gaa gga gag cgt aat gga ctc tat gct gat aat gac aat gac tcc acc      725
Glu Gly Glu Arg Asn Gly Leu Tyr Ala Asp Asn Asp Asn Asp Ser Thr
        220                 225                 230

ttc aca ggc ttt ctt ctc tac cat gac acc aac tga tcaccactaa           771
Phe Thr Gly Phe Leu Leu Tyr His Asp Thr Asn  *
    235                 240                 245

ctcagagcct cctccaggcc aaacagcccc aaagtcaatt aaaggctttc agtacggtta    831

ggaagttgat tattatttag ttggaggcct ttagatatta ttcattcatt tactcattca    891

tttattcatt cattcatcaa gtaactttaa aaaaatcata tgctatgttc ccagtcctgg    951

ggagcttcac aaacatgacc agataactga ctagaaagaa gtagttgaca gtgctatttt   1011

gtgcccactg tctctcctga tgctcatatc aatcctataa ggcacaggga acaagcattc   1071

tcctgttttt acagattgta tcctgaggct gagagagtta agtgaatgtc taaggtcaca   1131

cagtattaag tgacagtgct agaaatcaaa cccagagctg tggactttgt tcactagact   1191

gtgccctttt atagaggtac atgttctctt tggagtgttg gtaggtgtct gtttcccacc   1251

tcacctgaga gccattgaat ttgccttcct catgaattaa aacctccccc aagcagagct   1311

tcctcagaga aagtggttct atgatgaagt cctgtcttgg aaggactact actcaatggc   1371

ccctgcacta ctctacttcc tcttacctat gtcccttctc atgcctttcc ctccaacggg   1431

gaaagccaac tccatctcta agtgctgaac tcatccctgt tcctcaaggc cacctggcca   1491

ggagcttctc tgatgtgata tccacttttt tttttttttg agatggagtc tcactctgtc   1551

acccaggctg gagtacagtg acacgacctc ggctcactgc agcctccttc tcctgggtcc   1611

aagcaattat tgtgcctcag cctcccgagt agctgagact tcaggtgcat tccaccacac   1671

atggctaatt tttgtatttt tagtagaaat ggggtttcgt catgttggcc aggctggtct   1731

cgaactcctg gcctaggtga tccacccgcc tcgacctccc aaagtgctgg gattacaggc   1791

atgagccacc atgcccagtc gatatctcac tttttatttt gccatggatg agagtcctgg   1851

gtgtgaggaa cacctcccac caggctagag gcaactgccc aggaaggact gtgcttccgt   1911

cacctctaaa tcccttgcag atccttgata aatgcctcat gaagaccaat ctcttgaatc   1971

ccatatctac ccagaattaa ctccattcca gtctctgcat gtaatcagtt ttatccacag   2031

aaacattttc attttaggaa atccctggtt taagtatcaa tccttgttca gctggacaat   2091

atgaatcttt tccactgaag ttagggatga ctgtgatttt cagaacacgt ccagaatttt   2151

tcatcaagaa ggtagcttga gcctgaaatg caaaacccat ggaggaattc tgaagccatt   2211

gtctccttga gtaccaacag ggtcagggaa gactgggcct cctgaattta ttattgttct   2271

ttaagaatta caggttgagg tagttgatgg tggtaaacat tctctcagga gacaataact   2331

ccagtgatgt tttcaaaga ttttagcaaa aacagagtaa atagcattct ctatcaatat   2391

ataaatttaa aaaactatct ttttgcttac agttttaaat tctgaacaat ttctcttata   2451

tgtgtattgc taatcattaa ggtattattt tttccacata taaagctttg tctttttgtt   2511

gttgttgttg tttttaagat ggagtttccc tctgttgcca ggctagagtg cagtggcatg   2571

atctcggctt actgcaacct ttgcctccca ggtttaagcg attcttctgc ctcagcctcc   2631

cgagtagctg ggaccacagg tgcctaccac catgccaggc taatttttgt atttttagta   2691

aagacagggt ttcaccatat tggccaggct ggtctcgaac tcctgacctt gtgatctgcc   2751
```

-continued

```
cgcctccatt gtgttgttat ttgtgagaaa gatagatatg aggtttagag agggatgaag   2811

aggtgagagt aagccttgtg ttagtcagaa ctctgtgttg tgaatgtcat tcacaacaga   2871

aaacccaaaa tattatgcaa actactgtaa gcaagaaaaa taaaggaaaa atggaaacat   2931

ttattccttt gcataataga aattaccaga gttgttctgt ctttagataa ggtttgaacc   2991

aaagctcaaa acaatcaaga cccttttctg tatgtccttc tgttctgcct tccgcagtgt   3051

aggctttacc ctcaggtgct acacagtata gttctagggt ttccctcccg atatcaaaaa   3111

gactgtggcc tgcccagctc tcgtatcccc aagccacacc atctggctaa atggacatca   3171

tgttttctgg tgatgcccaa agaggagaga ggaagctctc tttcccagat gccccagcaa   3231

gtgtaacctt gcatctcatt gctctggctg agttgtgtgc ctgtttctga ccaatcactg   3291

agtcaggagg atgaaatatt catattgact taattgcagc ttaagttagg ggtatgtaga   3351

ggtattttcc ctaaagcaaa attgggacac tgttatcaga aataggagag tggatgatag   3411

atgcaaaata atacctgtcc acaacaaact cttaatgctg tgtttgagct ttcatgagtt   3471

tcccagagag acatagctgg aaaattccta ttgattttct ctaaaatttc aacaagtagc   3531

taaagtctgg ctatgctcac agtctcacat ctggtggggg tgggctcctt acagaacacg   3591

ctttcacagt taccctaaac tctctggggc agggttattc ctttgtggaa ccagaggcac   3651

agagacagtc aactgaggcc caacagaggc ctgagagaaa ctgaggtcaa gatttcagga   3711

ttaatggtcc tgtgatgctt tgaagtacaa ttgtggattt gtccaattct ctttagttct   3771

gtcagctttt gcttcatata ttttagcgct ctattattag atatatacat gtttagtatt   3831

atgtcttatt ggtgcattta ctctcttatc attatgtaat gtccttcttt atctgtgata   3891

attttctgtg ttctgaagtc tactttgtct aaaaataaca tacgcactca acttcctttt   3951

ctttcttcct tcctttcttt cttccttcct ttctttctct ctctctcttt ccttccttcc   4011

ttcctccttt tctctctctc tctctctctc tctcttttct tgacagactc tcgttctgtg   4071

gccctggctg gagttcagtg gtgtgatctt ggctcactgc tacctctacc atgagcaatt   4131

ctcctgcctc agcctcccaa gtagctggaa ctacaggctc atgccactgc gcccagctaa   4191

tttttgtatt tttcgtagag acggggtttc accacattcg tcaggttggt ttcaaactcc   4251

tgactttgtg atccacccgc ctcggcctcc caaagtgctg ggattacagg catgagccat   4311

cacacctggt caactttctt ttgattagtg tttttgtggt atatcttttt ccatcatgtt   4371

actttaaata tatctatatt attgtattta aaatgtgttt cttacagact gcatgtagtt   4431

gggtataatt tttatccagt ctaaaaatat ctgtctttta attggtgttt agacaattta   4491

tatttaataa aatggtggaa tttaaa                                        4517
```

```
<210> SEQ ID NO 6
<211> LENGTH: 244
<212> TYPE: PRT
<213> ORGANISM: Homo sapiens

<400> SEQUENCE: 6

Met Leu Leu Leu Gly Ala Val Leu Leu Leu Leu Ala Leu Pro Gly His
1               5                   10                  15

Asp Gln Glu Thr Thr Thr Gln Gly Pro Gly Val Leu Leu Pro Leu Pro
            20                  25                  30

Lys Gly Ala Cys Thr Gly Trp Met Ala Gly Ile Pro Gly His Pro Gly
        35                  40                  45

His Asn Gly Ala Pro Gly Arg Asp Gly Arg Asp Gly Thr Pro Gly Glu
```

-continued

```
    50                  55                  60

Lys Gly Glu Lys Gly Asp Pro Gly Leu Ile Gly Pro Lys Gly Asp Ile
65                  70                  75                  80

Gly Glu Thr Gly Val Pro Gly Ala Glu Gly Pro Arg Gly Phe Pro Gly
                85                  90                  95

Ile Gln Gly Arg Lys Gly Glu Pro Gly Glu Gly Ala Tyr Val Tyr Arg
            100                 105                 110

Ser Ala Phe Ser Val Gly Leu Glu Thr Tyr Val Thr Ile Pro Asn Met
        115                 120                 125

Pro Ile Arg Phe Thr Lys Ile Phe Tyr Asn Gln Gln Asn His Tyr Asp
    130                 135                 140

Gly Ser Thr Gly Lys Phe His Cys Asn Ile Pro Gly Leu Tyr Tyr Phe
145                 150                 155                 160

Ala Tyr His Ile Thr Val Tyr Met Lys Asp Val Lys Val Ser Leu Phe
                165                 170                 175

Lys Lys Asp Lys Ala Met Leu Phe Thr Tyr Asp Gln Tyr Gln Glu Asn
            180                 185                 190

Asn Val Asp Gln Ala Ser Gly Ser Val Leu Leu His Leu Glu Val Gly
        195                 200                 205

Asp Gln Val Trp Leu Gln Val Tyr Gly Glu Gly Glu Arg Asn Gly Leu
    210                 215                 220

Tyr Ala Asp Asn Asp Asn Asp Ser Thr Phe Thr Gly Phe Leu Leu Tyr
225                 230                 235                 240

His Asp Thr Asn


<210> SEQ ID NO 7
<211> LENGTH: 20966
<212> TYPE: DNA
<213> ORGANISM: Homo sapiens
<220> FEATURE:
<221> NAME/KEY: misc_feature
<222> LOCATION: 1..4811
<223> OTHER INFORMATION: 5' regulatory region
<220> FEATURE:
<221> NAME/KEY: exon
<222> LOCATION: 4812..4851
<223> OTHER INFORMATION: exon 1
<220> FEATURE:
<221> NAME/KEY: exon
<222> LOCATION: 15144..15365
<223> OTHER INFORMATION: exon 2
<220> FEATURE:
<221> NAME/KEY: exon
<222> LOCATION: 16277..20559
<223> OTHER INFORMATION: exon 3
<220> FEATURE:
<221> NAME/KEY: misc_feature
<222> LOCATION: 20560..20966
<223> OTHER INFORMATION: 3' regulatory region
<220> FEATURE:
<221> NAME/KEY: allele
<222> LOCATION: 3787
<223> OTHER INFORMATION: 9-27-261 : polymorphic base G or C
<220> FEATURE:
<221> NAME/KEY: allele
<222> LOCATION: 11118
<223> OTHER INFORMATION: 99-14387-129 : polymorphic base A or C
<220> FEATURE:
<221> NAME/KEY: allele
<222> LOCATION: 15120
<223> OTHER INFORMATION: 9-12-48 : polymorphic base C or T
<220> FEATURE:
<221> NAME/KEY: allele
<222> LOCATION: 15196
<223> OTHER INFORMATION: 9-12-124 : polymorphic base G or T
<220> FEATURE:
```

-continued

<221> NAME/KEY: allele
<222> LOCATION: 15427
<223> OTHER INFORMATION: 9-12-355 : polymorphic base G or T
<220> FEATURE:
<221> NAME/KEY: allele
<222> LOCATION: 15500
<223> OTHER INFORMATION: 9-12-428 : polymorphic base A or G
<220> FEATURE:
<221> NAME/KEY: allele
<222> LOCATION: 15863
<223> OTHER INFORMATION: 99-14405-105 : polymorphic base A or G
<220> FEATURE:
<221> NAME/KEY: allele
<222> LOCATION: 17170
<223> OTHER INFORMATION: 9-16-189 : polymorphic base deletion of A
<220> FEATURE:
<221> NAME/KEY: primer_bind
<222> LOCATION: 3528..3545
<223> OTHER INFORMATION: 9-27.pu
<220> FEATURE:
<221> NAME/KEY: primer_bind
<222> LOCATION: 3928..3946
<223> OTHER INFORMATION: 9-27.rp complement
<220> FEATURE:
<221> NAME/KEY: primer_bind
<222> LOCATION: 10990..11008
<223> OTHER INFORMATION: 99-14387.pu
<220> FEATURE:
<221> NAME/KEY: primer_bind
<222> LOCATION: 11423..11442
<223> OTHER INFORMATION: 99-14387.rp complement
<220> FEATURE:
<221> NAME/KEY: primer_bind
<222> LOCATION: 15073..15092
<223> OTHER INFORMATION: 9-12.pu
<220> FEATURE:
<221> NAME/KEY: primer_bind
<222> LOCATION: 15503..15520
<223> OTHER INFORMATION: 9-12.rp complement
<220> FEATURE:
<221> NAME/KEY: primer_bind
<222> LOCATION: 15759..15776
<223> OTHER INFORMATION: 99-14405.pu
<220> FEATURE:
<221> NAME/KEY: primer_bind
<222> LOCATION: 16191..16211
<223> OTHER INFORMATION: 99-14405.rp complement
<220> FEATURE:
<221> NAME/KEY: primer_bind
<222> LOCATION: 16982..17001
<223> OTHER INFORMATION: 9-16.pu
<220> FEATURE:
<221> NAME/KEY: primer_bind
<222> LOCATION: 17384..17402
<223> OTHER INFORMATION: 9-16.rp complement
<220> FEATURE:
<221> NAME/KEY: misc_binding
<222> LOCATION: 3775..3799
<223> OTHER INFORMATION: 9-27-261.probe
<220> FEATURE:
<221> NAME/KEY: misc_binding
<222> LOCATION: 11106..11130
<223> OTHER INFORMATION: 99-14387-129.probe
<220> FEATURE:
<221> NAME/KEY: misc_binding
<222> LOCATION: 15108..15132
<223> OTHER INFORMATION: 9-12-48.probe
<220> FEATURE:
<221> NAME/KEY: misc_binding
<222> LOCATION: 15184..15208
<223> OTHER INFORMATION: 9-12-124.probe
<220> FEATURE:
<221> NAME/KEY: misc_binding
<222> LOCATION: 15415..15439
<223> OTHER INFORMATION: 9-12-355.probe
<220> FEATURE:
<221> NAME/KEY: misc_binding
<222> LOCATION: 15488..15512
<223> OTHER INFORMATION: 9-12-428.probe
<220> FEATURE:
<221> NAME/KEY: misc_binding
<222> LOCATION: 15851..15875
<223> OTHER INFORMATION: 99-14405-105.probe
<220> FEATURE:
<221> NAME/KEY: misc_binding
<222> LOCATION: 17158..17182
<223> OTHER INFORMATION: 9-16-189.probe
<220> FEATURE:
<221> NAME/KEY: primer_bind
<222> LOCATION: 3768..3786
<223> OTHER INFORMATION: 9-27-261.mis
<220> FEATURE:
<221> NAME/KEY: primer_bind
<222> LOCATION: 3788..3806
<223> OTHER INFORMATION: 9-27-261.mis complement
<220> FEATURE:
<221> NAME/KEY: primer_bind
<222> LOCATION: 11099..11117
<223> OTHER INFORMATION: 99-14387-129.mis
<220> FEATURE:
<221> NAME/KEY: primer_bind
<222> LOCATION: 11119..11137
<223> OTHER INFORMATION: 99-14387-129.mis complement
<220> FEATURE:
<221> NAME/KEY: primer_bind
<222> LOCATION: 15101..15119
<223> OTHER INFORMATION: 9-12-48.mis
<220> FEATURE:
<221> NAME/KEY: primer_bind
<222> LOCATION: 15121..15139
<223> OTHER INFORMATION: 9-12-48.mis complement
<220> FEATURE:
<221> NAME/KEY: primer_bind
<222> LOCATION: 15177..15195
<223> OTHER INFORMATION: 9-12-124.mis
<220> FEATURE:
<221> NAME/KEY: primer_bind
<222> LOCATION: 15197..15215
<223> OTHER INFORMATION: 9-12-124.mis complement
<220> FEATURE:
<221> NAME/KEY: primer_bind
<222> LOCATION: 15408..15426
<223> OTHER INFORMATION: 9-12-355.mis
<220> FEATURE:
<221> NAME/KEY: primer_bind
<222> LOCATION: 15428..15446
<223> OTHER INFORMATION: 9-12-355.mis complement
<220> FEATURE:
<221> NAME/KEY: primer_bind
<222> LOCATION: 15481..15499
<223> OTHER INFORMATION: 9-12-428.mis
<220> FEATURE:
<221> NAME/KEY: primer_bind
<222> LOCATION: 15501..15519
<223> OTHER INFORMATION: 9-12-428.mis complement
<220> FEATURE:
<221> NAME/KEY: primer_bind
<222> LOCATION: 15844..15862
<223> OTHER INFORMATION: 99-14405-105.mis
<220> FEATURE:
<221> NAME/KEY: primer_bind
<222> LOCATION: 15864..15882
<223> OTHER INFORMATION: 99-14405-105.mis complement
<220> FEATURE:
<221> NAME/KEY: primer_bind
<222> LOCATION: 17151..17169
<223> OTHER INFORMATION: 9-16-189.mis
<220> FEATURE:
<221> NAME/KEY: primer_bind
<222> LOCATION: 17171..17189
<223> OTHER INFORMATION: 9-16-189.mis complement

<400> SEQUENCE: 7
gctgatctgc tgcctcagcc ttcccaaagt gctgtaattt attaggcata agccactgtg 60
cctgcctagt gttgtacatt ctgtgggttt tgacaattgt atgcatctac atgtatgtac 120

-continued

```
catttatagt attcctgttt ttaattttag ccattctagt aggcatgtag tgatatctca    180
tggtgatttt aatttgcgtt tccgtaatgg ttaataatgc tgaacatctt tgcatgtgct    240
tgtttgtcat ttgtgtttcc tacttggtga aataattgtt catgtccttt gtccattttc    300
taattgaatt tttttttacc atttagtttt gagatttctt tatacaatct agatccaaat    360
ctcttgtctc aaatatggtt tgcaaataca ttcctctaat tcatatattg ccttttcctc    420
ctcttaacag gatgtttcac agagcaaaag ttttagtttt gttgaaatct cacttttcat    480
ttttttcttt agtggattgt gcttttgttg tcatatgtaa gaactcttca ctggccctag    540
atccttgtat tggtttccta agattgccat agcaaatcac catgaactta gtgacaaaaa    600
gacagaaatt tattttcact tcctactgtg ggcagactag acgttaatta ttttcatgta    660
tgctcattcc tatgacatct ttctgatata ataattatag ttattcttaa gcttcaccct    720
tttttctatt agctttgtta ccttgggtgt cactttttct tttttgacat tgtgacctat    780
gccagatcat gtctgttagt acttagccct ccattcacct ctccataatc ccttttgtat    840
tcctggagct tgatgcctga aatgacacat cctacattcc tttgccagat gggtaccagt    900
tagcttgtgc acatgggaga caaccgtgaa aagactgaag tggggaagaa gggaggagct    960
gttgtgtttc agtgagcgcc cttggcagtg gcggtgacag tggctcctgt tcagtggcaa   1020
tggtggagca gctagcaaga catgcagtaa gcgcaggctc ataggctatg gtccaggagc   1080
agtcaccgat tcctggtctt taggcaatat catctccctt tgcttctcca gcctttctaa   1140
aattattgta ccttgactag tacaattttt tagtattggg ggtagtccaa ggacacaggc   1200
tttaaaaagt atgaattcag ggttgcctac ctgcattgac tgcgcttgaa tcatgatggc   1260
cttctggtcg gtggcaggag gtgacagtcc aaatcatgca gtagcaaacc agatacttaa   1320
attatcatct gagatacttc agaagtacag ccgtagccat accttcagaa gagataaaga   1380
aatgttctcc tggccaggcg cggtggctca cgcctgtcat tccagcactt tgggaggccg   1440
agggggtgga tcacctgagg tcgggagttc gagaccagcc tgaccaacat ggggaaaccc   1500
tgtctctact aaaaatacaa aattagcggg gcgtggtggc acatgcccat aatcccagct   1560
actcgggagg ctaaggcagg ataatcgctt gaacctgaga ggcagaggtt gcggtgaact   1620
gagatcatgc catagtactc cagcctgggc aacaagagtg aaactccatc tcaaaaaaaa   1680
aaaaaagaaa aaaagataaa gaaatgttct cctttcttgc catttctagg ggtttgggga   1740
tggcgtacat tgctgcaggg cgtgctcact ctaccatctt gctccaatct ttatttttca   1800
aaatacagtg cttatgcttg gttacttcag ttaagattat ttttaaaaat cataattaag   1860
caaaaatata tggccatgct taaacatatt taagataaat taagtgattt ggcctgtttc   1920
agtatcccaa ctcacatgct aacaggggct tgacctgtag ctacggtacc ctggaggaaa   1980
tgatcgcatt tatttggtta tttcggtcta agtagtaata gttctgtcct gggaaaaaga   2040
ctagcctcaa ggcatttctg attgaatgtt tttcaattac agtctttaaa ccagtatgcc   2100
acagaactgg ctctttccac atgacggcct ttgtggtggg tggcagattg ccctgaggcc   2160
tcgcaaaatg ctaggctttc acaatgtcac tgactgacag ccaggcccag cacagtcttg   2220
gtgtgattgt ggggctaaag ttattccacc ttgtgcaata gctacagcct tctctaacca   2280
gctgcattct tataaagtta gaagaaaata cttttttttt tttgagatgg attctcgctc   2340
tgttgcccag gctggagtgc aatggtgcga tctcggctcg ctgcaacctc cgcctcctgg   2400
gttcaaacga ttctcctccc tcagaccccc gagtagctgg gattgcaggt gcctgccacc   2460
acgcccggct aactttttttg tatttttagt ggagacgggg tttcaccatc ttcgtcaggc   2520
```

-continued

```
tggtctcaga ctcctgacct caagtgatct gcccgcctca gcctcccaaa atgctgggat   2580
tacaggcatg agctactgtg cccggccaaa gaaaatactt tttatgccag ccctgaaact   2640
accctgaagc acatacatca accttgaggc ctcacactcc atcaagaggg gtgaagggca   2700
tgaggaatta gaaagcatag ggatttttag ttagacagat ctggttcaaa tcctagactt   2760
gtgccttgaa caaattattt accctcattg aactctagat tcattatttg taaaatgaaa   2820
gacaataata gttatctcca aaggaaagtt gaatatgatc attcatttat tcattaattc   2880
aacatttatt attgcctact ttgtgccagg ttctattcta ggaactaagg gatacaactt   2940
tgaataggca aaatctctgc tctcctgaag tttacttttt tttttttttt ttgagacaga   3000
gtttcactct tgtcacccag gctggagcgc aatggtgctc ttggctcact gcaacctcca   3060
cctcctgggt tcaagtgatt ctcttgtctc agcctcccaa gtagctggga ctacaggtat   3120
gtgccaccac gcccggctat ttctgcattt ttagtagaga tggggtttca ccatgttggc   3180
cagactggtc tcaaactcct gatctcaggt gatatgcctg tcttggcctt ccaaagtact   3240
gggattacag gcctgagcca ctgcacctga cctgaagttt atgttctatt aaatagcaac   3300
agacagtaac ataaaccaaa aataaatagg aaaacaccat aacaaaaatc aaacagtgat   3360
ataattgaga gttgcttcta tttctttttg ttgtcttctt ggttcaatca gcctgctaaa   3420
ctatatggaa cctcattttc atgggccact tatttaagcc gggggacctt ggaaagtctc   3480
tcatgtctct catctcaacg gcctaatgtg acttctcttg aaatatttgg acattagcag   3540
gaagctgagg ctttacatca gatctttact ttaatggtgg acttgacttt actggtagat   3600
ttttaggctc tgtgtggact gtggagatga tatctggggg gcaggcagac acttgccctg   3660
cctctgtctg agaaaattct gttttggatg tcttgttgaa gttggtgctg gcatcctaag   3720
cccttgctgg ggtcgtaatt taattcatca gaatgtgtgg cttgcaagaa ccggctcaga   3780
tcctgcsctt caaaaacaaa acatgagcgt gccaagaaag tccaaggtgt tgaatgttgc   3840
cacttcaagc ctaaactttc taggaacacc taagtgggtg gcagcttcca gttctccagg   3900
ctgcttctag gccagagctg ggttccacaa gagacagaat aggcatatat atgcttaagg   3960
aactggaaaa acaggctctc tctctctcac aaacacacac acacacatac caaggtagct   4020
gtcaaaatgt tatccgaaat tttggaacca aaaaatcttg aaagatggta ttccaatatc   4080
acattttatg taagttttct attatattag attcaaatta cgattcgagg ccacaagctt   4140
taagaattca gggccttttt aacttgccaa gccccacacc actccaggaa cttccccaca   4200
ccccagttct cagaattcat gtgcaaggtc tttcctaaat ccagggtcca ggtcagagag   4260
tggaggatgt gctctatttc ttacctgatt gcagacccct ctgacagtgc tcccttctga   4320
agcactcact gtctgaacgt acacagtctc agacttaatc atgcacagtg agcaagactg   4380
tggtgtgata attggcgtcc ctgacttatt agggcaaatc tatgggaggg ggagacctcc   4440
tggaccactg agcaattaat tcatttacat taggaagttt ctccgtcaga tgcaggaaaa   4500
aaatcttgtt ttcctgctgt ggttttgact tttgccccat cttctgttgc tgttgtagga   4560
ggcaaaataa gggtcaaggc ctggaaacac aagtgctttg actgaagctc cacttggctt   4620
ccgaagccca agctgggttg taccaggttc cctagggtgc aggctgtggg caactgccag   4680
ggacatgtgc ctgcccaccg gcctctggcc ctcactgagt tggccaatgg gaaatgacaa   4740
ttgtgaggtg gggactgcct gcccccgtga gtaccaggct gttgaggctg ggccatctcc   4800
tcctcacttc cattctgact gcagtctgtg gttctgattc cataccagag ggtaagagca   4860
```

-continued

```
attctgtgaa gttccaggct gggtggggga tgcatgcata gcctctggct gggatcaccc   4920
aggctctccc gtccgtagta gtgtgggagt ggatacaggt ggatactctg gtcagagcag   4980
cactggtgga ggcagatatg cactgggctt cttcctccgt tctcccacag ccccaagaga   5040
gaaagggtta tttcagacat tccttctaag atgcatggaa ccattctgaa ttttacccag   5100
ttcgctctgt agcaggatac ctattgagaa aaagttaggg tcagtaaggt ggaagggtct   5160
gtccacagat gaagtccaat tcgattaagg gggataaggg aatacattgt ctcttagctt   5220
gaccaggtag ggcaaaggaa gaagcatata tgaaggcagc ttcagaaaag tcaagctgag   5280
cactgacttc agactggaat taggaatcca gctctgccac tttattctac tcagcaaata   5340
tttactgagc aaattctatg ggctagacag tggattgggt tcacaagata caatgagtgt   5400
gacatggttg ttgtctatgg atttggggat atatgtaggt atagggatat cttacaaggt   5460
aatcaagagg ttctaatgag gccagccatg gtggctcaca cctgtaatcc cagcaatttg   5520
ggagaccgag gcgggtggat cacctgaggt caggagttcc agactagcct gaccaacatg   5580
gtgaaacccc gcctctacca aaaatacaaa aattagttgg gcgtgatggc aggtgcctgt   5640
aatcccagct tctcgggagg ctgaggcagg agaattgtct gaacctggga ggcagaggtt   5700
gcagtgagcc gagattgttg ccactgcatt ccagcctggg tgacagagcg agactttgtg   5760
tcaaaaaaaa aaaaaaaaag aaagaaaaga aaaagaggct ctaatgagat aaaatgagaa   5820
aagcctggca tgtagtggca acttatgaaa aattgtaatt aaaaaaaaac attttctgac   5880
agaagaaact ggatctacct ggtttttctg aagcctaatc ctgctcgccc cagtgagtgc   5940
tgtttctgag gcatcctggt tgttttgagc tgtggatgct gaaggttaga gtgggaggga   6000
ttttagaggt taggtctgcc cctcttgtgt tagaggacat ggatccctgg tctggagagg   6060
ttctggtttt tggatcaagc ctcacaaggg gtggcaccaa ctcactccta ggaactccgc   6120
tagaaggaag gccagctctg cctaattcgg ttggggagat gggggtccct ttatgctagc   6180
agaatatgtc cgaaggagca tgatggtgtc agctttgttc atgaaggcca gtggtacaca   6240
gggagcccgg cagcttcctc agcagtccct gctgccactc ttccttaagt cttgaggagt   6300
cttttttttgg cacaatctca gctcactgca acctccgcct cccaggttca agcgattctc   6360
ctgcctcagt ctcccaagta gctgagacta caggcatgcg ccaccacgcc cagctaattt   6420
ttatattttt agtagagatg gggttcacca tattggccag gatggtctcg atctcttgac   6480
ctcatattcc acctgcctcg gcctcccaaa gtgctggtat tacaggtgtg agccactgcg   6540
cctggccgag gagtcttaag ctgagatcac agcattgcac tccagcctgg gcaaaaagag   6600
caaaactcca tctcaaaaaa aaaaaaaaaa tagacacaag actggctcct tgtctttttt   6660
ggggacaggg tctcactcta tcacccaggc tggagtgcag tggtgcaatc acagctcact   6720
gcagcctcga tttcccaggc tcaagtgacc ctcccatctt agcctcctga gtagctggga   6780
ctacaggtgt gtgcaaccat gcctggctaa tttttaaaaa ttttttgtag agatgaggtc   6840
tcactatatt ggctgggggg cctcaaactc ctgggctcag cagtcctccc acctcagcct   6900
cccaaaaggc tgggattata tgcttgctct ttttaaggtg gctgtaggga caaactttcc   6960
acctactcct tgtcaagcca gtggaccggt ggtcccagac atacggctaa agtcaagagg   7020
tgatgtcttt tggagagata ctttcaatca ggaatttcaa tcagaaattc aatcatgtgg   7080
agagagactt atcctaaaaa tgtggtggtg cgtgggatgc tctgttttat tagttccttg   7140
acagtatgta tgtgtgtgag tgtgtgtgtg tgcgcgcgca cactcatttg gatgggtgtg   7200
tatgtgtgtg ggggggtggt gcgtacgtat gtggatgtgt ggatgtggtg tgtgggtgtg   7260
```

-continued

```
cgcgtgcata ggtggaggtg tgtgtatggg tgcgggtatg tgtgtgtgtt gggcatggag   7320
atattgacag ctctcccagg gctgagtgaa ggctttcggg caaagctcct gggagctagg   7380
caaagctgag ttgattcctg gttatgccat ttattattgg gttgcaccgt gtgaaactgc   7440
caatattcta cactttgact tttatttatt tttattttta ttttttttga gacagagttt   7500
cacacttgtc acctaggctg gagtgcagtg gcgcgatctc agctcactgc aacctctgcc   7560
tcatggattc aagtgattct cctgcctcag cctcccaagt agctggaatt acaggtgccc   7620
gctaccacgc ctgactaatt tttgtatttt tggtagagac gggatttcac catgttgtcc   7680
aggctggtct gaaactcctg acatcaggta atccacccac ctcagcctcc caaagtgctg   7740
ggattacagg catgagccac tgcgcccggc ccattttgac ttttaaaaat gggagtttga   7800
tataattcaa tccagtggtt gaattagcta gcatcgttcc ctctccaagt ctcaggttct   7860
cctacacgtt agagtcaaaa gcagggctat gggaagatta agtaaaataa attttgaaaa   7920
tgccttatga aaattacact ccaaagaact cgcgccagtg tcagtgttct catgttcctc   7980
atctcacatg atcacatttc gcggattagg aagctgagtc tgagaagctc cgtgtagtgc   8040
tttttcggag gcaccgtgat gtgatggaag gctcactcgt taggaagtca gaacagagtc   8100
tctgagggat catttcctta atctgtcagt ttcctcatct ctgaagttgg gctcatttcc   8160
ttccttcatg gagttattgt aaagatgaag ataaataacg tgtaaaatct agcatgggaa   8220
ctggcttcta taaggttcta ataagtgcat tcctactcct tcccctcagc cttcccattt   8280
gtaaaagcaa ggcaggggtg aggtgatttc tggggctcct tttggctctg acatttgagg   8340
attttgtatc cttttttttt tcagagtctt gctctgtcac ccaggttgga gtgcagctca   8400
atgcaaattc cgcctcccag gctcaagcaa ttcttatgtc tcagcctcct gagtacctgg   8460
gattacaggc aggcaccacc acccccagct aattttttgt attttcagta gagacggggt   8520
tttgccatat tggccaggct ggtcttgaac tcctgacttc atgtgaccca cccatctcag   8580
cctcccaaag tgctgagatg acaggtgtga gctaccgtgc ctggccaatt ttgtgtgctt   8640
taatgccctt ttctgctgga agagttggca ccaggtttgg tgatctcttt cccccacacg   8700
gctctgcctc ctgccagtcc cagaggggac cctgtccttg catttcacag gattctgctg   8760
ttgcaactga aattccagta ggtcaaagtg aaatttctca tacactttaa catgaagata   8820
aatgatcaca gtatggccct ttaggatcct gagaacatca cggtcatccc ctggtataat   8880
tttaaaagca gatgaatcca tgcctgtgcg aggtttgcca ggaaagccag tgctgggatt   8940
acagtggaag tctttttatg ctactttttt cttgtatccc tcaccccatg gggtggcata   9000
ttgaaaggca ggatgtgtga ccacgatact tttctcctcc tggactatgt ctaagagtct   9060
gttattgggt tctgaagatc agagtttaat ttccgactcc tctctgtgta gctctgggat   9120
cttggaaagc cacttaacct ttctgaagtc ccctttcctc atctctaaaa tgcatacact   9180
catcactaac atttactgag cactgacatg tgccagacac cattctaagc attttacaca   9240
gactacacca tttgatcttc caacaaacag aacactgaaa cgcattacag gtcagaacaa   9300
atgatttgtg cctaagcacc aagaccgtag agcccgtgct ccctattcta ccctatcctg   9360
tctctcaaaa tgattgtgag aatcgaatga gacactaggt gagaaaaggg ttttataaat   9420
agcattttaa aaatttttta aagtccacaa aatttttaat tttaatacag ataaaataga   9480
tccctttgtt ttataaaaag taacaaaatt tgttatacaa caactatgtt atttattaat   9540
tttgcctttt tgtatgctgc caggaaagaa acattaagaa atcttaaatt gattatggtg   9600
```

-continued

```
aatcagaagg tctgcctgga ctttttattg ctctaactgt acagctgatc atactacctc   9660
atttttttt atgacacttc aagggtgcgc ttagcttcat cactccttcg ttgccaaaag   9720
ctttgtgacc aaaaacaatt aagcagattc ctgagtcact aaatgacaca taaccagagt   9780
tgagacttag gaacttttag tgccatgcta agcccacagg gacacaacaa atagcatttt   9840
acaaaggcaa agaattgtga cacttgagat ttagcttgtt gatccttgta aaagttttct   9900
ttttaggcat aattgagttt tagatcatag tactcactat tacttagtaa taattttttt   9960
ctgatagaaa tacagtgtaa caggccgggc gcagtggctc atgcctgtaa tcccagcact  10020
ttgggaggcc gaggcgggcg gatcacttga ggtcaggagt ttgagaccag cccggccaac  10080
atggtgaaat cccatctcta ctaaaaatac aaaaaattag ccaggtgtgg tcgtggattc  10140
ctgtgatccc agctacttgg gagggtgagg caggagcatc agttgaaccc aggaggcgga  10200
ggttgcagtg agccaagatg gtgccattgc actccagcct gggccacaaa gcgagactcc  10260
acttcagaaa caaaaaaaaa aagagagaga gagaaaagaa ggaaggaagg aaggaaggaa  10320
ggaaagaagg aaggaaggaa ggaaagaagg aaggaaggaa ggaaggaaag aaggaaggaa  10380
ggaaagaagg aaggaaggaa agaaggaagg aaggaaggaa ggaagggtaa caagcaaagt  10440
gtaacaatgg caatatctaa aaaaatagt attttttatat gtttgtcgtt ttatatatat  10500
gacccccact ttagagatga ggaaactgag agattaagga aacgatccct gagagactct  10560
gttctgactt ccaaatcggt gagctttcca tcgcatcacg gtgcctccga aagcatgaca  10620
cggagcttct cagacttagc ttcctaatcc gctaaacggg attatgtgag atgaggaaca  10680
tgagaacgct gacatgggtg agggttcctt ggagtatcat tttcatgtgg cattttcaaa  10740
acttatttta cctaatcttc ccaaagccct gcttttgact ctaatgtgtc tcctgagact  10800
tggagagcgc aagatgctag cgacagagca agactccatc tccagataaa taaataagta  10860
aaataaaaaa gaacacaaat aattttgaaa attttttga aaattaggca cgtttgcact  10920
gaccttcaat tgttattaat tgctggtttc ccacccagaa ttaagttgga atgcaacttt  10980
cttttacaat cagagtccgt tcttggtctt ggaaacttct gaggctcctg tgctaatccc  11040
actcttgtat ttttggcacc tctaccccgt gccactgtca tggaacccag gctgatcgca  11100
cctattagtg gagaaatmtg tccataatac tgaagtttgg ggacaaacag tgttccctta  11160
gggtaggaga aagagatctt tatttttaac aaagggggag gagccagaaa actccagaga  11220
cccctgagtt tgccctctct ccaaggtttg ggtaagccc cccgtcaccc tttatctctg  11280
gggctttcac atattctgga ttctctcctc ctgtttccca gcagaaaagg atggagcctc  11340
acagattctt cccatttctg gagaaaaaca tgcatggagc tcaaagttct tctcaggagt  11400
tttattgcca aagccataat aagaaagggt ggaggtgaca agcagtgagg aagtttaaag  11460
atgcatgaaa tctgtaaagt ctcagaacaa gaattctcct aaaatgcaaa aggggctttg  11520
ctggtctccc cttggcttct catgtagctc acctcttttt tcttatcttg agactagtca  11580
aacctaagct gtttctcatt ttatttccag aagctattga gaacactctc ctgaattctt  11640
caaattcagt agagggcgac aaatgtacat ataaatgatg gtagtgggtc ttaaataaag  11700
actcatgaca cctaaagggg cagcacctga gtctgattgc acctgtttct gttgctgttt  11760
ctgtctctct tctctctgtc tgccatttca ttatcaatgg ttactttact tataagatca  11820
tattagaacc tgatatttga taaatgatgc atcagatcta tagtgagaga aaaaattaat  11880
gcaattaaag gtgttgtaac agctagtctt caagtgggga gaaatcattt gagtacctta  11940
ggtcacagct tacatcaaaa caaaaaatca gagctacatt aaaaagtgaa attttaacta  12000
```

-continued

```
tatcaaacaa tagaaaaaaa cagaagaaaa ttgaatactt actaaatctt agcatgaata 12060
agaactgttt aacacttaga ggcaaggact gggcgtggtg gctcatgctt ttaatcccag 12120
gactttggga gcccaaggcg ggcggatcac ctgaggtcag gagtttgaga ctagcctggc 12180
caacatggtg aaaccccgtc tctactaaaa aatgcaaaaa ttagctgcgt gtggtggtgc 12240
atgcctgtaa tctcagctac ttgggaggct aaggcatgag aatcgcttga acctgggagg 12300
tggaggctgt agtgagccga gattgtgcca ctgcactaca gcctgggtga cagtgtgaaa 12360
tcctctctct caaaaaaaaa aaaaaaaaaa agcaaactag agcagtgagg taccattatt 12420
tcctttgctc actaaactga caacacacaa atgtttttta taatacccaa agctgatgag 12480
ggtagttaag gtatgccctt ttatacacac actaatgatg tactactggt tggcagtata 12540
acatatgctg ccatgtgggg atatgtatca ggagacttaa aaatgtgcat accttttggt 12600
ccagtaattt acttctggga atctgtcata acagaataat aatcttgggg aaagctacat 12660
gcctaaggat atttaaaata ttatttaaaa atcaaagtat aatttcttac agaatataaa 12720
ataatatttt aaaatgaaaa tatgctaaaa gtttgatgaa atataaatgg tcaaatatat 12780
attgattata tccacttact agactagcac tcactctgag acgttaaaaa tagtcattat 12840
aaaaactaga aaatgccaaa gacaaaataa aggaataaag ttttacataa agtatgattc 12900
cactatgttt aaaaataaac agagacattc ttggagttga gtattgtttt cttttctgtc 12960
atgtccaaag aactatataa ctattatttt taatgaacta tatatgtaat atatacatat 13020
agtttatatg tatatacaaa atttatctca tatatatgat aaagatgaaa gatgagttgg 13080
atgtgccacg tgaagtgggt agtatagaaa cccaggtaat ggggcatagg agtgggattc 13140
cagataccag gcccatgttt ttggggtgag attgccaatc acggtctttc ttccatccct 13200
cacagaggag taggtttgtc ttcaacaaac cttcagttgt cctgaagaca aacctaattc 13260
tggagacttc atataatcta gaagagacaa gcaaactgat gaaaaatagt gaatttttaa 13320
ggtaaaataa agtacatgga ctacactttg tttagaatca gattcttggg attaaccaca 13380
ttaacccaca gagggtctta gtgatgcctc taatccagga tcctaggacc tatttctctc 13440
tgtgagatgc tttctcccaa ctccttggtg agagtgggaa gactaagacc tcagcaatct 13500
gaggtggagg cctaagatcc ccctaagatc ggaggcagaa tctgagaggg gataaaagtc 13560
cctatacctg tattgggccc ttttctggga gggggatatc aaagaatgat tttgagacag 13620
ggaggctttt gactacctgt gccacttgag ctctttgcta gggctccaga atacatattt 13680
caaatacatt ccccctccct ccttccttcc ctcttccact cttccttttt atcttccttt 13740
cttcttttcc ttcctccttc ccttcctttc tctggctctc tcatgatttc ttttcctcat 13800
tataaaagtg cttatttagt ccctactctg ctattagtgt gttagtcttt gtcccctggt 13860
acttgctgtt taatggagaa atgggtgagc aaaacagaaa ttacagcaga gtgcaataat 13920
agagctaagc caggtgtata aatccattct cacactgctg taaaaaacta ctgggtaatt 13980
tataaagaaa agaggtttaa ttgactcaca gttccacagg ctgtacagga agcatggctg 14040
gggaggcctc agaaaactta caatcatggt ggaagaaaga gcgaagggga agcaagcaca 14100
tcacacagca gcaggagaga gagagagaaa gagagagaga gagaatatag gggaagtgct 14160
acacactttc aaccagatct tgtgagaatt cacctactat catgagaaca gcaagggata 14220
agtctgcctc catgattcag tcacctccta ccaggcccct tctccaacac atgtcgacgt 14280
gctatttggg tggggacaca gacccaaacc atattaccag ggcactggag aaacacagag 14340
```

-continued

```
gggaaagaac cagccaagga gtgagatgga gaacaaggag gacttcttga aacagatgac  14400
atccaaactg ggtcctgaaa gctgaataga gattagacag gggaggaggg gcagctaaag  14460
atggctcagg caaacaaagg gccaggggat atgttcatgg gatgatgtgt ctctcgttgt  14520
ctgcttaaca caaggtgagt ctctccctcc ctctctctct ctttttctct gtgtgtgttt  14580
gtgtgtgtgc atgtgtgcaa atgtaatata cccaatagtc aaacatgtgc cccaggagag  14640
gggtagagga agaaagagaa tgagagagta agaaggagga atagacacag aaaatgagag  14700
agaagggggg aaagaaaaag aagaaaggag ccagaggaga gaagctggtt agcattgaat  14760
ggagcaatct gtgtcatcgt acttgggaaa cccaaggatg gattcttggc aagtcgactc  14820
ttggagcttt ccctgtgctt ggtcctgtgc tcagacatgg gaaaattaga ggagtgtcat  14880
ctgtgcaatc actgaattca taatcttggt gaggaaagga gactacacac agggaataat  14940
gctaagtatt acagatttca gggcagaaag agatcaaggt gggctgcaat attcagaaaa  15000
gtcttcctgg aaaagttgaa tacttagaaa gcagctccta gaagtagact ctgctgagat  15060
ggacggagtc ctttgtaggt cccaactggg tgtgtgtgtg gggtctgtct ctccatggcy  15120
gacagtgcac atgtggattc cagggctcag gatgctgttg ctgggagctg ttctactgct  15180
attagctctg cccggkcatg accaggaaac cacgactcaa gggcccggag tcctgcttcc  15240
cctgcccaag gggcctgca caggttggat ggcgggcatc ccagggcatc cgggccataa  15300
tggggcccca ggccgtgatg gcagagatgg cacccctggt gagaagggtg agaaaggaga  15360
tccaggtaag aatgtttctg gcctctttca tcacagacct cctacactga tataaactat  15420
atgaagkcat tcattattaa ctaaggccta gacacaggga gaaagcaaag ctttttttatg  15480
ttaaccataa gcaacctgar gtgatttggg gttggtcttc caaggatgag tgtagatggt  15540
gcctctataa ccaagacttt ggctttgctg catctgcagc tccttttcca tcccctttcc  15600
catcttcacc ctcatcccta ttcccagtac attcatattc tgattcctct ttctgtctgc  15660
ttaacttcca tttcacccag tggcattcaa ccacatttac tgcacacccc ctgaaaggct  15720
cagtcctgcc tttggggaac tcttgatcta ggtaagatgt ctaatgtgca aggctctgtt  15780
ggtggttacc acaagaaagt ctactctaaa aatgtcaaac tgaatgtgaa caagtattca  15840
aagtatggag catagagaaa atrtactcac cgtggacctg atgaagaatg aaggcttcaa  15900
ggaggaggca gagcttcagc taggccttga atgatgggta ggcagaatag aggaggagag  15960
acatcctaga tggagggggt agaattgcaa aaccagggtt gatggtgcca gcacataaag  16020
ggctggcagg gtggagggtc tatgatagag acctatagga gataaagata gagttgaaat  16080
tatgggagcc tccatgtctg tgggagatat agaaggagga ggtaacacct ctctcctttt  16140
gggagctctt attggtttct tgatctataa gtcaagaagg ttgtgagtgg gagccacagg  16200
gatggtaatt taggctgtaa ccaacctagg caggagttct gttctttgta gtcactgagg  16260
tcttctcatt ccttaggtct tattggtcct aagggagaca tcggtgaaac cggagtaccc  16320
ggggctgaag gtccccgagg ctttccggga atccaaggca ggaaaggaga acctggagaa  16380
ggtgcctatg tataccgctc agcattcagt gtgggattgg agacttacgt tactatcccc  16440
aacatgccca ttcgctttac caagatcttc tacaatcagc aaaaccacta tgatggctcc  16500
actggtaaat tccactgcaa cattcctggg ctgtactact ttgcctacca catcacagtc  16560
tatatgaagg atgtgaaggt cagcctcttc aagaaggaca aggctatgct cttcacctat  16620
gatcagtacc aggaaaataa tgtggaccag gcctccggct ctgtgctcct gcatctggag  16680
gtgggcgacc aagtctggct ccaggtgtat ggggaaggag agcgtaatgg actctatgct  16740
```

gataatgaca atgactccac cttcacaggc tttcttctct accatgacac caactgatca 16800
ccactaactc agagcctcct ccaggccaaa cagccccaaa gtcaattaaa ggctttcagt 16860
acggttagga agttgattat tatttagttg gaggccttta gatattattc attcatttac 16920
tcattcattt attcattcat tcatcaagta actttaaaaa aatcatatgc tatgttccca 16980
gtcctgggga gcttcacaaa catgaccaga taactgacta gaaagaagta gttgacagtg 17040
ctattttgtg cccactgtct ctcctgatgc tcatatcaat cctataaggc acagggaaca 17100
agcattctcc tgtttttaca gattgtatcc tgaggctgag agagttaagt gaatgtctaa 17160
ggtcacacaa gtattaagtg acagtgctag aaatcaaacc cagagctgtg gactttgttc 17220
actagactgt gcccttttat agaggtacat gttctctttg gagtgttggt aggtgtctgt 17280
ttcccacctc acctgagagc cattgaattt gccttcctca tgaattaaaa cctcccccaa 17340
gcagagcttc ctcagagaaa gtggttctat gatgaagtcc tgtcttggaa ggactactac 17400
tcaatggccc ctgcactact ctacttcctc ttacctatgt cccttctcat gcctttccct 17460
ccaacgggga aagccaactc catctctaag tgctgaactc atccctgttc ctcaaggcca 17520
cctggccagg agcttctctg atgtgatatc cacttttttt ttttttgag atggagtctc 17580 actctgtcac ccaggctgga gtacagtgac acgacctcgg ctcactgcag cctccttctc 17640
ctgggtccaa gcaattattg tgcctcagcc tcccgagtag ctgagacttc aggtgcattc 17700
caccacacat ggctaatttt tgtattttta gtagaaatgg ggtttcgtca tgttggccag 17760
gctggtctcg aactcctggc ctaggtgatc cacccgcctc gacctcccaa agtgctggga 17820
ttacaggcat gagccaccat gcccagtcga tatctcactt tttattttgc catggatgag 17880
agtcctgggt gtgaggaaca cctcccacca ggctagaggc aactgcccag gaaggactgt 17940
gcttccgtca cctctaaatc ccttgcagat ccttgataaa tgcctcatga agaccaatct 18000
cttgaatccc gtatctaccc agaattaact ccattccagt ctctgcatgt aatcagtttt 18060
atccacagaa acattttcat tttaggaaat ccctggtttt aagtatcaat ccttgttcag 18120
ctggacaata tgaatctttt ccactgaagt tagggatgac tgtgattttc agaacacgtc 18180
cagaattttt catcaagaag gtagcttgag cctgaaatgc aaaacccatg gaggaattct 18240
gaagccattg tctccttgag taccaacagg gtcagggaag actgggcctc ctgaatttat 18300
tattgttctt taagaattac aggttgaggt agttgatggt ggtaaacatt ctctcaggag 18360
acaataactc cagtgatgtt cttcaaagat tttagcaaaa acagagtaaa tagcattctc 18420
tatcaatata taaatttaaa aaactatctt tttgcttaca gttttaaatc ctgaacaatt 18480
ctctcttaca tgtgtattgc taatcattaa ggtattattt tttccacata taaagctttg 18540
tctttttgtt gttgttgttg tttttaagat ggagtttccc tctgttgcca ggctagagtg 18600
cagtggcatg atctcggctt actgcaacct ttgcctccca ggttcaagcg attcttctgc 18660
ctcagcctcc cgagtagctg ggaccacagg tgcctaccac catgccaggc taatttttgt 18720
atttttagta aagacagggt ttcaccatat tggccaggct ggtctcgaac tcctgacctt 18780
gtgatctgcc cacctccatt tttgttgtta ttttttgaga aagatagata tgaggtttag 18840
agagggatga agaggtgaga gtaagccttg tgttagtcag aactctgtgt tgtgaatgtc 18900
attcacaaca gaaaacccaa aatattatgc aaactactgt aagcaagaaa aataaaggaa 18960

-continued

```
aaatggaaac atttattcct ttgcataata gaaattacca gagttgttct gtctttagat  19020
aaggtttgaa ccaaagctca aaacaatcaa gacccttttc tgtatgtcct tctgttctgc  19080
cttccgcagt gtaggcttta ccctcaggtg ctacacagta tagttctagg gtttccctcc  19140
cgatatcaaa aagactgtgg cctgcccagc tctcgtatcc ccaagccaca ccatctggct  19200
aaatggacat catgttttct ggtgatgccc aaagaggaga gaggaagctc tctttcccag  19260
atgccccagc aagtgtaacc ttgcatctca ttgctctggc tgagttgtgt gcctgtttct  19320
gaccaatcac tgagtcagga ggatgaaata ttcatattga cttaattgca gcttaagtta  19380
ggggtatgta gaggtatttt ccctaaagca aaattgggac actgttatca gaaataggag  19440
agtggatgat agatgcaaaa taatacctgt ccacaacaaa ctcttaatgc tgtgtttgag  19500
ctttcatgag tttcccagag agacatagct ggaaaattcc tattgatttt ctctaaaatt  19560
tcaacaagta gctaaagtct ggctatgctc acagtctcac atctggttgg ggtgggctcc  19620
ttacagaaca cgctttcaca gttaccctaa actctctggg gcaggggtat tcctttgtgg  19680
aaccagaggc acagagagag tcaactgagg ccaaaagagg cctgagagaa actgaggtca  19740
agatttcagg attaatggtc ctgtgatgct ttgaagtaca attgtggatt tgtccaattc  19800
tctttagttc tgtcagcttt tgcttcatat attttagcgc tctattatta gatatataca  19860
tgtttagtat tatgtcttat tggtgcattt actctcttat cattatgtaa tgtccttctt  19920
tatctgtgat aatttttctgt gttctgaagt ctactttgtc taaaaataac atacgcactc  19980
aacttccttt tctttcttcc ttcctttctt tcttccttcc tttctttctc tctctctctc  20040
tttccttcct tccttcctcc ttttctttct ctctctctct ctctctcttt ttttgacaga  20100
ctctcgttct gtggccctgg ctggagttca gtggtgtgat cttggctcac tgctacctct  20160
accatgagca attctcctgc ctcagcctcc caagtagctg gaactacagg ctcatgccac  20220
tgcgcccagc taatttttgt atttttcgta gagacggggt ttcaccacat tcgtcaggtt  20280
ggtttcaaac tcctgacttt gtgatccacc cgcctcggcc tcccaaagtg ctgggattac  20340
aggcatgagc catcacacct ggtcaacttt cttttgatta gtgtttttgt ggtatatctt  20400
tttccatcat gttactttaa atatatctat attattgtat ttaaaatgtg tttcttacag  20460
actgcatgta gttgggtata atttttatcc agtctaaaaa tatctgtctt ttaattggtg  20520
tttagacaat ttatatttaa taaaattgtt gaatttaaga tggatgactg ttttatttgt  20580
ttgctgttca ccacttctgt tttattctct ttccagaatt cttttggatt gtttaaatat  20640
ttcataatat tttatcttaa tttatttatt gggtatttgc ctatatctct ttgtggtatt  20700
ttttagtggt tgcttgaggg attacaatgt acttaacttt tcacagtgtg cataaagtta  20760
atattttgcc acttgcagta aaccgtagaa ggcttataat catattagta cctctatcca  20820
ctttctttta tgttgtagtt gtcatatata ttacatctat atacactgaa acattatagg  20880
caatgttatg atttttgcat tcgtcagtca tatatatatt ttaaagaatt taagaggaga  20940
aaaatacata ttcagatatt catcat                                       20966
```

OBG3 GLOBULAR HEAD AND USES THEREOF

FIELD OF THE INVENTION

The present invention relates to the field of metabolic research, in particular the discovery of compounds effective for reducing body mass and useful for treating obesity-related diseases and disorders. The obesity-related diseases or disorders envisioned to be treated by the methods of the invention include, but are not limited to, hyperlipidemia, atherosclerosis, diabetes, and hypertension.

BACKGROUND OF THE INVENTION

The following discussion is intended to facilitate the understanding of the invention, but is not intended nor admitted to be prior art to the invention.

Obesity is a public health problem that is serious, widespread, and increasing. In the United States, 20 percent of the population is obese; in Europe, a slightly lower percentage is obese [Friedman (2000) Nature 404:632–634]. Obesity is associated with increased risk of hypertension, cardiovascular disease, diabetes, and cancer as well as respiratory complications and osteoarthritis [Kopelman (2000) Nature 404:635–643]. Even modest weight loss ameliorates these associated conditions.

While still acknowledging that lifestyle factors including environment, diet, age and exercise play a role in obesity, twin studies, analyses of familial aggregation, and adoption studies all indicate that obesity is largely the result of genetic factors [Barsh et al. (2000) Nature 404:644–651]. In agreement with these studies, is the fact that an increasing number of obesity-related genes are being identified. Some of the more extensively studied genes include those encoding leptin (ob) and its receptor (db), pro-opiomelanocortin (Pomc), melanocortin-4-receptor (Mc4r), agouti protein ($A^y$), carboxypeptidase E (fat), 5-hydroxytryptamine receptor 2C (Htr2c), nescient basic helix-loop-helix 2 (Nhlh2), prohormone convertase 1 (PCSK1), and tubby protein (tubby) [rev'd in Barsh et al. (2000) Nature 404:644–651].

SUMMARY OF THE INVENTION

The instant invention is based on the discovery that portions of the full-length OBG3 polypeptide, termed OBG3 polypeptide fragments or gOBG3 polypeptide fragments, have unexpected effects in vitro and in vivo, including utility for weight reduction, prevention of weight gain, and control of blood glucose levels in humans and other mammals. These unexpected effects of OBG3 or gOBG3 polypeptide fragment administration in mammals also include reduction of elevated free fatty acid levels caused by administration of epinephrine, i.v. injection of "intralipid", or administration of a high fat test meal, as well as increased fatty acid oxidation in muscle cells, and weight reduction in mammals consuming a high fat/high sucrose diet. These effects are unexpected and surprising given that administration of full-length OBG3 polypeptide typically has no effect or a significantly reduced effect in vivo or in vitro depending on the specific biological activity and the amount administered. To the extent that any effect is observed following administration of full-length OBG3 polypeptide, the levels of full-length OBG3 polypeptide required for an effect render it unfeasible in most instances as a potential treatment for humans at this time. In contrast, the OBG3 and gOBG3 polypeptide fragments of the invention are radically more effective and thus can be provided at levels that are feasible for treatments in humans.

Thus, the invention is drawn to OBG3 and gOBG3 polypeptide fragments, polynucleotides encoding said OBG3 and gOBG3 polypeptide fragments, vectors comprising said OBG3 and gOBG3 polynucleotides, and cells recombinant for said OBG3 and gOBG3 polynucleotides, as well as to pharmaceutical and physiologically acceptable compositions comprising said OBG3 and gOBG3 polypeptide fragments and methods of administering said OBG3 and gOBG3 pharmaceutical and physiologically acceptable compositions in order to reduce body weight or to treat obesity-related diseases and disorders. Assays for identifying agonists and antagonists of obesity-related activity are also part of the invention.

In a first aspect, the invention features a purified, isolated, or recombinant OBG3 or gOBG3 polypeptide fragment that has significantly greater activity than a full-length OBG3 polypeptide, wherein said activity is selected from the group consisting of lipid partitioning, lipid metabolism, and insulin-like activity. In preferred embodiments, said polypeptide fragment comprises, consists essentially of, or consists of, at least 6 and not more than 238 consecutive amino acids of SEQ ID NO:6 or at least 6 and not more than 241 consecutive amino acids of SEQ ID NO:2 or SEQ ID NO:4. In other preferred embodiments, OBG3 or gOBG3 polypeptide fragments having unexpected activity are selected from amino acids 84–244, 85–244, 86–244, 87–244, 88–244, 89–244, 90–244, 91–244, 92–244, 93–244, 94–244, 95–244, 96–244, 97–244, 98–244,99–244, 100–244, 101–244, 102–244, or 103–244 of SEQ ID NO:6. In other preferred embodiments, OBG3 or gOBG3 polypeptide fragments having unexpected activity are selected from amino acids 88–247, 89–247, 90–247, 91–247, 92–247, 93–247, 94–247, 95–247, 96–247, 97–247, 98–247, 99–247, 100–247, 101–247, 102–247, 103–247, 104–247, 105–247, or 106–247 of SEQ ID NO:2 or SEQ ID NO:4. In other preferred embodiments, OBG3 or gOBG3 polypeptide fragments are selected from amino acids about 84 to 244, 85 to 244, 101 to 244, 102 to 244, or 103 to 244 of SEQ ID NO:6 and amino acids 88 to 247, 104 to 247, 105 to 247, or 106 to 247 of SEQ ID NO:2 or SEQ ID NO:4. In further preferred embodiments, gOBG3 polypeptide fragments are said selected gOBG3 polypeptide fragments made resistant to dipeptidyl peptidase cleavage by N-terminal modification. In other further preferred embodiments, said polypeptide fragment comprises an amino acid sequence at least 70%, 75%, 80%, 85%, 90%, 91%, 92%, 93%, 94%, 95%, 96%, 97%, 98%, or 99% identical to the corresponding consecutive amino acids of SEQ ID NO:6, SEQ ID NO:2 or SEQ ID NO:4.

In other highly preferred embodiments, said polypeptide fragment comprises, consists essentially of, or consists of, a purified, isolated, or recombinant gOBG3 fragment. Preferably, said gOBG3 polypeptide fragment comprises, consists essentially of, or consists of, at least 6 consecutive amino acids of amino acids 84 to 244 of SEQ ID NO:6 or at least 6 consecutive amino acids of amino acids 88 to 247 of SEQ ID NO:2 or SEQ ID NO:4. In other preferred embodiments, gOBG3 polypeptide fragments having unexpected activity are selected from amino acids 84–244, 85–244, 86–244, 87–244, 88–244, 89–244, 90–244, 91–244, 92–244, 93–244, 94–244, 95–244, 96–244, 97–244, 98–244, 99–244, 100–244, 101–244, 102–244, or 103–244 of SEQ ID NO:6. In other preferred embodiments, gOBG3 polypeptide fragments having unexpected activity are selected from amino acids 88–247, 89–247, 90–247, 91–247, 92–247, 93–247, 94–247, 95–247, 96–247, 97–247, 98–247, 99–247, 100–247, 101–247, 102–247, 103–247, 104–247, 105–247, or 106–247 of SEQ ID NO:2 or SEQ ID NO:4. In other preferred embodiments, gOBG3 polypeptide fragments are selected from amino acids 84 to 244, 85 to 244, 101 to 244, 102 to 244, or 103 to 244 of SEQ ID NO:6 and amino acids 88 to 247, 104 to 247, 105 to 247, or 106 to 247 of SEQ ID NO:2 or SEQ ID NO:4. In further preferred embodiments, gOBG3 polypeptide fragments are said selected gOBG3 polypeptide fragments made resistant to dipeptidyl peptidase cleavage by N-terminal modification. Alternatively, said gOBG3 fragment comprises, consists essentially of, or consists of, an amino acid sequence at least 90%, 91%, 92%, 93%, 94%, 95%, 96%, 97%, 98%, or 99% identical to the corresponding amino acids 84 to 244 of SEQ ID NO:6 or at least 75% identical to amino acids 88 to 247 of SEQ ID NO:2 or SEQ ID NO:4. In a further preferred embodiment, the OBG3 polypeptide fragment is identical to an APM1 proteolytic cleavage product from human plasma. Preferably, the proteolytic cleavage product comprises the C1q globular head or a portion thereof. More preferably, the proteolytic cleavage product is identical to a proteolytic cleavage product isolated from human plasma by immunoprecipitation using antibodies specific for the C1q globular head. More preferably the proteolytic cleavage product cannot be immunoprecipitated from human plasma using an antibody directed against the human non-homologous region (HDQETTTQGPGVLLPLPKGA) of APM1. Still more preferably, the APM1 proteolytic cleavage product has an apparent molecular weight of 27 kDa using SDS-PAGE.

In a further preferred embodiment, the OBG3 or gOBG3 polypeptide fragment is able to lower circulating (either blood, serum or plasma) levels (concentration) of: (i) free fatty acids, (ii) glucose, and/or (iii) triglycerides. Further preferred polypeptide fragments demonstrating free fatty acid level lowering activity, glucose level lowering activity, and/or triglyceride level lowering activity, have an activity that is significantly greater than full-length OBG3 at the same molar concentration, have a greater than transient activity and/or have a sustained activity.

Further preferred OBG3 or gOBG3 polypeptide fragments are those that significantly stimulate muscle lipid or free fatty acid oxidation as compared to full-length OBG3 polypeptides at the same molar concentration. Further preferred OBG3 or gOBG3 polypeptide fragments are those that cause C2C12 cells differentiated in the presence of said fragments to undergo at least 10%, 20%, 30%, 35%, or 40% more oleate oxidation as compared to untreated cells or cells treated with full-length OBG3.

Further preferred OBG3 or gOBG3 polypeptide fragments are those that are at least 30% more efficient than full-length OBG3 at increasing leptin uptake in a liver cell line (preferably BPRCL mouse liver cells (ATCC CRL-2217)).

Further preferred OBG3 or gOBG3 polypeptide fragments are those that significantly reduce the postprandial increase in plasma free fatty acids, particularly following a high fat meal.

Further preferred OBG3 or gOBG3 polypeptide fragments are those that significantly reduce or eliminate ketone body production, particularly following a high fat meal.

Further preferred OBG3 or gOBG3 polypeptide fragments are those that increase glucose uptake in skeletal muscle cells.

Further preferred OBG3 or gOBG3 polypeptide fragments are those that increase glucose uptake in adipose cells.

Further preferred OBG3 or gOBG3 polypeptide fragments are those that increase glucose uptake in neuronal cells.

Further preferred OBG3 or gOBG3 polypeptide fragments are those that increase glucose uptake in red blood cells.

Further preferred OBG3 or gOBG3 polypeptide fragments are those that increase glucose uptake in the brain.

Further preferred OBG3 or gOBG3 polypeptide fragments are those that significantly reduce the postprandial increase in plasma glucose following a meal, particularly a high carbohydrate meal.

Further preferred OBG3 or gOBG3 polypeptide fragments are those that significantly prevent the postprandial increase in plasma glucose following a meal, particularly a high fat or a high carbohydrate meal.

Further preferred OBG3 or gOBG3 polypeptide fragments are those that improve insulin sensitivity.

Further preferred OBG3 or gOBG3 polypeptide fragments are those that inhibit the progression from impaired glucose tolerance to insulin resistance.

Further preferred OBG3 or gOBG3 polypeptide fragments are those that increase muscle mass, preferably those that increase muscle cell number, more preferably those that increase muscle fiber number.

Further preferred OBG3 or gOBG3 polypeptide fragments are those that promote an increase in body girth, preferably fragments that promote an increase in muscle mass. Further preferred OBG3 or gOBG3 polypeptide fragments promote growth rate, preferably promoting an increase in growth rate greater than an average growth rate in the absence of OBG3 or gOBG3 polypeptide fragments.

Further preferred OBG3 or gOBG3 polypeptide fragments are those that promote growth rate in newborn mammals, preferably cow, goat, sheep, rabbit, mouse, rat, pig, dog, or human newborns, more preferably human newborns between the ages of 0–6 months of age, most preferably human newborn between the ages of 0–3 months. Further preferred OBG3 or gOBG3 polypeptide fragments are those that promote growth rate in newborn underweight or premature mammals, preferably cow, goat, sheep, rabbit, mouse, rat, pig, dog, or human underweight or premature newborns, more preferably human underweight or premature newborns between the ages of 0–6 months of age, most preferably human underweight or premature newborns between the ages of 0–3 months of age.

Further preferred OBG3 or gOBG3 polypeptide fragments are those that form multimers (e.g., heteromultimers or homomultimers) in vitro and/or in vivo. Preferred multimers axe homodimers or homotrimers. Other preferred multimers are homomultimers comprising at least 4, 6, 8, 9, 10 or 12 OBG3 or gOBG3 polypeptide fragment subunits. Other preferred multimers are hetero multimers comprising a OBG3 or gOBG3 polypeptide fragment of the invention.

Further preferred embodiments include heterologous polypeptides comprising an OBG3 or gOBG3 polypeptide fragment of the invention.

In a second aspect, the invention features a purified, isolated, or recombinant polynucleotide encoding said OBG3 polypeptide fragment described in the first aspect, or the complement thereof. In further embodiments the polynucleotides are DNA, RNA, DNA/RNA hybrids, single-stranded, and double-stranded.

In a third aspect, the invention features a recombinant vector comprising, consisting essentially of, or consisting of, said polynucleotide described in the second aspect.

In a fourth aspect, the invention features a recombinant cell comprising, consisting essentially of, or consisting of, said recombinant vector described in the third aspect. A further embodiment includes a host cell recombinant for a polynucleotide of the invention.

In a fifth aspect, the invention features a pharmaceutical or physiologically acceptable composition comprising, consisting essentially of, or consisting of, said OBG3 or gOBG3 polypeptide fragment described in the first aspect and, alternatively, a pharmaceutical or physiologically acceptable diluent.

In a sixth aspect, the invention features a method of reducing body mass comprising providing or administering to individuals in need of reducing body mass said pharmaceutical or physiologically acceptable composition described in the fifth aspect. Further preferred is a method of reducing body fat mass comprising providing or administering to individuals in need thereof said pharmaceutical or physiologically acceptable composition described in the fifth aspect. Further preferred is a method of increasing lean body mass comprising providing or administering to individuals in need thereof said pharmaceutical or physiologically acceptable composition described in the fifth aspect. Further preferred is a method of increasing the growth rate of body girth or length comprising providing or administering to individuals in need thereof said pharmaceutical or physiologically acceptable composition described in the fifth aspect.

In preferred embodiments, the identification of said individuals in need of reducing body mass to be treated with said pharmaceutical or physiologically acceptable composition comprises genotyping OBG3 single nucleotide polymorphisms (SNPs) or measuring OBG3 or gOBG3 polypeptide or mRNA levels in clinical samples from said individuals. Preferably, said clinical samples are selected from the group consisting of plasma, urine, and saliva. Preferably, an OBG3 or gOBG3 polypeptide fragment of the present invention is administered to an individual with at least a 10%, 20%, 30%, 40%, 50%, 60%, 70%, 80%, 90%, or 100% reduction in blood, serum or plasma levels of full-length OBG3 or the naturally proteolytically cleaved OBG3 fragment as compared to healthy, non-obese patients.

In a seventh aspect, the invention features a method of preventing or treating an obesity-related disease or disorder comprising providing or administering to an individual in need of such treatment said pharmaceutical or physiologically acceptable composition described in the fifth aspect. In preferred embodiments, the identification of said individuals in need of such treatment to be treated with said pharmaceutical or physiologically acceptable composition comprises genotyping OBG3 single nucleotide polymorphisms (SNPs) or measuring OBG3 or gOBG3 polypeptide or mRNA levels in clinical samples from said individuals. Preferably, said clinical samples are selected from the group consisting of blood, serum, plasma, urine, and saliva. Preferably, said obesity-related disease or disorder is selected from the group consisting of obesity, impaired glucose tolerance, insulin resistance, atherosclerosis, atheromatous disease, heart disease, hypertension, stroke, Syndrome X, Noninsulin Dependent Diabetes Mellitus (NIDDM, or Type II diabetes) and Insulin Dependent Diabetes Mellitus (IDDM or Type I diabetes). Diabetes-related complications to be treated by the methods of the invention include microangiopathic lesions, ocular lesions, retinopathy, neuropathy, and renal lesions. Heart disease includes, but is not limited to, cardiac insufficiency, coronary insufficiency, and high blood pressure. Other obesity-related disorders to be treated by compounds of the invention include hyperlipidemia and hyperuricemia. Yet other obesity-related diseases or disorders of the invention include cachexia, wasting, AIDS-related weight loss, cancer-related weight loss, anorexia, and bulimia. In preferred embodiments, said individual is a mammal, preferably a human.

In related aspects, embodiments of the present invention includes methods of causing or inducing a desired biological response in an individual comprising the steps of: providing or administering to an individual a composition comprising an OBG3 or gOBG3 polypeptide fragment, wherein said biological response is selected from the group consisting of:

(a) lowering circulating (either blood, serum, or plasma) levels (concentration) of free fatty acids;

(b) lowering circulating (either blood, serum or plasma) levels (concentration) of glucose;

(c) lowering circulating (either blood, serum or plasma) levels (concentration) of triglycerides;

(d) stimulating muscle lipid or free fatty acid oxidation;

(c) increasing leptin uptake in the liver or liver cells;

(e) reducing the postprandial increase in plasma free fatty acids, particularly following a high fat meal; and, (f) reducing or eliminating ketone body production, particularly following a high fat meal;

(g) increasing tissue sensitivity to insulin, particularly muscle, adipose, liver or brain;

(h) inhibiting the progression from impaired glucose tolerance to insulin resistance;

(i) increasing muscle cell protein synthesis;

(j) reducing adipocyte triglyceride content;

(k) increasing utilization of energy from foodstuffs or metabolic stores;

(l) increasing growth rate, preferably growth in girth or length;

(m) increasing muscle growth; and (n) increasing skeletal growth;

and further wherein said biological response is significantly greater than, or at least 10%, 20%, 30%, 35%, or 40% greater than, the biological response caused or induced by a full-length OBG3 polypeptide at the same molar concentration; or alternatively wherein said biological response is greater than a transient response; or alternativley wherein said biological response is sustained. In further preferred embodiments, the present invention of said pharmaceutical or physiologically acceptable composition can be used as a method to control blood glucose in some persons with Noninsulin Dependent Diabetes Mellitus (NIDDM, Type II diabetes) in combination with insulin therapy.

In further preferred embodiments, the present invention of said pharmaceutical or physiologically acceptable composition can be used as a method to control blood glucose in some persons with Insulin Dependent Diabetes Mellitus (IDDM, Type I diabetes) in combination with insulin therapy.

In further preferred embodiments, the present invention of said pharmaceutical or physiologically acceptable composition can be used as a method to control body weight in some persons with Noninsulin Dependent Diabetes Mellitus (NIDDM, Type II diabetes) in combination with insulin therapy.

In further preferred embodiments, the present invention of said pharmaceutical or physiologically acceptable composition can be used as a method to control body weight in some persons with Insulin Dependent Diabetes Mellitus (IDDM, Type I diabetes) in combination with insulin therapy.

In further preferred embodiments, the present invention of said pharmaceutical or physiologically acceptable composition can be used as a method to control blood glucose in some persons with Noninsulin Dependent Diabetes Mellitus (NIDDM, Type II diabetes) alone, without combination of insulin therapy.

In further preferred embodiments, the present invention of said pharmaceutical or physiologically acceptable composition can be used as a method to control blood glucose in some persons with Insulin Dependent Diabetes Mellitus (IDDM, Type I diabetes) alone, without combination of insulin therapy.

In further preferred embodiments, the present invention of said pharmaceutical or physiologically acceptable composition can be used as a method to control body weight in some persons with Noninsulin Dependent Diabetes Mellitus (NIDDM, Type II diabetes) alone, without combination of insulin therapy.

In further preferred embodiments, the present invention of said pharmaceutical or physiologically acceptable composition can be used as a method to control body weight in some persons with Insulin Dependent Diabetes Mellitus (IDDM, Type I diabetes) alone, without combination of insulin therapy.

In a further preferred embodiment, the present invention may be used in complementary therapy of NIDDM patients to improve their weight or glucose control in combination with an oral insulin secretagogue or an insulin sensitising agent. Preferably, the oral insulin secretagogue is 1,1-dimethyl-2-(2-morpholino phenyl)guanidine fumarate (BTS67582) or a sulphonylurea selected from tolbutamide, tolazamide, chlorpropamide, glibenclamide, glimepiride, glipizide and glidazide. Preferably, the insulin sensitising agent is selected from metformin, ciglitazone, troglitazone and pioglitazone.

The present invention further provides a method of improving the body weight or glucose control of NIDDM patients alone, without an oral insulin secretagogue or an insulin sensitising agent.

In a further preferred embodiment, the present invention may be used in complementary therapy of IDDM patients to improve their weight or glucose control in combination with an oral insulin secretagogue or an insulin sensitising agent. Preferably, the oral insulin secretagogue is 1,1-dimethyl-2-(2-morpholino phenyl)guanidine fumarate (BTS67582) or a sulphonylurea selected from tolbutamide, tolazamide, chlorpropamide, glibenclamide, glimepiride, glipizide and glidazide. Preferably, the insulin sensitising agent is selected from metformin, ciglitazone, troglitazone and pioglitazone.

The present invention further provides a method of improving the body weight or glucose control of IDDM patients alone, without an oral insulin secretagogue or an insulin sensitising agent.

In a further preferred embodiment, the present invention may be administered either concomitantly or concurrently, with the oral insulin secretagogue or insulin sensitising agent for example in the form of separate dosage units to be used simultaneously, separately or sequentially (either before or after the secretagogue or either before or after the sensitising agent). Accordingly, the present invention further provides for a composition of pharmaceutical or physiologically acceptable composition and an oral insulin secretagogue or insulin sensitising agent as a combined preparation for simultaneous, separate or sequential use for the improvement of body weight or glucose control in NIDDM or IDDM patients.

In further preferred embodiments, the present invention of said pharmaceutical or physiologically acceptable composition further provides a method for the use as an insulin sensitiser.

In further preferred embodiments, the present invention of said pharmaceutical or physiologically acceptable composition can be used as a method to improve insulin sensitivity in some persons with Noninsulin Dependent Diabetes Mellitus (NIDDM, Type II diabetes) in combination with insulin therapy.

In further preferred embodiments, the present invention of said pharmaceutical or physiologically acceptable composition can be used as a method to improve insulin sensitivity in some persons with Insulin Dependent Diabetes Mellitus (IDDM, Type I diabetes) in combination with insulin therapy.

In further preferred embodiments, the present invention of said pharmaceutical or physiologically acceptable composition can be used as a method to improve insulin sensitivity in some persons with Noninsulin Dependent Diabetes Mellitus (NIDDM, Type II diabetes) without insulin therapy.

In an eighth aspect, the invention features a method of making the OBG3 polypeptide fragment described in the first aspect, wherein said method is selected from the group consisting of: proteolytic cleavage, recombinant methodology and artificial synthesis.

In a ninth aspect, the present invention provides a method of making a recombinant OBG3 or gOBG3 polypeptide fragment or a full-length OBG3 polypeptide, the method comprising providing a transgenic, non-human mammal whose milk contains said recombinant OBG3 or gOBG3 polypeptide fragment or full-length protein, and purifying said recombinant OBG3 or gOBG3 polypeptide fragment or said full-length OBG3 polypeptide from the milk of said non-human mammal. In one embodiment, said non-human mammal is a cow, goat, sheep, rabbit, or mouse. In another embodiment, the method comprises purifying a recombinant full-length OBG3 polypeptide from said milk, and further comprises cleaving said protein in vitro to obtain a desired OBG3 or gOBG3 polypeptide fragment.

In a tenth aspect, the invention features a use of the polypeptide described in the first aspect for treatment of obesity-related diseases and disorders and/or reducing or increasing body mass. Preferably, said obesity-related diseases and disorders are selected from the group consisting of obesity, impaired glucose tolerance, insulin resistance, atherosclerosis, atheromatous disease, heart disease, hypertension, stroke, Syndrome X, Noninsulin Dependent Diabetes Mellitus (NIDDM, or Type II diabetes) and Insulin Dependent Diabetes Mellitus (IDDM or Type I diabetes). Diabetes-related complications to be treated by the methods of the invention include microangiopathic lesions, ocular lesions, retinopathy, neuropathy, and renal lesions. Heart disease includes, but is not limited to, cardiac insufficiency, coronary insufficiency, and high blood pressure. Other obesity-related disorders to be treated by compounds of the invention include hyperlipidemia and hyperuricemia. Yet other obesity-related diseases or disorders of the invention include cachexia, wasting, AIDS-related weight loss, cancer-related weight loss, anorexia, and bulimia.

In an eleventh aspect, the invention features a use of the polypeptide described in the first aspect for the preparation of a medicament for the treatment of obesity-related diseases and disorders and/or for reducing body mass. Preferably, said obesity-related disease or disorder is selected from the group consisting of obesity, impaired glucose tolerance, insulin resistance, atherosclerosis, atheromatous disease, heart disease, hypertension, stroke, Syndrome X, Noninsulin Dependent Diabetes Mellitus (NIDDM, or Type II diabetes) and Insulin Dependent Diabetes Mellitus (IDDM or Type I diabetes). Diabetes-related complications to be treated by the methods of the invention include microangiopathic lesions, ocular lesions, retinopathy, neuropathy, and renal lesions. Heart disease includes, but is not limited to, cardiac insufficiency, coronary insufficiency, and high blood pressure. Other obesity-related disorders to be treated by compounds of the invention include hyperlipidemia and hyperuncemia. Yet other obesity-related diseases or disorders of the invention include cachexia, wasting, AIDS-related weight loss, cancer-related weight loss, anorexia, and bulimia. In preferred embodiments, said individual is a mammal, preferably a human.

In a twelfth aspect, the invention provides a polypeptide of the first aspect of the invention, or a composition of the fifth aspect of the invention, for use in a method of treatment of the human or animal body.

In a thirteenth aspect, the invention features methods of reducing body weight comprising providing to an individual said pharmaceutical or physiologically acceptable composition described in the fifth aspect, or the polypeptide described in the first aspect. Where the reduction of body weight is practiced for cosmetic purposes, the individual has a BMI of at least 20 and no more than 25. In embodiments for the treatment of obesity, the individual may have a BMI of at least 20. One embodiment for the treatment of obesity provides for the treatment of individuals with BMI values of at least 25. Another embodiment for the treatment of obesity provides for the treatment of individuals with BMI values of at least 30. Yet another embodiment provides for the treatment of individuals with BMI values of at least 40. Alternatively, for increasing the body weight of an individual, the BMI value should be at least 15 and no more than 20.

In a fourteenth aspect, the invention features the pharmaceutical or physiologically acceptable composition described in the fifth aspect for reducing body mass and/or for treatment or prevention of obesity-related diseases or disorders. Preferably, said obesity-related disease or disorder is selected from the group consisting of obesity, impaired glucose tolerance, insulin resistance, atherosclerosis, atheromatous disease, heart disease, hypertension, stroke, Syndrome X, Noninsulin Dependent Diabetes Mellitus (NIDDM, or Type II diabetes) and Insulin Dependent Diabetes Mellitus (IDDM or Type I diabetes). Diabetes-related complications to be treated by the methods of the invention include microangiopathic lesions, ocular lesions, retinopathy, neuropathy, and renal lesions. Heart disease includes, but is not limited to, cardiac insufficiency, coronary insufficiency, and high blood pressure. Other obesity-related disorders to be treated by compounds of the invention include hyperlipidemia and hyperuricemia. Yet other obesity-related diseases or disorders of the invention include cachexia, wasting, AIDS-related weight loss, cancer-related weight loss, anorexia, and bulimia. In preferred embodiments, said individual is a mammal, preferably a human. In preferred embodiments, the identification of said individuals to be treated with said pharmaceutical or physiologically acceptable composition comprises genotyping OBG3 single nucleotide polymorphisms (SNPs) or measuring OBG3 or gOBG3 polypeptide or mRNA levels in clinical samples from said individuals. Preferably, said clinical samples are selected from the group consisting of blood, serum, plasma, urine, and saliva.

In a fifteenth aspect, the invention features the pharmaceutical or physiologically acceptable composition described in the fifth aspect for reducing body weight for cosmetic reasons.

In a sixteenth aspect, the OBG3 or gOBG3 polypeptide fragments of the invention features methods treating insulin resistance comprising providing to an individual said pharmaceutical or physiologically acceptable composition described in the fifth aspect, or the polypeptide described in the first aspect.

In a seventeenth aspect, the invention features the pharmaceutical or physiologically acceptable composition described in the fifth aspect in a method of treating individuals with normal glucose tolerance (NGT) who are obese or who have fasting hyperinsulinemia, or who have both.

In further preferred embodiments, the invention features the pharmaceutical or physiologically acceptable composition described in the fifth aspect in a method of treating individuals with gestational diabetes. Gestational diabetes refers to the development of diabetes in an individual during pregnancy, usually during the second or third trimester of pregnancy.

In further preferred embodiments, the invention features the pharmaceutical or physiologically acceptable composition described in the fifth aspect in a method of treating individuals with impaired fasting glucose (IFG). Impaired fasting glucose (IFG) is that condition in which fasting plasma glucose levels in an individual are elevated but not diagnostic of overt diabetes, i.e. plasma glucose levels of less than 126 mg/dl and greater than or equal to 110 mg/dl.

In further preferred embodiments, the invention features the pharmaceutical or physiologically acceptable composition described in the fifth aspect in a method of treating impaired glucose tolerance (IGT) in an individual. In other further preferred embodiments, the invention features the pharmaceutical or physiologically acceptable composition described in the fifth aspect in a method of preventing IGT in an individual. By providing therapeutics and methods for reducing or preventing IGT, i.e., for normalizing insulin resistance, the progression to NIDDM can be delayed or prevented. Furthermore, by providing therapeutics and methods for reducing or preventing insulin resistance, the invention provides methods for reducing and/or preventing the appearance of Insulin-Resistance Syndrome.

In further preferred embodiments, the invention features the pharmaceutical or physiologically acceptable composition described in the fifth aspect in a method of treating a subject having polycystic ovary syndrome (PCOS). PCOS is among the most common disorders of premenopausal women. Insulin-sensitizing agents have been shown to be effective in PCOS. Accordingly, the invention provides methods for reducing insulin resistance, normalizing blood glucose thus treating and/or preventing PCOS.

In further preferred embodiments, the invention features the pharmaceutical or physiologically acceptable composition described in the fifth aspect in a method of treating a subject having insulin resistance. In still further preferred embodiments, a subject having insulin resistance is treated according to the methods of the invention to reduce or cure the insulin-resistance. As insulin resistance is also often associated with infections and cancer, prevention or reducing insulin resistance according to the methods of the invention may prevent or reduce infections and cancer.

In further preferred embodiment, the methods of the invention are used to prevent the development of insulin resistance in a subject, e.g., those known to have an increased risk of developing insulin-resistance.

In an eighteenth aspect, the invention features a method of using OBG3 or gOBG3 polypeptide fragment in a method of screening compounds for one or more antagonists of dipeptidyl peptidase cleavage said polypeptide fragment.

In preferred embodiment, said compound is selected from but is not restricted to small molecular weight organic or inorganic compound, protein, peptide, carbohydrate, or lipid.

In preferred embodiment, said polypeptide fragment is gOBG3 polypeptide fragment. In further preferred embodiment, said gOBG3 polypeptide fragment is gOBG3 polypeptide fragment of SEQ ID NO:6.

In preferred embodiment, said antagonist of dipeptidyl peptidase cleavage of said gOBG3 polypeptide fragment is specific for said dipeptidyl peptidase.

In further preferred embodiment, said antagonist of dipeptidyl peptidase cleavage of said gOBG3 polypeptide fragment is specific for said gOBG3 polypeptide fragment.

In a nineteenth aspect, the invention features a method of using OBG3 or gOBG3 polypeptide fragment in a method of screening compounds for one or more antagonists of OBG3 or gOBG3 activity, wherein said activity is selected from but not restricted to lipid partitioning, lipid metabolism, and insulin-like activity.

In preferred embodiment, said compound is selected from but is not restricted to small molecular weight organic or inorganic compound, protein, peptide, carbohydrate, or lipid.

In a twentieth aspect, the present invention provides a mammal, preferably a newborn human, with a supplement to promote, improve, enhance or increase the assimilation, utilization or storage of energy and other nutrients present in foodstuffs consumed by newborn mammals, particularly newborn humans, and particularly energy and other nutrients in infant formula or breast milk. A further preferred embodiment of the present invention is to provide a mammal, preferably a newborn human, with a supplement to promote, improve, enhance, or increase growth rate. Preferred methods of supplementation with OBG3 or gOBG3 polypeptides of the invention include but is not limited to:

(a) direct addition of OBG3 or gOBG3 polypeptides to synthetic infant formula or to breast milk;

(b) administration of OBG3 or gOBG3 polypeptides prior to feeding, preferably 1–15 minutes prior to feeding, more preferably 1–5 minutes prior to feeding; and (c) administration of OBG3 or gOBG3 polypeptides following feeding, preferably 1–15 minutes following feeding, more preferably 1–5 minutes following feeding;

wherein routes of administration of OBG3 or gOBG3 polypeptides are selected from oral, buccal, nasal and intramuscular routes, preferably oral routes.

A further preferred embodiment is directed to using OBG3 or gOBG3 polypeptides of the invention in methods to promote, improve, enhance or increase the assimilation, utilization or storage of energy and other nutrients present in foodstuffs consumed by newborn mammals, particularly newborn humans, and particularly energy and other nutrients in infant formula or breast milk. A further preferred embodiment is directed to using OBG3 or gOBG3 polypeptides of the invention in methods to promote, improve, enhance or increase the growth rate of a newborn mammal, preferably a human newborn. Further preferred are compositions comprising OBG3 or gOBG3 polypeptides which can be used in methods to promote, improve, enhance or increase the assimilation, utilization or storage of energy and other nutrients present in foodstuffs consumed by newborn mammals, particularly newborn humans, and particularly energy and other nutrients in infant formula or breast milk. Further preferred are compositions comprising OBG3 or gOBG3 polypeptides which can be used in methods to promote, improve, enhance or increase the growth rate of a newborn mammal, preferably a human newborn. A still further preferred embodiment of the present invention is directed to compositions comprising synthetic infant milk formula and OBG3 or gOBG3 polypeptides of the invention.

Another embodiment of the invention is to provide OBG3 or gOBG3 polypeptide compositions useful for enhancing or improving the nutritional value of synthetic infant milk formulas or breast milk. Further preferred are compositions useful for incorporation into the diet of a newborn mammal so as to enhance and improve the nutritional value of the diet. Still another embodiment of the invention is to provide techniques and routines for improving the diet and feeding of newborn mammals, particularly premature, underweight or very-low-birth-weight newborns, preferably human newborns.

In preferred embodiments of the invention, said polypeptide fragment is gOBG3 polypeptide fragment. In further preferred embodiment, said gOBG3 polypeptide fragment is gOBG3 polypeptide fragment of SEQ ID NO:6.

In preferred aspects of the methods of the invention disclosed herein, the amount of OBG3 or gOBG3 polypeptide fragment or polynucleotide administered to an individual is sufficient to bring circulating (blood, serum, or plasma) levels (concentration) of OBG3 polypeptides to their normal levels (levels in non-obese individuals). "Normal levels" may be specified as the total concentration of all circulating OBG3 polypeptides (full-length OBG3 and fragments thereof) or the concentration of all circulating proteolytically cleaved OBG3 polypeptides only.

In preferred embodiments of the compositions of the invention disclosed herein, compositions of the invention may further comprise any combination of OBG3 polypeptide fragments, insulin, insulin secretagogues or insulin sensitising agents such that the composition produces a biological effect greater than the expected effect for an OBG3 polypeptide administered alone rather than in combination with insulin, insulin secretagogues or insulin sensitising agents.

In a further embodiment, said biological function includes, but is not limited to, free fatty acid level lowering activity, glucose level lowering activity, triglyceride level lowering activity, stimulating adipose lipolysis, stimulating muscle lipid or free fatty acid oxidation, increasing leptin uptake in a liver cell line, significantly reducing the postprandial increase in plasma free fatty acids or glucose due to a high fat meal, significantly reducing or eliminate ketone body production as the result of a high fat meal, increasing glucose uptake in skeletal muscle cells, adipose cells, red blood cells or the brain, increasing insulin sensitivity, inhibiting the progression from impaired glucose tolerance to insulin resistance, reducing body mass, decreasing fat mass, increasing lean muscle mass, preventing or treating an metabolic-related disease or disorder, controlling blood glucose in some persons with Noninsulin Dependent Diabetes Mellitus or Noninsulin Dependent Diabetes Mellitus, treating insulin resistance or preventing the development of insulin resistance.

Full-length OBG3 (ACRP30, AdipoQ, APM1) polypeptides and polynucleotides encoding the same may be specifically substituted for an OBG3 or gOBG3 polypeptide fragment or polynucleotide encoding the same in any embodiment of the present invention.

BRIEF DESCRIPTION OF THE FIGURES

FIG. 1 shows an alignment of the sequences of the human (APM1), and mouse (AdipoQ and ACRP30) OBG3 polypeptides.

FIG. 2 shows the nucleic acid sequence of AdipoQ cloned into the BamHI and XhoI sites of pTrcHisB. AdipoQ begins at 510 and ends at 1214 (insert in bold). This construct does not contain the N-term signal sequence (MLLLQALLFLLILP).

FIG. 4 shows the nucleic acid sequence of the globular region of AdipoQ cloned into pTrcHisB. AdipoQ globular region begins at 510 and ends at 927 bp. The insert is in bold.

FIG. 7 shows a protein sequence alignment of the obg3 clone (obg3 clone; the insert in FIG. 2) with the published sequences of human (APM1) and mouse (AdipoQ and ACRP30) obg3. In the alignment, amino acids (AAs) 45 to 110 contain the collagen-like region; AAs 111–247 contain the globular region. The cut sites from lysine-blocked trypsin fall after AAs 58, 61, 95, 103, 115, 125, and 134. As determined by amino-terminal sequencing of the gOBG3 product, the gOBG3 start site is at AA 104 (101 for human gOBG3 or APM1).

FIG. 9A shows TG in mg/dl; FIG. 9B shows TG as a percent of the starting value.

FIGS. 11A and 11B show graphical representations of the effect of gOBG3 (3×25 μg ip) on plasma FFA in C57BL6/J mice following a high fat meal. FIG. 1A shows FFA as mM; FIG. 11B shows FFA as a percent of the starting value.

FIG. 12A shows leptin as ng/mL; FIG. 12B shows leptin as a percent of the starting value.

FIG. 13A shows insulin levels in ng/mL; FIG. 13B shows insulin as a percent of the starting value.

FIG. 14A shows FFA levels in mM; FIG. 14B shows FFA as a percent of the starting value.

FIG. 15A shows TG levels in mg/dl; FIG. 15B shows TG as a percent of the starting value.

FIG. 16A shows glucose levels as mg/dl; FIG. 16B shows glucose levels as a percent of the starting value.

FIG. 17 shows a table identifying additional APM1 SNPs. Information concerning Known Base Changes, Location, Prior Markers, Amplicon, and Forward and Reverse primers for microsequencing are shown.

FIG. 21A shows results of treatment of mice after 19 days on a high fat diet. FIG. 21B shows results of treatment of mice after 6 months on a high fat diet.

FIG. 22 shows a table of the tested blood chemistry values with saline injections, ACRP30 injections, or gACRP30 injections.

FIG. 23A, Lane II shows the complete form of ACRP30 purified by FPLC. Lane I shows the proteolytic cleavage product gACRP30. FIG. 23B shows a cleavage product of APM1 after immunoprecipitation followed by Western blotting. The apparent molecular weight of this truncated form is 27 kDa, corresponding to about 70% of the complete form of APM1 (Lane IV). This truncated form was not detectable when a second antiserum, specific for the human non-homologous region (HDQETTTQGPGVLLPLPKGA) of the protein was used for immunoprecipitation (Lane V) and the same anti-globular head antiserum for detection. A preimmune serum of the same animal did not detect any protein; a dimer of APM1 was seen with both specific antibodies (apparent MW 74 kDa).

DETAILED DISCLOSURE OF THE INVENTION

Figure 3:
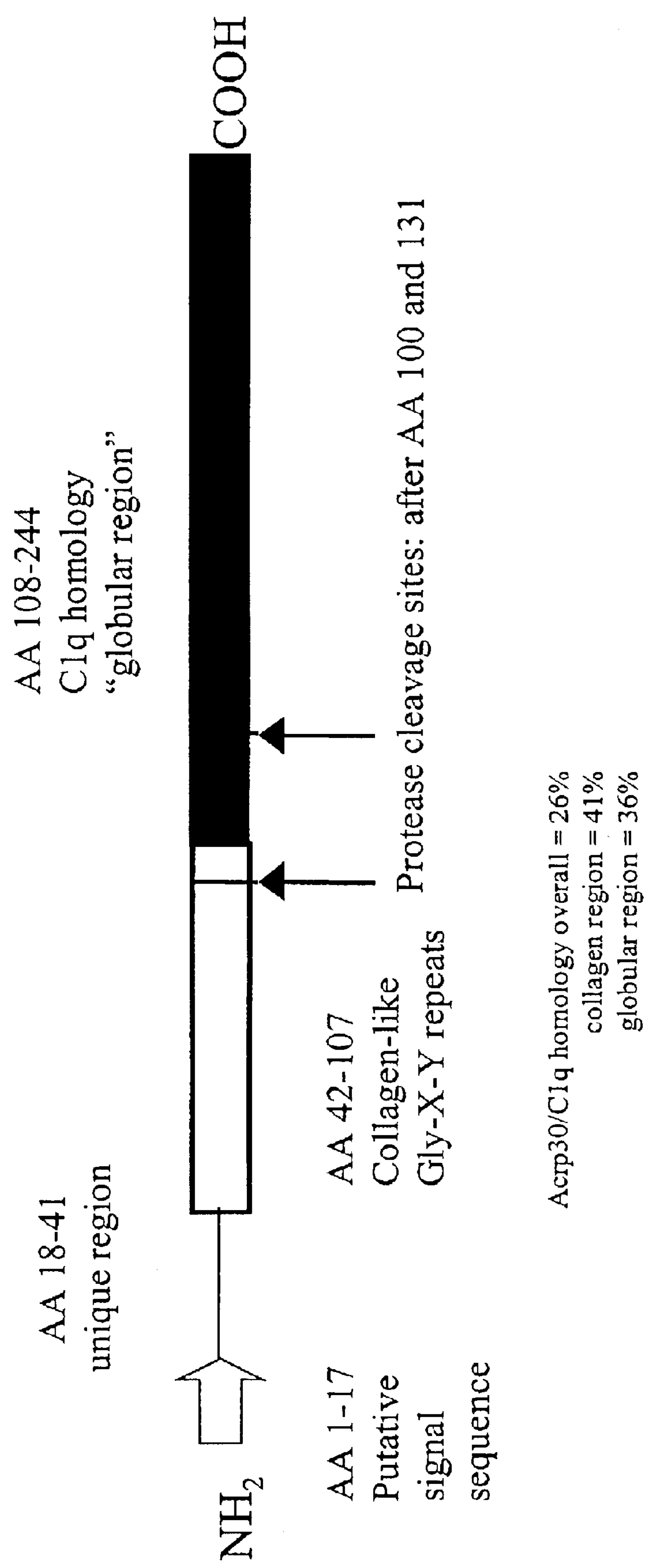
FIG. 3 shows a schematic drawing of the protein structure of APM1. The putative signal sequence at the N-terminus (AA 1–17), the unique region (AA 18–41), the collagen region (AA 42–107), and the globular region (AA 108–244) at the carboxy terminus are shown. Two protease cleavage sites after AA 100 and AA 131 are also shown.

Before describing the invention in greater detail, the following definitions are set forth to illustrate and define the meaning and scope of the terms used to describe the invention herein.

As used interchangeably herein, the terms "oligonucleotides", and "polynucleotides" and nucleic acid include RNA, DNA, or RNA/DNA hybrid sequences of more than one nucleotide in either single chain or duplex form. The terms encompass "modified nucleotides" which comprise at least one modification, including by way of example and not limitation: (a) an alternative linking group, (b) an analogous form of purine, (c) an analogous form of pyrimidine, or (d) an analogous sugar. For examples of analogous linking groups, purines, pyrimidines, and sugars see for example PCT publication No. WO 95/04064. The polynucleotide sequences of the invention may be prepared by any known method, including synthetic, recombinant, ex vivo generation, or a combination thereof, as well as utilizing any purification methods known in the art.

The terms polynucleotide construct, recombinant polynucleotide and recombinant polypeptide are used herein consistently with their use in the art. The terms "upstream" and "downstream" are also used herein consistently with their use in the art. The terms "base paired" and "Watson & Crick base paired" are used interchangeably herein and consistently with their use in the art. Similarly, the terms "complementary", "complement thereof", "complement", "complementary polynucleotide", "complementary nucleic acid" and "complementary nucleotide sequence" are used interchangeably herein and consistently with their use in the art.

The term "purified" is used herein to describe a polynucleotide or polynucleotide vector of the invention that has been separated from other compounds including, but not limited to, other nucleic acids, carbohydrates, lipids and proteins (such as the enzymes used in the synthesis of the polynucleotide). Purified can also refer to the separation of covalently closed polynucleotides from linear polynucleotides, or vice versa, for example. A polynucleotide is substantially pure when at least about 50%, 60%, 75%, or 90% of a sample contains a single polynucleotide sequence. In some cases this involves a determination between conformations (linear versus covalently closed). A substantially pure polynucleotide typically comprises about 50, 60, 70, 80, 90, 95, 99% weight/weight of a nucleic acid sample. Polynucleotide purity or homogeneity may be indicated by a number of means well known in the art, such as agarose or polyacrylamide gel electrophoresis of a sample, followed by visualizing a single polynucleotide band upon staining the gel. For certain purposes higher resolution can be provided by using HPLC or other means well known in the art.

Similarly, the term "purified" is used herein to describe a polypeptide of the invention that has been separated from other compounds including, but not limited to, nucleic acids, lipids, carbohydrates and other proteins. In some preferred embodiments, a polypeptide is substantially pure when at least about 50%, 60%, 75%, 85%, 90%, 95%, 96%, 97%, 98%, 99%, or 99.5% of the polypeptide molecules of a sample have a single amino acid sequence. In some preferred embodiments, a substantially pure polypeptide typically comprises about 50%, 60%, 70%, 80%, 90% 95%, 96%, 97%, 98%, 99% or 99.5% weight/weight of a protein sample. Polypeptide purity or homogeneity is indicated by a number of methods well known in the art, such as agarose or polyaciylamide gel electrophoresis of a sample, followed by visualizing a single polypeptide band upon staining the gel. For certain purposes higher resolution can be provided by using HPLC or other methods well known in the art.

Further, as used herein, the term "purified" does not require absolute purity; rather, it is intended as a relative definition. Purification of starting material or natural material to at least one order of magnitude, preferably two or three orders, and more preferably four or five orders of magnitude is expressly contemplated. Alternatively, purification may be expressed as "at least" a percent purity relative to heterologous polynucleotides (DNA, RNA or both) or polypeptides. As a preferred embodiment, the polynucleotides or polypeptides of the present invention are at least; 10%, 20%, 30%, 40%, 50%, 60%, 70%, 80%, 90%, 95%, 96%, 97%, 98%, 99%, 99.5% or 100% pure relative to heterologous polynucleotides or polypeptides. As a further preferred embodiment the polynucleotides or polypeptides have an "at least" purity ranging from any number, to the thousandth position, between 90% and 100% (e.g., at least 99.995% pure) relative to heterologous polynucleotides or polypeptides. Additionally, purity of the polynucleotides or polypeptides may be expressed as a percentage (as described above) relative to all materials and compounds other than the carrier solution. Each number, to the thousandth position, maybe claimed as individual species of purity.

The term "isolated" requires that the material be removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that the vector or composition is not part of its natural environment.

Specifically excluded from the definition of "isolated" are: naturally occurring chromosomes (e.g., chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a 5' EST makes up less than 5% (or alternatively 1%, 2%, 3%, 4%, 10%, 25%, 50%, 75%, or 90%, 95%, or 99%) of the number of nucleic acid inserts in the vector molecules. Further specifically excluded are whole cell genomic DNA or whole cell RNA preparations (including said whole cell preparations which are mechanically sheared or enzymatically digested). Further specifically excluded are the above whole cell preparations as either an in vitro preparation or as a heterogeneous mixture separated by electrophoresis (including blot transfers of the same) wherein the polynucleotide of the invention have not been further separated from the heterologous polynucleotides in the electrophoresis medium (e.g., further separating by excising a single band from a heterogeneous band population in an agarose gel or nylon blot).

The term "primer" denotes a specific oligonucleotide sequence that is complementary to a target nucleotide sequence and used to hybridize to the target nucleotide sequence. A primer serves as an initiation point for nucleotide polymerization catalyzed by DNA polymerase, RNA polymerase, or reverse transcriptase.

The term "probe" denotes a defined nucleic acid segment (or nucleotide analog segment, e.g., PNA as defined hereinbelow) which can be used to identify a specific polynucleotide sequence present in a sample, said nucleic acid segment comprising a nucleotide sequence complementary to the specific polynucleotide sequence to be identified.

The term "polypeptide" refers to a polymer of amino acids without regard to the length of the polymer. Thus, peptides, oligopeptides, and proteins are included within the definition of polypeptide. This term also does not specify or exclude post-expression modifications of polypeptides. For example, polypeptides that include the covalent attachment of glycosyl groups, acetyl groups, phosphate groups, lipid groups and the like are expressly encompassed by the term polypeptide. Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring. As used herein, the term "OBG3" refers generically to the murine or human OBG3, unless otherwise specified. The terms "ACRP30" and "AdipoQ" refer specifically to the murine form of OBG3 and the term "APM1" refers specifically to the human form of the gene.

Without being limited by theory, the compounds/polypeptides of the invention are capable of modulating the partitioning of dietary lipids between the liver and peripheral tissues, and are thus believed to treat "diseases involving the partitioning of dietary lipids between the liver and peripheral tissues." The term "peripheral tissues" is meant to include muscle and adipose tissue. In preferred embodiments, the compounds/polypeptides of the invention partition the dietary lipids toward the muscle. In alternative preferred embodiments, the dietary lipids are partitioned toward the adipose tissue. In other preferred embodiments, the dietary lipids are partitioned toward the liver. In yet other preferred embodiments, the compounds/polypeptides of the invention increase or decrease the oxidation of dietary lipids, preferably free fatty acids (FFA) by the muscle. Dietary lipids include, but are not limited to triglycerides and free fatty acids.

Preferred diseases believed to involve the partitioning of dietary lipids include obesity and obesity-related diseases and disorders such as obesity, impaired glucose tolerance, insulin resistance, atherosclerosis, atheromatous disease, heart disease, hypertension, stroke, Syndrome X, Noninsulin Dependent Diabetes Mellitus (NIDDM, or Type II diabetes) and Insulin Dependent Diabetes Mellitus (IDDM or Type I diabetes). Diabetes-related complications to be treated by the methods of the invention include microangiopathic lesions, ocular lesions, retinopathy, neuropathy, and renal lesions. Heart disease includes, but is not limited to, cardiac insufficiency, coronary insufficiency, and high blood pressure. Other obesity-related disorders to be treated by compounds of the invention include hyperlipidemia and hyperuricemia. Yet other obesity-related diseases or disorders of the invention include cachexia, wasting, AIDS-related weight loss, cancer-related weight loss, anorexia, and bulimia.

The term "heterologous", when used herein, is intended to designate any polypeptide or polynucleotide other than an OBG3 or gOBG3 polypeptide or a polynucleotide encoding an OBG3 or gOBG3 polypeptide of the present invention.

The terms "comprising", "consisting of" and "consisting essentially of" are defined according to their standard meaning. A defined meaning set forth in the M.P.E.P. controls over a defined meaning in the art and a defined meaning set forth in controlling Federal Circuit case law controls over a meaning set forth in the M.P.E.P. With this in mind, the terms may be substituted for one another throughout the instant application in order to attach the specific meaning associated with each term.

The term "host cell recombinant for" a particular polynucleotide of the present invention, means a host cell that has been altered by the hands of man to contain said polynucleotide in a way not naturally found in said cell. For example, said host cell may be transiently or stably transfected or transduced with said polynucleotide of the present invention.

The term "obesity" as used herein is defined in the WHO classifications of weight (Kopehnan (2000) Nature 404:635–643). Underweight is less than 18.5 (thin); Healthy is 18.5–24.9 (normal); grade 1 overweight is 25.0–29.9 (overweight); grade 2 overweight is 30.0–39.0 (obesity); grade 3 overweight is greater than or equal to 40.0 BMI. BMI is body mass index (morbid obesity) and is $kg/m^2$. Waist circumference can also be used to indicate a risk of metabolic complications where in men a circumference of greater than or equal to 94 cm indicates an increased risk, and greater than or equal to 102 cm indicates a substantially increased risk. Similarly for women, greater than or equal to 88 cm indicates an increased risk, and greater than or equal to 88 cm indicates a substantially increased risk. The waist circumference is measured in cm at midpoint between lower border of ribs and upper border of the pelvis. Other measures of obesity include, but are not limited to, skinfold thickness which is a measurement in cm of skinfold thickness using calipers, and bioimpedance, which is based on the principle that lean mass conducts current better than fat mass because it is primarily an electrolyte solution; measurement of resistance to a weak current (impedance) applied across extremities provides an estimate of body fat using an empirically derived equation.

The term "diabetes" as used herein is intended to encompass the usual diagnosis of diabetes made from any of the methods included, but not limited to, the following list: symptoms of diabetes (eg. polyuria, polydipsia, polyphagia) plus casual plasma glucose levels of greater than or equal to 200 mg/dl, wherein casual plasma glucose is defined any time of the day regardless of the timing of meal or drink consumption; 8 hour fasting plasma glucose levels of less than or equal to 126 mg/dl; and plasma glucose levels of greater than or equal to 200 mg/dl 2 hours following oral administration of 75 g anhydrous glucose dissolved in water.

The term "impaired glucose tolerance (IGT)" as used herein is intended to indicate that condition associated with insulin-resistance that is intermediate between frank, NIDDM and normal glucose tolerance (NGT). A high percentage of the IGT population is known to progress to NIDDM relative to persons with normal glucose tolerance (Sad et al., New Engl J Med 1988; 319:1500–6 which disclosure is hereby incorporated by reference in its entirety). Thus, by providing therapeutics and methods for reducing or preventing IGT, i.e., for normalizing insulin resistance, the progression to NIDDM can be delayed or prevented. IGT is diagnosed by a procedure wherein an affected person's postprandial glucose response is determined to be abnormal as assessed by 2-hour postprandial plasma glucose levels. In this test, a measured amount of glucose is given to the patient and blood glucose levels measured regular intervals, usually every half hour for the first two hours and every hour thereafter. In a "normal" or non-IGT individual, glucose levels rise during the first two hours to a level less than 140 mg/dl and then drop rapidly. In an IGT individual, the blood glucose levels are higher and the drop-off level is at a slower rate.

The term "Insulin-Resistance Syndrome" as used herein is intended to encompass the cluster of abnormalities resulting from an attempt to compensate for insulin resistance that sets in motion a series of events that play an important role in the development of both hypertension and coronary artery disease (CAD), such as premature atherosclerotic vascular disease. Increased plasma triglyceride and decreased HDL-cholesterol concentrations, conditions that are known to be associated with CAD, have also been reported to be associated with insulin resistance. Thus, by providing therapeutics and methods for reducing or preventing insulin resistance, the invention provides methods for reducing and/or preventing the appearance of insulin-resistance syndrome.

The term "polycystic ovary syndrome (PCOS)" as used herein is intended to designate that etiologically unassigned disorder of premenopausal women, affecting 5–10% of this population, characterized by hyperandrogenism, chronic anovulation, defects in insulin action, insulin secretion, ovarian steroidogenesis and fibrinolysis. Women with PCOS frequently are insulin resistant and at increased risk to develop glucose intolerance or NIDDM in the third and fourth decades of life (Dunaif et al. (1996) J Clin Endocrinol Metab 81:3299 which disclosure is hereby incorporated by reference in its entirety). Hyperandrogenism also is a feature of a variety of diverse insulin-resistant states, from the type A syndrome, through leprechaunism and lipoatrophic diabetes, to the type B syndrome, when these conditions occur in premenopausal women. It has been suggested that hyperinsulinemia per se causes hyperandrogenism. Insulin-sensitizing agents, e.g., troglitazone, have been shown to be effective in PCOS and that, in particular, the defects in insulin action, insulin secretion, ovarian steroidogenosis and fibrinolysis are improved (Ehrman et al. (1997) J Clin Invest 100:1230 which disclosure is hereby incorporated by reference in its entirety), such as in insulin-resistant humans.

The term "insulin resistance" as used herein is intended to encompass the usual diagnosis of insulin resistance made by any of a number of methods, such as the intravenous glucose tolerance test or measurement of the fasting insulin level. It is well known that there is an excellent correlation between the height of the fasting insulin level and the degree of insulin resistance. Therefore, one could use elevated fasting insulin levels as a surrogate marker for insulin resistance for the purpose of identifying which normal glucose tolerance (NGT) individuals have insulin resistance. Another way to do this is to follow the approach as disclosed in The New England Journal of Medicine, No. 3, pp. 1188 (1995) (which disclosure is hereby incorporated by reference in its entirety), i.e. to select obese subjects as an initial criterion for entry into the treatment group. Some obese subjects have impaired glucose tolerance (IGT) while others have normal glucose tolerance (NGT). Since essentially all obese subjects are insulin resistant, i.e. even the NGT obese subjects are insulin resistant and have fasting hyperinsulinemia. Therefore, the target of the treatment according to the present invention can be defined as NGT individuals who are obese or who have fasting hyperinsulinemia, or who have both.

A diagnosis of insulin resistance can also be made using the euglycemic glucose clamp test. This test involves the simultaneous administration of a constant insulin infusion and a variable rate glucose infusion. During the test, which lasts 3–4 hours, the plasma glucose concentration is kept constant at euglycemic levels by measuring the glucose level every 5–10 minutes and then adjusting the variable rate glucose infusion to keep the plasma glucose level unchanged. Under these circumstances, the rate of glucose entry into the bloodstream is equal to the overall rate of glucose disposal in the body. The difference between the rate of glucose disposal in the basal state (no insulin infusion) and the insulin infused state, represents insulin mediated glucose uptake. In normal individuals, insulin causes brisk and large increase in overall body glucose disposal, whereas in NIDDM subjects, this effect of insulin is greatly blunted, and is only 20–30% of normal. In insulin resistant subjects with either IGT or NGT, the rate of insulin stimulated glucose disposal is about half way between normal and NIDDM. For example, at a steady state plasma insulin concentration of about 100 μU/ml (a physiologic level) the glucose disposal rate in normal subjects is about 7 mg/kg/min. In NIDDM subjects, it is about 2.5 mg/kg/min., and in patients with IGT (or insulin resistant subjects with NGT) it is about 4–5 mg/kg/min. This is a highly reproducible and precise test, and can distinguish patients within these categories. It is also known that as subjects become more insulin resistant, the fasting insulin level rises. There is an excellent positive correlation between the height of the fasting insulin level and the magnitude of the insulin resistance as measured by euglycemic glucose clamp tests and, therefore, this provides the rationale for using fasting insulin levels as a surrogate measure of insulin resistance.

The term "agent acting on the partitioning of dietary lipids between the liver and peripheral tissues" refers to a compound or polypeptide of the invention that modulates the partitioning of dietary lipids between the liver and the peripheral tissues as previously described. Preferably, the agent increases or decreases the oxidation of dietary lipids, preferably free fatty acids (FFA) by the muscle. Preferably the agent decreases or increases the body weight of individuals or is used to treat or prevent an obesity-related disease or disorder such as obesity, impaired glucose tolerance, insulin resistance, atherosclerosis, atheromatous disease, heart disease, hypertension, stroke, Syndrome X, Noninsulin Dependent Diabetes Mellitus (NIDDM, or Type II diabetes) and Insulin Dependent Diabetes Mellitus (IDDM or Type I diabetes). Diabetes-related complications to be treated by the methods of the invention include microangiopathic lesions, ocular lesions, retinopathy, neuropathy, and renal lesions. Heart disease includes, but is not limited to, cardiac insufficiency, coronary insufficiency, and high blood pressure. Other obesity-related disorders to be treated by compounds of the invention include hyperlipidemia and hyperuricemia. Yet other obesity-related diseases or disorders of the invention include cachexia, wasting, AIDS-related weight loss, cancer-related weight loss, anorexia, and bulimia.

The terms "response to an agent acting on the partitioning of dietary lipids between the liver and peripheral tissues" refer to drug efficacy, including but not limited to, ability to metabolize a compound, ability to convert a pro-drug to an active drug, and the pharmacokinetics (absorption, distribution, elimination) and the pharmacodynamics (receptor-related) of a drug in an individual.

The terms "side effects to an agent acting on the partitioning of dietary lipids between the liver and peripheral tissues" refer to adverse effects of therapy resulting from extensions of the principal pharmacological action of the drug or to idiosyncratic adverse reactions resulting from an interaction of the drug with unique host factors. "Side effects to an agent acting on the partitioning of dietary lipids between the liver and peripheral tissues" can include, but are not limited to, adverse reactions such as dermatologic, hematologic or hepatologic toxicities and further includes gastric and intestinal ulceration, disturbance in platelet function, renal injury, nephritis, vasomotor rhinitis with profuse watery secretions, angioneurotic edema, generalized urticaria, and bronchial asthma to laryngeal edema and bronchoconstriction, hypotension, and shock.

The term "OBG3-related diseases and disorders" as used herein refers to any disease or disorder comprising an aberrant functioning of OBG3, or which could be treated or prevented by modulating OBG3 levels or activity. "Aberrant functioning of OBG3" includes, but is not limited to, aberrant levels of expression of OBG3 (either increased or decreased, but preferably decreased), aberrant activity of OBG3 (either increased or decreased), and aberrant interactions with ligands or binding partners (either increased or decreased). By "aberrant" is meant a change from the type, or level of activity seen in normal cells, tissues, or patients, or seen previously in the cell, tissue, or patient prior to the onset of the illness. In preferred embodiments, these OBG3-related diseases and disorders include obesity and the obesity-related diseases and disorders described previously.

The term "cosmetic treatments" is meant to include treatments with compounds or polypeptides of the invention that increase or decrease the body mass of an individual where the individual is not clinically obese or clinically thin. Thus, these individuals have a body mass index (BMI) below the cut-off for clinical obesity (e.g. below 25 kg/$M^2$) and above the cut-off for clinical thinness (e.g. above 18.5 kg/$M^2$). In addition, these individuals are preferably healthy (e.g. do not have an obesity-related disease or disorder of the invention). "Cosmetic treatments" are also meant to encompass, in some circumstances, more localized increases in adipose tissue, for example, gains or losses specifically around the waist or hips, or around the hips and thighs, for example. These localized gains or losses of adipose tissue can be identified by increases or decreases in waist or hip size, for example.

The term "preventing" as used herein refers to administering a compound prior to the onset of clinical symptoms of a disease or condition so as to prevent a physical manifestation of aberrations associated with obesity or OBG3. Alternatively, the term "preventing" can also be used to signify the reduction, or severity, of clinical symptoms associated with a disease or condition.

The term "treating" as used herein refers to administering a compound after the onset of clinical symptoms.

The term "in need of treatment" as used herein refers to a judgment made by a caregiver (e.g. physician, nurse, nurse practitioner, etc in the case of humans; veterinarian in the case of animals, including non-human mammals) that an individual or animal requires or will benefit from treatment. This judgment is made based on a variety of factors that are in the realm of a caregiver's expertise, but that include the knowledge that the individual or animal is ill, or will be ill, as the result of a condition that is treatable by the compounds of the invention.

The term "perceives a need for treatment" refers to a sub-clinical determination that an individual desires to reduce weight for cosmetic reasons as discussed under "cosmetic treatment" above. The term "perceives a need for treatment" in other embodiments can refer to the decision that an owner of an animal makes for cosmetic treatment of the animal.

The term "individual" or "patient" as used herein refers to any animal, including mammals, preferably mice, rats, other rodents, rabbits, dogs, cats, swine, cattle, sheep, horses, or primates, and most preferably humans. The term may specify male or female or both, or exclude male or female.

The term "non-human animal" refers to any non-human vertebrate, including birds and more usually mammals, preferably primates, animals such as swine, goats, sheep, donkeys, horses, cats, dogs, rabbits or rodents, more preferably rats or mice. Both the terms "animal" and "mammal" expressly embrace human subjects unless preceded with the term "non-human".

The inventors have found that a fragment of OBG3, called gOBG3, is able to significantly reduce the postprandial response of plasma free fatty acids, glucose, and triglycerides in mice fed a high fat/sucrose meal. There was no significant effect on leptin, insulin or glucagon levels. In addition, gOBG3 was found to increase muscle free fatty acid oxidation in vitro and ex vivo. Further, gOBG3 was shown to decrease and then to prevent an increase in weight gain in mice that had been fed a high fat/sucrose diet for 19 days. In mice that had been maintained on the same high fat/sucrose diet for 6 months, gOBG3 treatment resulted in a sustained weight loss over 16 days that was significant, despite being maintained on the high fat/sucrose diet.

The instant invention encompasses the use of OBG3 polypeptide fragments in the partitioning of free fatty acid (FFA) and as an important new tool to control energy homeostasis. Of the tissues that can significantly remove lipids from circulation and cause FFA oxidation, muscle is quantitatively the most important. Globular OBG3 is a unique and novel pharmacological tool that controls body weight without interfering with food intake.

PREFERRED EMBODIMENTS OF THE INVENTION

I. OBG3 Polypeptide Fragments of the Invention

OBG3 polypeptide fragments that have measurable activity in vitro and in vivo have been identified. These activities include, but are not limited to, reduction of the postprandial response of plasma free fatty acids, glucose, and triglycerides in mice fed a high fat/sucrose meal (Example 8), increase in muscle free fatty acid oxidation in vitro and ex vivo (Example 12), and sustained weight loss in mice on a high fat/sucrose diet (Example 14). Other assays for OBG3 polypeptide fragment activity in vitro and in vivo are also provided (Examples 4, 7, 9, 11, 13, for example), and equivalent assays can be designed by those of ordinary skill in the art.

In contrast, the "intact" or "full-length" OBG3 polypeptide does not have either the in vivo or the in vitro activities that have been identified for OBG3 and gOBG3 polypeptide fragments of the invention. In most cases, the activities are either not present or at a minimum are undetectable over control values in the assays used. In other cases, the activities can be measured, but are present either at extremely reduced levels and/or require significantly more protein on a molar basis compared with the OBG3 and gOBG3 polypeptide fragments of the invention (see, e.g. Example 10). By "intact" or "full-length" OBG3 polypeptide as used herein is meant the full-length polypeptide sequence of any OBG3 polypeptide, from the N-terminal methionine to the C-terminal stop codon. Examples of intact or full-length OBG3 polypeptides are found in SEQ ID NO:2 (mouse), SEQ ID NO:4 (mouse), and SEQ ID NO:6 (human). The term "OBG3 polypeptide fragments" as used herein refers to fragments of the "intact" or "full-length" OBG3 polypeptide that have "obesity-related activity". The term "gOBG3 polypeptide fragments" refers to polypeptide fragments comprised of part or all of the globular region and is thus a narrower term than "OBG3 polypeptide fragments". The term "fragment" means a polypeptide having a sequence that is entirely the same as part, but not all, of an intact or full-length OBG3 polypeptide. Such fragments may be "free-standing" (i.e. not part of or fused to other polypeptides), or one or more fragments may be present in a single polypeptide. OBG3 or gOBG3 fragments are contiguous fragments of the full-length OBG3 polypeptide unless otherwise specified.

The term "obesity-related activity" as used herein refers to at least one, and preferably all, of the activities described herein for OBG3 polypeptide fragments. Assays for the determination of these activities are provided herein (e.g. Examples 4, 7–9, 11–14), and equivalent assays can be designed by those with ordinary skill in the art. Optionally, "obesity-related activity" can be selected from the group consisting of lipid partitioning, lipid metabolism, and insulin-like activity, or an activity within one of these categories. By "lipid partitioning" activity is meant the ability to effect the location of dietary lipids among the major tissue groups including, adipose tissue, liver, and muscle. The inventors have shown that OBG3 polypeptide fragments of the invention play a role in the partitioning of lipids to the muscle, liver or adipose tissue. By "lipid metabolism" activity is meant the ability to influence the metabolism of lipids. The inventors have shown that OBG3 polypeptide fragments of the invention have the ability to affect the level of free fatty acids in the plasma as well as to increase the metabolism of lipids in the muscle through free fatty acid oxidation experiments. (Examples 4, 8, 10, 11, 12) and to transiently affect the levels of triglycerides in the plasma and the muscle (Examples 8, 10 13). By "insulin-like" activity is meant the ability of OBG3 polypeptide fragments to modulate the levels of glucose in the plasma. The inventors have found that OBG3 polypeptide fragments do not significantly impact insulin levels but do impact glucose levels similarly to the effects of insulin (Examples 9 & 10). These effects are not seen in the presence of the intact (full-length) OBG3 polypeptide or are significantly greater in the presence of the OBG3 polypeptide fragments compared with the full-length OBG3 polypeptide.

The term "significantly greater" as used herein refers to a comparison of the activity of an OBG3 polypeptide fragment in an obesity-related assay compared with the activity of a full-length OBG3 polypeptide in the same assay. By "significantly" as used herein is meant statistically significant as it is typically determined by those with ordinary skill in the art. For example, data are typically calculated as a mean±SEM, and a p-value≦0.05 is considered statistically significant. Statistical analysis is typically done using either the unpaired Student's t test or the paired Student's t test, as appropriate in each study. Examples of a significant change in activity as a result of the presence of an OBG3 polypeptide fragment of the invention compared to the presence of a full-length OBG3 polypeptide include an increase or a decrease in a given parameter of at least 5%, 10%, 15%, 20%, 25%, 30%, 35%, 40%, 45%, 50%, 55%, 60%, 65%, 70%, or 75%. One or more, but not necessarily all, of the measurable parameters will change significantly in the presence of OBG3 polypeptide fragments as compared to in the presence of an intact OBG3 polypeptide.

Representative "obesity-related assays" are provided in Examples 4, 7–9, and 11–14. These assays include, but are not limited to, methods of measuring the postprandial response, methods of measuring free fatty acid oxidation, and methods of measuring weight modulation. In preferred embodiments, the post-prandial response is measured in non-human animals, preferably mice. In preferred embodiments changes in dietary lipids are measured, preferably free fatty acids and/or triglycerides. In other embodiments, other physiologic parameters are measured including, but not limited to, levels of glucose, insulin, and leptin. In other preferred embodiments, free fatty acid oxidation is measured in cells in vitro or ex vivo, preferably in muscle cells or tissue of non-human animals, preferably mice. In yet other preferred embodiments weight modulation is measured in human or non-human animals, preferably rodents (rats or mice), primates, canines, felines or procines on a high fat/sucrose diet. Optionally, "obesity-related activity" includes other activities not specifically identified herein. In general, "measurable parameters" relating to obesity and the field of metabolic research can be selected from the group consisting of free fatty acid levels, free fatty acid oxidation, triglyceride levels, glucose levels, insulin levels, leptin levels, food intake, weight, leptin and lipoprotein binding, uptake and degradation and lipolysis stimulated receptor (LSR) expression.

In these obesity-related assays, preferred OBG3 polypeptide fragments of the invention, but not full-length OBG3 polypeptides, would cause a significant change in at least one of the measurable parameters selected from the group consisting of post-prandial lipemia, free fatty acid levels, triglyceride levels, glucose levels, free fatty acid oxidation, and weight. Alternatively, preferred OBG3 polypeptide fragments of the invention, but not full-length OBG3 polypeptides, would have a significant change in at least one of the measurable parameters selected from the group consisting of an increase in LSR activity, an increase in leptin activity and an increase in lipoprotein activity. By "LSR" activity is meant expression of LSR on the surface of the cell, or in a particular conformation, as well as its ability to bind, uptake, and degrade leptin and lipoprotein. By "leptin" activity is meant its binding, uptake and degradation by LSR, as well as its transport across a blood brain barrier, and potentially these occurrences where LSR is not necessarily the mediating factor or the only mediating factor. Similarly, by "lipoprotein" activity is meant its binding, uptake and degradation by LSR, as well as these occurrences where LSR is not necessarily the mediating factor or the only mediating factor.

The invention is drawn, inter alia, to isolated, purified or recombinant OBG3 polypeptide fragments. OBG3 polypeptide fragments of the invention are useful for reducing or increasing (using antagonists of OBG3 polypeptides) body weight either as a cosmetic treatment or for treatment or prevention of obesity-related diseases and disorders. OBG3 polypeptide fragments are also useful inter alia in screening assays for agonists or antagonists of OBG3 fragment activity; in screening assays for antagonists of dipeptidyl peptidase cleavage of OBG3 fragments, preferably cleavage of the N-terminal EP dipeptide of OBG3 polypeptide fragment 103–244 of SEQ ID NO:6, cleavage of the N-terminal VP dipeptide of OBG3 fragment 85–244 of SEQ ID NO:6, or cleavage of the N-terminal EP dipeptide of OBG3 polypeptide fragment 106–247 of SEQ ID NO:2 or SEQ ID NO:4; for raising OBG3 fragment-specific antibodies; and in diagnostic assays. When used for cosmetic treatments, or for the treatment or prevention of obesity-related diseases, disorders, or conditions, one or more OBG3 polypeptide fragments can be provided to a subject. Thus, various fragments of the full-length protein can be combined into a "cocktail" for use in the various treatment regimens.

The full-length OBG3 polypeptide is comprised of at least four distinct regions including:

1. an N-terminal putative signal sequence about from amino acids 1–17 of SEQ ID NO:6, SEQ ID NO:2, or SEQ ID NO:4;

2. a unique region about from amino acids 18–41 of SEQ ID NO:6 or 18–44 of SEQ ID NO:2, or SEQ ID NO:4;
3. a collagen-like region about from amino acids 42–107 of SEQ ID NO:6 or 45–110 of SEQ ID NO:2 or SEQ ID NO:4; and
4. a globular region about from amino acids 108–244 of SEQ ID NO:6 or 111–247 of SEQ ID NO:2 or SEQ ID NO:4.

The term "collagen residues" is used in the manner standard in the art to mean the amino acid triplet glycine, X, Y, where X and Y can be any amino acid.

The OBG3 polypeptide fragments of the present invention are preferably provided in an isolated form, and may be partially or substantially purified. A recombinantly produced version of an OBG3 polypeptide fragment can be substantially purified by the one-step method described by Smith et al. ((1988) Gene 67(1):31–40) or by the methods described herein or known in the art (see, e.g., Examples 1–3). Fragments of the invention also can be purified from natural or recombinant sources using antibodies directed against the polypeptide fragments of the invention by methods known in the art of protein purification.

Preparations of OBG3 polypeptide fragments of the invention involving a partial purification of or selection for the OBG3 polypeptide fragments are also specifically contemplated. These crude preparations are envisioned to be the result of the concentration of cells expressing OBG3 polypeptide fragments with perhaps a few additional purification steps, but prior to complete purification of the fragment. The cells expressing OBG3 polypeptide fragments are present in a pellet, they are lysed, or the crude polypeptide is lyophilized, for example.

OBG3 or gOBG3 polypeptide fragments, and polynucleotides encoding the same, can be any integer in length from at least 6 consecutive amino acids to 1 amino acid less than a full-length OBG3 polypeptide. Thus, for human OBG3 (SEQ ID NO:6), an OBG3 or gOBG3 polypeptide fragment can be any integer of consecutive amino acids from 6 to 243; for mouse OBG3 (SEQ ID NO:2 or SEQ ID NO:4) an OBG3 or gOBG3 fragment can be any integer of consecutive amino acids from 6 to 246, for example. The term "integer" is used herein in its mathematical sense and thus representative integers include: 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 234, 235, 236, 237, 238, 239, 240, 241, 242, 243, 244, 245, and 246.

Each OBG3 fragment as described above can be further specified in terms of its N-terminal and C-terminal positions. For example, every combination of a N-terminal and C-terminal position that fragments of from 6 contiguous amino acids to 1 amino acids less than the full-length OBG3 polypeptide could occupy, on any given intact and contiguous full-length OBG3 polypeptide sequence are included in the present invention. Thus, a 6 consecutive amino acid fragment could occupy positions selected from the group consisting of 1–6, 2–7, 3–8, 4–9, 5–10, 6–11, 7–12, 8–13, 9–14, 10–15, 11–16, 12–17, 13–18, 14–19, 15–20, 16–21, 17–22, 18–23, 19–24, 20–25, 21–26, 22–27, 23–28, 24–29, 25–30, 26–31, 27–32, 28–33, 29–34, 30–35, 31–36, 32–37, 33–38, 34–39, 35–40, 36–41, 37–42, 38–43, 39–44, 40–45, 41–46, 42–47, 43–48, 44–49, 45–50, 46–51, 47–52, 48–53, 49–54, 50–55, 51–56, 52–57, 53–58, 54–59, 55–60, 56–61, 57–62, 58–63, 59–64, 60–65, 61–66, 62–67, 63–68, 64–69, 65–70, 66–71, 67–72, 68–73, 69–74, 70–75, 71–76, 72–77, 73–78, 74–79, 75–80, 76–81, 77–82, 78–83, 79–84, 80–85, 81–86, 82–87, 83–88, 84–89, 85–90, 86–91, 87–92, 88–93, 89–94, 90–95, 91–96, 92–97, 93–98, 94–99, 95–100, 96–101, 97–102, 98–103, 99–104, 100–105, 101–106, 102–107, 103–108, 104–109, 105–110, 106–111, 107–112, 108–113, 109–114, 110–115, 111–116, 112–117, 113–118, 114–119, 115–120, 116–121, 117–122, 118–123, 119–124, 120–125, 121–126, 122–127, 123–128, 124–129, 125–130, 126–131, 127–132, 128–133, 129–134, 130–135, 131–136, 132–137, 133–138, 134–139, 135–140, 136–141, 137–142, 138–143, 139–144, 140–145, 141–146, 142–147, 143–148, 144–149, 145–150, 146–151, 147–152, 148–153, 149–154, 150–155, 151–156, 152–157, 153–158, 154–159, 155–160, 156–161, 157–162, 158–163, 159–164, 160–165, 161–166, 162–167, 163–168, 164–169, 165–170, 166–171, 167–172, 168–173, 169–174, 170–175, 171–176, 172–177, 173–178, 174–179, 175–180, 176–181, 177–182, 178–183, 179–184, 180–185, 181–186, 182–187, 183–188, 184–189, 185–190, 186–191, 187–192, 188–193, 189–194, 190–195, 191–196, 192–197, 193–198, 194–199, 195–200, 196–201, 197–202, 198–203, 199–204, 200–205, 201–206, 202–207, 203–208, 204–209, 205–210, 206–211, 207–212, 208–213, 209–214, 210–215, 211–216, 212–217, 213–218, 214–219, 215–220, 216–221, 217–222, 218–223, 219–224, 220–225, 221–226, 222–227, 223–228, 224–229, 225–230, 226–231, 227–232, 228–233, 229–234, 230–235, 231–236, 232–237, 233–238, 234–239, 235–240, 236–241, 237–242, 238–243, and 239–244 of SEQ ID NO:6.

Further preferred polypeptide fragments of SEQ ID NO:6, and polynucleotides encoding the same, are selected from the group consisting of fragments comprising any 50 consecutive amino acids numbered from 1–50, 2–51, 3–52, 4–53, 5–54, 6–55, 7–56, 8–57, 9–58, 10–59, 11–60, 12–61, 13–62, 14–63, 15–64, 16–65, 17–66, 18–67, 19–68, 20–69, 21–70, 22–71, 23–72, 24–73, 25–74, 26–75, 27–76, 28–77, 29–78, 30–79, 31–80, 32–81, 33–82, 34–83, 35–84, 36–85, 37–86, 38–87, 39–88, 40–89, 41–90, 42–91, 43–92, 44–93, 45–94, 46–95, 47–96, 48–97, 49–98, 50–99, 51–100, 52–101, 53–102, 54–103, 55–104, 56–105, 57–106, 58–107, 59–108, 60–109, 61–110, 62–111, 63–112, 64–113, 65–114, 66–115, 67–116, 68–117, 69–118, 70–119, 71–120, 72–121, 73–122, 74–123, 75–124, 76–125, 77–126, 78–127, 79–128, 80–129, 81–130, 82–131, 83–132, 84–133, 85–134, 86–135, 87–136, 88–137, 89–138, 90–139, 91–140, 92–141, 93–142, 94–143, 95–144, 96–145, 97–146, 98–147, 99–148, 100–149, 101–150, 102–151, 103–152, 104–153, 105–154, 106–155, 107–156, 108–157, 109–158, 110–159, 111–160, 112–161, 113–162, 114–163, 115–164, 116–165, 117–166, 118–167, 119–168, 120–169, 121–170, 122–171, 123–172, 124–173, 125–174, 126–175, 127–176, 128–177, 129–178, 130–179, 131–180, 132–181, 133–182, 134–183, 135–184, 136–185, 137–186, 138–187, 139–188, 140–189, 141–190, 142–191, 143–192, 144–193, 145–194, 146–195, 147–196, 148–197, 149–198, 150–199, 151–200, 152–201, 153–202, 154–203, 155–204, 156–205, 157–206, 158–207, 159–208, 160–209, 161–210, 162–211, 163–212, 164–213, 165–214, 166–215, 167–216, 168–217, 169–218, 170–219, 171–220, 172–221, 173–222, 174–223, 175–224, 176–225, 177–226, 178–227, 179–228, 180–229, 181–230, 182–231, 183–232, 184–233, 185–234, 186–235, 187–236, 188–237, 189–238, 190–239, 191–240, 192–241, 193–242, 194–243, 195–244 of SEQ ID NO:6.

Further preferred polypeptide fragments of SEQ ID NO:6, and polynucleotides encoding the same, are selected from the group consisting of fragments comprising any 100 consecutive amino acids numbered from 1–100, 2–101, 3–102, 4–103, 5–104, 6–105, 7–106, 8–107, 9–108, 10–109, 11–110, 12–111, 13–112, 14–113, 15–114, 16–115, 17–116, 18–117, 19–118, 20–119, 21–120, 22–121, 23–122, 24–123, 25–124, 26–125, 27–126, 28–127, 29–128, 30–129, 31–130, 32–131, 33–132, 34–133, 35–134, 36–135, 37–136, 38–137, 39–138, 40–139, 41–140, 42–141, 43–142, 44–143, 45–144, 46–145, 47–146, 48–147, 49–148, 50–149, 51–150, 52–151, 53–152, 54–153, 55–154, 56–155, 57–156, 58–157, 59–158, 60–159, 61–160, 62–161, 63–162, 64–163, 65–164, 66–165, 67–166, 68–167, 69–168, 70–169, 71–170, 72–171, 73–172, 74–173, 75–174, 76–175, 77–176, 78–177, 79–178, 80–179, 81–180, 82–181, 83–182, 84–183, 85–184, 86–185, 87–186, 88–187, 89–188, 90–189, 91–190, 92–191, 93–192, 94–193, 95–194, 96–195, 97–196, 98–197, 99–198, 100–199, 101–200, 102–201, 103–202, 104–203, 105–204, 106–205, 107–206, 108–207, 109–208, 110–209, 111–210, 112–211, 113–212, 114–213, 115–214, 116–215, 117–216, 118–217, 119–218, 120–219, 121–220, 122–221, 123–222, 124–223, 125–224, 126–225, 127–226, 128–227, 129–228, 130–229, 131–230, 132–231, 133–232, 134–233, 135–234, 136–235, 137–236, 138–237, 139–238, 140–239, 141–240, 142–241, 143–242, 144–243, and 145–244.

A 238 consecutive amino acid fragment could occupy positions selected from the group consisting of 1–238, 2–239, 3–240, 4–241, 5–242, 6–243 and 7–244 of SEQ ID NO:6. Similarly, the positions occupied by all the other fragments of sizes between 6 amino acids and 243 amino acids on SEQ ID NO:6 are included in the present invention and can also be immediately envisaged based on the examples for fragments of 6, 50, 100 or 238 consecutive amino acids listed above, and therefore, are not individually listed solely for the purpose of not unnecessarily lengthening the specification. Furthermore, the positions occupied by fragments of 6 to 241 consecutive amino acids on SEQ ID NO:2 or SEQ ID NO:4 are included in the present invention and can also be immediately envisaged based on these two examples and therefore are not individually listed solely for the purpose of not unnecessarily lengthening the specification. In addition, the positions occupied by fragments of 6 consecutive amino acids to 1 amino acid less than any other full-length OBG3 polypeptide can also be envisaged based on these two examples and therefore are not individually listed solely for the purpose of not unnecessarily lengthening the specification. In preferred embodiments, OBG3 or gOBG3 polypeptide fragments, and polynucleotides encoding the same, having unexpected activity are selected from amino acids numbered from 84–244, 85–244, 86–244, 87–244, 88–244, 89–244, 90–244, 91–244, 92–244, 93–244, 94–244, 95–244, 96–244, 97–244, 98–244, 99–244, 100–244, 101–244, 102–244, or 103–244 of SEQ ID NO:6. Still further preferred are OBG3 or gOBG3 polypeptide fragments, and polynucleotides encoding the same, having unexpected activity, selected from amino acids numbered from 111–191, 144–199, or 191–244 of SEQ ID NO:6. In preferred embodiments, OBG3 or gOBG3 polypeptide fragments, and polynucleotides encoding the same, having unexpected activity are selected from amino acids numbered from 88–247, 89–247, 90–247, 91–247, 92–247, 93–247, 94–247, 95–247, 96–247, 97–247, 98–247, 99–247, 100–247, 101–247, 102–247, 103–247, 104–247, 105–247, or 106–247 of SEQ ID NO:2 or SEQ ID NO:4.

The OBG3 or gOBG3 polypeptide fragments of the present invention may alternatively be described by the formula "n to c" (inclusive); where "n" equals the N-terminal most amino acid position (as defined by the sequence listing) and "c" equals the C-terminal most amino acid position (as defined by the sequence listing) of the polypeptide; and further where "n" equals an integer between 1 and the number of amino acids of the full length polypeptide sequence of the present invention minus 6 (238 for SEQ ID NO: 6 and 241 for SEQ ID NOs: 2 or 4); and where "c" equals an integer between 7 and the number of amino acids of the full-length polypeptide sequence (244 for SEQ ID NO: 6 and 247 for SEQ ID NOs: 2 or 4); and where "n" is an integer smaller then "c" by at least 6. Therefore, for SEQ ID NO: 6, "n" is any integer selected from the list consisting of: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 234, 235, 236, 237 and 238; and "c" is any integer selected from the group consisting of: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 234, 235, 236, 237, 238, 239, 240, 241, 242, 243, 244. Every combination of "n" and "c" positions are included as specific embodiments of the invention. Moreover, the formula "n" to "c" may be modified as '"n1–n2" to "c1–c2"', wherein "n1–n2" and "c1–c2" represent positional ranges selected from any two integers above which represent amino acid positions of the sequence listing. Alternative formulas include '"n1–n2" to "c"' and '"n" to "c1–c2"'. In a preferred embodiment, OBG3 or gOBG3 polypeptide fragments of the invention may be described by the formula where n1=84, n2=103, and c=244 of SEQ ID NO:6 or by the formula n1=88, n2=106, and c=247 of SEQ ID NO: 2 or SEQ ID NO:4.

These specific embodiments, and other polypeptide and polynucleotide fragment embodiments described herein may be modified as being "at least", "equal to", "equal to or less than", "less than", "at least_but not greater than_" or "from_to_". A specified size or specified N-terminal and/or C-terminal positions. It is noted that all ranges used to describe any embodiment of the present invention are inclusive unless specifically set forth otherwise.

The present invention also provides for the exclusion of any individual fragment specified by N-terminal and C-terminal positions or of any fragment specified by size in amino acid residues as described above. In addition, any number of fragments specified by N-terminal and C-terminal positions or by size in amino acid residues as described above may be excluded as individual species. Further, any number of fragments specified by N-terminal and C-terminal positions or by size in amino acid residues as described above may make up a polypeptide fragment in any combination and may optionally include non-OBG3 polypeptide sequence as well.

In particularly preferred embodiments, the OBG3 polypeptide fragment is a "globular OBG3" (gOBG3) fragment. The term "gOBG3 fragment" or "gOBG3" or "gOBG3 polypeptide" as used herein refers to fragments of a full-length OBG3 polypeptide that comprise at least 6 and any other integer number of amino acids up to 137 of the globular region of a full-length OBG3 polypeptide (defined above). In preferred embodiments, gOBG3 polypeptide fragments also comprise at least 1 and any other integer number of amino acids up 66 of the collagen region of a full-length OBG3 polypeptide, preferably 1, 2, 3, 4, 5, 6, 7, 8, 9, 10, 11, 12, 13, 14, 15, 16, 17, 18, 19, 20, 21, 22, 23, or 24 consecutive amino acid residues from the collagen region of the intact OBG3 polypeptide that are adjacent to the globular region. By "adjacent" to the globular region is meant the first collagen amino acid immediately N-terminal to the globular region and adding each collagen amino acid consecutively in the N-terminal direction. Thus, for example, if there is only one collagen amino acid in the gOBG3 polypeptide fragment, it is the collagen amino acid 107 of SEQ ID NO: 6 or amino acid 110 of SEQ ID NO:2 or SEQ ID NO:4 located adjacent and 5' to the first amino acid of the globular region. If there are 24 collagen amino acids adjacent to the globular region in the gOBG3 fragment they would be the collagen amino acids 84–107 of SEQ ID NO: 6 or amino acids 87–110 of SEQ ID NO:2 or SEQ ID NO:4.

In preferred embodiments, OBG3 or gOBG3 polypeptide fragments having unexpected activity are selected from amino acids 85–244, 86–244, 87–244, 88–244, 89–244, 90–244, 91–244, 92–244, 93–244, 94–244, 95–244, 96–244, 97–244, 98–244, 99–244, 100–244, 101–244, 102–244, or 103–244 of SEQ ID NO:6. In further preferred embodiments, OBG3 or gOBG3 polypeptide fragments having unexpected activity are selected from amino acids 111–191, 144–199, or 191–244 of SEQ ID NO:6. In other preferred embodiments, OBG3 or gOBG3 polypeptide fragments having unexpected activity are selected from amino acids 88–247, 89–247, 90–247, 91–247, 92–247, 93–247, 94–247, 95–247, 96–247, 97–247, 98–247, 99–247, 100–247, 101–247, 102–247, 103–247, 104–247, 105–247, or 106–247 of SEQ ID NO:2 or SEQ ID NO:4. In further preferred embodiments, gOBG3 polypeptide fragments are selected from amino acids 111 to 191, 144 to 199, 191 to 244, 84 to 244, 85 to 244, 101 to 244, 102 to 244, or 103 to 244 of SEQ ID NO:6 and amino acids 88 to 247, 104 to 247, 105 to 247, or 106 to 247 of SEQ ID NO:2 or SEQ ID NO:4.

In yet other preferred embodiments, the invention features a gOBG3 polypeptide fragment comprising at least 115, but not more than 175 contiguous amino acids of any one of the gOBG3 fragment sequences set forth in FIG. 1, wherein no more than 24 of said at least 115 and no more than 175 contiguous amino acids are present in the collagen-like region of OBG3. Preferably, the gOBG3 polypeptide fragment comprises at least 125, but not more than 165, or at least 140, but not more than 165 amino acids, and no more than 24 amino acids are in the collagen-like region; more preferably at least 125 but not more than 165, or at least 140 but not more than 165 amino acids, and no more than 12 amino acids are in the collagen-like region; or at least 140 and not more than 150 amino acids, and no more than 8 amino acids are present in the collagen-like region. Preferably the gOBG3 fragment is mammalian, preferably human or mouse, but most preferably human.

In further preferred embodiments of the invention, OBG3 polypeptide fragments having unexpected biological activity comprise at least 50 contiguous amino acids, but no more than 137 amino acids of the globular region of SEQ ID NO:6. More preferred are fragments comprising at least 50, but not more than OBG3 and gOBG3 polypeptide fragments of the invention include variants, fragments, analogs and derivatives of the OBG3 and gOBG3 polypeptide fragments described above, including modified OBG3 and gOBG3 polypeptide fragments. Particularly preferred are proteolytically cleaved fragments of OBG3 of SEQ ID NO:6, SEQ ID NO:2, or SEQ ID NO:4. More preferred is OBG3 fragment of about amino acids 85–244 of SEQ ID NO:6 made by collagenase cleavage of SEQ ID NO:6 at about position 84. More preferred is OBG3 fragment of about amino acids 88–247 of SEQ ID NO:2 or of SEQ ID NO:4 made by collagenase cleavage of SEQ ID NO:2 or SEQ ID NO:4 at about position 87. More preferred is OBG3 fragment of about amino acids 85–244 of SEQ ID NO:6 made by matrix metalloproteinase-1 (MMP-1) cleavage of SEQ ID NO:6 at about position 84. More preferred is OBG3 fragment of about amino acids 88–247 of SEQ ID NO:2 or of SEQ ID NO:4 made by matrix metalloproteinase-1 (MMP-1) cleavage of SEQ ID NO:2 or SEQ ID NO:4 at about position 87. More preferred is OBG3 fragment of about amino acids 101–244 of SEQ ID NO:6 made by plasmin cleavage of SEQ ID NO:6 at about position 100. More preferred is OBG3 fragment of about amino acids 104–247 of SEQ ID NO:2 or of SEQ ID NO:4 made by plasmin cleavage of SEQ ID NO:2 or SEQ ID NO:4 at about position 103. More preferred is OBG3 fragment of about amino acids 103–244 of SEQ ID NO:6 made by precerebellin processing protease cleavage of SEQ ID NO:6 at about position 102. More preferred is OBG3 fragment of about amino acids 106–247 of SEQ ID NO:2 or of SEQ ID NO:4 made by precerebellin processing protease cleavage of SEQ ID NO:2 or SEQ ID NO:4 at about position 105. Most preferred is APM1 proteolytic fragment of SEQ ID NO:6, wherein said APM1 fragment isolated from human plasma migrates with an apparent molecular weight of about 27 kDa on SDS-PAGE under reducing conditions.

Variants

It will be recognized by one of ordinary skill in the art that some amino acids of the OBG3 and gOBG3 fragment sequences of the present invention can be varied without significant effect on the structure or function of the protein; there will be critical amino acids in the fragment sequence that determine activity. Thus, the invention further includes variants of OBG3 and gOBG3 polypeptide fragments that have obesity-related activity as described above. Such variants include OBG3 fragment sequences with one or more amino acid deletions, insertions, inversions, repeats, and substitutions either from natural mutations or human manipulation selected according to general rules known in the art so as to have little effect on activity. Guidance concerning how to make phenotypically silent amino acid substitutions is provided below.

There are two main approaches for studying the tolerance of an amino acid sequence to change (see, Bowie, et al. (1990) Science, 247, 1306–10). The first method relies on the process of evolution, in which mutations are either accepted or rejected by natural selection. The second approach uses genetic engineering to introduce amino acid changes at specific positions of a cloned gene and selections or screens to identify sequences that maintain functionality.

These studies have revealed that proteins are surprisingly tolerant of amino acid substitutions and indicate which amino acid changes are likely to be permissive at a certain position of the protein. For example, most buried amino acid residues require nonpolar side chains, whereas few features of surface side chains are generally conserved. Other such phenotypically silent substitutions are described by Bowie et al. (supra) and the references cited therein.

Typically seen as conservative substitutions are the replacements, one for another, among the aliphatic amino acids Ala, Val, Leu and Phe; interchange of the hydroxyl residues Ser and Thr; exchange of the acidic residues Asp and Glu; substitution between the amide residues Asn and Gln; exchange of the basic residues Lys and Arg; and replacements among the aromatic residues Phe, Tyr. In addition, the following groups of amino acids generally represent equivalent changes: (1) Ala, Pro, Gly, Glu, Asp, Gln, Asn, Ser, Thr; (2) Cys, Ser, Tyr, Thr; (3) Val, Ile, Leu, Met, Ala, Phe; (4) Lys, Arg, His; (5) Phe, Tyr, Trp, His.

Similarly, amino acids in the OBG3 and gOBG3 polypeptide fragment sequences of the invention that are essential for function can also be identified by methods known in the art, such as site-directed mutagenesis or alanine-scanning mutagenesis (see, e.g., Cunningham, et al. (1989) Science 244(4908):1081–5). The latter procedure introduces single alanine mutations at every residue in the molecule. The resulting mutant molecules are then tested for obesity-related activity using assays as described above. Of special interest are substitutions of charged amino acids with other charged or neutral amino acids that may produce proteins with highly desirable improved characteristics, such as less aggregation. Aggregation may not only reduce activity but also be problematic when preparing pharmaceutical or physiologically acceptable formulations, because aggregates can be immunogenic (see, e.g., Pinckard, et al., (1967) Clin. Exp. Immunol 2:331–340; Robbins, et al., (1987) Diabetes July;36(7):838–41; and Cleland, et al., (1993) Crit Rev Ther Drug Carrier Syst. 10(4):307–77).

Thus, the fragment, derivative, analog, or homolog of the OBG3 or gOBG3 fragment of the present invention may be, for example: (i) one in which one or more of the amino acid residues are substituted with a conserved or non-conserved amino acid residue (preferably a conserved amino acid residue) and such substituted amino acid residue may or may not be one encoded by the genetic code (i.e. may be a non-naturally occurring amino acid); or (ii) one in which one or more of the amino acid residues includes a substituent group; or (iii) one in which the OBG3 or gOBG3 fragment is fused with another compound, such as a compound to increase the half-life of the fragment (for example, polyethylene glycol); or (iv) one in which the additional amino acids are fused to the above form of the fragment, such as an IgG Fc fusion region peptide or leader or secretory sequence or a sequence which is employed for purification of the above form of the fragment or a pro-protein sequence. Such fragments, derivatives and analogs are deemed to be within the scope of those skilled in the art from the teachings herein.

A further embodiment of the invention relates to a polypeptide which comprises the amino acid sequence of an OBG3 or gOBG3 polypeptide fragment having an amino acid sequence which contains at least one conservative amino acid substitution, but not more than 50 conservative amino acid substitutions, not more than 40 conservative amino acid substitutions, not more than 30 conservative amino acid substitutions, and not more than 20 conservative amino acid substitutions. Also provided are polypeptides which comprise the amino acid sequence of a OBG3 or gOBG3 fragment, having at least one, but not more than 10, 9, 8, 7, 6, 5, 4, 3, 2 or 1 conservative amino acid substitutions.

Another specific embodiment of a modified OBG3 or gOBG3 fragment of the invention is a polypeptide that is resistant to proteolysis, for example a OBG3 or gOBG3 fragment in which a —CONH— peptide bond is modified and replaced by one or more of the following: a (CH2NH) reduced bond; a (NHCO) retro inverso bond; a (CH2-O) methylene-oxy bond; a (CH2-S) thiomethylene bond; a (CH2CH2) carba bond; a (CO—CH2) cetomethylene bond; a (CHOH—CH2) hydroxyethylene bond); a (N—N) bound; a E-alcene bond; or a —CH═CH— bond. Thus, the invention also encompasses an OBG3 or gOBG3 fragment or a variant thereof in which at least one peptide bond has been modified as described above.

A further embodiment of the invention relates to an OBG3 or gOBG3 polypeptide fragment made resistant to dipeptidyl peptidase cleavage through N-terminal modification of said polypeptide fragment. In preferred embodiment, said OBG3 or gOBG3 polypeptide fragment is selected from amino acids 85–244 or 103–244 of SEQ ID NO:6 or amino acids 106–247 of SEQ ID NO:2 or SEQ ID NO:4. In preferred embodiment, said dipeptidyl peptidase cleavage leads to removal of the N-terminal dipeptide EP by dipeptidyl peptidase from said preferred gOBG3 polypeptide fragment 103–244 of SEQ ID NO:6 or 106–247 of SEQ ID NO:2 or SEQ ID NO:4. In preferred embodiment, said dipeptidyl peptidase cleavage leads to removal of the N-terminal dipeptide VP by dipeptidyl peptidase from said preferred gOBG3 polypeptide fragment 85–244 of SEQ ID NO:6. In preferred embodiment, said dipeptidyl peptidase is human plasma comprised of dipeptidyl peptidase. In preferred embodiment, said dipeptidyl peptidase is selected from but not restricted to human CD26 or human Attractin. In further preferred embodiment, said dipeptidyl peptidase is selected from soluble human CD26 or soluble human Attractin. In preferred embodiment, said N-terminal modification is selected from but not restricted to glycation [Harte (2001) Regulatory Peptides 96:95–104 which disclosure is hereby incorporated by reference in its entirety], N-methylation, alpha-methylation, desamidation [Gallwitz (2000) Regulatory Peptides 86:103–111 which disclosure is hereby incorporated by reference in its entirety], or alternation of the chirality of one or more N-terminal amino acids [Siegel (1999) European Journal of Clinical Investigation 29:610–614 which disclosure is hereby incorporated by reference in its entirety]. Thus, the invention also encompasses an OBG3 or gOBG3 polypeptide fragment or a variant thereof that has been made resistant to dipeptidyl peptidase cleavage through N-terminal modification of said polypeptide fragment.

In addition, amino acids have chirality within the body of either L or D. In some embodiments it is preferable to alter the chirality of the amino acids in the OBG3 or gOBG3 polypeptide fragments of the invention in order to extend half-life within the body. In other embodiments, it is preferable to alter the chirality of one or more amino acid in order to render the OBG3 or gOBG3 polypeptide fragment resistant to dipeptidyl peptidase cleavage [Siegel (1999) European Journal of Clinical Investigation 29:610–614 which disclosure is hereby incorporated by reference in its entirety]. In further embodiments, it is preferable to alter the chirality of the penultimate N-terminal amino acid in order to render the OBG3 or gOBG3 polypeptide fragment resistant to dipeptidyl peptidase cleavage. Thus, in some embodiments, one or more of the amino acids are preferably in the L configuration. In other embodiments, one or more of the amino acids are preferably in the D configuration.

Percent Identity

The polypeptides of the present invention also include polypeptides having an amino acid sequence at least 50% identical, at least 60% identical, or 70%, 80%, 85%, 90%, 91%, 92%, 93%, 94%, 95%, 96%, 97%, 98% or 99% identical to an OBG3 or gOBG3 fragment as described above. By a polypeptide having an amino acid sequence at least, for example, 95% "identical" to an OBG3 or gOBG3 fragment amino acid sequence is meant that the amino acid sequence is identical to the OBG3 or gOBG3 polypeptide fragment sequence except that it may include up to five amino acid alterations per each 100 amino acids of the OBG3 or gOBG3 polypeptide fragment amino acid sequence. The reference sequence is the OBG3 or gOBG3 polypeptide fragment with a sequence corresponding to the sequence of the sequence listing. Thus, to obtain a polypeptide having an amino acid sequence at least 95% identical to an OBG3 or gOBG3 fragment amino acid sequence, up to 5% (5 of 100) of the amino acid residues in the sequence may be inserted, deleted, or substituted with another amino acid compared with the OBG3 or gOBG3 polypeptide fragment sequence. These alterations may occur at the amino or carboxy termini or anywhere between those terminal positions, interspersed either individually among residues in the sequence or in one or more contiguous groups within the sequence.

As a practical matter, whether any particular polypeptide is a percentage identical to an OBG3 or gOBG3 fragment can be determined conventionally using known computer programs. Such algorithms and programs include, but are by no means limited to, TBLASTN, BLASTP, FASTA, TFASTA, and CLUSTALW (Pearson and Lipman, (1988) Proc Natl Acad Sci USA 85(8):2444–8; Altschul et al., (1990) J Mol Biol 215(3):403–410; Thompson et al., (1994) Nucleic Acids Res 22(2):4673–4680; Higgins et al., (1996) Meth Enzymol 266:383–402; Altschul et al., (1997) Nuc Acids Res 25:3389–3402; Altschul et al., (1993) Nature Genetics 3:266–272). In a particularly preferred embodiment, protein and nucleic acid sequence homologies are evaluated using the Basic Local Alignment Search Tool ("BLAST"), which is well known in the art (See, e.g., Karlin and Altschul (1990) Proc Natl Acad Sci USA 87(6):2264–8; Altschul et al., 1990, 1993, 1997, all supra). In particular, five specific BLAST programs are used to perform the following tasks:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (see, Gonnet et al., (1992) Science 256(5062):1443–5; Henikoff and Henikoff (1993) Proteins 17(1):49–61). Less preferably, the PAM or PAM250 matrices may also be used (See, e.g., Schwartz and Dayhoff, eds, (1978) Matrices for Detecting Distance Relationships: Atlas of Protein Sequence and Structure, Washington: National Biomedical Research Foundation). The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (See, e.g., Karlin and Altschul, (1990) Proc Natl Acad Sci USA 87(6):2264–8). The BLAST programs may be used with the default parameters or with modified parameters provided by the user. Preferably, the parameters are default parameters.

A preferred method for determining the best overall match between a query sequence (a sequence of the present invention) and a subject sequence, also referred to as a global sequence alignment, can be determined using the FASTDB computer program based on the algorithm of Brutlag et al. (1990) Comp. App. Biosci. 6:237–245. In a sequence alignment the query and subject sequences are both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group=25 Length=0, Cutoff Score=1, Window Size=sequence length, Gap Penalty=5, Gap Size Penalty=0.05, Window Size=247 or the length of the subject amino acid sequence, whichever is shorter.

If the subject sequence is shorter than the query sequence due to N-or C-terminal deletions, not because of internal deletions, the results, in percent identity, must be manually corrected because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, that are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query amino acid residues outside the farthest N- and C-terminal residues of the subject sequence.

For example, a 90 amino acid residue subject sequence is aligned with a 100-residue query sequence to determine percent identity. The deletion occurs at the N-terminus of the subject sequence and therefore, the FASTDB alignment does not match/align with the first residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90-residue subject sequence is compared with a 100-residue query sequence. This time the deletions are internal so there are no residues at the N- or C-termini of the subject sequence, which are not matched/aligned with the query. In this case, the percent identity calculated by FASTDB is not manually corrected. Once again, only residue positions outside the N- and C-terminal ends of the subject sequence, as displayed in the FASTDB alignment, which are not matched/aligned with the query sequence are manually corrected. No other manual corrections are made for the purposes of the present invention.

Production

Note, throughout the disclosure, wherever OBG3 polypeptide fragments are discussed, gOBG3fragments are specifically intended to be included as a preferred subset of OBG3 polypeptide fragments.

OBG3 polypeptide fragments are preferably isolated from human or mammalian tissue samples or expressed from human or mammalian genes in human or mammalian cells. The OBG3 polypeptide fragments of the invention can be made using routine expression methods known in the art. The polynucleotide encoding the desired polypeptide fragments is ligated into an expression vector suitable for any convenient host. Both eukaryotic and prokaryotic host systems are used in forming recombinant polypeptide fragments. The polypeptide fragment is then isolated from lysed cells or from the culture medium and purified to the extent needed for its intended use. Purification is by any technique known in the art, for example, differential extraction, salt fractionation, chromatography, centrifugation, and the like. See, for example, Methods in Enzymology for a variety of methods for purifying proteins. Also, see Examples 1–3 for methods previously used for OBG3 polypeptide fragments.

In an alternative embodiment, the polypeptides of the invention are isolated from milk. The polypeptides can be purified as full-length OBG3 polypeptides, which can then be cleaved, if appropriate, in vitro to generate an OBG3 fragment, or, alternatively, OBG3 fragments themselves can be purified from the milk. Any of a large number of methods can be used to purify the present polypeptides from milk, including those taught in Protein Purification Applications, A Practical Approach (New Edition), Edited by Simon Roe, AEA Technology Products and Systems, Biosciences, Harwell; Clark (1998) J Mammary Gland Biol Neoplasia 3:337–50; Wilkins and Velander (1992) 49:333–8; U.S. Pat. Nos. 6,140,552; 6,025,540; Hennighausen, Protein Expression and Purification, vol. 1, pp. 3–8 (1990); Harris et al. (1997) Bioseparation 7:31–7; Degener et al. (1998) J Chromatog 799:125–37; Wilkins (1993) J Cell Biochem Suppl. 0 (17 part A):39; the entire disclosures of each of which are herein incorporated by reference. In a typical embodiment, milk is centrifuged, e.g. at a relatively low speed, to separate the lipid fraction, and the aqueous supernatant is then centrifuged at a higher speed to separate the casein in the milk from the remaining, "whey" fraction. Often, biomedical proteins are found in this whey fraction, and can be isolated from this fraction using standard chromatographic or other procedures commonly used for protein purification, e.g. as described elsewhere in the present application. In one preferred embodiment, OBG3 polypeptides are purified using antibodies specific to OBG3 polypeptides, e.g. using affinity chromatography. In addition, methods can be used to isolate particular OBG3 fragments, e.g. electrophoretic or other methods for isolating proteins of a particular size. The OBG3 polypeptides isolating using these methods can be naturally occurring, as OBG3 polypeptides have been discovered to be naturally present in the milk of mammals (see, e.g. Example 17), or can be the result of the recombinant production of the protein in the mammary glands of a non-human mammal, as described infra. In one such embodiment, the OBG3 fragment is produced as a fusion protein with a heterologous, antigenic polypeptide sequence, which antigenic sequence can be used to purify the protein, e.g., using standard immuno-affinity methodology.

In addition, shorter protein fragments may be produced by chemical synthesis. Alternatively, the proteins of the invention are extracted from cells or tissues of humans or non-human animals. Methods for purifying proteins are known in the art, and include the use of detergents or chaotropic agents to disrupt particles followed by differential extraction and separation of the polypeptides by ion exchange chromatography, affinity chromatography, sedimentation according to density, and gel electrophoresis.

Any OBG3 fragment cDNA, including that in FIG. 4, can be used to express OBG3 polypeptide fragments. The nucleic acid encoding the OBG3 fragment to be expressed is operably linked to a promoter in an expression vector using conventional cloning technology. The OBG3 fragment cDNA insert in the expression vector may comprise the coding sequence for: the full-length OBG3 polypeptide (to be later modified); from 6 amino acids to 6 amino acids less than the full-length OBG3 polypeptide; a gOBG3 fragment; or variants and % similar polypeptides.

The expression vector is any of the mammalian, yeast, insect or bacterial expression systems known in the art, some of which are described herein, and examples of which are given in the Examples (Examples 1–3). Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence can be optimized for the particular expression organism into which the expression vector is introduced, as explained by Hatfield, et al., U.S. Pat. No. 5,082,767, the disclosures of which are incorporated by reference herein in their entirety.

If the nucleic acid encoding OBG3 polypeptide fragments lacks a methionine to serve as the initiation site, an initiating methionine can be introduced next to the first codon of the nucleic acid using conventional techniques. Similarly, if the insert from the OBG3 polypeptide fragment cDNA lacks a poly A signal, this sequence can be added to the construct by, for example, splicing out the Poly A signal from pSG5 (Stratagene) using BglI and SalI restriction endonuclease enzymes and incorporating it into the mammalian expression vector pXT1 (Stratagene). pXT1 contains the LTRs and a portion of the gag gene from Moloney Murine Leukemia Virus. The position of the LTRs in the construct allow efficient stable transfection. The vector includes the Herpes Simplex Thymidine Kinase promoter and the selectable neomycin gene.

The nucleic acid encoding an OBG3 fragment can be obtained by PCR from a vector containing the OBG3 nucleotide sequence using oligonucleotide primers complementary to the desired OBG3 cDNA and containing restriction endonuclease sequences for Pst I incorporated into the 5' primer and BglII at the 5' end of the corresponding cDNA 3' primer, taking care to ensure that the sequence encoding the OBG3 fragment is positioned properly with respect to the poly A signal. The purified fragment obtained from the resulting PCR reaction is digested with PstI, blunt ended with an exonuclease, digested with BglII, purified and ligated to pXT1, now containing a poly A signal and digested with BglII. Alternative methods are presented in Examples 1–3.

Transfection of an OBG3 fragment-expressing vector into mouse NIH 3T3 cells is one embodiment of introducing polynucleotides into host cells. Introduction of a polynucleotide encoding a polypeptide into a host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al. ((1986) Methods in Molecular Biology, Elsevier Science Publishing Co., Inc., Amsterdam). It is specifically contemplated that the polypeptides of the present invention may in fact be expressed by a host cell lacking a recombinant vector. Methods of expressing OBG3 fragment of the invention in cells are described in Examples 1–3.

A polypeptide of this invention (i.e. an OBG3 or gOBG3 fragment) can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells.

Depending upon the host employed in a recombinant production procedure, the polypeptides of the present invention may be glycosylated or may be non-glycosylated. Preferably the polypeptides of the invention are non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination, see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., (1989) Proc Natl Acad Sci USA 86(22):8932–5; Koller et al., (1989) Proc Natl Acad Sci USA 86(22):8927–31; and Zijlstra et al. (1989) Nature 342(6248):435–8; the disclosures of each of which are incorporated by reference in their entireties).

Modifications

In addition, polypeptides of the invention can be chemically synthesized using techniques known in the art (See, e.g., Creighton, 1983 Proteins. New York, N.Y.: W.H. Freeman and Company; and Hunkapiller et al., (1984) Nature 310(5973):105–11). For example, a relative short fragment of the invention can be synthesized by use of a peptide synthesizer. Furthermore, if desired, nonclassical amino acids or chemical amino acid analogs can be introduced as a substitution or addition into the fragment sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, omithine, norleucine, norvaline, hydroxyproline, sarcosine, citrulline, homocitrulline, cysteic acid, t-butylglycine, t-butylalanine, phenylglycine, cyclohexylalanine, b-alanine, fluoroamino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptide fragments which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptide fragments may also be modified with a detectable label, such as an enzymatic, fluorescent, isotopic or affinity label to allow for detection and isolation of the polypeptide.

Also provided by the invention are chemically modified derivatives of the polypeptides of the invention that may provide additional advantages such as increased solubility, stability and circulating time of the polypeptide, or decreased immunogenicity. See U.S. Pat. No. 4,179,337.

The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the polypeptide with consideration of effects on functional or antigenic domains of the polypeptide. There are a number of attachment methods available to those skilled in the art, e.g., EP 0 401 384, herein incorporated by reference (coupling PEG to G-CSF), see also Malik et al. (1992) Exp Hematol 20(8):1028–35, reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues, glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus may be accomplished by reductive alkylation, which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

In further preferred embodiment, the invention features a method of reducing body mass comprising providing or administering to individuals in need of reducing body mass said pharmaceutical or physiologically acceptable composition described in the fifth aspect in combination with provision or administration of an antagonist of dipeptidyl peptidase cleavage of OBG3 or gOBG3 polypeptide fragment of the first aspect.

Preferred said antagonist is a peptidyl derivative of a diester of alpha-minoalkylphosphonic acid (U.S. Pat. No. 5,543,396 which disclosure is hereby incorporated by reference in its entirety). More preferred said peptidyl derivative is selected from Ala-Pro$^P$(OZ)$_2$, AcOH.Ala-Pip$^P$(Oph)$_2$, HCl.Ala-Pro$^P$(Oph-4Cl)$_2$, HCl.Ala-Pip$^P$(Oph-4Cl)$_2$, or 2HCl.Lys-Pip$^P$(Oph-4Cl)$_2$, where Z represents an aryl group, a substituted aryl group or a highly flourinated alkyl group, Pro$^P$ represents a proline phosphonate derivative, and Pip$^P$ represents piperidyl phosphonate (U.S. Pat. No. 5,543,396 which disclosure is hereby incorporated by reference in its entirety).

Other preferred said antagonist is a compound of the general formula Z-Xaa-Y', in which Xaa is an amino acid, Z is a protecting group, and Y' is one of various types of ring structures (U.S. Pat. No. 6,090,786 which disclosure is hereby incorporated by reference in its entirety). More preferred is said compound wherein Z may or may not be present and represents a protecting group, such as benzyloxycarbonyl; Xaa represents alanine, methionine, arginine, phenylalanine, aspartic acid, proline, asparagine, serine, cysteine, threonine, glycine, tyrosine, glutamic acid, tryptophan, glutamine, valine, isoleucine, lysine, leucine, L-thioproline, L-homoproline, L-1,2,3,4, tetrahydroisoquinoline-3-carboxylic acid (Tic), L-2,3-dihydroindol-2-carboxylic acid, L-naphthylglycine, L-phenylglycine, L-4-phenylproline, O-benzyl tyrosine, omega-Z lysine, or omega-acetyl lysine; and Y' represents a pyrrolidide, a phosphonate or phosphinate derivative, or reduced peptide; or pharmaceutically acceptable salts thereof (U.S. Pat. No. 6,090,786 which disclosure is hereby incorporated by reference in its entirety).

Other preferred said antagonist is sulphostin (U.S. Pat. No. 6,214,340 which disclosure is hereby incorporated by reference in its entirety).

Other preferred said antagonist is N-(substituted glycyl)-2-cyanopyrrolidine (U.S. Pat. No. 6,166,063). More preferred said N-(substituted glycyl)-2-cyanopyrrolidine is selected from pyrrolidine, 1-[[(3,5-dimethyl-1-adamantyl) amino]-acetyl]-2-cyano-, (S)—; pyrrolidine, 1-[[(3-ethyl-1-adamantyl)amino]-acetyl]-2-cyano-, (S)—; pyrrolidine, 1-[[(3-methoxy-1-adamantyl)amino]-acetyl]-2-cyano-, (S)—; pyrrolidine, 1-[[[3-[[(t-butylamino)carbonyl]oxy]-1-adamantyl]amino]-acetyl]-2-cyano-, (S)—; pyrrolidine, 1-[[[3-[[[(4-methoxyphenyl)amino]-carbonyl]oxy]-1-adamantyl]amino]-acetyl]-2-cyano-, (S)—; pyrrolidine, 1-[[[(3-[[(phenylamino)carbonyl]oxy]-1-adamantyl] amino]-acetyl]-2-cyano-, (S)—; pyrrolidine, 1-[[(5-hydroxy-2-adamantyl))amino]-acetyl]-2-cyano-, (S)—; pyrrolidine, 1-[[(3-acetyloxy-1-adamantyl)amino]-acetyl]-2-cyano-, (S)—; pyrrolidine, 1-[[[(3-[[[(diisopropyl)amino] carbonyl]oxy]-1-adamantyl]amino]-acetyl]-2-cyano-, (S)—; pyrrolidine, 1-[[[3-[[[(cyclohexyl)amino]carbonyl] oxy]-1-adamantyl]amino]-acetyl]-2-cyano-, (S)—; pyrrolidine, 1-[[(3-ethyoxy-1-adamantyl)amino]-acetyl]-2-cyano-, (S)—; or, in each case, a pharmaceutically acceptable acid addition salt thereof (U.S. Pat. No. 6,166,063).

Other preferred said antagonist is tetrahydroisoquinoline 3-carboxamide derivative of formula ##STR1## (U.S. Pat. No. 6,172,081). More preferred is said derivative and pharmaceutically acceptable salts thereof wherein X is $CH_2$, S, O, or $C(CH_3)_2$; $R_1$ and $R_2$ are independently hydrogen, hydroxy, alkyl, alkoxy, aralkoxy, or halogen (U.S. Pat. No. 6,172,081).

Other preferred said antagonist is valine-pyrrolidide [Deacon (2001) Diabetes 50:1588–1597 which disclosure is hereby incorporated by reference in its entirety].

Multimers

The polypeptide fragments of the invention may be in monomers or multimers (i.e., dimers, trimers, tetramers and higher multimers). Accordingly, the present invention relates to monomers and multimers of the polypeptide fragments of the invention, their preparation, and compositions (preferably, pharmaceutical or physiologically acceptable compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the OBG3 polypeptide fragments of the invention (including polypeptide fragments, variants, splice variants, and fusion proteins corresponding to these polypeptide fragments as described herein). These homomers may contain polypeptide fragments having identical or different amino acid sequences. In a specific embodiment, a homomer of the invention is a multimer containing only polypeptide fragments having an identical amino acid sequence. In another specific embodiment, a homomer of the invention is a multimer containing polypeptide fragments having different amino acid sequences. In specific embodiments, the multimer of the invention is a homodimer (e.g., containing polypeptide fragments having identical or different amino acid sequences) or a homotrimer (e.g., containing polypeptide fragments having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., corresponding to different proteins or polypeptide fragments thereof) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in the sequence listing, or contained in the polypeptide encoded by a deposited clone). In one instance, the covalent associations are cross-linking between cysteine residues located within the polypeptide sequences, which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the invention.

In one example, covalent associations are between the heterologous sequence contained in a fusion protein of the invention (see, e.g., U.S. Pat. No. 5,478,925). In a specific example, the covalent associations are between the heterologous sequence contained in an Fc fusion protein of the invention (as described herein). In another specific example, covalent associations of fusion proteins of the invention are between heterologous polypeptide sequence from another protein that is capable of forming covalently associated multimers, such as for example, oseteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins, and have since been found in a variety of different proteins (Landschulz et al., (1988) Genes Dev. July;2(7):786–800). Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. FEBS Letters (1994) 344(2–3):191–5 and in U.S. patent application Ser. No. 08/446,922, hereby incorporated by reference. Other peptides derived from naturally occurring trimeric proteins may be employed in preparing trimeric polypeptides of the invention. In another example, proteins of the invention are associated by interactions between Flag® & polypeptide sequence contained in fusion proteins of the invention containing Flag® polypeptide sequence. In a further embodiment, proteins of the invention are associated by interactions between heterologous polypeptide sequence contained in Flag® fusion proteins of the invention and anti Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C-terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, at least 30 techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hyrophobic or signal peptide) and which can be incorporated by membrane reconstitution techniques into liposomes (See, e.g., U.S. Pat. No. 5,478,925, which is herein incorporated by reference in its entirety).

II. OBG3 Polynucleotides of the Invention

Preferred polynucleotides are those that encode OBG3 and gOBG3 polypeptide fragments of the invention. The recombinant polynucleotides encoding OBG3 and gOBG3 polypeptide fragments can be used in a variety of ways, including, but not limited to, expressing the polypeptide in recombinant cells for use in screening assays for antagonists and agonists of its activity as well as to facilitate its purification for use in a variety of ways including, but not limited to screening assays for agonists and antagonists of its activity, diagnostic screens, and raising antibodies, as well as treatment and/or prevention of obesity-related diseases and disorders and/or to reduce body mass.

The invention relates to the polynucleotides encoding OBG3 and gOBG3 polypeptide fragments and variant polypeptide fragments thereof as described herein. These polynucleotides may be purified, isolated, and/or recombinant. In all cases, the desired OBG3 and gOBG3 polynucleotides of the invention are those that encode OBG3 and gOBG3 polypeptide fragments of the invention have obesity-related activity as described and discussed herein.

Fragments

A polynucleotide fragment is a polynucleotide having a sequence that entirely is the same as part, but not all, of the full-length OBG3 polypeptide or a specified OBG3 or gOBG3 polypeptide nucleotide sequence. Such fragments may be "free-standing", i.e. not part of or fused to other polynucleotides, or they may be comprised within another non-OBG3 or non-gOBG3 (heterologous) polynucleotide of which they form a part or region. However, several OBG3 or gOBG3 polynucleotide fragments may be comprised within a single polynucleotide.

The OBG3 polynucleotides of the invention comprise from 18 consecutive bases to 18 consecutive bases less than the full-length polynucleotide sequence encoding the intact OBG3 polypeptide, for example the full-length OBG3 polypeptide polynucleotide sequences in SEQ ID NO: 1, SEQ ID NO:3, or SEQ ID NO:5. In one aspect of this embodiment, the polynucleotide comprises at least 18, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, or 740 consecutive nucleotides of a polynucleotide of the present invention.

In addition to the above preferred nucleic acid sizes, further preferred nucleic acids comprise at least 18 nucleotides, wherein "at least 18" is defined as any integer between 18 and the integer representing 18 nucleotides less than the 3' most nucleotide position of the intact OBG3 polypeptide cDNA as set forth in the sequence listing (SEQ ID NO:1, SEQ ID NO:3, or SEQ ID NO:5) or elsewhere herein.

Further included as preferred polynucleotides of the present invention are nucleic acid fragments at least 18 nucleotides in length, as described above, that are further specified in terms of their 5' and 3' position. The 5' and 3' positions are represented by the position numbers set forth in the sequence listing below. For allelic and degenerate and other variants, position 1 is defined as the 5' most nucleotide of the ORF, i.e., the nucleotide "A" of the start codon (ATG) with the remaining nucleotides numbered consecutively. Therefore, every combination of a 5' and 3' nucleotide position that a polynucleotide fragment invention, at least 18 contiguous nucleotides in length, could occupy on an intact OBG3 polypeptide polynucleotide of the present invention is included in the invention as an individual species. The polynucleotide fragments specified by 5' and 3' positions can be immediately envisaged and are therefore not individually listed solely for the purpose of not unnecessarily lengthening the specification.

It is noted that the above species of polynucleotide fragments of the present invention may alternatively be described by the formula "x to y"; where "x" equals the 5' most nucleotide position and "y" equals the 3' most nucleotide position of the polynucleotide; and further where "x" equals an integer between 1 and the number of nucleotides of the polynucleotide sequence of the present invention minus 18, and where "y" equals an integer between 19 and the number of nucleotides of the polynucleotide sequence of the present invention minus 18 nucleotides; and where "x" is an integer smaller then "y" by at least 18.

The present invention also provides for the exclusion of any species of polynucleotide fragments of the present invention specified by 5' and 3' positions or polynucleotides specified by size in nucleotides as described above. Any number of fragments specified by 5' and 3' positions or by size in nucleotides, as described above, may be excluded.

The gOBG3 polynucleotide fragments of the invention comprise from 18 consecutive bases to the full-length polynucleotide sequence encoding the gOBG3 fragments described in Section II of the Preferred Embodiments of the Invention. In one aspect of this embodiment, the polynucleotide comprises at least 18, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, or 465 consecutive nucleotides of a polynucleotide of the present invention.

In addition to the above preferred nucleic acid sizes, further preferred nucleic acids comprise at least 18 nucleotides, wherein "at least 18" is defined as any integer between 18 and the integer corresponding to the 3' most nucleotide position of a gOBG3 fragment cDNA herein.

Further included as preferred polynucleotides of the present invention are nucleic acid fragments at least 18 nucleotides in length, as described above, that are further specified in terms of their 5' and 3' position. The 5' and 3' positions are represented by the position numbers set forth in the sequence listing below. For allelic and degenerate and other variants, position 1 is defined as the 5' most nucleotide of the open reading frame (ORF), i.e., the nucleotide "A" of the start codon (ATG) with the remaining nucleotides numbered consecutively. Therefore, every combination of a 5' and 3' nucleotide position that a polynucleotide fragment invention, at least 18 contiguous nucleotides in length, could occupy on a gOBG3 fragment polynucleotide of the present invention is included in the invention as an individual species. The polynucleotide fragments specified by 5' and 3' positions can be immediately envisaged and are therefore not individually listed solely for the purpose of not unnecessarily lengthening the specification.

It is noted that the above species of polynucleotide fragments of the present invention may alternatively be described by the formula "x to y"; where "x" equals the 5' most nucleotide position and "y" equals the 3' most nucleotide position of the polynucleotide; and further where "x" equals an integer between 1 and the number of nucleotides of the gOBG3 polynucleotide sequence of the present invention minus 18, and where "y" equals an integer between 9 and the number of nucleotides of the gOBG3 polynucleotide sequence of the present invention; and where "x" is an integer smaller than "y" by at least 18. Every combination of "x" and "y" positions are included as specific embodiments of the invention. Moreover, the formula "x" to "y" may be modified as '"x1–x2" to "y1–y2"', wherein '"x1–x2" and "y1–y2"' represent positional ranges selected from any two nucleotide positions of the sequence listing. Alternative formulas include '"x1–x2" to "y"' and '"x" to "y1–y2"'.

These specific embodiments, and other polynucleotide fragment embodiments described herein may be modified as being "at least", "equal to", "equal to or less than", "less than", "at least_but not greater than_" or "from_to_", a specified size or specified 5' and/or 3' positions.

The present invention also provides for the exclusion of any species of polynucleotide fragments of the present invention specified by 5' and 3' positions or polynucleotides specified by size in nucleotides as described above. Any number of fragments specified by 5' and 3' positions or by size in nucleotides, as described above, may be excluded.

Variants

In other preferred embodiments, variants of OBG3 and gOBG3 polynucleotides encoding OBG3 and gOBG3 fragments are envisioned. Variants of polynucleotides, as the term is used herein, are polynucleotides whose sequence differs from a reference polynucleotide. A variant of a polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms. Generally, differences are limited so that the nucleotide sequences of the reference and the variant are closely similar overall and, in many regions, identical.

Polynucleotide variants that comprise a sequence substantially different from those described above but that, due to the degeneracy of the genetic code, still encode OBG3 and gOBG3 polypeptide fragments of the present invention are also specifically envisioned. It would also be routine for one skilled in the art to generate the degenerate variants described above, for instance, to optimize codon expression for a particular host (e.g., change codons in the human mRNA to those preferred by other mammalian or bacterial host cells).

As stated above, variant polynucleotides may occur naturally, such as a natural allelic variant, or by recombinant methods. By an "allelic variant" is intended one of several alternate forms of a gene occupying a given locus on a chromosome of an organism (See, e.g., B. Lewin, (1990) Genes IV, Oxford University Press, New York). Non-naturally occurring variants may be produced using art-known mutagenesis techniques. Such nucleic acid variants include those produced by nucleotide substitutions, deletions, or additions. The substitutions, deletions, or additions may involve one or more nucleotides. Alterations in the coding regions may produce conservative or non-conservative amino acid substitutions, deletions or additions. Especially preferred among these are silent substitutions, additions and deletions, which do not alter the properties and activities of an OBG3 or gOBG3 polypeptide fragment of the invention. Also preferred in this regard are conservative substitutions.

Nucleotide changes present in a variant polynucleotide are preferably silent, which means that they do not alter the amino acids encoded by the polynucleotide. However, nucleotide changes may also result in amino acid substitutions, additions, deletions, fusions and truncations in the polypeptide encoded by the reference sequence.

In cases where the nucleotide substitutions result in one or more amino acid changes, preferred OBG3 and gOBG3 polypeptide fragments include those that retain one or more obesity-related activity as described in Section I of the Preferred Embodiments of the Invention.

By "retain the same activities" is meant that the activity measured using the polypeptide encoded by the variant OBG3 or gOBG3 polynucleotide in assays is at least 75%, 80%, 85%, 90%, 95%, 96%, 97%, 98%, 99%, or 100%, and not more than 101%, 102%, 103%, 104%, 105%, 110%, 115%, 120% or 125% of the activity measured using a gOBG3 fragment described in the Examples Section herein.

By the activity being "increased" is meant that the activity measured using the polypeptide encoded by the variant OBG3 or gOBG3 polynucleotide in assays is at least 125%, 130%, 135%, 140%, 145%, 150%, 155%, 160%, 170%, 180%, 190%, 200%, 225%, 250%, 275%, 300%, 325%, 350%, 375%, 400%, 450%, or 500% of the activity measured using a gOBG3 fragment described in the Examples Section herein.

By the activity being "decreased" is meant that the activity measured using the polypeptide encoded by the variant OBG3 or gOBG3 polynucleotide in assays is decreased by at least 25%, 30%, 35%, 40%, 45%, or 50% of the activity measured using a gOBG3 fragment described in the Examples Section herein.

Percent Identity

The present invention is further directed to nucleic acid molecules having sequences at least 50%, 60%, 70%, 80%, 90%, 95%, 96%, 97%, 98% or 99% identical to the polynucleotide sequences of SEQ ID NO:1, SEQ ID NO:3, or SEQ ID NO:5 or fragments thereof that encode a polypeptide having obesity-related activity as described in Section I of the Preferred Embodiments of the Invention. Of course, due to the degeneracy of the genetic code, one of ordinary skill in the art will immediately recognize that a large number of the nucleic acid molecules at least 50%, 60%, 70%, 80%, 90%, 95%, 96%, 97%, 98%, or 99% identical to the nucleic acid sequences shown in SEQ ID NO:1, SEQ ID NO:3, or SEQ ID NO:5 or fragments thereof will encode a polypeptide having biological activity. In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having biological activity. This is because the skilled artisan is fully aware of amino acid substitutions that are either less likely or not likely to significantly affect protein function (e.g., replacing one aliphatic amino acid with a second aliphatic amino acid), as further described previously in Section I of the Preferred Embodiments of the Invention.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the OBG3 or gOBG3 fragment. In other words, to obtain a polynucleotide having a nucleotide sequence at least 95% identical to a reference nucleotide sequence, up to 5% of the nucleotides in the reference sequence may be deleted, inserted, or substituted with another nucleotide. The query sequence may be an entire sequence or any fragment specified as described herein.

The methods of determining and defining whether any particular nucleic acid molecule or polypeptide is at least 50%, 60%, 70%, 80%, 90%, 95%, 96%, 97%, 98% or 99% identical to a nucleotide sequence of the present invention can be done by using known computer programs. A preferred method for determining the best overall match between a query sequence (a sequence of the present invention) and a subject sequence, also referred to as a global sequence alignment, can be determined using the FASTDB computer program based on the algorithm of Brutlag et al., ((1990) Comput Appl Biosci 6(3):237–45). In a sequence alignment the query and subject sequences are both DNA sequences. An RNA sequence can be compared by first converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only nucleotides outside the 5' and 3' nucleotides of the subject sequence, as displayed by the FASTDB alignment, which are not matched/aligned with the query sequence, are calculated for the purposes of manually adjusting the percent identity score.

For example, a 90-nucleotide subject sequence is aligned to a 100-nucleotide query sequence to determine percent identity. The deletions occur at the 5' end of the subject sequence and therefore, the FASTDB alignment does not show a matched/alignment of the first 10 nucleotides at 5' end. The 10 unpaired nucleotides represent 10% of the sequence (number of nucleotides at the 5' and 3' ends not matched/total number of nucleotides in the query sequence) so 10% is subtracted from the percent identity score calculated by the FASTDB program. If the remaining 90 nucleotides were perfectly matched the final percent identity would be 90%. In another example, a 90 nucleotide subject sequence is compared with a 100 nucleotide query sequence. This time the deletions are internal deletions so that there are no nucleotides on the 5' or 3' of the subject sequence which are not matched/aligned with the query. In this case the percent identity calculated by FASTDB is not manually corrected. Once again, only nucleotides 5' and 3' of the subject sequence which are not matched/aligned with the query sequence are manually corrected for. No other manual corrections are made for the purposes of the present invention.

Fusions

Further included in the present invention are polynucleotides encoding the polypeptides of the present invention that are fused in frame to the coding sequences for additional heterologous amino acid sequences. Also included in the present invention are nucleic acids encoding polypeptides of the present invention together with additional, non-coding sequences, including for example, but not limited to non-coding 5' and 3' sequences, vector sequence, sequences used for purification, probing, or priming. For example, heterologous sequences include transcribed, nontranslated sequences that may play a role in transcription, and mRNA processing, for example, ribosome binding and stability of mRNA. The heterologous sequences may alternatively comprise additional coding sequences that provide additional functionalities. Thus, a nucleotide sequence encoding a polypeptide may be fused to a tag sequence, such as a sequence encoding a peptide that facilitates purification of the fused polypeptide. In certain preferred embodiments of this aspect of the invention, the tag amino acid sequence is a hexa-histidine peptide, such as the tag provided in a pQE vector (QIAGEN, Inc., 9259 Eton Avenue, Chatsworth, Calif., 91311), among others, many of which are commercially available. For instance, hexa-histidine provides for convenient purification of the fusion protein (See, Gentz et al., (1989) Proc Natl Acad Sci USA 86(3):821–4). The "HA" tag is another peptide useful for purification which corresponds to an epitope derived from the influenza hemagglutinin protein (See, Wilson et al., (1984) Cell 37(3):767–78). As discussed above, other such fusion proteins include OBG3 or gOBG3 fragment cDNA fused to Fc at the N- or C-terminus.

III. Recombinant Vectors of the Invention

The term "vector" is used herein to designate either a circular or a linear DNA or RNA molecule, that is either double-stranded or single-stranded, and that comprises at least one polynucleotide of interest that is sought to be transferred in a cell host or in a unicellular or multicellular host organism.

The present invention relates to recombinant vectors comprising any one of the polynucleotides described herein.

The present invention encompasses a family of recombinant vectors that comprise polynucleotides encoding OBG3 polypeptide fragments of the invention.

In a first preferred embodiment, a recombinant vector of the invention is used to amplify the inserted polynucleotide in a suitable cell host, this polynucleotide being amplified every time that the recombinant vector replicates. The inserted polynucleotide can be one that encodes gOBG3 polypeptide fragments of the invention.

A second preferred embodiment of the recombinant vectors according to the invention consists of expression vectors comprising polynucleotides encoding OBG3 polypeptide fragments of the invention. Within certain embodiments, expression vectors are employed to express an OBG3 fragment of the invention, preferably a modified OBG3 fragment described in the present invention, which can be then purified and, for example, be used as a treatment for obesity-related diseases, or simply to reduce body mass of individuals.

Expression requires that appropriate signals are provided in the vectors, said signals including various regulatory elements, such as enhancers/promoters from both viral and mammalian sources, that drive expression of the genes of interest in host cells. Dominant drug selection markers for establishing permanent, stable, cell clones expressing the products are generally included in the expression vectors of the invention, as they are elements that link expression of the drug selection markers to expression of the polypeptide.

More particularly, the present invention relates to expression vectors which include nucleic acids encoding an OBG3 fragment of the invention, or a modified OBG3 fragment as described herein, or variants or fragments thereof, under the control of a regulatory sequence selected among OBG3 polypeptide fragments, or alternatively under the control of an exogenous regulatory sequence.

Consequently, preferred expression vectors of the invention are selected from the group consisting of: (a) an OBG3 fragment regulatory sequence and driving the expression of a coding polynucleotide operably linked thereto; and (b) an OBG3 fragment coding sequence of the invention, operably linked to regulatory sequences allowing its expression in a suitable cell host and/or host organism.

Some of the elements that can be found in the vectors of the present invention are described in further detail in the following sections.

1) General Features of the Expression Vectors of the Invention:

A recombinant vector according to the invention comprises, but is not limited to, a YAC (Yeast Artificial Chromosome), a BAC (Bacterial Artificial Chromosome), a phage, a phagemid, a cosmid, a plasmid, or even a linear DNA molecule which may consist of a chromosomal, non-chromosomal, semi-synthetic or synthetic DNA. Such a recombinant vector can comprise a transcriptional unit comprising an assembly of:

(1) a genetic element or elements having a regulatory role in gene expression, for example promoters or enhancers. Enhancers are cis-acting elements of DNA, usually from about 10 to 300 bp in length that act on the promoter to increase the transcription;

(2) a structural or coding sequence which is transcribed into mRNA and eventually translated into a polypeptide, said structural or coding sequence being operably linked to the regulatory elements described in (1); and (3) appropriate transcription initiation and termination sequences. Structural units intended for use in yeast or eukaryotic expression systems preferably include a leader sequence enabling extracellular secretion of translated protein by a host cell. Alternatively, when a recombinant protein is expressed without a leader or transport sequence, it may include a N-terminal residue. This residue may or may not be subsequently cleaved from the expressed recombinant protein to provide a final product.

Generally, recombinant expression vectors will include origins of replication, selectable markers permitting transformation of the host cell, and a promoter derived from a highly expressed gene to direct transcription of a downstream structural sequence. The heterologous structural sequence is assembled in appropriate phase with translation initiation and termination sequences, and preferably a leader sequence capable of directing secretion of the translated protein into the periplasmic space or the extracellular medium. In a specific embodiment wherein the vector is adapted for transfecting and expressing desired sequences in mammalian host cells, preferred vectors will comprise an origin of replication in the desired host, a suitable promoter and enhancer, and also any necessary ribosome binding sites, polyadenylation sites, splice donor and acceptor sites, transcriptional termination sequences, and 5'-flanking non-transcribed sequences. DNA sequences derived from the SV40 viral genome, for example SV40 origin, early promoter, enhancer, splice and polyadenylation sites may be used to provide the required non-transcribed genetic elements.

2) Regulatory Elements

Promoters

The suitable promoter regions used in the expression vectors of the present invention are chosen taking into account the cell host in which the heterologous gene is expressed. The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell, such as, for example, a human or a viral promoter. The promoter used may be constitutive or inducible.

A suitable promoter may be heterologous with respect to the nucleic acid for which it controls the expression or alternatively can be endogenous to the native polynucleotide containing the coding sequence to be expressed.

Additionally, the promoter is generally heterologous with respect to the recombinant vector sequences within which the construct promoter/coding sequence has been inserted.

Promoter regions can be selected from any desired gene using, for example, CAT (chloramphenicol transferase) vectors and more preferably pKK232–8 and pCM7 vectors. Preferred bacterial promoters are the LacI, LacZ, the T3 or T7 bacteriophage RNA polymerase promoters, the gpt, lambda PR, PL and trp promoters (EP 0036776), the polyhedrin promoter, or the p10 protein promoter from baculovirus (Kit Novagen) (Smith et al., (1983) Mol Cell Biol 3(12):2156–65; O'Reilly et al., 1992), the lambda PR promoter or also the trc promoter.

Eukaryotic promoters include CMV immediate early, HSV thymidine kinase, early and late SV40, LTRs from retrovirus, and mouse metallothionein-L. In addition, promoters specific for a particular cell type may be chosen, such as those facilitating expression in adipose tissue, muscle tissue, or liver. Selection of a convenient vector and promoter is well within the level of ordinary skill in the art.

The choice of a promoter is well within the ability of a person skilled in the field of genetic engineering. For example, one may refer to Sambrook et al. (1989) Molecular Cloning: A Laboratory Manual, Cold Spring Harbor Laboratory Press, NY, Vol. 1, 2, 3 (1989), or also to the procedures described by Fuller et al. (1996) Immunology in Current Protocols in Molecular Biology.

Other Regulatory Elements

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

Vectors containing the appropriate DNA sequence as described above can be utilized to transform an appropriate host to allow the expression of the desired polypeptide or polynucleotide.

3) Selectable Markers

Such markers would confer an identifiable change to the cell permitting easy identification of cells containing the expression construct. The selectable marker genes for selection of transformed host cells are preferably dihydrofolate reductase or neomycin resistance for eukaryotic cell culture, TRP1 for *S. cerevisiae* or tetracycline, rifampicin or ampicillin resistance in *E. coli*, or levan saccharase for mycobacteria, this latter marker being a negative selection marker.

4) Preferred Vectors

Bacterial Vectors

As a representative but non-limiting example, useful expression vectors for bacterial use can comprise a selectable marker and a bacterial origin of replication derived from commercially available plasmids comprising genetic elements of pBR322 (ATCC 37017). Such commercial vectors include, but are not limited to, pKK223–3 (Pharmacia, Uppsala, Sweden) and pGEM1 (Promega Biotec, Madison, Wis., USA).

Large numbers of other suitable vectors are known to those of skill in the art, and are commercially available, such as the following bacterial vectors: pTrc-His, pET30-His, pQE70, pQE60, pQE-9 (Qiagen), pbs, pD10, phagescript, psiX174, pbluescript SK, pbsks, pNH8A, pNH16A, pNH18A, pNH46A (Stratagene); ptrc99a, pKK223–3, pKK233–3, pDR540, pRIT5 (Pharmacia); pWLNEO, pSV2CAT, pOG44, pXT1, pSG (Stratagene); pSVK3, pBPV, pMSG, pSVL (Pharmacia); pQE-30 (QIAexpress).

Baculovirus Vectors

A suitable vector for the expression of polypeptides of the invention is a baculovirus vector that can be propagated in insect cells and in insect cell lines. A specific suitable host vector system is the pVL 1392/1393 baculovirus transfer vector (Pharmingen) that is used to transfect the SF9 cell line (ATCC N°CRL 1711) which is derived from *Spodoptera frugiperda*. Further suitable baculovirus vectors are known to those skilled in the art, for example, FastBacHT. Other suitable vectors for the expression of an APM1 globular head polypeptide in a baculovirus expression system include, but are not limited to, those described by Chai et al. (1993; Biotechnol Appl Biochem. December;18 (Pt 3):259–73); Vlasak et al. (1983; Eur J Biochem September 1;135(1):123–6); and Lenhard et al. (1996; Gene March 9;169(2):187–90).

Mammalian Vectors

Further suitable vectors for the expression of polypeptides of the invention are mammalian vectors. A number of suitable vector systems are known to those skilled in the art, for example, pcDNA4HisMax, pcDNA3.1Hygro-His and pcDNA3.1Hygro.

Viral Vectors

In one specific embodiment, the vector is derived from an adenovirus. Preferred adenovirus vectors according to the invention are those described by Feldman and Steg (1996; Semin Interv Cardiol 1(3):203–8) or Ohno et al. (1994; Science 265(5173):781–4). Another preferred recombinant adenovirus according to this specific embodiment of the present invention is the human adenovirus type 2 or 5 (Ad 2 or Ad 5) or an adenovirus of animal origin (French patent application No. FR-93.05954).

Retrovirus vectors and adeno-associated virus vectors are generally understood to be the recombinant gene delivery systems of choice for the transfer of exogenous polynucleotides in vivo, particularly to mammals, including humans. These vectors provide efficient delivery of genes into cells, and the transferred nucleic acids are stably integrated into the chromosomal DNA of the host.

Particularly preferred retroviruses for the preparation or construction of retroviral in vitro or in vivo gene delivery vehicles of the present invention include retroviruses selected from the group consisting of Mink-Cell Focus Inducing Virus, Murine Sarcoma Virus, Reticuloendotheliosis virus and Rous Sarcoma virus. Particularly preferred Murine Leukemia Viruses include the 4070A and the 1504A viruses, Abelson (ATCC No VR-999), Friend (ATCC No VR-245), Gross (ATCC No VR-590), Rauscher (ATCC No VR-998) and Moloney Murine Leukemia Virus (ATCC No VR-190; PCT Application No WO 94/24298). Particularly preferred Rous Sarcoma Viruses include Bryan high titer (ATCC Nos VR-334, VR-657, VR-726, VR-659 and VR-728). Other preferred retroviral vectors are those described in Roth et al. (1996), PCT Application No WO 93/25234, PCT Application No WO 94/06920, Roux et al., ((1989) Proc Natl Acad Sci USA 86(23):9079–83), Julan et al., (1992) J. Gen. Virol. 3:3251–3255 and Neda et al. ((1991) J Biol Chem 266(22):14143–6).

Yet another viral vector system that is contemplated by the invention consists of the adeno-associated virus (AAV). The adeno-associated virus is a naturally occurring defective virus that requires another virus, such as an adenovirus or a herpes virus, as a helper virus for efficient replication and a productive life cycle (Muzyczka et al., (1992) Curr Top Microbiol Immunol 158:97–129). It is also one of the few viruses that may integrate its DNA into non-dividing cells, and exhibits a high frequency of stable integration (Flotte et al., (1992) Am J Respir Cell Mol Biol 7(3):349–56; Samulski et al., (1989) J Virol 63(9):3822–8; McLaughlin et al., (1989) Am J Hum Genet 59:561–569). One advantageous feature of AAV derives from its reduced efficacy for transducing primary cells relative to transformed cells.

5) Delivery of the Recombinant Vectors

In order to effect expression of the polynucleotides of the invention, these constructs must be delivered into a cell. This delivery may be accomplished in vitro, as in laboratory procedures for transforming cell lines, or in vivo or ex vivo, as in the treatment of certain disease states.

One mechanism is viral infection where the expression construct is encapsulated in an infectious viral particle.

Several non-viral methods for the transfer of polynucleotides into cultured mammalian cells are also contemplated by the present invention, and include, without being limited to, calcium phosphate precipitation (Graham et al., (1973) Virology 54(2):536–9; Chen et al., (1987) Mol Cell Biol 7(8):2745–52), DEAE-dextran (Gopal, (1985) Mol Cell Biol 5(5):1188–90), electroporation (Tur-Kaspa et al., (1986) Mol Cell Biol 6(2):716–8; Potter et al., (1984) Proc Natl Acad Sci USA 81(22):7161–5.), direct microinjection (Harland et al., (1985) J Cell Biol 101(3):1094–9), DNA-loaded liposomes (Nicolau et al., (1982) Biochim Biophys Acta 721(2):185–90; Fraley et al., (1979) Proc Natl Acad Sci USA 76(7):3348–52), and receptor-mediated transfection (Wu and Wu, (1987) J Biol Chem 262(10):4429–32; Wu and Wu (1988) Biochemistry 27(3):887–92). Some of these techniques may be successfully adapted for in vivo or ex vivo use.

Once the expression polynucleotide has been delivered into the cell, it may be stably integrated into the genome of the recipient cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle.

One specific embodiment for a method for delivering a protein or peptide to the interior of a cell of a vertebrate in vivo comprises the step of introducing a preparation comprising a physiologically acceptable carrier and a naked polynucleotide operatively coding for the polypeptide of interest into the interstitial space of a tissue comprising the cell, whereby the naked polynucleotide is taken up into the interior of the cell and has a physiological effect. This is particularly applicable for transfer in vitro but it may be applied to in vivo as well.

Compositions for use in vitro and in vivo comprising a "naked" polynucleotide are described in PCT application No. WO 90/11092 (Vical Inc.) and also in PCT application No. WO 95/11307 (Institut Pasteur, INSERM, Universite d'Ottawa) as well as in the articles of Tascon et al. (1996) Nature Medicine 2(8):888–892 and of Huygen et al. ((1996) Nat Med 2(8):893–8).

In still another embodiment of the invention, the transfer of a naked polynucleotide of the invention, including a polynucleotide construct of the invention, into cells may be proceeded with a particle bombardment (biolistic), said particles being DNA-coated microprojectiles accelerated to a high velocity allowing them to pierce cell membranes and enter cells without killing them, such as described by Klein et al. ((1990) Curr Genet February;17(2):97–103).

In a further embodiment, the polynucleotide of the invention may be entrapped in a liposome (Ghosh and Bacchawat, (1991) Targeted Diagn Ther 4:87–103; Wong et al., (1980) Gene 10:87–94; Nicolau et al., (1987) Methods Enzymol 149:157–76). These liposomes may further be targeted to cells expressing LSR by incorporating leptin, triglycerides, ACRP30, or other known LSR ligands into the liposome membrane.

In a specific embodiment, the invention provides a composition for the in vivo production of an APM1 globular head polypeptide described herein. It comprises a naked polynucleotide operatively coding for this polypeptide, in solution in a physiologically acceptable carrier, and suitable for introduction into a tissue to cause cells of the tissue to express the said polypeptide.

The amount of vector to be injected to the desired host organism varies according to the site of injection. As an indicative dose, it will be injected between 0.1 and 100 μg of the vector in an animal body, preferably a mammal body, for example a mouse body.

In another embodiment of the vector according to the invention, it may be introduced in vitro in a host cell, preferably in a host cell previously harvested from the animal to be treated and more preferably a somatic cell such as a muscle cell. In a subsequent step, the cell that has been transformed with the vector coding for the desired APM1 globular head polypeptide or the desired fragment thereof is reintroduced into the animal body in order to deliver the recombinant protein within the body either locally or systemically.

IV. Recombinant Cells of the Invention

Another object of the invention consists of host cells recombinant for, i.e., that have been transformed or transfected with one of the polynucleotides described herein, and more precisely a polynucleotide comprising a polynucleotide encoding an OBG3 polypeptide fragment of the invention such as any one of those described in "Polynucleotides of the Invention". These polynucleotides can be present in cells as a result of transient or stable transfection. The invention includes host cells that are transformed (prokaryotic cells) or that are transfected (eukaryotic cells) with a recombinant vector such as any one of those described in "Recombinant Vectors of the Invention".

Generally, a recombinant host cell of the invention comprises at least one of the polynucleotides or the recombinant vectors of the invention that are described herein.

Preferred host cells used as recipients for the recombinant vectors of the invention are the following:

a) Prokaryotic host cells: *Escherichia coli* strains (I.E. DH5-α strain), *Bacillus subtilis, Salmonella typhimurium*, and strains from species like *Pseudoimonas, Streptomyces* and *Staphylococcus*, and b) Eukaryotic host cells: HeLa cells (ATCC N°CCL2; N°CCL2.1; N°CCL2.2), Cv 1 cells (ATCC N°CCL70), COS cells (ATCC N°CRL1650; N°CRL1651), Sf-9 cells (ATCC N°CRL1711), C127 cells (ATCC N°CRL-1804), 3T3 (ATCC N° CRL-6361), CHO (ATCC N° CCL-61), human kidney 293 (ATCC N° 45504; N° CRL-1573), BHK (ECACC N° 84100501; N°84111301), PLC cells, HepG2, and Hep3B.

The constructs in the host cells can be used in a conventional manner to produce the gene product encoded by the recombinant sequence.

Following transformation of a suitable host and growth of the host to an appropriate cell density, the selected promoter is induced by appropriate means, such as temperature shift or chemical induction, and cells are cultivated for an additional period.

Cells are typically harvested by centrifugation, disrupted by physical or chemical means, and the resulting crude extract retained for further purification.

Microbial cells employed in the expression of proteins can be disrupted by any convenient method, including freeze-thaw cycling, sonication, mechanical disruption, or use of cell lysing agents. Such methods are well known by the skilled artisan.

Further, according to the invention, these recombinant cells can be created in vitro or in vivo in an animal, preferably a mammal, most preferably selected from the group consisting of mice, rats, dogs, pigs, sheep, cattle, and primates, not to include humans. Recombinant cells created in vitro can also be later surgically implanted in an animal, for example. Methods to create recombinant cells in vivo in animals are well known in the art.

The present invention also encompasses primary, secondary, and immortalized homologously recombinant host cells of vertebrate origin, preferably mammalian origin and particularly human origin, that have been engineered to: a) insert exogenous (heterologous) polynucleotides into the endogenous chromosomal DNA of a targeted gene, b) delete endogenous chromosomal DNA, and/or c) replace endogenous chromosomal DNA with exogenous polynucleotides. Insertions, deletions, and/or replacements of polynucleotide sequences may be to the coding sequences of the targeted gene and/or to regulatory regions, such as promoter and enhancer sequences, operably associated with the targeted gene.

The present invention further relates to a method of making a homologously recombinant host cell in vitro or in vivo, wherein the expression of a targeted gene not normally expressed in the cell is altered. Preferably the alteration causes expression of the targeted gene under normal growth conditions or under conditions suitable for producing the polypeptide encoded by the targeted gene. The method comprises the steps of: (a) transfecting the cell in vitro or in vivo with a polynucleotide construct, the polynucleotide construct comprising; (i) a targeting sequence; (ii) a regulatory sequence and/or a coding sequence; and (iii) an unpaired splice donor site, if necessary, thereby producing a transfected cell; and (b) maintaining the transfected cell in vitro or in vivo under conditions appropriate for homologous recombination.

The present invention further relates to a method of altering the expression of a targeted gene in a cell in vitro or in vivo wherein the gene is not normally expressed in the cell, comprising the steps of: (a) transfecting the cell in vitro or in vivo with a polynucleotide construct, the polynucleotide construct comprising: (i) a targeting sequence; (ii) a regulatory sequence and/or a coding sequence; and (iii) an unpaired splice donor site, if necessary, thereby producing a transfected cell; and (b) maintaining the transfected cell in vitro or in vivo under conditions appropriate for homologous recombination, thereby producing a homologously recombinant cell; and (c) maintaining the homologously recombinant cell in vitro or in vivo under conditions appropriate for expression of the gene.

The present invention further relates to a method of making a polypeptide of the present invention by altering the expression of a targeted endogenous gene in a cell in vitro or in vivo wherein the gene is not normally expressed in the cell, comprising the steps of: a) transfecting the cell in vitro with a polynucleotide construct, the polynucleotide construct comprising: (i) a targeting sequence; (ii) a regulatory sequence and/or a coding sequence; and (iii) an unpaired splice donor site, if necessary, thereby producing a transfected cell; (b) maintaining the transfected cell in vitro or in vivo under conditions appropriate for homologous recombination, thereby producing a homologously recombinant cell; and c) maintaining the homologously recombinant cell in vitro or in vivo under conditions appropriate for expression of the gene thereby making the polypeptide.

The present invention further relates to a polynucleotide construct that alters the expression of a targeted gene in a cell type in which the gene is not normally expressed. This occurs when a polynucleotide construct is inserted into the chromosomal DNA of the target cell, wherein the polynucleotide construct comprises: a) a targeting sequence; b) a regulatory sequence and/or coding sequence; and c) an unpaired splice-donor site, if necessary. Further included are polynucleotide constructs, as described above, wherein the construct further comprises a polynucleotide that encodes a polypeptide and is in-frame with the targeted endogenous gene after homologous recombination with chromosomal DNA.

The compositions may be produced, and methods performed, by techniques known in the art, such as those described in U.S. Pat. Nos. 6,054,288; 6,048,729; 6,048,724; 6,048,524; 5,994,127; 5,968,502; 5,965,125; 5,869,239; 5,817,789; 5,783,385; 5,733,761; 5,641,670; 5,580,734; International Publication Nos: WO96/29411, WO 94/12650; and scientific articles described by Koller et al., (1994) Annu. Rev. Immunol. 10:705–730; the disclosures of each of which are incorporated by reference in their entireties).

The OBG3 gene expression in mammalian, and typically human, cells may be rendered defective, or alternatively it may be enhanced, with the insertion of an OBG3 genomic or cDNA sequence with the replacement of the OBG3 gene counterpart in the genome of an animal cell by an OBG3 polynucleotide according to the invention. These genetic alterations may be generated by homologous recombination events using specific DNA constructs that have been previously described.

One kind of host cell that may be used are mammalian zygotes, such as murine zygotes. For example, murine zygotes may undergo microinjection with a purified DNA molecule of interest, for example a purified DNA molecule that has previously been adjusted to a concentration range from 1 ng/ml—for BAC inserts—3 ng/μl—for P1 bacteriophage inserts—in 10 mM Tris-HCl, pH 7.4, 250 μM EDTA containing 100 mM NaCl, 30 μM spermine, and 70 μM spermidine. When the DNA to be microinjected has a large size, polyamines and high salt concentrations can be used in order to avoid mechanical breakage of this DNA, as described by Schedl et al ((1993) Nature 362(6417):258–61).

Any one of the polynucleotides of the invention, including the DNA constructs described herein, may be introduced in an embryonic stem (ES) cell line, preferably a mouse ES cell line. ES cell lines are derived from pluripotent, uncommitted cells of the inner cell mass of pre-implantation blastocysts. Preferred ES cell lines are the following: ES-E14TG2a (ATCC No.CRL-1821), ES-D3 (ATCC No.CRL1934 and No. CRL-11632), YS001 (ATCC No. CRL-11776), 36.5 (ATCC No. CRL-11116). To maintain ES cells in an uncommitted state, they are cultured in the presence of growth inhibited feeder cells that provide the appropriate signals to preserve this embryonic phenotype and serve as a matrix for ES cell adherence. Preferred feeder cells are primary embryonic fibroblasts that are established from tissue of day 13- day 14 embryos of virtually any mouse strain, that are maintained in culture, such as described by Abbondanzo et al. (1993; Methods Enzymol 225:803–23) and are inhibited in growth by irradiation, such as described by Robertson ((1987) Embryo-derived stem cell lines. In: E. J. Robertson Ed. Teratocarcinomas and Embryonic Stem Cells: A Practical Approach, IRL Press, Oxford), or by the presence of an inhibitory concentration of LIF, such as described by Pease and Williams (1990; Exp Cell Res 190(2):209–11).

The constructs in the host cells can be used in a conventional manner to produce the gene product encoded by the recombinant sequence.

Following transformation of a suitable host and growth of the host to an appropriate cell density, the selected promoter is induced by appropriate means, such as temperature shift or chemical induction, and cells are cultivated for an additional period. Cells are typically harvested by centrifugation, disrupted by physical or chemical means, and the resulting crude extract retained for further purification. Microbial cells employed in the expression of proteins can be disrupted by any convenient method, including freeze-thaw cycling, sonication, mechanical disruption, or use of cell lysing agents. Such methods are well known by the skilled artisan.

IV. Transgenic Animals

The present invention also provides methods and compositions for the generation of non-human animals and plants that express recombinant OBG3 polypeptides, i.e. recombinant OBG3 fragments or full-length OBG3 polypeptides. The animals or plants can be transgenic, i.e. each of their cells contains a gene encoding the OBG3 polypeptide, or, alternatively, a polynucleotide encoding the polypeptide can be introduced into somatic cells of the animal or plant, e.g. into mammary secretory epithelial cells of a mammal. In preferred embodiments, the non-human animal is a mammal such as a cow, sheep, goat, pig, or rabbit.

Methods of making transgenic animals such as mammals are well known to those of skill in the art, and any such method can be used in the present invention. Briefly, transgenic mammals can be produced, e.g., by transfecting a pluripotential stem cell such as an ES cell with a polynucleotide encoding a polypeptide of interest. Successfully transformed ES cells can then be introduced into an early stage embryo that is then implanted into the uterus of a mammal of the same species. In certain cases, the transformed ("transgenic") cells will comprise part of the germ line of the resulting animal, and adult animals comprising the transgenic cells in the germ line can then be mated to other animals, thereby eventually producing a population of transgenic animals that have the transgene in each of their cells, and which can stably transmit the transgene to each of their offspring. Other methods of introducing the polynucleotide can be used, for example introducing the polynucleotide encoding the polypeptide of interest into a fertilized egg or early stage embryo via microinjection. Alternatively, the transgene may be introduced into an animal by infection of zygotes with a retrovirus containing the transgene (Jaenisch, R. (1976) Proc Natl Acad Sci USA 73, 1260–1264). Methods of making transgenic mammals are described, e.g., in Wall et al. (1992) J Cell Biochem 1992 49(2):113–20; Hogan, et al. (1986) in Manipulating the Mouse Embryo: A Laboratory Manual, Cold Spring Harbor Laboratory Press, Cold Spring Harbor, N.Y.; in WO 91/08216; or in U.S. Pat. No. 4,736,866.

In a preferred method, the polynucleotides are microinjected into the fertilized oocyte. Typically, fertilized oocytes are microinjected using standard techniques, and then cultured in vitro until a "pre-implantation embryo" is obtained. Such pre-implantation embryos preferably contain approximately 16 to 150 cells. Methods for culturing fertilized oocytes to the pre-implantation stage are described, e.g., by Gordon et al. ((1984) Methods in Enzymology, 101, 414); Hogan et al. ((1986) in Manipulating the Mouse Embryo. A Laboratory Manual. Cold Spring Harbor Laboratory Press, Cold Spring Harbor, N.Y.) (for the mouse embryo); Hammer et al. ((1985) Nature, 315, 680) (for rabbit and porcine embryos); Gandolfi et al. ((1987) J. Reprod. Fert. 81, 23–28); Rexroad et al. ((1988) J. Anim. Sci. 66, 947–953) (for ovine embryos); and Eyestone et al. ((1989) J. Reprod. Fert. 85, 715–720); Camous et al. ((1984) J. Reprod. Fert. 72, 779–785); and Heyman et al. ((1987) Theriogenology 27, 5968) (for bovine embryos); the disclosures of each of which are incorporated herein in their entireties. Pre-implantation embryos are then transferred to an appropriate female by standard methods to permit the birth of a transgenic or chimeric animal, depending upon the stage of development when the transgene is introduced.

As the frequency of transgene incorporation is often low, the detection of transgene integration in pre-implantation embryos is often desirable using any of the herein-described methods. Any of a number of methods can be used to detect the presence of a transgene in a pre-implantation embryo. For example, one or more cells may be removed from the pre-implantation embryo, and the presence or absence of the transgene in the removed cell or cells can be detected using any standard method e.g. PCR. Alternatively, the presence of a transgene can be detected in utero or post partum using standard methods.

In a particularly preferred embodiment of the present invention, transgenic mammals are generated that secrete recombinant OBG3 polypeptides in their milk. As the mammary gland is a highly efficient protein-producing organ, such methods can be used to produce protein concentrations in the gram per liter range, and often significantly more. Preferably, expression in the mammary gland is accomplished by operably linking the polynucleotide encoding the OBG3 polypeptide to a mammary gland specific promoter and, optionally, other regulatory elements. Suitable promoters and other elements include, but are not limited to, those derived from mammalian short and long WAP, alpha, beta, and kappa, casein, alpha and beta lactoglobulin, beta-CN 5' genes, as well as the the mouse mammary tumor virus (MMTV) promoter. Such promoters and other elements may be derived from any mammal, including, but not limited to, cows, goats, sheep, pigs, mice, rabbits, and guinea pigs. Promoter and other regulatory sequences, vectors, and other relevant teachings are provided, e.g., by Clark (1998) J Mammary Gland Biol Neoplasia 3:337–50; Jost et al. (1999) Nat Biotechnol 17:160–4; U.S. Pat. Nos. 5,994,616; 6,140,552; 6,013,857; Sohn et al. (1999) DNA Cell Biol. 18:845–52; Kim et al. (1999) J Biochem (Japan) 126:320–5; Soulier et al. (1999) Euro J Biochem 260:533–9; Zhang et al. (1997) Chin J Biotech 13:271–6; Rijnkels et al. (1998) Transgen Res 7:5–14; Korhonen et al. (1997) Euro J Biochem 245:482–9; Uusi-Oukari et al. (1997) Transgen Res 6:75–84; Hitchin et al. (1996) Prot Expr Purif 7:247–52; Platenburg et al. (1994) Transgen Res 3:99–108; Heng-Cherl et al. (1993) Animal Biotech 4:89–107; and Christa et al. (2000) Euro J Biochem 267:1665–71; the entire disclosures of each of which is herein incorporated by reference.

In another embodiment, the polypeptides of the invention can be produced in milk by introducing polynucleotides encoding the polypeptides into somatic cells of the mammary gland in vivo, e.g. mammary secreting epithelial cells. For example, plasmid DNA can be infused through the nipple canal, e.g. in association with DEAE-dextran (see, e.g., Hens et al. (2000) Biochim. Biophys. Acta 1523:161–171), in association with a ligand that can lead to receptor-mediated endocytosis of the construct (see, e.g., Sobolev et al. (1998) 273:7928–33), or in a viral vector such as a retroviral vector, e.g. the Gibbon ape leukemia virus (see, e.g., Archer et al. (1994) PNAS 91:6840–6844). In any of these embodiments, the polynucleotide may be operably linked to a mammary gland specific promoter, as described above, or, alternatively, any strongly expressing promoter such as CMV or MoMLV LTR.

The suitability of any vector, promoter, regulatory element, etc. for use in the present invention can be assessed beforehand by transfecting cells such as mammary epithelial cells, e.g. MacT cells (bovine mammary epithelial cells) or GME cells (goat mammary epithelial cells), in vitro and assessing the efficiency of transfection and expression of the transgene in the cells.

For in vivo administration, the polynucleotides can be administered in any suitable formulation, at any of a range of concentrations (e.g. 1–500 μg/ml, preferably 50–100 μg/ml), at any volume (e.g. 1–100 ml, preferably 1 to 20 ml), and can be administered any number of times (e.g. 1, 2, 3, 5, or 10 times), at any frequency (e.g. every 1, 2, 3, 5, 10, or any number of days). Suitable concentrations, frequencies, modes of administration, etc. will depend upon the particular polynucleotide, vector, animal, etc., and can readily be determined by one of skill in the art.

In a preferred embodiment, a retroviral vector such as Gibbon ape leukemia viral vector is used, as described in Archer et al. ((1994) PNAS 91:6840–6844). As retroviral infection typically requires cell division, cell division in the mammary glands can be stimulated in conjunction with the administration of the vector, e.g. using a factor such as estrodiol benzoate, progesterone, reserpine, or dexamethasone. Further, retroviral and other methods of infection can be facilitated using accessory compounds such as polybrene.

In any of the herein-described methods for obtaining OBG3 polypeptides from milk, the quantity of milk obtained, and thus the quantity of OBG3 polypeptides produced, can be enhanced using any standard method of lacation induction, e.g. using hexestrol, estrogen, and/or progesterone.

The polynucleotides used in such embodiments can either encode a full-length OBG3 polypeptide or an OBG3 fragment. Typically, the encoded polypeptide will include a signal sequence to ensure the secretion of the protein into the milk. Where a full-length OBG3 sequence is used, the full-length protein can, e.g., be isolated from milk and cleaved in vitro using a suitable protease. Alternatively, a second, protease-encoding polynucleotide can be introduced into the animal or into the mammary gland cells, whereby expression of the protease results in the cleavage of the OBG3 polypeptide in vivo, thereby allowing the direct isolation of OBG3 fragments from milk.

V. Pharmaceutical or Physiologically Acceptable Compositions of the Invention

The OBG3 and gOBG3 polypeptide fragments of the invention can be administered to non-human animals and/or humans, alone or in pharmaceutical or physiologically acceptable compositions where they are mixed with suitable carriers or excipient(s). The pharmaceutical or physiologically acceptable composition is then provided at a therapeutically effective dose. A therapeutically effective dose refers to that amount of OBG3 or gOBG3 fragment sufficient to result in prevention or amelioration of symptoms or physiological status of obesity-related diseases or disorders as determined by the methods described herein. A therapeutically effective dose can also refer to the amount of OBG3 or gOBG3 fragment necessary for a reduction in weight or a prevention of an increase in weight or prevention of an increase in the rate of weight gain in persons desiring this affect for cosmetic reasons. A therapeutically effective dosage of an OBG3 or gOBG3 fragment of the invention is that dosage that is adequate to promote weight loss or weight gain with continued periodic use or administration. Techniques for formulation and administration of OBG3 polypeptide fragments may be found in "Remington's Pharmaceutical Sciences," Mack Publishing Co., Easton, Pa., latest edition.

Other diseases or disorders that OBG3 polypeptide fragments of the invention could be used to treat or prevent include, but are not limited to, obesity and obesity-related diseases and disorders such as obesity, impaired glucose tolerance, insulin resistance, atherosclerosis, atheromatous disease, heart disease, hypertension, stroke, Syndrome X, Noninsulin Dependent Diabetes Mellitus (NIDDM, or Type II diabetes) and Insulin Dependent Diabetes Mellitus (IDDM or Type I diabetes). Diabetes-related complications to be treated by the methods of the invention include microangiopathic lesions, ocular lesions, retinopathy, neuropathy, and renal lesions. Heart disease includes, but is not limited to, cardiac insufficiency, coronary insufficiency, and high blood pressure. Other obesity-related disorders to be treated by compounds of the invention include hyperlipidemia and hyperuricemia. Yet other obesity-related diseases or disorders of the invention include cachexia, wasting, AIDS-related weight loss, cancer-related weight loss, anorexia, and bulimia. The OBG3 or gOBG3 polypeptide fragments may also be used to enhance physical performance during work or exercise or enhance a feeling of general well-being. Physical performance activities include walking, running, jumping, lifting and/or climbing.

The OBG3 or gOBG3 polypeptide fragments or antagonists thereof may also be used to treat dyslexia, attention-deficit disorder (ADD), attention-deficit/hyperactivity disorder (ADHD), and psychiatric disorders such as schizophrenia by modulating fatty acid metabolism, more specifically, the production of certain long-chain polyunsaturated fatty acids.

It is expressly considered that the OBG3 or gOBG3 polypeptide fragments of the invention may be provided alone or in combination with other pharmaceutically or physiologically acceptable compounds. Other compounds useful for the treatment of obesity and other diseases and disorders are currently well-known in the art.

In a preferred embodiment, the OBG3 or gOBG3 polypeptide fragments are useful for, and used in, the treatment of insulin resistance and diabetes using methods described herein and known in the art. More particularly, a preferred embodiments relates to process for the therapeutic modification and regulation of glucose metabolism in an animal or human subject, which comprises administering to a subject in need of treatment (alternatively on a timed daily basis) an OBG or OBG3 polypeptide fragment (or polynucleotide encoding said polypeptide) in dosage amount and for a period sufficient to reduce plasma glucose levels in said animal or human subject.

Further preferred embodiments relate to methods for the prophylaxis or treatment of diabetes comprising administering to a subject in need of treatment (alternatively on a timed daily basis) an OBG or OBG3 polypeptide fragment (or polynucleotide encoding said polypeptide) in dosage amount and for a period sufficient to reduce plasma glucose levels in said animal or human subject.

Routes of Administration.

Suitable routes of administration include oral, nasal, rectal, transmucosal, or intestinal administration, parenteral delivery, including intramuscular, subcutaneous, intramedullary injections, as well as intrathecal, direct intraventricular, intravenous, intraperitoneal, intranasal, intrapulmonary (inhaled) or intraocular injections using methods known in the art. A particularly useful method of administering compounds for promoting weight loss involves surgical implantation, for example into the abdominal cavity of the recipient, of a device for delivering OBG3 or gOBG3 polypeptide fragments over an extended period of time. Other particularly preferred routes of administration are aerosol and depot formulation. Sustained release formulations, particularly depot, of the invented medicaments are expressly contemplated.

Composition/Formulation

Pharmaceutical or physiologically acceptable compositions and medicaments for use in accordance with the present invention may be formulated in a conventional manner using one or more physiologically acceptable carriers comprising excipients and auxiliaries. Proper formulation is dependent upon the route of administration chosen.

Certain of the medicaments described herein will include a pharmaceutically or physiologically acceptable carrier and at least one polypeptide that is a OBG3 polypeptide fragment of the invention. For injection, the agents of the invention may be formulated in aqueous solutions, preferably in physiologically compatible buffers such as Hanks's solution, Ringer's solution, or physiological saline buffer such as a phosphate or bicarbonate buffer. For transmucosal administration, penetrants appropriate to the bamer to be permeated are used in the formulation. Such penetrants are generally known in the art.

Pharmaceutical or physiologically acceptable preparations that can be taken orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable gaseous propellant, e.g., carbon dioxide. In the case of a pressurized aerosol the dosage unit may be determined by providing a valve to deliver a metered amount. Capsules and cartridges of, e.g., gelatin, for use in an inhaler or insufflator, may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in aqueous vehicles, and may contain formulatory agents such as suspending, stabilizing and/or dispersing agents.

Pharmaceutical or physiologically acceptable formulations for parenteral administration include aqueous solutions of the active compounds in water-soluble form. Aqueous suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder or lyophilized form for constitution with a suitable vehicle, such as sterile pyrogen-free water, before use.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Additionally, the compounds may be delivered using a sustained-release system, such as semipermeable matrices of solid hydrophobic polymers containing the therapeutic agent. Various sustained release materials have been established and are well known by those skilled in the art. Sustained-release capsules may, depending on their chemical nature, release the compounds for a few weeks up to over 100 days.

Depending on the chemical nature and the biological stability of the therapeutic reagent, additional strategies for protein stabilization may be employed.

The pharmaceutical or physiologically acceptable compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Effective Dosage

Pharmaceutical or physiologically acceptable compositions suitable for use in the present invention include compositions wherein the active ingredients are contained in an effective amount to achieve their intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes or encompasses a concentration point or range shown to increase leptin or lipoprotein uptake or binding in an in vitro system. Such information can be used to more accurately determine useful doses in humans.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the LD50, (the dose lethal to 50% of the test population) and the ED50 (the dose therapeutically effective in 50% of the population). The dose ratio between toxic and therapeutic effects is the therapeutic index and it can be expressed as the ratio between LD50 and ED50. Compounds that exhibit high therapeutic indices are preferred.

The data obtained from these cell culture assays and animal studies can be used in formulating a range of dosage for use in humans. The dosage of such compounds lies preferably within a range of circulating concentrations that include the ED50, with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, in "The Pharmacological Basis of Therapeutics", Ch. 1).

Dosage amount and interval may be adjusted individually to provide plasma levels of the active compound which are sufficient to maintain or prevent weight loss or gain, depending on the particular situation. Dosages necessary to achieve these effects will depend on individual characteristics and route of administration.

Dosage intervals can also be determined using the value for the minimum effective concentration. Compounds should be administered using a regimen that maintains plasma levels above the minimum effective concentration for 10–90% of the time, preferably between 30–90%; and most preferably between 50–90%. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

A preferred dosage range for the amount of an OBG3 polypeptide fragment of the invention, which can be administered on a daily or regular basis to achieve desired results, including a reduction in levels of circulating plasma triglyceride-rich lipoproteins, range from 0.01–0.5 mg/kg body mass. A more preferred dosage range is from 0.05–0.1 mg/kg. Of course, these daily dosages can be delivered or administered in small amounts periodically during the course of a day. It is noted that these dosage ranges are only preferred ranges and are not meant to be limiting to the invention.

VI. Methods of Treatment

Treatment of mice with gOBG3 polypeptide fragments results in decreased triglyceride levels, decreased free fatty acid levels, decreased glucose levels, and decreased body weight as well as increased muscle oxidation.

The invention is drawn inter alia to methods of preventing or treating obesity-related diseases and disorders comprising providing an individual in need of such treatment with an OBG3 or gOBG3 polypeptide fragment of the invention. Preferably, the OBG3 polypeptide fragment has obesity-related activity either in vitro or in vivo. Preferably the OBG3 polypeptide fragment is provided to the individual in a pharmaceutical composition that is preferably taken orally. Preferably the individual is a mammal, and most preferably a human. In preferred embodiments, the obesity-related disease or disorder is selected from the group consisting of atherosclerosis, cardiovascular disease, impaired glucose tolerance, insulin resistance, hypertension, stroke, Syndrome X, Type I diabetes, Type II diabetes and lipoatrophic diabetes. Diabetes-related complications to be treated by the methods of the invention include microangiopathic lesions, ocular lesions, retinopathy, neuropathy and renal lesions. Heart disease includes, but is not limited to, cardiac insufficiency, coronary insufficiency, and high blood pressure. Other obesity-related disorders to be treated by compounds of the invention include hyperlipidemia, hypertriglyceridemia, and hyperuricemia. Yet other obesity-related diseases or disorders of the invention include cachexia, wasting, AIDS-related weight loss, neoplasia-related weight loss, anorexia, and bulimia. In highly preferred embodiments, OBG3 polypeptide fragments in pharmaceutical compositions are used to modulate body weight in healthy individuals for cosmetic reasons.

The invention also features a method of preventing or treating obesity-related diseases and disorders comprising providing an individual in need of such treatment with a compound identified by assays of the invention (described in Section VI of the Preferred Embodiments of the Invention and in the Examples). Preferably these compounds antagonize or agonize effects of OBG3 or gOBG3 polypeptide fragments in cells in vitro, muscles ex vivo, or in animal models. Alternatively, these compounds agonize or antagonize the effects of OBG3 or gOBG3 polypeptide fragments on leptin and/or lipoprotein uptake and/or binding. Optionally, these compounds prevent the interaction, binding, or uptake of OBG3 or gOBG3 polypeptide fragments with LSR in vitro or in vivo. Preferably, the compound is provided to the individual in a pharmaceutical composition that is preferably taken orally. Preferably the individual is a mammal, and most preferably a human. In preferred embodiments, the obesity-related disease or disorder is selected from the group consisting of obesity and obesity-related diseases and disorders such as atherosclerosis, heart disease, impaired glucose tolerance, insulin resistance, hypertension, stroke, Syndrome X, Type I diabetes, Type II diabetes, and lipoatrophic diabetes. Diabetes-related complications to be treated by the methods of the invention include microangiopathic lesions, ocular lesions, retinopathy, neuropathy and renal lesions. Heart disease includes, but is not limited to, cardiac insufficiency, coronary insufficiency, and high blood pressure. Other obesity-related disorders to be treated by compounds of the invention include hyperlipidemia, hypertriglyceridemia, and hyperuricemia. Yet other obesity-related diseases or disorders of the invention include cachexia, wasting, AIDS-related weight loss, neoplasia-related weight loss, anorexia, and bulimia. In highly preferred embodiments, the pharmaceutical compositions are used to modulate body weight for cosmetic reasons.

In further preferred embodiments, the present invention of said pharmaceutical or physiologically acceptable composition can be used as a method to control blood glucose in some individuals, particularly those with Type I diabetes, Type II diabetes, or insulin resistance, in combination with insulin therapy.

In further preferred embodiments, the present invention of said pharmaceutical or physiologically acceptable composition can be used as a method to control body weight in some individuals, particularly those with Type I diabetes, Type II diabetes, or insulin resistance, in combination with insulin therapy.

In further preferred embodiments, the present invention of said pharmaceutical or physiologically acceptable composition can be used as a method to control blood glucose in some individuals, particularly those with Type I diabetes, Type II diabetes, or insulin resistance, alone, without combination of insulin therapy.

In further preferred embodiments, the present invention of said pharmaceutical or physiologically acceptable composition can be used as a method to control body weight in some individuals, particularly those with Type II diabetes or insulin resistance, alone, without combination of insulin therapy.

In a further preferred embodiment, the present invention may be used in complementary therapy, particularly in some individuals, particularly those with Type I diabetes, Type II diabetes, or insulin resistance, to improve their weight or glucose control in combination with an oral insulin secretagogue or an insulin sensitising agent. Preferably, the oral insulin secretagogue is 1,1-dimethyl-2-(2-morpholino phenyl)guanidine fumarate (BTS67582) or a sulphonylurea selected from tolbutamide, tolazamide, chlorpropamide, glibenclamide, glimepiride, glipizide and glidazide. Preferably, the insulin sensitising agent is selected from metformin, ciglitazone, troglitazone and pioglitazone.

The present invention further provides a method of improving the body weight or glucose control of some individuals, particularly those with Type I diabetes, Type II diabetes, or insulin resistance, alone, without an oral insulin secretagogue or an insulin sensitising agent.

In a further preferred embodiment, the present invention may be administered either concomitantly or concurrently, with the oral insulin secretagogue or insulin sensitising agent for example in the form of separate dosage units to be used simultaneously, separately or sequentially (either before or after the secretagogue or either before or after the sensitising agent). Accordingly, the present invention further provides for a composition of pharmaceutical or physiologically acceptable composition and an oral insulin secretagogue or insulin sensitising agent as a combined preparation for simultaneous, separate or sequential use for the improvement of body weight or glucose control in some individuals, particularly those with Type I diabetes, Type II diabetes, or insulin resistance.

In further preferred embodiments, the present invention of said pharmaceutical or physiologically acceptable composition further provides a method for the use as an insulin sensitiser.

In further preferred embodiments, the present invention of said pharmaceutical or physiologically acceptable composition can be used as a method to improve insulin sensitivity in some individuals, particularly those with Type I diabetes, Type II diabetes, or insulin resistance, in combination with insulin therapy.

In further preferred embodiments, the present invention of said pharmaceutical or physiologically acceptable composition can be used as a method to improve insulin sensitivity in some individuals, particularly those with Type II diabetes or insulin resistance, without insulin therapy.

In further preferred embodiments, the present invention of said pharmaceutical or physiologically acceptable composition further provides a method for the use as an inhibitor of the progression from impaired glucose tolerance to insulin resistance.

More generally, the instant invention is drawn to treatment with OBG3 and gOBG3 polypeptide fragments where an individual is shown to have a particular genotype for an APM1 marker (APM1 designates the human homolog of the full-length OBG3 polypeptide), or where they have been shown to have a reduced amount of plasma APM1, either full-length or preferably a more biologically active fragment of APM1, as compared to control values, e.g. values representative of non-diseased individuals, or as compared to that individual prior to the onset of a disease or condition. In either case, treatment comprises providing pharmaceutically acceptable gOBG3 or OBG3 polypeptide fragments to the individual. The exact amount of OBG3 or gOBG3 fragment provided would be determined through clinical trials under the guidance of qualified physicians, but would be expected to be in the range of 5–7 mg per individual per day. In general, a preferred range would be from 0.5 to 14 mg per individual per day, with a highly preferred range being between 1 and 10 mg per individual per day. Individuals who could benefit from treatment with gOBG3 or OBG3 polypeptide fragments could be identified through at least two methods: plasma serum level determinations and genotyping.

OBG3/APM1 Levels

Preliminary studies have shown that obese people have lower levels of full-length OBG3/Apm1 than non-obese people. The invention envisions treatment of individuals (preferably obese) that have low levels of full-length OBG3/Apm1 with OBG3 or gOBG3 polypeptide fragments of the invention. In addition, the invention preferably is drawn to treatment of individuals with low levels of the biologically active fragment of OBG3/Apm1 with OBG3 or gOBG3 polypeptide fragments of the invention. In further embodiments, OBG3 or gOBG3 polypeptide fragments of the present invention are administered to individuals, preferably obese individuals, that levels of full-length OBG3 (or alternatively a mature OBG3 polypeptide fragment) at least 10%, 20%, 30%, 40%, 50%, 60%, 70%, 80%, 90%, about 100% or 100% lower than non-obese individuals, preferably healthy individuals as determined by a physician using normal standards in the art. Methods to determine and compare the levels of full-length OBG3 in individuals are well-known in the art and include, but are not limited to using an antibody specific for Apml in a format such as a Radio Immune Assay, ELISA, Western blot, dotblot, or as part of an array, for example. Methods of generating antibodies to, and detection of, APM1 and fragments thereof (such as the 27 kDa APM1 product in human plasma) as well as to proteins with SNPs are included in the present invention and are discussed in PCT/IB99/01858, U.S. application Ser. No. 09/434,848, and WO 99/07736, hereby incorporated herein by reference in its entirety including drawings, figures, or tables. Further, antibodies specific for OBG3/gOBG3 polypeptide fragments of the invention (e.g., antibodies that bind the 27 kDa APM1 fragment as well as full-length APM1 and antibodies that bind the 27 kDa APM1 fragment but not the full-length APM1), their generation, and their use are described herein. Particularly included in the present invention are methods of binding an antibody specific for the 27 kDa APM1 fragment to the 27 kDa APM1 fragment comprising the steps of: obtaining a biological sample comprising the 27 kDa APM1 fragment, contacting said 27 kDa fragment with said antibody under conditions that allow specific binding of the antibody and the 27 kDa fragment to occur, and specifically binding said antibody to said 27 kDa fragment.

Also particularly included in the present invention are monoclonal antibodies that specifically bind an APM1 polypeptide fragment comprised of the C-terminal globular domain (gAPM1) but not said fragment from which the N-terminal dipeptide EP has been proteolytically removed by dipeptidyl peptidase [Deacon (2000) Journal of Clinical Endocrinology and Metabolism 85:3575–3581 which disclosure is hereby incorporated by reference in its entirety]. Preferred said gAPM1 polypeptide fragment is selected from amino acids 85–244 or 103–244 of SEQ ID NO:6. Methods of making monoclonal antibodies are known to those of ordinary skill in the art. Further particularly included are methods of using gAPM1 of the invention to select monoclonal antibodies, wherein said monoclonal antibody specifically binds to gAPM1 (85–244) but not to gAPM1 (87–244) of SEQ ID NO:6 comprising the steps of: obtaining a sample comprising gAPM1 (85–244) and obtaining a sample comprising gAPM1 (87–244); contacting said antibody with gAPM1 (85–244) and contacting said antibody with gAPM1 (87–244); and quantifying the level of antibody binding to gAPM1 (85–244) and the level of antibody binding to gAPM1 (87–244) by enzyme-linked immunosorbent assay (ELISA). Further particularly included are methods of selecting monoclonal antibodies, wherein said monoclonal antibody specifically binds to gAPM1 (103–247) but not to gAPM1 (105–247) of SEQ ID NO:2 or SEQ ID NO:4 comprising the steps of: obtaining a sample comprising gAPM1 (103–247) and obtaining a sample comprising gAPM1 (87–244); contacting said antibody with gAPM1 (105–247) and contacting said antibody with gAPM1 (87–244); and quantifying the level of antibody binding to gAPM1 (103–247) and the level of antibody binding to gAPM1 (105–247) by ELISA.

APM1 Genotyping

The methods treatment using genotyping to identify individuals that would benefit from treatments of the invention are based on the finding that single nucleotide polymorphisms (SNPs) in the APM1 gene have been identified that show an association in obese adolescents with free fatty acid (FFA) and respiratory quotient levels, others that show an association with the relationship between BMI and leptin, and still others that show an association with glucose levels. Further, a combination of the APM1 SNPs associated with FFA and leptin metabolism also predicts people who will be seriously overweight (data not shown).

APM1 SNPs and methods of genotyping are described in PCT/IB99/01858 as well as U.S. application Ser. No. 09/434,848, both of which are hereby incoporated herein in their entirety including any drawings, figure, or tables. Briefly, the term "genotype" as used herein refers to the identity of the alleles present in an individual or a sample. The term "genotyping" a sample or an individual for a biallelic marker consists of determining the specific allele or the specific nucleotide carried by an individual at a biallelic marker.

Methods of genotyping comprise determining the identity of a nucleotide at an APM1 biallelic marker site by any method known in the art. Preferably, microsequencing is used. The genotype is used to determine whether an individual should be treated with gOBG3 or OBG3 polypeptide fragments. Thus, these genotyping methods are performed on nucleic acid samples derived from a single individual. These methods are well-known in the art, and discussed fully in the applications referenced above and briefly below.

Any method known in the art can be used to identify the nucleotide present at a biallelic marker site. Since the biallelic marker allele to be detected has been identified and specified in the present invention, detection will prove simple for one of ordinary skill in the art by employing any of a number of techniques. Many genotyping methods require the previous amplification of the DNA region carrying the biallelic marker of interest. While the amplification of target or signal is often preferred at present, ultrasensitive detection methods that do not require amplification are also encompassed by the present genotyping methods.

Methods well-known to those skilled in the art that can be used to detect biallelic polymorphisms include methods such as conventional dot blot analysis, single strand conformational polymorphism analysis (SSCP; Orita et al. (1989) Proc Natl Acad Sci USA 86(8):2766–70), denaturing gradient gel electrophoresis (DGGE), heteroduplex analysis, mismatch cleavage detection, and other conventional techniques as described in Sheffield et al. (1991; Am J Hum Genet 49(4):699–706); White et al. (1992), Grompe et al. ((1989) Proc Natl Acad Sci USA 86(15):5888–92; (1993) Nat Genet 5(2):111–7). Another method for determining the identity of the nucleotide present at a particular polymorphic site employs a specialized exonuclease-resistant nucleotide derivative as described in U.S. Pat. No. 4,656,127.

Preferred methods involve directly determining the identity of the nucleotide present at a biallelic marker site by sequencing assay, allele-specific amplification assay, or hybridization assay. The following is a description of some preferred methods. A highly preferred method is the microsequencing technique. The term "sequencing" is used herein to refer to polymerase extension of duplex primer/template complexes and includes both traditional sequencing and microsequencing.

1) Sequencing Assays

The nucleotide present at a polymorphic site can be determined by sequencing methods. In a preferred embodiment, DNA samples are subjected to PCR amplification before sequencing using any method known in the art. Preferably, the amplified DNA is subjected to automated dideoxy terminator sequencing reactions using a dye-primer cycle sequencing protocol. Sequence analysis allows the identification of the base present at the biallelic marker site.

2) Microsequencing Assays

In microsequencing methods, the nucleotide at a polymorphic site in a target DNA is detected by a single nucleotide primer extension reaction. This method involves appropriate microsequencing primers that hybridize just upstream of the polymorphic base of interest in the target nucleic acid. A polymerase is used to specifically extend the 3' end of the primer with one single ddNTP (chain terminator) complementary to the nucleotide at the polymorphic site. The identity of the incorporated nucleotide is then determined in any suitable way.

Typically, microsequencing reactions are carried out using fluorescent ddNTPs and the extended microsequencing primers are analyzed by electrophoresis on ABI 377 sequencing machines to determine the identity of the incorporated nucleotide as described in EP 412 883. Alternatively capillary electrophoresis can be used in order to process a higher number of assays simultaneously.

Different approaches can be used for the labeling and detection of ddNTPs. A homogeneous phase detection method based on fluorescence resonance energy transfer has been described by Chen and Kwok ((1997) Nucleic Acids Res 25(2):347–53) and Chen et al. ((1997) Proc Natl Acad Sci USA 94(20): 10756–61). In this method, amplified genomic DNA fragments containing polymorphic sites are incubated with a 5'-fluorescein-labeled primer in the presence of allelic dye-labeled dideoxyribonucleoside triphosphates and a modified Taq polymerase. The dye-labeled primer is extended one base by the dye-terminator specific for the allele present on the template. At the end of the genotyping reaction, the fluorescence intensities of the two dyes in the reaction mixture are analyzed directly without separation or purification. All these steps can be performed in the same tube and the fluorescence changes can be monitored in real time. Alternatively, the extended primer may be analyzed by MALDI-TOF Mass Spectrometry. The base at the polymorphic site is identified by the mass added onto the microsequencing primer (see Haff and Smirnov, (1997) Nucleic Acids Res 25(18):3749–50; (1997) Genome Res 7(4):378–88).

Microsequencing may be achieved by the established microsequencing method or by developments or derivatives thereof. Alternative methods include several solid-phase microsequencing techniques. The basic microsequencing protocol is the same as described previously, except that the method is conducted as a heterogeneous phase assay, in which the primer or the target molecule is immobilized or captured onto a solid support. To simplify the primer separation and the terminal nucleotide addition analysis, oligonucleotides are attached to solid supports or are modified in such ways that permit affinity separation as well as polymerase extension. The 5' ends and internal nucleotides of synthetic oligonucleotides can be modified in a number of different ways to permit different affinity separation approaches, e.g., biotinylation. If a single affinity group is used on the oligonucleotides, the oligonucleotides can be separated from the incorporated terminator regent. This eliminates the need of physical or size separation. More than one oligonucleotide can be separated from the terminator reagent and analyzed simultaneously if more than one affinity group is used. This permits the analysis of several nucleic acid species or more nucleic acid sequence information per extension reaction. The affinity group need not be on the priming oligonucleotide but could alternatively be present on the template.

For example, immobilization can be carried out via an interaction between biotinylated DNA and streptavidin-coated microtitration wells or avidin-coated polystyrene particles. In the same manner, oligonucleotides or templates may be attached to a solid support in a high-density format. In such solid phase microsequencing reactions, incorporated ddNTPs can be radiolabeled (Syvänen, (1994) Clin Chim Acta 226(2):225–36) or linked to fluorescein (Livak and Hainer, (1994) Hum Mutat 3(4):379–85). The detection of radiolabeled ddNTPs can be achieved through scintillation-based techniques. The detection of fluorescein-linked ddNTPs can be based on the binding of antifluorescein antibody conjugated with alkaline phosphatase, followed by incubation with a chromogenic substrate (such as p-nitrophenyl phosphate).

Other possible reporter-detection pairs include: ddNTP linked to dinitrophenyl (DNP) and anti-DNP alkaline phosphatase conjugate (Harju et al., (1993) Clin Chem 39(11 Pt 1):2282–7) or biotinylated ddNTP and horseradish peroxidase-conjugated streptavidin with o-phenylenediamine as a substrate (WO 92/15712). As yet another alternative solid-phase microsequencing procedure, Nyren et al. ((1993) Anal Biochem 208(1):171–5) described a method relying on the detection of DNA polymerase activity by an enzymatic luminometric inorganic pyrophosphate detection assay (ELIDA).

Pastinen et al. ((1997) Genome Res 7(6):606–14) describe a method for multiplex detection of single nucleotide polymorphism in which the solid phase minisequencing principle is applied to an oligonucleotide array format. High-density arrays of DNA probes attached to a solid support (DNA chips) are further described below.

It will be appreciated that any primer having a 3' end immediately adjacent to the polymorphic nucleotide may be used. Similarly, it will be appreciated that microsequencing analysis may be performed for any biallelic marker or any combination of biallelic markers of the present invention.

3) Allele-Specific Amplification Assay Methods

Discrimination between the two alleles of a biallelic marker can also be achieved by allele specific amplification, a selective strategy, whereby one of the alleles is amplified without, or at a much higher rate than, amplification of the other allele. This is accomplished by placing the polymorphic base at the 3' end of one of the amplification primers. Because the extension forms from the 3'end of the primer, a mismatch at or near this position has an inhibitory effect on amplification. Therefore, under appropriate amplification conditions, these primers only direct amplification on their complementary allele. Determining the precise location of the mismatch and the corresponding assay conditions are well with the ordinary skill in the art.

The "Oligonucleotide Ligation Assay" (OLA) uses two oligonucleotides that are designed to be capable of hybridizing to abutting sequences of a single strand of a target molecule. One of the oligonucleotides is biotinylated, and the other is detectably labeled. If the precise complementary sequence is found in a target molecule, the oligonucleotides will hybridize such that their termini abut, and create a ligation substrate that can be captured and detected. OLA is capable of detecting single nucleotide polymorphisms and may be advantageously combined with PCR as described by Nickerson et al. ((1990) Proc Natl Acad Sci USA 87(22):8923–7). In this method, PCR is used to achieve the exponential amplification of target DNA, which is then detected using OLA.

Other amplification methods that are particularly suited for the detection of single nucleotide polymorphism include LCR (ligase chain reaction) and Gap LCR (GLCR). LCR uses two pairs of probes to exponentially amplify a specific target. The sequences of each pair of oligonucleotides are selected to permit the pair to hybridize to abutting sequences of the same strand of the target. Such hybridization forms a substrate for a template-dependant ligase. In accordance with the present invention, LCR can be performed with oligonucleotides having the proximal and distal sequences of the same strand of a biallelic marker site.

In one embodiment, either oligonucleotide will be designed to include the biallelic marker site. In such an embodiment, the reaction conditions are selected such that the oligonucleotides can be ligated together only if the target molecule either contains or lacks the specific nucleotide that is complementary to the biallelic marker on the oligonucleotide.

In an alternative embodiment, the oligonucleotides will not include the biallelic marker, such that when they hybridize to the target molecule, a "gap" is created as described in WO 90/01069. This gap is then "filled" with complementary dNTPs (as mediated by DNA polymerase), or by an additional pair of oligonucleotides. Thus at the end of each cycle, each single strand has a complement capable of serving as a target during the next cycle and exponential allele-specific amplification of the desired sequence is obtained. Ligase/Polymerase-mediated Genetic Bit Analysis™ is another method for determining the identity of a nucleotide at a preselected site in a nucleic acid molecule (WO 95/21271). This method involves the incorporation of a nucleoside triphosphate that is complementary to the nucleotide present at the preselected site onto the terminus of a primer molecule, and their subsequent ligation to a second oligonucleotide. The reaction is monitored by detecting a specific label attached to the reaction's solid phase or by detection in solution.

4) Hybridization Assay Methods

A preferred method of determining the identity of the nucleotide present at a biallelic marker site involves nucleic acid hybridization. The hybridization probes, which can be conveniently used in such reactions, preferably include probes specific for APM1 cDNA surrounding APM1 biallelic markers. Any hybridization assay may be used including Southern hybridization, Northern hybridization, dot blot hybridization and solid-phase hybridization (see Sambrook et al., supra).

Hybridization refers to the formation of a duplex structure by two single stranded nucleic acids due to complementary base pairing. Hybridization can occur between exactly complementary nucleic acid strands or between nucleic acid strands that contain minor regions of mismatch. Specific probes can be designed that hybridize to one form of a biallelic marker and not to the other and therefore are able to discriminate between different allelic forms. Allele-specific probes are often used in pairs, one member of a pair showing perfect match to a target sequence containing the original allele and the other showing a perfect match to the target sequence containing the alternative allele.

Hybridization conditions should be sufficiently stringent that there is a significant difference in hybridization intensity between alleles, and preferably an essentially binary response, whereby a probe hybridizes to only one of the alleles. Stringent, sequence specific hybridization conditions, under which a probe will hybridize only to the exactly complementary target sequence are well known in the art (Sambrook et al., supra). Stringent conditions are sequence dependent and will be different in different circumstances. Generally, stringent conditions are selected to be about 5° C. lower than the thermal melting point (Tm) for the specific sequence at a defined ionic strength and pH. Although such hybridizations can be performed in solution, it is preferred to employ a solid-phase hybridization assay. The target DNA comprising a biallelic marker of the present invention may be amplified prior to the hybridization reaction.

The presence of a specific allele in the sample is determined by detecting the presence or the absence of stable hybrid duplexes formed between the probe and the target DNA. The detection of hybrid duplexes can be carried out by a number of methods. Various detection assay formats are well known which utilize detectable labels bound to either the target or the probe to enable detection of the hybrid duplexes. Typically, hybridization duplexes are separated from unhybridized nucleic acids and the labels bound to the duplexes are then detected. Those skilled in the art will recognize that wash steps may be employed to wash away excess target DNA or probe as well as unbound conjugate. Further, standard heterogeneous assay formats are suitable for detecting the hybrids using the labels present on the primers and probes.

Two recently developed assays allow hybridization-based allele discrimination with no need for separations or washes (see Landegren U. et al., (1998) Genome Res 8(8):769–76). The TaqMan assay takes advantage of the 5' nuclease activity of Taq DNA polymerase to digest a DNA probe annealed specifically to the accumulating amplification product. TaqMan probes are labeled with a donor-acceptor dye pair that interacts via fluorescence resonance energy transfer (FRET). Cleavage of the TaqMan probe by the advancing polymerase during amplification dissociates the donor dye from the quenching acceptor dye, greatly increasing the donor fluorescence. All reagents necessary to detect two allelic variants can be assembled at the beginning of the reaction and the results are monitored in real time (see Livak et al., 1995).

In an alternative homogeneous hybridization based procedure, molecular beacons are used for allele discriminations. Molecular beacons are hairpin-shaped oligonucleotide probes that report the presence of specific nucleic acids in homogeneous solutions. When they bind to their targets they undergo a conformational reorganization that restores the fluorescence of an internally quenched fluorophore (Tyagi et al., (1998) Nat Biotechnol 16(1):49–53).

The polynucleotides provided herein can be used to produce probes that can be used in hybridization assays for the detection of biallelic marker alleles in biological samples. These probes are characterized in that they preferably comprise between 8 and 50 nucleotides, and in that they are sufficiently complementary to a sequence comprising a biallelic marker of the present invention to hybridize thereto and preferably sufficiently specific to be able to discriminate the targeted sequence for only one nucleotide variation. A particularly preferred probe is 25 nucleotides in length. Preferably the biallelic marker is within 4 nucleotides of the center of the polynucleotide probe. In particularly preferred probes, the biallelic marker is at the center of said polynucleotide. In preferred embodiments the polymorphic base is within 5, 4, 3, 2, 1, nucleotides of the center of the said polynucleotide, more preferably at the center of said polynucleotide. Preferably the probes of the present invention are labeled or immobilized on a solid support.

By assaying the hybridization to an allele specific probe, one can detect the presence or absence of a biallelic marker allele in a given sample. High-Throughput parallel hybridizations in array format are specifically encompassed within "hybridization assays" and are described below.

5) Hybridization to Addressable Arrays of Oligonucleotides

Hybridization assays based on oligonucleotide arrays rely on the differences in hybridization stability of short oligonucleotides to perfectly matched and mismatched target sequence variants. Efficient access to polymorphism information is obtained through a basic structure comprising high-density arrays of oligonucleotide probes attached to a solid support (e.g., the chip) at selected positions. Each DNA chip can contain thousands to millions of individual synthetic DNA probes arranged in a grid-like pattern and miniaturized to the size of a dime.

The chip technology has already been applied with success in numerous cases. For example, the screening of mutations has been undertaken in the BRCA1 gene, in *S. cerevisiae* mutant strains, and in the protease gene of HIV-1 virus (Hacia et al., (1996) Nat Genet 14(4):441–7; Shoemaker et al., (1996) Nat Genet 14(4):450–6; Kozal et al., (1996) Nat Med 2(7):753–9). Chips of various formats for use in detecting biallelic polymorphisms can be produced on a customized basis by Affymetrix (GeneChip™), Hyseq (HyChip and HyGnostics), and Protogene Laboratories.

In general, these methods employ arrays of oligonucleotide probes that are complementary to target nucleic acid sequence segments from an individual, which target sequences include a polymorphic marker. EP 785280 describes a tiling strategy for the detection of single nucleotide polymorphisms.

Briefly, arrays may generally be "tiled" for a large number of specific polymorphisms. By "tiling" is generally meant the synthesis of a defined set of oligonucleotide probes which is made up of a sequence complementary to the target sequence of interest, as well as preselected variations of that sequence, e.g., substitution of one or more given positions with one or more members of the basis set of monomers, i.e. nucleotides. Tiling strategies are further described in PCT application No. WO 95/11995. In a particular aspect, arrays are tiled for a number of specific, identified biallelic marker sequences. In particular, the array is tiled to include a number of detection blocks, each detection block being specific for a specific biallelic marker or a set of biallelic markers.

For example, a detection block may be tiled to include a number of probes, which span the sequence segment that includes a specific polymorphism. To ensure probes that are complementary to each allele, the probes are synthesized in pairs differing at the biallelic marker. In addition to the probes differing at the polymorphic base, monosubstituted probes are also generally tiled within the detection block. These mono substituted probes have bases at and up to a certain number of bases in either direction from the polymorphism, substituted with the remaining nucleotides (selected from A, T, G, C and U). Typically the probes in a tiled detection block will include substitutions of the sequence positions up to and including those that are 5 bases away from the biallelic marker. The monosubstituted probes provide internal controls for the tiled array, to distinguish actual hybridization from artifactual cross-hybridization. Upon completion of hybridization with the target sequence and washing of the array, the array is scanned to determine the position on the array to which the target sequence hybridizes. The hybridization data from the scanned array is then analyzed to identify which allele or alleles of the biallelic marker are present in the sample. Hybridization and scanning may be carried out as described in PCT application No. WO 92/10092 and WO 95/11995 and U.S. Pat. No. 5,424,186.

Thus, in some embodiments, the chips may comprise an array of nucleic acid sequences of fragments of about 15 nucleotides in length. In preferred embodiments the polymorphic base is within 5, 4, 3, 2, 1, nucleotides of the center of the said polynucleotide, more preferably at the center of said polynucleotide. In some embodiments, the chip may comprise an array of at least 2, 3, 4, 5, 6, 7, 8 or more of these polynucleotides.

6) Integrated Systems

Another technique, which may be used to analyze polymorphisms, includes multicomponent integrated systems, which miniaturize and compartmentalize processes such as PCR and capillary electrophoresis reactions in a single functional device. An example of such technique is disclosed in U.S. Pat. No. 5,589,136, which describes the integration of PCR amplification and capillary electrophoresis in chips.

Integrated systems can be envisaged mainly when microfluidic systems are used. These systems comprise a pattern of microchannels designed onto a glass, silicon, quartz, or plastic wafer included on a microchip. The movements of the samples are controlled by electric, electroosmotic or hydrostatic forces applied across different areas of the microchip to create functional microscopic valves and pumps with no moving parts. Varying the voltage controls the liquid flow at intersections between the micro-machined channels and changes the liquid flow rate for pumping across different sections of the microchip.

For genotyping biallelic markers, the microfluidic system may integrate nucleic acid amplification, microsequencing, capillary electrophoresis and a detection method such as laser-induced fluorescence detection.

In a first step, the DNA samples are amplified, preferably by PCR. Then, the amplification products are subjected to automated microsequencing reactions using ddNTPs (specific fluorescence for each ddNTP) and the appropriate oligonucleotide microsequencing primers which hybridize just upstream of the targeted polymorphic base. Once the extension at the 3' end is completed, the primers are separated from the unincorporated fluorescent ddNTPs by capillary electrophoresis. The separation medium used in capillary electrophoresis can for example be polyacrylamide, polyethyleneglycol or dextran. The incorporated ddNTPs in the single-nucleotide primer extension products are identified by fluorescence detection. This microchip can be used to process at least 96 to 384 samples in parallel. It can use the usual four-color laser induced fluorescence detection of the ddNTPs.

APM1 Biallellic Markers

The APM1 biallelic markers currently identified are shown in Table 1 below. The markers that have been linked with either FFA levels or changes in the leptin/BMI index are A5, A6, A7 and A3, A4, respectively. A5, A6, and A7 are in complete linkage disequilibrium. Thus, if an individual's genotype at A6 is GG, then A7 will be AA, and both are linked with decreased FFA levels and would indicate that treatment with gOBG3 or OBG3 polypeptide fragments was appropriate for example. Similarly, if an individual's genotype at A4 is AC or CC, treatment with gOBG3 or OBG3 polypeptide fragments could be expected to be beneficial. Alternatively, if an individual has both an AA genotype at A7 and an AC or CC genotype at A4, treatment with gOBG3 or OBG3 polypeptide fragments is indicated.

The above-described associations between genotypes and risk factors and treatment are exemplary, only. Other associations that would also indicate individuals appropriate for gOBG3 or OBG3 fragment treatment (or inappropriate) can also be identified using the methods described in the art or PCT/IB99/01858. Associations that would indicate treatment would be those genotypes associated with changes in parameters that gOBG3 or OBG3 fragment administration has been shown to affect in a "positive" direction, e.g. the association with decrease in weight for treatment of obesity. Associations that would indicate that treatment should not be performed would be genotypes that indicated an adverse affect for diabetes treatment (negative effect on insulin levels for example) or weight loss.

TABLE 1

| Amplicon | Biallelic marker | Marker Name | Localization in APM1 gene | Polymorphism | Marker position in SEQ ID No 7 |
|---|---|---|---|---|---|
| 9-27 | A1 | 9-27/261 | 5' regulatory region | Allele 1: G<br>Allele 2: C | 3787 |
| 99-14387 | A2 | 99-14387/129 | Intron 1 | Allele 1: A<br>Allele 2: C | 11118 |
| 9-12 | A3 | 9-12/48 | Intron 1 | Allele 1: T<br>Allele 2: C | 15120 |
| 9-12 and 9-13 | A4 | 9-12/124 or 9-13/66 | Exon 2 | Allele 1: T<br>Allele 2: G | 15196 |
| 9-12 and 9-13 | A5 | 9-12/355 or 9-13/297 | Intron 2 | Allele 1: G<br>Allele 2: T | 15427 |
| 9-12 and 9-13 | A6 | 9-12/428 or 9-13/370 | Intron 2 | Allele 1: A<br>Allele 2: G | 15500 |
| 99-14405 | A7 | 99-14405/105 | Intron 2 | Allele 1: G<br>Allele 2: A | 15863 |
| 9-16 | A8 | 9-16/189 | Exon 3 | Allele 1: A<br>Allele 2: Del | 17170 |

APM1 Association Studies

Association studies focus on population frequencies and rely on the phenomenon of linkage disequilibrium. Linkage disequilibrium is the deviation from random of the occurrence of pairs of specific alleles at different loci on the same chromosome. If a specific allele in a given gene is directly associated with a particular trait, its frequency will be statistically increased in an affected (trait positive)

population, when compared to the frequency in a trait negative population or in a random control population. As a consequence of the existence of linkage disequilibrium, the frequency of all other alleles present in the haplotype carrying the trait-causing allele will also be increased in trait positive individuals compared to trait negative individuals or random controls. Therefore, association between the trait and any allele (specifically a biallelic marker allele) in linkage disequilibrium with the trait-causing allele will suffice to suggest the presence of a trait-related gene in that particular region.

Case-control populations can be genotyped for biallelic markers to identify associations that narrowly locate a trait causing allele, as any marker in linkage disequilibrium with one given marker associated with a trait will be associated with the trait. Linkage disequilibrium allows the relative frequencies in case-control populations of a limited number of genetic polymorphisms (specifically biallelic markers) to be analyzed as an alternative to screening all possible functional polymorphisms in order to find trait-causing alleles. Association studies compare the frequency of marker alleles in unrelated case-control populations, and represent powerful tools for the dissection of complex traits.

Case-Control Populations (Inclusion Criteria)

Population-based association studies do not concern familial inheritance, but compare the prevalence of a particular genetic marker, or a set of markers, in case-control populations. They are case-control studies based on comparison of unrelated case (affected or trait positive) individuals and unrelated control (unaffected, trait negative or random) individuals. Preferably, the control group is composed of unaffected or trait negative individuals. Further, the control group is ethnically matched to the case population. Moreover, the control group is preferably matched to the case-population for the main known confusion factor for the trait under study (for example age-matched for an age-dependent trait). Ideally, individuals in the two samples are paired in such a way that they are expected to differ only in their disease status. The terms "trait positive population", "case population" and "affected population" are used interchangeably herein.

An important step in the dissection of complex traits using association studies is the choice of case-control populations (see, Lander and Schork, (1994) Science 265(5181) :2037–48). A major step in the choice of case-control populations is the clinical definition of a given trait or phenotype. Any genetic trait may be analyzed by the association method proposed here by carefully selecting the individuals to be included in the trait positive and trait negative phenotypic groups. Four criteria are often useful: clinical phenotype, age at onset, family history and severity.

The selection procedure for continuous or quantitative traits (such as blood pressure for example) involves selecting individuals at opposite ends of the phenotype distribution of the trait under study, so as to include in these trait positive and trait negative populations individuals with non-overlapping phenotypes. Preferably, case-control populations consist of phenotypically homogeneous populations. Trait positive and trait negative populations consist of phenotypically uniform populations of individuals representing each between 1 and 98%, preferably between 1 and 80%, more preferably between 1 and 50%, and more preferably between 1 and 30%, most preferably between 1 and 20% of the total population under study, and preferably selected among individuals exhibiting non-overlapping phenotypes. The clearer the difference between the two trait phenotypes, the greater the probability of detecting an association with biallelic markers. The selection of those drastically different but relatively uniform phenotypes enables efficient comparisons in association studies and the possible detection of marked differences at the genetic level, provided that the sample sizes of the populations under study are significant enough.

In preferred embodiments, a first group of between 50 and 300 trait positive individuals, preferably about 100 individuals, are recruited according to their phenotypes. A similar number of trait negative individuals are included in such studies.

In the present invention, typical examples of inclusion criteria include obesity and disorders related to obesity as well as physiologic parameters associated with obesity, such as free fatty acid levels, glucose levels, insulin levels, leptin levels, triglyceride levels, free fatty acid oxidation levels, and weight loss.

Association Analysis

The general strategy to perform association studies using biallelic markers derived from a region carrying a candidate gene is to scan two groups of individuals (case-control populations) in order to measure and statistically compare the allele frequencies of the biallelic markers of the present invention in both groups.

If a statistically significant association with a trait is identified for at least one or more of the analyzed biallelic markers, one can assume that: either the associated allele is directly responsible for causing the trait (i.e. the associated allele is the trait causing allele), or more likely the associated allele is in linkage disequilibrium with the trait causing allele. The specific characteristics of the associated allele with respect to the candidate gene function usually give further insight into the relationship between the associated allele and the trait (causal or in linkage disequilibrium). If the evidence indicates that the associated allele within the candidate gene is most probably not the trait-causing allele but is in linkage disequilibrium with the real trait-causing allele, then the trait-causing allele can be found by sequencing the vicinity of the associated marker, and performing further association studies with the polymorphisms that are revealed in an iterative manner.

Association studies are usually run in two successive steps. In a first phase, the frequencies of a reduced number of biallelic markers from the candidate gene are determined in the trait positive and trait negative populations. In a second phase of the analysis, the position of the genetic loci responsible for the given trait is further refined using a higher density of markers from the relevant region. However, if the candidate gene under study is relatively small in length, as is the case for APM1, a single phase may be sufficient to establish significant associations.

Haplotype Analysis

As described above, when a chromosome carrying a disease allele first appears in a population as a result of either mutation or migration, the mutant allele necessarily resides on a chromosome having a set of linked markers: the ancestral haplotype. This haplotype can be tracked through populations and its statistical association with a given trait can be analyzed. Complementing single point (allelic) association studies with multi-point association studies also called haplotype studies increases the statistical power of association studies. Thus, a haplotype association study allows one to define the frequency and the type of the ancestral carrier haplotype. A haplotype analysis is important in that it increases the statistical power of an analysis involving individual markers.

In a first stage of a haplotype frequency analysis, the frequency of the possible haplotypes based on various combinations of the identified biallelic markers of the invention is determined. The haplotype frequency is then compared for distinct populations of trait positive and control individuals. The number of trait positive individuals, which should be, subjected to this analysis to obtain statistically significant results usually ranges between 30 and 300, with a preferred number of individuals ranging between 50 and 150. The same considerations apply to the number of unaffected individuals (or random control) used in the study. The results of this first analysis provide haplotype frequencies in case-control populations, for each evaluated haplotype frequency a p-value and an odds ratio are calculated. If a statistically significant association is found the relative risk for an individual carrying the given haplotype of being affected with the trait under study can be approximated.

Interaction Analysis

The biallelic markers of the present invention may also be used to identify patterns of biallelic markers associated with detectable traits resulting from polygenic interactions. The analysis of genetic interaction between alleles at unlinked loci requires individual genotyping using the techniques described herein. The analysis of allelic interaction among a selected set of biallelic markers with appropriate level of statistical significance can be considered as a haplotype analysis. Interaction analysis consists in stratifying the case-control populations with respect to a given haplotype for the first loci and performing a haplotype analysis with the second loci with each subpopulation.

VII. Assays for Identifying Modulators of OBG3 Polypeptide Fragment Activity

The invention features methods of screening for one or more compounds that modulate OBG3 or gOBG3 polypeptide fragment activity in cells, that includes providing potential compounds to be tested to the cells, and where modulation of an OBG3 polypeptide fragment effect or activity indicates the one or more compounds. Exemplary assays that may be used are described in the Examples 4–5, 7–14, 16, and 18. To these assays would be added compounds to be tested for their inhibitory or stimulatory activity as compared to the effects of OBG3 polypeptide fragment alone. Other assays in which an effect is observed based on the addition of OBG3 polypeptide fragment can also be used to screen for modulators of OBG3 polypeptide fragment activity or effects of the presence of OBG3 polypeptide fragment on cells. The essential step is to apply an unknown compound and then to monitor an assay for a change from what is seen when only OBG3 polypeptide fragment is applied to the cell. A change is defined as something that is significantly different in the presence of the compound plus OBG3 polypeptide fragment compared to OBG3 polypeptide fragment alone. In this case, significantly different would be an "increase" or a "decrease" in a measurable effect of at least 25%, 30%, 35%, 40%, 45%, 50%, 55%, 60%, 65%, 70%, or 75%.

The term "modulation" as used herein refers to a measurable change in an activity. Examples include, but are not limited to, lipolysis stimulated receptor (LSR) modulation, leptin modulation, lipoprotein modulation, plasma FFA levels, FFA oxidation, TG levels, glucose levels, and weight. These effects can be in vitro or preferably in vivo. Modulation of an activity can be either an increase or a decrease in the activity. Thus, LSR activity can be increased or decreased, leptin activity can be increased or decreased, and lipoprotein activity can be increased or decreased. Similarly, FFA, TG, and glucose levels (and weight) can be increased or decreased in vivo. Free Fatty Acid oxidation can be increased or decreased in vivo or ex vivo.

By "LSR" activity is meant expression of LSR on the surface of the cell, or in a particular conformation, as well as its ability to bind, uptake, and degrade leptin and lipoprotein. By "leptin" activity is meant its binding, uptake and degradation by LSR, as well as its transport across a blood brain barrier, and potentially these occurrences where LSR is not necessarily the mediating factor or the only mediating factor. Similarly, by "lipoprotein" activity is meant its binding, uptake and degradation by LSR, as well as these occurrences where LSR is not necessarily the mediating factor or the only mediating factor. Exemplary assays are provided in Example 4–5, 7–14, 16, and 18. These assay and other comparable assays can be used to determine/identify compounds that modulate OBG3 polypeptide fragment activity. In some cases it may be important to identify compounds that modulate some but not all of the OBG3 polypeptide fragment activities, although preferably all activities are modified.

The term "increasing" as used herein refers to the ability of a compound to increase an OBG3 polypeptide fragment activity in some measurable way compared to the effect of an OBG3 polypeptide fragment in its absence. As a result of the presence of the compound leptin binding and/or uptake might increase, for example, as compared to controls in the presence of the OBG3 polypeptide fragment alone. Preferably, an increase in activity is at least 25%, 30%, 35%, 40%, 45%, 50%, 55%, 60%, 65%, 70%, or 75% compared to the level of activity in the presence of the OBG3 fragment.

Similarly, the term "decreasing" as used herein refers to the ability of a compound to decrease an activity in some measurable way compared to the effect of an OBG3 fragment in its absence. For example, the presence of the compound decreases the plasma concentrations of FFFA, TG, and glucose in mice. Also as a result of the presence of a compound leptin binding and/or uptake might decrease, for example, as compared to controls in the presence of the OBG3 fragment alone. Preferably, a decrease in activity is at least 25%, 30%, 35%, 40%, 45%, 50%, 55%, 60%, 65%, 70%, or 75% as compared to the level of activity in the presence of the OBG3 fragment alone.

The invention features a method for identifying a potential compound to modulate body mass in individuals in need of modulating body mass comprising: a) contacting a cell with a gOBG3 fragment and a candidate compound; b) detecting a result selected from the group consisting of LSR modulation, leptin modulation, lipoprotein modulation, FFA oxidation modulation; and c) wherein said result identifies said potential compound if said result differs from said result when said cell is contacted with the gOBG3 polypeptide fragment alone.

In preferred embodiments, said contacting further comprises a ligand of said LSR. Preferably said ligand is selected from the group consisting of cytokine, lipoprotein, free fatty acids, and C1q, and more preferably said cytokine is leptin, and most preferably said leptin is a leptin polypeptide fragment as described in U.S. Provisional application No. 60/155,506 hereby incorporated by reference herein in its entirety including any figures, drawings, or tables.

In other preferred embodiments, said OBG3 or gOBG3 polypeptide fragment is mouse or is human. In other preferred embodiments, said cell is selected from the group consisting of PLC, CHO-K1, Hep3B, and HepG2.

In yet other preferred embodiments, said lipoprotein modulation is selected from the group consisting of binding, uptake, and degradation. Preferably, said modulation is an increase in said binding, uptake, or degradation. Alternatively, said modulation is a decrease in said binding, uptake, or degradation.

In other preferred embodiments, leptin modulation is selected from the group consisting of binding, uptake, degradation, and transport. Preferably, said modulation is an increase in said binding, uptake, degradation, or transport. Alternatively, said modulation is a decrease in said binding, uptake, degradation, or transport. Preferably, said transport is across a blood-brain barrier.

In yet other preferred embodiments, said LSR modulation is expression on the surface of said cell. Preferably, said detecting comprises FACS, more preferably said detecting further comprises antibodies that bind specifically to said LSR, and most preferably said antibodies bind specifically to the carboxy terminus of said LSR.

In still other preferred embodiments, said potential compound is selected from the group consisting of peptides, peptide libraries, non-peptide libraries, peptoids, fatty acids, lipoproteins, medicaments, antibodies, small molecules, and proteases. Other characteristics and advantages of the invention are described in the Brief Description of the Figures and the Examples. These are meant to be exemplary only, and not to limit the invention in any way. Throughout this application, various publications, patents and published patent applications are cited. The disclosures of these publications, patents and published patent specifications referenced in this application are hereby incorporated by reference into the present disclosure.

VIII. Assays for Identifying Antagonists of Dipeptidyl Peptidase Cleavage of gOBG3 Polypeptide Fragment The invention features methods of screening for one or more antagonist compounds that block N-terminal cleavage of gOBG3 polypeptide fragment by dipeptidyl peptidase. Preferred said compound is selected from but is not restricted to small molecular weight organic or inorganic compound, protein, peptide, carbohydrate, or lipid. Preferred said dipeptidyl peptidase is human plasma comprised of dipeptidyl peptidase. Preferred dipeptidyl peptidase is selected from but not restricted to human CD26 or human Attractin. Further preferred dipeptidyl peptidase is selected from but is not restricted to soluble human CD26 or soluble human Attractin. Soluble human CD26 is produced by recombinant means using methods well known to those of ordinary skill in the art (U.S. Pat. No. 6,265,551 which disclosure is hereby incorporated by reference in its entirety). Soluble human Attractin is produced by recombinant means using methods well known to those of ordinary skill in the art (International Patent Application No. WO15651A1 which disclosure is hereby incorporated by reference in its entirety). Preferred said gOBG3 polypeptide fragment is selected from gOBG3 (85–244) or gOBG3 (103–244) of SEQ ID NO:6. Said dipeptidyl peptidase cleavage of said preferred gOBG3 polypeptide fragment (85–244) of SEQ ID NO:6 removes the N-terminal dipeptide VP. Said dipeptidyl peptidase cleavage of said preferred gOBG3 polypeptide fragment (103–244) of SEQ ID NO:6 removes the N-terminal dipeptide EP. An exemplary assay that may be used is described in Example 19.

Said methods of screening for an antagonist compound that blocks N-terminal cleavage of gOBG3 polypeptide fragment by dipeptidyl peptidase comprises: a) incubating and thereby contacting gOBG3 polypeptide fragment with or without a candidate compound and with dipeptidyl peptidase; b) detecting the result, wherein said result is cleavage of the N-terminal dipeptide of OBG3 polypeptide fragment, using a technology selected from but not restricted to enzyme-linked immunosorbent assay (ELISA), mass spectrometry, chromatography, radioisotopic counting, N-terminal sequencing, or functionality wherein said functionality is selected from the group consisting of LSR modulation, leptin modulation, lipoprotein modulation, FFA oxidation modulation; and c) wherein said result identifies said potential compound if said result differs from said result when gOBG3 polypeptide fragment is contacted with dipeptidyl peptidase alone. Preferred said gOBG3 polypeptide fragment is gOBG3 polypeptide fragment selected from amino acids 106–247 of SEQ ID NO:2 or SEQ ID NO:4. Most preferred said gOBG3 polypeptide fragment is gOBG3 polypeptide fragment selected from amino acids 85–244 or 103–244 of SEQ ID NO:6. Preferred said technology is ELISA, wherein said ELISA utilizes a monoclonal antibody that specifically binds to intact but not to dipeptidyl peptidase cleaved gOBG3 polypeptide fragment. Further preferred said technology is ELISA, wherein said ELISA utilizes a monoclonal antibody that specifically binds to intact (106–247) but not to dipeptidyl peptidase cleaved (108–247) gOBG3 polypeptide fragment of SEQ ID NO:2 or SEQ ID NO:4. Most preferred said technology is ELISA, wherein said ELISA utilizes a monoclonal antibody that specifically binds to intact (85–244) but not to dipeptidyl peptidase cleaved (87–244) gAPM1 polypeptide fragment of SEQ ID NO:6. Other most preferred said technology is ELISA, wherein said ELISA utilizes a monoclonal antibody that specifically binds to intact (103–244) but not to dipeptidyl peptidase cleaved (105–244) gAPM1 polypeptide fragment of SEQ ID NO:6.

The invention further features methods for determining the specificity of said antagonist of said dipeptidyl peptidase cleavage of said gOBG3 polypeptide fragment comprising: a) contacting said gOBG3 polypeptide fragment with said antagonist and said dipeptidyl peptidase; b) contacting an alternative substrate of said dipeptidyl peptidase with said antagonist and said dipeptidyl peptidase; c) detecting a result on the basis of a technology selected from but not restricted to enzyme-linked immunosorbent assay (ELISA), mass spectrometry, chromatography, radioisotopic counting, N-terminal sequencing, or functionality; and d) wherein said result identifies said antagonist as specific for gOBG3 polypeptide fragment if said result differs from said result for said alternative substrate of said dipeptidyl peptidase contacted with said dipeptidyl peptidase and said antagonist. Preferred said gOBG3 polypeptide fragment is gACRP30 polypeptide fragment of amino acids 106–247 of SEQ ID NO:2 or SEQ ID NO:4; preferred said alternative substrate of said dipeptidyl peptidase is selected from gAPM1 polypeptide fragment of amino acids 85–244 or 103–244 of SEQ ID NO:6. Most preferred said gOBG3 polypeptide fragment is gAPM1 polypeptide fragment of amino acids 85–244 of SEQ ID NO:6; preferred said alternative substrate of said dipeptidyl peptidase is selected from gAPM1 polypeptide fragment of amino acids 103–244 of SEQ ID NO: 6 and gOBG3 polypeptide fragment of amino acids 106–247 of SEQ ID NO:2 or SEQ ID NO:4. Other most preferred said gOBG3 polypeptide fragment is gAPM1 polypeptide fragment of amino acids 103–244 of SEQ ID NO:6; preferred said alternative substrate of said dipeptidyl peptidase is selected from gAPM1 polypeptide fragment of amino acids 85–244 of SEQ ID NO: 6 and gOBG3 polypeptide fragment of amino acids 106–247 of SEQ ID NO:2 or SEQ ID NO:4.

IX. Assays for Identifying Antagonists of OBG3 or gOBG3 Polypeptide Fragment Activity The invention features methods of screening compounds for one or more antagonists of OBG3 or gOBG3 polypeptide fragment activity, wherein said activity is selected from but not restricted to lipid partitioning, lipid metabolism, and insulin-like activity. Preferred said compound is selected from but is not restricted to small molecular weight organic or inorganic compound, protein, peptide, carbohydrate, or lipid. Preferred said polypeptide fragment is gOBG3 polypeptide fragment. Preferred said polypeptide fragment is gOBG3 polypeptide fragment. Preferred said gOBG3 polypeptide fragment is gOBG3 (104–247) of SEQ ID NO:2 or SEQ ID NO:4. Most preferred said gOBG3 polypeptide fragment is gAPM1 (101–244) of SEQ ID NO:6.

The invention further features methods of screening compounds for said antagonist of OBG3 or gOBG3 polypeptide fragment activity comprising: a) contacting said gOBG3 polypeptide fragment with or without said compound; b) detecting a result on the basis of activity, wherein said activity is selected from but not restricted to lipid partitioning, lipid metabolism, and insulin-like activity; and c) wherein said result identifies said antagonist as specific for gOBG3 polypeptide fragment if said result with compound differs from said result for said result without compound. Exemplary assays that may be used are described in Examples 4 and 18.

EXAMPLES

The following Examples are provided for illustrative purposes and not as a means of limitation. One of ordinary skill in the art would be able to design equivalent assays and methods based on the disclosure herein all of which form part of the instant invention.

It should be noted that the term full-length OBG3 polypeptide used throughout the specification is intended to encompass the protein homologs ACRP30 [Scherer, et al., "A novel serum protein similar to C1q, produced exclusively in adipocytes"; J Biol Chem 270, 26746–26749 (1995)], AdipoQ [Hu, et al., "AdipoQ is a novel adipose-specific gene dysregulated in obesity", J Biol Chem 271, 10697–10703 (1996)] and the human homolog APM1 [Maeda, et al., "cDNA cloning and expression of a novel adipose specific collagen-like factor, APM1 (AdiPose Most abundant Gene transcript 1)", Biochem Biophys Res Commun 221, 286–289 (1996)] or GBP28 [Nakano, et al., "Isolation and characterization of GBP28, a novel gelatin-binding protein purified from human plasma", J Biochem (Tokyo) 120, 803–812 (1996)]. OBG3 is also intended to encompass other homologs.

Example 1

Production of Recombinant OBG3

An exemplary method for generating recombinant OBG3 is given below. Although the method describes the production of the mouse analog, a person with skill in the art would be able to use the information provided to produce other OBG3 analogs, including but not limited to the human analog. An alignment of the amino acid sequences of the human (APM1) and mouse (AdipoQ and ACRP30) OBG3 is shown in FIG. 1.

The recombinant OBG3 analog is cloned in pTRC His B (Invitrogen) between BamH1 and Xho1 (FIG. 2) and maintained in *E. coli* DH5-alpha. The sequence of the OBG3 insert corresponds to ACRP30 genbank U37222 bases 88 to 791 except in position 382 where in #3 G replaces A found in ACRP 30 (V instead of M). The corresponding nucleotide in AdipoQ U49915 is G as in clone #3. The amino acid V is also conserved in the human sequence APM1 D45371.

Culture:

Plate out bacteria in LB agar media containing 100 μg/mL ampicillin. Inoculate 1 colony into 5 mL media (no agar) at 37° C. overnight. Add 2 mL of this initial culture into 500 mL Erlenmeyer flasks containing 200 mL LB media and 100 μg/mL ampicillin. Incubate at 37° C. in an orbital shaker until the $OD_{600}$=0.2. Add IPTG to a final concentration of 1 mM (stock solution=1 M). Incubate at 37° C. overnight.

Lysis:

Pellet the bacteria by centrifugation (Sorvall, 3500 rpm, 15 min, 4° C.) in a pre-weighed tube.

At 4° C. resuspend the pellet in 3 mL/g of lysis buffer

Add 40 μL/g PMSF 10 mM

Add 80 μL/g of lysozyme 10 mg/mL

Incubate 20 min on ice, shaking intermittently

Add 30 μL/g 10% sodium deoxycholate

Incubate at 37° C. until the lysate is viscous

Freeze in liquid Nitrogen and thaw at 37° C. three times

Sonicate 2×, 30 sec, 25% cycle, 2.5 power level

Centrifuge 30 min, 15000 rpm, 4° C.

Recover the supernatant

Note: The lysate can be stored frozen before or after the sonication step.

Batch Purification:

1. Pack 1 mL of Probond resin (Invitrogen; 1 mL=2 mL suspended gel) into a 5 ml column. Wash with 5 mL PBS.

2. Apply 5 mL bacterial supernatant to the 1 mL of gel. (If volume is very high, use several small columns.)

3. Wash with 24 mL phosphate buffer, pH 7.8, followed by a wash with 24 mL phosphate buffer, pH 6.

4. Elute with imidazole buffer and collect fractions of 1 mL.

5. Analyze fractions by OD at 280 nm or by SDS-PAGE (12.5%; dilution ½ in 2× sample buffer) under reducing conditions (100° C., 5 min)

6. Pool the fractions containing protein (usually fraction numbers 2–4 for concentrations of 0.8–1 mg/mL and fractions 1, 5 and 6 for concentrations of 0.2–0.4 mg/mL).

7. Dialyze thoroughly against 1×PBS, 24 mM ammonium bicarbonate or 50 mM Tris, pH 7.4 containing 250 nM NaCl. Concentrate by Speed-Vac if needed.

8. Analyze protein by the Lowry method.

9. Aliquot and store at −20° C.

Purification on Liquid Chromatography System

1. Pack 5 mL of Probond resin into a 5 mL column.

2. Wash with 4 bed volumes of phosphate buffer pH 7.8, 1 mL/min.

3. Inject 25 mL lysate (filtered on 0.45μ or centrifuged at 3000 rpm, 30 min, 4° C., Beckman Allegra 6R) at 0.5 mL/min.

4. Wash with 4 bed volumes of phosphate buffer, pH 7.8 at 1 mL/min.

5. Wash with 12 bed volumes of phosphate buffer pH 5.5 at 1 mL/min.

6. Elute bound fraction with phosphate buffer, pH 5.5, containing 1 M imidazole at 1 mL/min.

7. Collect fractions, dialyze and analyze protein as described for batch purification, steps 7–9.

Example 2

Generation of Globular OBG3 by Enzymatic Cleavage

Incubate purified OBG3 (obtained as described above or through equivalent method) with acetylated Trypsin-Type V-S from Bovine Pancreas (Sigma E.C.=3.4.21.4) at 400 u/mg protein at 25° C. for 10 min.

Stop reaction by running the sample over a Poly-Prep Column (Biorad 731-1550) at +4° C. containing immobilized Trypsin inhibitor.

Collect 1.0 mL fractions. Determine protein concentration.

Pool the protein containing fractions and dialyze extensively against PBS using dialysis tubing with M.W. cutoff=10,000 da.

Concentrate on Amicon YM-10 Centricon Filter (Millipore, M. W. cutoff=10,000 da). Sterile filter.

Determine final protein concentration using Markwell's modified Lowry procedure (1981) or BCA protein assay (Pierce Chemical Co, Rockford, Ill.) and BSA as standard.

Check purity and efficiency of cleavage by SDS-PAGE analysis using a 4–20% gradient gel. The intact OBG3 migrates as a single band at approximately 37 kDa apparently due to co-transcribed vector sequences attached to the histidine tag at the N-terminus of AdipoQ, and forms a dimer at 74 kDa. The cleaved OBG3 forms a band at approx. 18 kDa (gOBG3). Additional degradation products, all smaller than 10 kda are also generated from the N-terminal region. These are separated from the desired 18 kDa band by dialysis with semipermeable membranes with a MW cutoff of 10,000. The two potential cleavage sites for gOBG3 are shown in FIG. 3. The actual cleavage site has been identified as the one after amino acid 103 (amino acid 100 for human gOBG3 or APM1) (FIG. 7). That is, the N-terminus of the gOBG3 cleavage product is Lys 104 (Lys 101 for human gOBG3 or APM1).

Other enzymatic/proteolytic methods can also be used that yield a preferred OBG3 or gOBG3 polypeptide fragment, e.g. clostripain, adipsin, plasmin, collagenase, matrix metalloproteinase-1 (MMP-1), or precerebellin processing protease. Other preferred enzymes would preferably cleave OBG3 at a site close to the junction between the collagen-like tail and the globular head (about amino acid 108 for human gOBG3 and about amino acid 111 for murine gOBG3), preferably permit the reaction to be easily stopped, preferably be easily removed using an immobilized inhibitor, or similar method, and preferably cuts the N-terminal fragment into small pieces (less than 10,000 MW). The cleavage preferably results in the presence of no more than 8 collagen repeats, more preferably no more than 3 collagen repeats, and most preferably no collagen repeats. A collagen repeat consists of GLY-X-Y. A determination of whether an active gOBG3 has been generated can be checked using the in vitro and in vivo assays described herein (Examples 4–6, 8–10).

Example 3

Generation of gOBG3 by Recombinant Methodology Restriction Site Cloning

A first approach is to look for unique restriction sites near the beginning of the globular head region (nucleic acid sequences of mouse and human OBG3 polypeptides are provided in the sequence listing). If present, it can be used to cleave within the 5' collagen-like region and generate a C-terminal fragment comprised of the globular head region. If a unique site is not present, it is also possible, although more difficult, to do this using restriction enzymes that cut in more than one location by doing partial digestions. The 3' end of the globular head can be cut from its vector backbone using an appropriate enzyme. The globular head can then be cloned into an expression vector and constructs containing the correct fragments can be identified. For AdipoQ, Tau I seems to be a unique enzyme that would separate the collagen tail from the globular head.

PCR Cloning

Another approach is to PCR the region of interest from the intact sequence (if cDNA is available) using primers with restriction sites on the end so that PCR products can be directly cloned into vectors of interest. Alternatively, gOBG3 can also be generated using RT-PCR to isolate it from adipose tissue RNA.

*E. coli* Vector

For example, the AdipoQ globular region can be cloned into pTrcHisB, by putting a Bam HI site on the sense oligo and a Xho I site on the antisense oligo. This allows isolation of the PCR product, digestion of that product, and ligation into the pTrcHisB vector that has also been digested with Bam HI and Xho I (FIG. 4). The vector, pTrcHisB, has an N-terminal 6-Histidine tag, that allows purification of the over expressed protein from the lysate using a Nickel resin column. The pTrcHisB vector is used for over-expression of proteins in *E. coli.*

Exemplary oligos for cloning into the *E. coli* vector include:

A) OBG3 sense CTTAGTGGATCCCGCTTATGTG-TATCGCTCAG 6 base pairs from the left there is a 6 bp BamHI site. Thus the region that is homologous to the gene begins at nucleotide 13.

B) OBG3 antisense GCTGTTCTCGAGTCAGTTGG-TATCATGG 6 base pairs from the left there is a 6 bp. XhoI site. Thus the region that is homologous to the gene begins at nucleotide 13.

The following are exemplary PCR conditions.

Final concentrations in the reaction are:

1×PE Biosystems buffer A 1.5 mM $MgCl_2$ 200 uM of each dNTP (dATP, dCTP, dGTP, dTTP)

2.5 Units of Amplitaq Gold from PE Biosystems 0.4 uM of each primer (sense and antisense)

10 ng of plasmid template

Cycling Parameters:

95° C. 10 min—1 cycle

95° C. 30 sec

56° C. 30 sec

72° C. 30 sec repeat above 3 steps for 30 cycles

72° C. 7 min—1 cycle.

BAC Vector

The globular head can also be over expressed in a Baculovirus system using the 6×His Baculovirus kit (Pharmingen), for example. The AdipoQ globular region is cloned into the appropriate vector using enzymes available in the multiple cloning site. This allows over-expression of the protein in a eukaryotic system which has some advantages over the *E. coli* system, including: Multiple gene expression, Signal peptide cleavage, Intron splicing, Nuclear transport, Functional protein, Phosphorylation, Glycosylation, and Acylation.

Exemplary oligos for cloning into the Baculovirus vector are the following:

A). OBG3 sense CTTAGTGAATTCGCTTATGTG-TATCGCTCAGA 6 base pairs from the left there is a 6 bp. EcoRI site. Thus the region that is homologous to the gene begins at nucleotide 13.

B). OBG3 antisense GCTGTTCTGCAGTCAGTTGG-TATCATGG 6 base pairs from the left there is a 6 bp. PstI site. Thus the region that is homologous to the gene begins at nucleotide 13.

The following are exemplary PCR conditions.

Final concentrations in the reaction are:

1×PE Biosystems buffer A 1.5 mM $MgCl_2$ 200 uM of each dNTP (dATP, dCTP, dGTP, dTTP)

2.5 Units of Amplitaq Gold from PE Biosystems 0.4 uM of each primer (sense and antisense)

10 ng of plasmid template

Cycling Parameters:

95° C. 10 min—1 cycle

95° C. 30 sec

60° C. 30 sec

72° C. 30 sec repeat above 3 steps for 30 cycles

72° C. 7 min—1 cycle.

Mammalian Vector

Globular OBG3 can also be cloned into a mammalian expression vector and expressed in and purified from mammalian cells, for example 3T3-L1 cells (undifferentiated adipocyte precursors). The globular head is then generated in an environment very close to its endogenous environment. However, this is not necessarily the most efficient way to make protein.

Example 4

In Vitro Tests of Obesity-Related Activity

The activity of various preparations and various sequence variants of gOBG3 polypeptide fragments are assessed using various in vitro assays including those provided below. These assays are also exemplary of those that can be used to develop gOBG3 polypeptide fragment antagonists and agonists. To do that, the effect of gOBG3 polypeptide fragments in the above assays, e.g. on leptin and/or LSR activity, in the presence of the candidate molecules would be compared with the effect of gOBG3 polypeptide fragments in the assays in the absence of the candidate molecules. Since gOBG3 polypeptide fragments have been shown to reduce body weight in mice on a high-cafeteria diet (Example 5), these assays also serve to identify candidate treatments for reducing (or increasing) body weight.

Liver Cell Line:

Tests of efficacy of gOBG3 polypeptide fragments on LSR can be performed using liver cell lines, including for example, PLC, HepG2, Hep3B (human), Hepa 1–6, BPRCL (mouse), or MCA-RH777, MCA-RH8994 (rat). For human cell lines, APM1 and globular APM1 would be used preferentially; for rodents, full-length and globular AdipoQ/ACRP30 would be used preferentially.

BPRCL mouse liver cells (ATCC Repository) were plated at a density of 300,000 cells/well in 6-well plates (day 0) in DMEM (high glucose) containing glutamine and penicillin-streptomycin (Bihain & Yen, 1992). Media was changed on day 2. On day 3, the confluent monolayers were washed once with phosphate-buffered saline (PBS, pH 7.4) (2 mL/well). Cells were incubated at 37° C. for 30 min with increasing concentrations of recombinant AdipoQ (AQ) or globular AdipoQ (AQ-GH) in DMEM containing 0.2% (w/v) BSA, 5 mM Hepes, 2 mM $CaCl_2$, 3.7 g/L sodium bicarbonate, pH 7.5. Incubations were continued for 3 h at 37° C. after addition of 10 ng/mL $^{125}$I-mouse leptin (specific activity, 22100 cpm/ng). Monolayers were washed 2 times consecutively with PBS containing 0.2% BSA, followed by 1 wash with PBS/BSA, and then 2 times consecutively with PBS. Cells were lysed with 0.1 N NaOH containing 0.24 mM EDTA. Lysates were collected into tubes, and counted in a gamma-counter. Results of an exemplary experiment are shown as the mean of triplicate determinations in FIG. 5.

Figure 5:
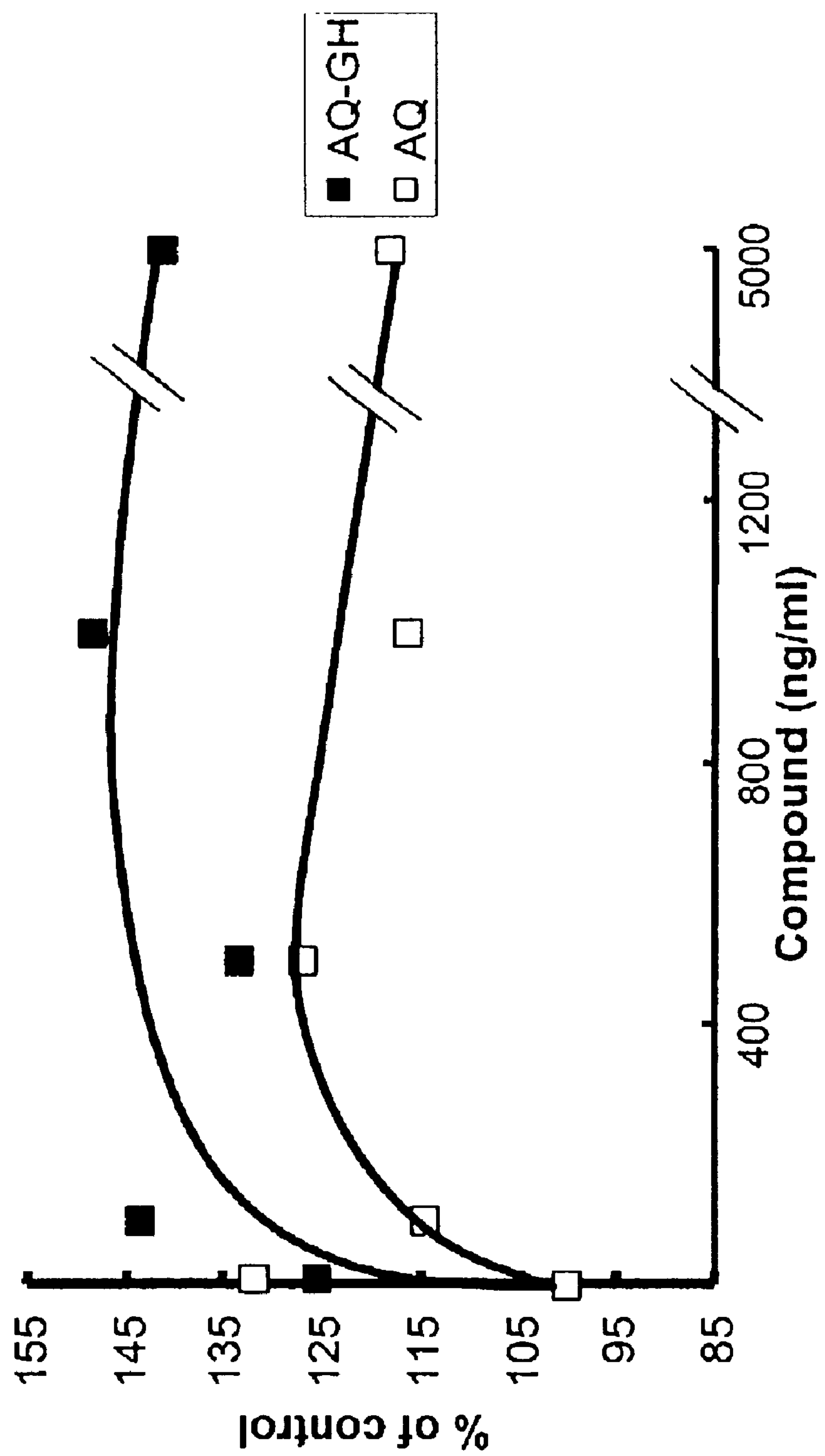
FIG. 5 is a graph showing a comparison of the effect of AdipoQ (AQ) and AdipoQ globular head (AQ-GH) on cell-associated $^{125}$I-leptin in the mouse liver cell line BPRCL. Results are shown as percent of control values in the presence of increasing amounts of compound (AQ or AQ-GH), and are the mean of triplicate determinations.

The results indicate that gOBG3 polypeptide fragments are at least 30% more efficient than OBG3 in increasing leptin uptake in a liver cell line (FIG. 5). This assay could be used to determine the efficiency of gOBG3 polypeptide fragments and related compounds (or agonists or antagonists) to increase or decrease leptin uptake into the liver, as well as the mechanism by which the gOBG3 polypeptide fragment/compound exerts this effect.

Blood Brain Barrier Model:

The effect of gOBG3 polypeptide fragments on leptin transport in the brain can be determined using brain-derived cells. One method that is envisioned is to use the blood/brain barrier model described by Dehouck, et al., "An easier, reproducible, and mass-production method to study the blood-brain barrier in vitro", J Neurochem 54, 1798–1801 (1990); hereby incorporated herein by reference in its entirety (including any figures, tables, or drawings) that uses a co-culture of brain capillary endothelial cells and astrocytes to test the effects of gOBG3 polypeptide fragments on leptin (or other molecules) transport via LSR or other receptors.

This assay would be an indicator of the potential effect of gOBG3 polypeptide fragments on leptin transport to the brain and could be used to screen gOBG3 polypeptide fragment variants for their ability to modulate leptin transport through LSR or other receptors in the brain. In addition, putative agonists and antagonists of the effect of gOBG3 polypeptide fragments on leptin transport through LSR or other receptors could also be screened using this assay. Increased transport of leptin across the blood/brain barrier would presumably increase its action as a satiety factor.

FACS Analysis of LSR Expression

The effect of gOBG3 polypeptide fragments on LSR can also be determined by measuring the level of LSR expression at the cell surface by flow surface cytometry, using anti-LSR antibodies and fluorescent secondary antibodies. Flow cytometry is a laser-based technology that is used to measure characteristics of biological particles. The underlying principle of flow cytometry is that light is scattered and fluorescence is emitted as light from the excitation source strikes the moving particles.

This is a high through-put assay that could be easily adapted to screen OBG3 and gOBG3 polypeptide fragments and variants as well as putative agonists or antagonists of gOBG3 polypeptide fragments. Two assays are provided below. The antibody, cell-line and gOBG3 polypeptide fragment analog would vary depending on the experiment, but a human cell-line, human anti-LSR antibody and globular APM1 could be used to screen for variants, agonists, and antagonists to be used to treat humans.

Assay 1:

Cells are pretreated with either intact OBG3 or gOBG3 polypeptide fragments (or untreated) before harvesting and analysis by FACs. Cells are harvested using non-enzymatic dissociation solution (Sigma), and then are incubated for 1 h at 4° C. with a 1:200 dilution of anti-LSR 81B or an irrelevant anti-serum in PBS containing 1% (w/v) BSA. After washing twice with the same buffer, goat anti-rabbit FITC-conjugated antibody (Rockland, Gilbertsville, Pa.) is added to the cells, followed by a further incubation for 30 mm at 4° C. After washing, the cells are fixed in 2% formalin. Flow cytometly analysis is done on FACsCalibur cytometer (Becton-Dickinson, Franklin Lakes, N.J.).

The in vitro Liver Cell Line assay (described above) has shown that LSR activity (leptin binding) increases with increasing concentrations of gOBG3 polypeptide fragments. While not wishing to be bound by any particular theory, this could either be the result of an increased number of LSR binding sites on the cell surface, or a change in affinity for leptin. The FACs assay would presumably be detecting changes in the number of LSR binding sites, although changes in conformation reflecting changes in affinity might also be detected. Preferably the antibody would be to the C-terminus of LSR.

Assay 2:

Cells are cultured in T175 flasks according to manufacturer's instructions for 48 hours prior to analysis.

Cells are washed once with FACS buffer (1×PBS/2% FBS, filter sterilized), and manually scraped from the flask in 10 mLs of FACS buffer. The cell suspension is transferred to a 15 mL conical tube and centrifuged at 1200 rpm, 4° C. for 5 minutes. Supernatant is discarded and cells are resuspended in 10 mL FACS buffer chilled to 4° C. A cell count is performed and the cell density adjusted with FACS buffer to a concentration of $1\times10^6$ cells/mL. One milliliter of cell suspension was added to each well of a 48 well plate for analysis. Cells are centrifuged at 1200 rpm for 5 minutes at 4° C. Plates are checked to ensure that cells are pelleted, the supernatant is removed and cells resuspended by running plate over a vortex mixer. One milliliter of FACS buffer is added to each well, followed by centrifugation at 1200 rpm for 5 minutes at 4° C. This described cell washing was performed a total of 3 times.

Primary antibody, titered in screening experiments to determine proper working dilutions (for example 1:25, 1:50, 1:100, 1:200, 1:400, 1:500, 1:800, 1:1000, 1:2000,1:4000, 1:5000, or 1:10000), is added to cells in a total volume of 50 μL FACs buffer. Plates are incubated for 1 h at 4° C. protected from light. Following incubation, cells are washed 3 times as directed above. Appropriate secondary antibody, titered in screening experiments to determine proper working dilutions (for example 1:25, 1:50, 1:100, 1:200, 1:400, 1:500, 1:800, 1:1000, 1:2000, 1:4000, 1:5000, or 1:10000), is added to cells in a total volume of 50 μL FAGs buffer. Plates are incubated for lh at 4° C. protected from light. Following incubation, cells are washed 3 times as directed above. Upon final wash, cells are resuspended in 500 μL FACs buffer and transferred to a FACs acquisition tube. Samples are placed on ice protected from light and analyzed within 1 hour.

Cellular Binding and Uptake of gOBG3 as Detected by Fluorescence Microscopy

Fluorecein isothiocyanate (FITC) conjugation of gOBG3: Purified gOBG3 at 1 mg/mL concentration was labeled with FITC using Sigma's FluoroTag FITC conjugation kit (Stock No. FITC-1). Protocol outlined in the Sigma Handbook for small-scale conjugation was followed for gOBG3 labeling.

Cell Culture: C2C12 mouse skeletal muscle cells (ATCC, Manassas, Va. CRL-1772) and Hepa-1–6 mouse hepatocytes (ATCC, Manassas, Va. CRL-1830) were seeded into 6 well plates at a cell density of $2\times10^5$ cells per well. C2C12 and Hepa-1–6 cells were cultured according to repository's instructions for 24–48 hours prior to analysis. Assay was performed when cells were 80% confluent.

FITC labeled gOBG3 cellular binding and uptake using microscopy: C2C12 and Hepa 16 cells were incubated in the presence/absence of antibody directed against human LSR (81B: N-terminal sequence of human LSR; does not cross react with mouse LSR and 93A: c-terminal sequence, cross reacts with mouse LSR) or an antiserum directed against gC1qr (953) for 1 hour at 37° C., 5% $CO_2$. LSR antibodies were added to the media at a concentration of 2 μg/mL. The anti-gc1qr antiserum was added to the media at a volume of 2.5 μL undiluted serum (high concentration) or 1:100 dilution (low concentration). Following incubation with specified antibody, FITC-gOBG3 (50 nM/mL) was added to each cell culture well. Cells were again incubated for 1 hour at 37° C., 5% $CO_2$. Cells were washed 2× with PBS, cells were scraped from well into 1 mL of PBS. Cell suspension was transferred to an eppendorf tube and centrifuged at 1000 rpm for 2 minutes. Supernatant was removed and cells resuspended in 200 μL of PBS. Binding and uptake of FITC-gOBG3 was analyzed by fluorescence microscopy under 40× magnification.

Analysis of C2C12 and Hepa 1–6 cells reveals identical phenotypes with respect to FITC-gOBG3 binding and uptake profiles both in the presence or absence of LSR antibodies. FITC-gOBG3 appears to be localized within vesicles in the cytoplasm of both mouse hepatocytes and mouse myoblasts, suggesting that binding and uptake of FITC-gOBG3 is occurring. FITC-gOBG3 uptake appears to be blocked when cells were pre-treated with the anti-LSR antibody that recognizes mouse LSR. However, binding of FITC-gOBG3 to the cell surface does occur in a small portion of the cells (C2C12 and Hepa 1–6). At low concentration of the gC1qr antiserum, FITC-gOBG3 appears to be localized within vesicles in the cytoplasm of both cell types, similarly to the phenotype of cells that have not received antibody pre-treatment prior to addition of FITC-gOBG3. FITC-gOBG3 uptake and binding phenotype is not affected by pre-treatment with an LSR antibody that does not recognize mouse LSR. Together, these data suggest that uptake of FITC-gOBG3 can be blocked by a human LSR antibody which cross-reacts with mouse LSR. However, this phenotype is not reproduced with other non cross-reactive LSR antibodies. Thus, this assay may be useful for identifying agents that facilitate or prevent the uptake and/or binding of OBG3 or gOBG3 polypeptide fragments to cells.

Effect on LSR as a Lipoprotein Receptor

The effect of gOBG3 on the lipoprotein binding, internalizing and degrading activity of LSR can also be tested. Measurement of LSR as lipoprotein receptor is described in Bihain & Yen, ((1992) Biochemistry 31(19):4628–36; hereby incorporated herein in its entirety including any drawings, tables, or figures). The effect of gOBG3 on the lipoprotein binding, internalizing and degrading activity of LSR (or other receptors) can be compared with that of intact OBG3, with untreated cells as an additional control. This assay can also be used to screen for active and inhibitory variants of gOBG3, as well as agonists and antagonists of obesity-related activity.

Human liver PLC cells (ATCC Repository) were plated at a density of 300,000 cells/well in 6-well plates (day 0) in DMEM (high glucose) containing glutamine and penicillin-streptomycin (Bihain & Yen, 1992). Media was changed on day 2. On day 3, the confluent monolayers were washed once with phosphate-buffered saline (PBS, pH 7.4) (2 mL/well). Cells were incubated at 37° C. for 30 min with 10 ng/mL human recombinant leptin in DMEM containing 0.2% (w/v) BSA, 5 mM Hepes, 2 mM $CaCl_2$, 3.7 g/L sodium bicarbonate, pH 7.5, followed by another 30 min incubation at 37° C. with increasing concentrations of gOBG3. Incubations were continued for 2 h at 37° C. after addition of 0.8 mM oleate and 20 μg/mL $^{125}$I-LDL. Monolayers were washed 2 times consecutively with PBS containing 0.2%

BSA, followed by 1 wash with PBS/BSA, and then 2 times consecutively with PBS. The amounts of oleate-induced binding, uptake and degradation of $^{125}$I-LDL were measured as previously described (Bihain & Yen, 1992, supra). Results are shown as the mean of triplicate determinations.

Figures 6A, 6B, 6C:
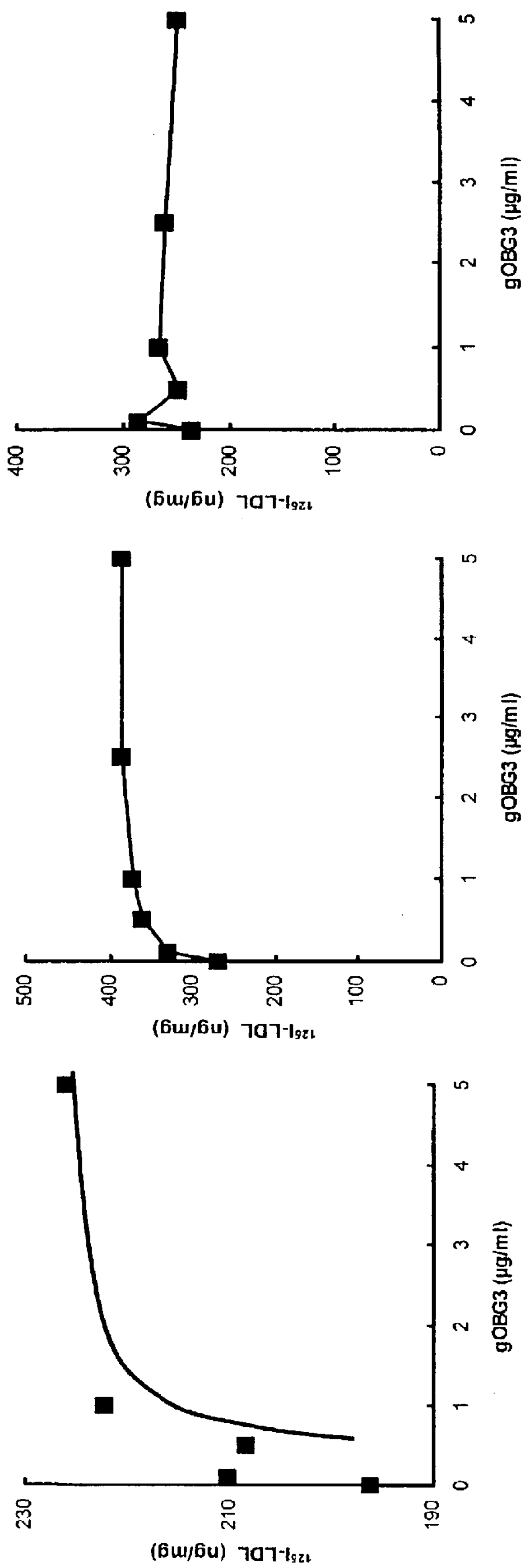
FIGS. 6A, 6B, and 6C show graphs of $^{125}$I-LDL binding, uptake, and degradation, respectively, in the mouse liver cell line BPRCL in the presence of increasing amounts of gOBG3.

As shown in FIG. 6, the addition of gOBG3 leads to an increased activity of LSR as a lipoprotein receptor. The oleate-induced binding and uptake of LDL appears more affected by gOBG3 as compared to the degradation. This increased LSR activity would potentially result in an enhanced clearance of triglyceride-rich lipoproteins during the postprandial state. Thus, more dietary fat would be removed through the liver, rather than being deposited in the adipose tissue. This assay could be used to determine the efficiency of a compound (or agonists or antagonists) to increase or decrease LSR activity (or lipoprotein uptake, binding and degradation through other receptors), and thus affect the rate of clearance of triglyceride-rich lipoproteins.

Effect on Muscle Differentiation

C2C12 cells (murine skeletal muscle cell line; ATCC CRL 1772, Rockville, Md.) are seeded sparsely (about 15–20%) in complete DMEM (w/glutamine, pen/strep, etc)+10% FCS. Two days later they become 80–90% confluent. At this time, the media is changed to DMEM+2% horse serum to allow differentiation. The media is changed daily. Abundant myotube formation occurs after 3–4 days of being in 2% horse serum, although the exact time course of C2C12 differentiation depends on how long they have been passaged and how they have been maintained, among other things.

To test the effect of the presence of gACRP30 on muscle differentiation, gACRP30 (1 to 2.5 μg/mL) was added the day after seeding when the cells were still in DMEM w/10% FCS. Two days after plating the cells (one day after gACRP30 was first added), at about 80–90% confluency, the media was changed to DMEM+2% horse serum plus gACRP30. The results show that the addition of gACRP30 causes the cells to begin organizing within one day after its addition. In contrast to the random orientation of the cells not treated with gACRP30, those treated with gACRP30 aligned themselves in relation to each other. In addition, differentiation occurred after only 2 days of gACRP30 treatment, in contrast to the 3 to 4 days needed in its absence.

Effect on Muscle Cell Fatty Acid Oxidation

C2C12 cells were differentiated in the presence or absence of 2 μg/mL gACRP30 for 4 days. On day 4, oleate oxidation rates were determined by measuring conversion of 1-$^{14}$C-oleate (0.2 mM) to $^{14}CO_2$ for 90 min. C2C12 cells differentiated in the presence of gACRP30 undergo 40% more oleate oxidation than controls differentiated in the absence of gACRP30. This experiment can be used to screen for active fragments and peptides as well as agonists and antagonists or activators and inhibitors of OBG3 and gOBG3 polypeptides.

The effect of gACRP30 on the rate of oleate oxidation was compared in differentiated C2C12 cells (murine skeletal muscle cells; ATCC, Manassas, Va. CRL-1772) and in a hepatocyte cell line (Hepa 1–6; ATCC, Manassas, Va. CRL-1830). Cultured cells were maintained according to manufacturer's instructions. The oleate oxidation assay was performed as previously described (Muoio et al (1999) Biochem J 338; 783–791). Briefly, nearly confluent myocytes were kept in low serum differentiation media (DMEM, 2.5% Horse serum) for 4 days, at which time formation of myotubes became maximal. Hepatocytes were kept in the same DMEM medium supplemented with 10% FCS for 2 days. One hour prior to the experiment the media was removed and 1 mL of preincubation media (MEM, 2.5% Horse serum, 3 mM glucose, 4 mM Glutamine, 25 mM Hepes, 1% FFA free BSA, 0.25 mM Oleate, 5 μg/mL gentamycin) was added. At the start of the oxidation experiment $^{14}$C-Oleic acid (1 μCi/mL, American Radiolabeled Chemical Inc., St. Louis, Mo.) was added and cells were incubated for 90 min at 37° C. in the absence/presence of 2.5 μg/mL gACRP30. After the incubation period 0.75 mL of the media was removed and assayed for $^{14}$C-oxidation products as described below for the muscle FFA oxidation experiment.

Oleate oxidation in C2C12 cells determined over 90 min increased significantly (39%; p=0.036, two-tailed t-Test) in cells treated with gACRP30. In contrast, no detectable increase in the rate of FFA oxidation was seen in hepatocytes incubated with gACRP30.

Triglyceride and Protein Analysis Following Oleate Oxidation in Cultured Cells

Following transfer of media for oleate oxidation assay, cells were placed on ice. To determine triglyceride and protein content, cells were washed with 1 mL of 1× PBS to remove residual media. To each well 300 μL of cell dissociation solution (Sigma) was added and incubated at 37° C. for 10 min. Plates were tapped to loosen cells, and 0.5 mL of 1× PBS was added. The cell suspension was transferred to an eppendorf tube, each well was rinsed with an additional 0.5 mL of 1× PBS, and was transferred to appropriate eppendorf tube. Samples were centrifuged at 1000 rpm for 10 minutes at room temperature. Supernatant was discarded and 750 μL of 1× PBS/2% chaps was added to cell pellet. Cell suspension was vortexed and placed on ice for 1 hour. Samples were then centrifuged at 13000 rpm for 20 mm at 4° C. Supernatants were transferred to new tube and frozen at −20° C. until analyzed. Quantitative measure of triglyceride level in each sample was determined using Sigma Diagnostics GPO-TRINDER enzymatic kit. The procedure outlined in the manual was adhered to, with the following exceptions: assay was performed in 48 well plate, 350 μL of sample volume was assayed, control blank consisted of 350 μL PBS/2% chaps, and standard contained 10 μL standard provided in kit plus 690 μL PBS/2% chaps. Analysis of samples was carried out on a Packard Spectra Count at a wavelength of 550 nm. Protein analysis was carried out on 25 μL of each supernatant sample using the BCA protein assay (Pierce) following manufacturer's instructions. Analysis of samples was carried out on a Packard Spectra Count at a wavelength of 550 nm.

Triglyceride production in both C2C12 and Hepa 1–6 cells did not change significantly in the absence/presence of ACRP30 and gACRP30. The protein content of all cells analyzed was equivalent in the absence/presence of ACRP30 and gACRP30.

In Vitro Glucose Uptake by Muscle Cells

L6 Muscle cells are obtained from the European Culture Collection (Porton Down) and are used at passages 7–11. Cells are maintained in standard tissue culture medium DMEM, and glucose uptake is assessed using [$^{3}$H]-2-deoxyglucose (2DG) with or without OBG3 or gOBG3 polypeptide fragment in the presence or absence of insulin ($10^{-8}$ M) as has been previously described (Walker, P. S. et al. (1990) Glucose transport activity in L6 muscle cells is regulated by the coordinate control of subcellular glucose transporter distribution, biosynthesis, and mRNA transcription. JBC 265(3):1516–1523; and Kilp, A. et al. (1992) Stimulation of hexose transport by metformin in L6 muscle cells in culture. Endocrinology 130(5):2535–2544, which disclosures are hereby incorporated by reference in their entireties). Uptake of 2DG is expressed as the percentage change compared with control (no added insulin or OBG3 or gOBG3 polypeptide fragment). Values are presented as mean±SEM of sets of 4 wells per experiment. Differences between sets of wells are evaluated by Student's t test, probability values $p<0.05$ are considered to be significant.

Example 5

Effect of gOBG3 on Mice Fed a High-Fat Diet

Experiments are performed using approximately 6 week old C57B1/6 mice (8 per group). All mice are housed individually. The mice are maintained on a high fat diet throughout each experiment. The high fat diet (cafeteria diet; D12331 from Research Diets, Inc.) has the following composition: protein kcal % 16, sucrose kcal % 26, and fat kcal % 58. The fat was primarily composed of coconut oil, hydrogenated.

After the mice are fed a high fat diet for 6 days, micro-osmotic pumps are inserted using isoflurane anesthesia, and are used to provide gOBG3, OBG3, saline, and an irrelevant peptide to the mice subcutaneously (s.c.) for 18 days. gOBG3 is provided at doses of 50, 25, and 2.5 μg/day; OBG3 is provided at 100, 50, and 5 μg/day; and the irrelevant peptide is provided at 10 μg/day. Body weight is measured on the first, third and fifth day of the high fat diet, and then daily after the start of treatment. Final blood samples are taken by cardiac puncture and are used to determine triglyceride (TG), total cholesterol (TC), glucose, leptin, and insulin levels. The amount of food consumed per day is also determined for each group.

In a preliminary experiment, mice treated with 2.5 μg/day gOBG3 had significantly lowered body weight.

Example 6

Tests of Obesity-Related Activity in Humans

Tests of the efficacy of gOBG3 in humans are performed in accordance with a physician's recommendations and with established guidelines. The parameters tested in mice are also tested in humans (e.g. food intake, weight, TG, TC, glucose, insulin, leptin, FFA). It is expected that the physiological factors would show changes over the short term. Changes in weight gain might require a longer period of time. In addition, the diet would need to be carefully monitored. Globular OBG3 would be given in daily doses of about 6 mg protein per 70 kg person or about 10 mg per day. Other doses would also be tested, for instance 1 mg or 5 mg per day up to 20 mg, 50 mg, or 100 mg per day.

Example 7

In Vivo Tests for Obesity-Related Activity in Rodent Diabetes Models

As metabolic profiles differ among various animal models of obesity and diabetes, analysis of multiple models is undertaken to separate the effects of OBG3 or gOBG3 polypeptide fragment on hyperglycemia, hyperinsulinemia, hyperlipidemia, and obesity. Mutation in colonies of laboratory animals and different sensitivities to dietary regimens have made the development of animal models with non-insulin dependent diabetes associated with obesity and insulin resistance possible. Genetic models such as db/db and ob/ob (See Diabetes (1982) 31(1):1–6) in mice and fa/fa in zucker rats have been developed by the various laboratories for understanding the pathophysiology of disease and for testing the efficacy of new antidiabetic compounds (Diabetes (1983) 32: 830–838; Annu Rep Sankyo Res Lab (1994) 46:1–57). Homozygous C57 BL/KsJ-db/db mice developed by Jackson Laboratory are obese, hyperglycemic, hyperinsulinemic, and insulin resistant (J Clin Invest (1990) 85:962–967), whereas heterozygous mice are lean and normoglycemic. In db/db model, mice progressively develop insulinopenia with age, a feature commonly observed in late stages of human type II diabetes when blood sugar levels are insufficiently controlled. The state of the pancreas and its course vary according to the models. Since this model resembles that of type II diabetes mellitus, the compounds of the present invention are tested for blood sugar and triglycerides lowering activities. Zucker (fa/fa) rats are severely obese, hyperinsulinemic, and insulin resistant (Coleman, Diabetes 31:1, 1982; E. Shafrir, in Diabetes Mellitus; H. Rifkin and D. Porte, Jr. Eds. (Elsevier Science Publishing Co., Inc., New York, ed. 4, 1990), pp. 299–340), and the fa/fa mutation may be the rat equivalent of the murine db mutation (Friedman et al. Cell 69:217–220, 1992; Truett et al., Proc Natl Acad Sci USA 88:7806, 1991). Tubby (tub/tub) mice are characterized by obesity, moderate insulin resistance and hyperinsulinemia without significant hyperglycemia (Coleman et al., J Heredity 81:424, 1990).

Previously, leptin was reported to reverse insulin resistance and diabetes mellitus in mice with congenital lipodystrophy (Shimomura et al. Nature 401:73–76 (1999); hereby incorporated herein in its entirety including any drawings, figures, or tables). Leptin was found to be less effective in a different lipodystrophic mouse model of lipoatrophic diabetes (Gavrilova et al Nature 403:850 (2000); hereby incorporated herein in its entirety including any drawings, figures, or tables). The instant invention encompasses the use of OBG3 or gOBG3 polypeptide fragments for reducing the insulin resistance and hyperglycaemia in this model either alone or in combination with leptin, the leptin peptide (U.S. Provisional Application No. 60/155,506), or other compounds. Assays include that described previously in Gavrilova et al. ((2000) Diabetes 49(11): 1910–6; (2000) Nature 403(6772):850) using A-ZIP/F-1 mice, except that OBG3 or gOBG3 polypeptide fragment would be administered using the methods previously described in Example 5 (or Examples 8–10). The glucose and insulin levels of the mice would be tested, and the food intake and liver weight monitored, as well as other factors, such as leptin, FFA, and TG levels, typically measured in our experiments (see Example 5, above, or Examples 8–10).

The streptozotocin (STZ) model for chemically-induced diabetes is tested to examine the effects of hyperglycemia in the absence of obesity. STZ-treated animals are deficient in insulin and severely hyperglycemic (Coleman, Diabetes 31:1, 1982; E. Shafrir, in Diabetes Mellitus; H. Riflkin and D. Porte, Jr. Eds. (Elsevier Science Publishing Co., Inc., New York, ed. 4, 1990), pp. 299–340). The monosodium glutamate (MSG) model for chemically-induced obesity (Olney, Science 164:719, 1969; Cameron et al., Clin Exp Pharmacol Physiol 5:41, 1978), in which obesity is less severe than in the genetic models and develops without hyperphagia, hyperinsulinemia and insulin resistance, is also examined. Finally, a non-chemical, non-genetic model for induction of obesity includes feeding rodents a high fat/high carbohydrate (cafeteria diet) diet ad libitum.

The instant invention encompasses the use of OBG3 and gOBG3 polypeptide fragment for reducing the insulin resistance and hyperglycemia in any or all of the above rodent diabetes models or in humans with Type I or Type II diabetes or other preferred metabolic diseases described previously or models based on other mammals. In the compositions of the present invention the OBG3 or gOBG3 polypeptide fragment may, if desired, be associated with other compatible pharmacologically-active antidiabetic agents such as insulin, leptin (U.S. Provisional Application No. 60/155,506), or troglitazone, either alone or in combination. Assays include that described previously in Gavrilova et al. ((2000) Diabetes 49(11):1910–6; (2000) Nature 403(6772):850) using A-ZIP/F-I mice, except that OBG3 or gOBG3 polypeptide fragment is administered intraperitoneally (i.p.), subcutaneously (s.c.), intramuscularly (i.m.), or intravenously (i.v.). The glucose and insulin levels of the mice would be tested, and the food intake and liver weight monitored, as well as other factors, such as leptin, FFA, and TG levels, typically measured in our experiments.

In Vivo Assay for Anti-Hyperglycemic Activity of OBG3 or gOBG3 Polypeptide Fragment Genetically altered obese diabetic mice (db/db) (male, 7–9 weeks old) are housed (7–9 mice/cage) under standard laboratory conditions at 22° C. and 50% relative humidity, and maintained on a diet of Purina rodent chow and water ad libitum. Prior to treatment, blood is collected from the tail vein of each animal and blood glucose concentrations are determined using One Touch Basic Glucose Monitor System (Lifescan). Mice that have plasma glucose levels between 250 to 500 mg/dl are used. Each treatment group consists of seven mice that are distributed so that the mean glucose levels are equivalent in each group at the start of the study. db/db mice are dosed by micro-osmotic pumps, inserted using isoflurane anesthesia, to provide OBG3 or gOBG3 polypeptide fragment, saline, and an irrelevant peptide to the mice subcutaneously (s.c.). Blood is sampled from the tail vein hourly for 4 hours and at 24, 30 h post-dosing and analyzed for blood glucose concentrations. Food is withdrawn from 04 h post dosing and reintroduced thereafter. Individual body weights and mean food consumption (each cage) are also measured after 24 h. Significant differences between groups (comparing OBG3 or gOBG3 fragment treated to saline-treated) are evaluated using Student t-test.

In Vivo Insulin Sensitivity Assay

In vivo insulin sensitivity is examined by utilizing two-step hyperinsulinemic-euglycemic clamps according to the following protocol. Rodents from any or all of the various models described in Example 2 are housed for at least a week prior to experimental procedures. Surgeries for the placement of jugular vein and carotid artery catheters are performed under sterile conditions using ketamine and xylazine (i.m.) anesthesia. After surgery, all rodents are allowed to regain consciousness and placed in individual cages. OBG3 or gOBG3 polypeptide fragment or vehicle is administered through the jugular vein after complete recovery and for the following two days. Sixteen hours after the last treatment, hyperinsulinemic-euglycemic clamps are performed. Rodents are placed in restrainers and a bolus of 4 μCi [3-$^3$H] glucose (NEN) is administered, followed by a continuous infusion of the tracer at a dose of 0.2 μCi/min (20 μl/min). Two hours after the start of the tracer infusion, 3 blood samples (0.3 ml each) are collected at 10 minute intervals (−20-0 min) for basal measurements. An insulin infusion is then started (5 mL/kg/min), and 100 μl blood samples are taken every 10 min. to monitor plasma glucose. A 30% glucose solution is infused using a second pump based on the plasma glucose levels in order to reach and maintain euglycemia. Once a steady state is established at 5 mL/kg/min insulin (stable glucose infusion rate and plasma glucose), 3 additional blood samples (0.3 ml each) are obtained for measurements of glucose, [3-$^3$H] glucose and insulin (100–120 min.). A higher dose of insulin (25 mL/kg/min.) is then administered and glucose infusion rates are adjusted for the second euglycemic clamp and blood samples are taken at 220–240 min. Glucose specific activity is determined in deproteinized plasma and the calculations of Rd and hepatic glucose output (HGO) are made, as described (Lang et al., Endocrinology 130:43, 1992). Plasma insulin levels at basal period and after 5 and 25 mL/kg/min. infusions are then determined and compared between OBG3 or gOBG3 fragment treated and vehicle treated rodents. Insulin regulation of glucose homeostasis has two major components; stimulation of peripheral glucose uptake and suppression of hepatic glucose output. Using tracer studies in the glucose clamps, it is possible to determine which portion of the insulin response is affected by OBG3 or gOBG3 polypeptide fragment.

Example 8

Effect of gOBG-3 on Plasma Free Fatty Acid in C57 BL/6 Mice

The effect of the globular head of ACRP30 on postprandial lipemia (PPL) in normal C57BL6/J mice was tested. ACRP30 is another name for adipo Q and is the mouse protein homologue to the human APM1 protein. OBG3 is a generic way to refer to all of these forms. The globular head form is indicated by placing a 'g' in front, e.g. gACRP30 or gOBG3. The gOBG3 used was prepared by proteolytic digestion of recombinant OBG3 as described previously in Example 2. Acetylated trypsin was used as protease.

The mice used in this experiment were fasted for 2 hours prior to the experiment after which a baseline blood sample was taken. All blood samples were taken from the tail using EDTA coated capillary tubes (50 μL each time point). At time 0 (8:30 AM), a standard high fat meal (6 g butter, 6 g sunflower oil, 10 g nonfat dry milk, 10 g sucrose, 12 mL distilled water prepared fresh following Nb#6, JF, pg. 1) was given by gavage (vol.=1% of body weight) to all animals.

Immediately following the high fat meal, 25 μg gOBG3 was injected i.p. in 100 μL saline. The same dose (25 μg/mL in 100 μL) was again injected at 45 min and at 1 hr 45 min (treated group, n=8). Control animals (n=8) were injected with saline (3×100 μL). Untreated and treated animals were handled in an alternating mode.

Blood samples were taken in hourly intervals, and were immediately put on ice. Plasma was prepared by centrifugation following each time point. Plasma was kept at −20° C. and free fatty acids (FFA), triglycerides (TG) and glucose were determined within 24 hours using standard test kits (Sigma and Wako). Due to the limited amount of plasma available, glucose was determined in duplicate using pooled samples. For each time point, equal volumes of plasma from all 8 animals per treatment group were pooled. Error bars shown for glucose therefore represent the SD of the duplicate determination and not the variation between animals as for TG and FFA.

Results

Figure 8:
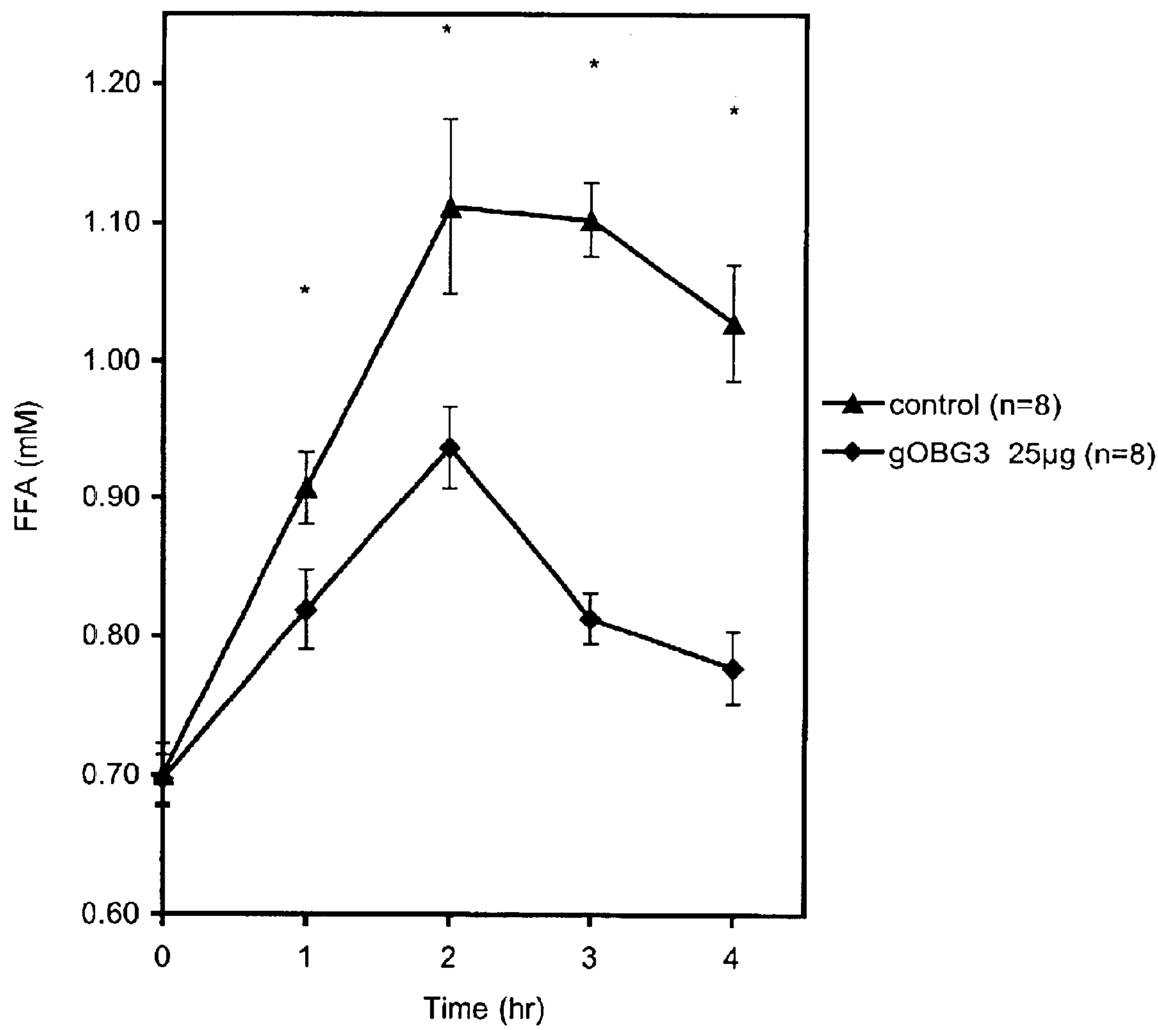
FIG. 8 shows a graphical representation of the effect of gOBG3 (3×25 μg ip) on plasma free fatty acids (FFA) in C57BL6/J mice following a high fat meal (* $p<0.02$).

The increase in plasma FFA due to the high fat meal was significantly lower in mice treated with gOBG3 at all time points between 1 and 4 hr. This can be interpreted as increase in FFA oxidation (FIG. 8).

Figure 9A:
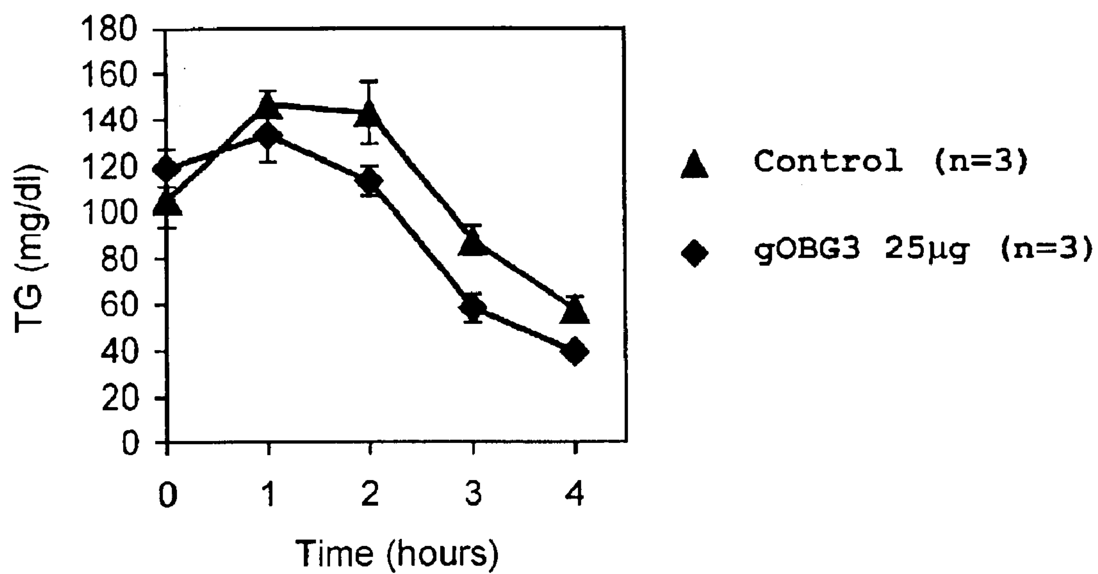
FIGS. 9A and 9B show graphical representations of the effect of gOBG3 (3×25 μg ip) on plasma triglycerides (TG) in C57BL6/J mice following a high fat meal ($p<0.05$ at 2, 3 and 4 hours).
Figure 9B:
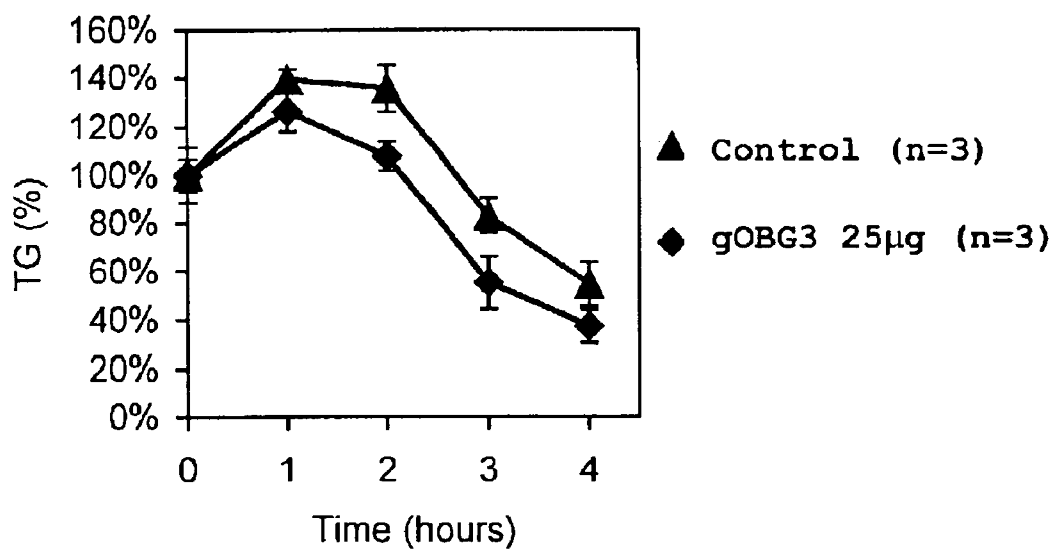

Treatment with gOBG3 also led to a significantly smaller increase in plasma TG compared to untreated mice. However, this effect was less pronounced than the effect on FFA (FIG. 9).

Figure 10:
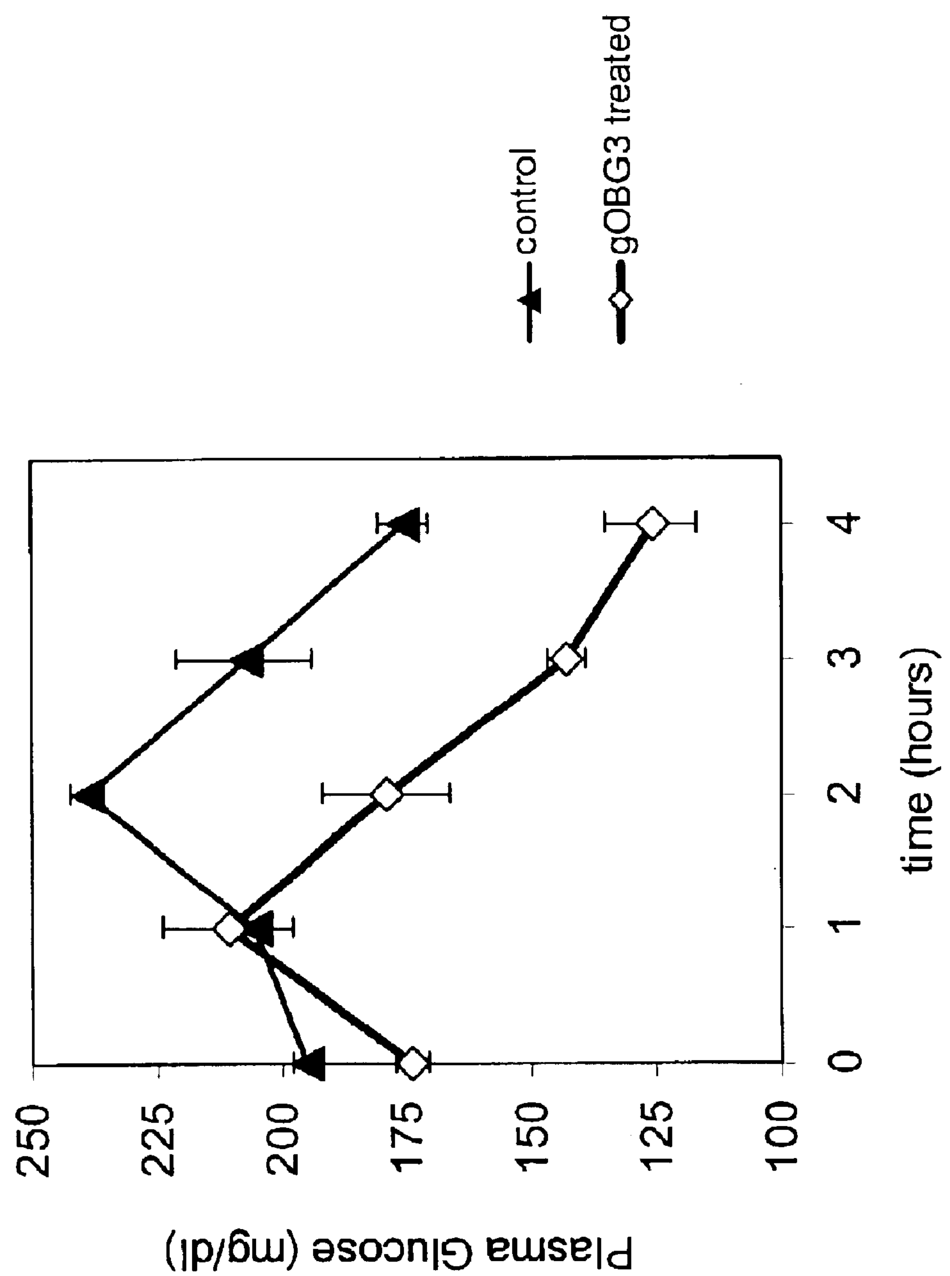
FIG. 10 shows a graphical representation of the effect of gOBG3 (3×25 μg ip) on plasma glucose in C57BL6/J mice following a high fat meal.

Glucose turnover was significantly improved following treatment with gOBG3; this effect can be interpreted as improved insulin sensitivity possibly due to the decrease in FFA (FIG. 10).

Similar results were seen previously in a prior experiment involving only 2 treatments (at 0 and at 45 minutes; data not shown). A strong FFA lowering effect of gOBG3 coupled with a less dominant TG lowering effect was observed.

Example 9

Effect of gOBG3 on Plasma Leptin and Insulin in C57 BL/6 Mice

The effect of the globular head of ACRP30 on plasma leptin and insulin levels during postprandial lipemia (PPL) in normal C57BL6/J mice was tested. The experimental procedure was the same as that described in Example 8, except that blood was drawn only at 0, 2 and 4 hours to allow for greater blood samples needed for the determination of leptin and insulin by RIA.

Briefly, 16 mice were fasted for 2 hours prior to the experiment after which a baseline blood sample was taken. All blood samples were taken from the tail using EDTA coated capillary tubes (100 μL each time point). At time 0 (9:00 AM), a standard high fat meal (see Example 8) was given by gavage (vol.=1% of body weight) to all animals. Immediately following the high fat meal, 25 μg gOBG3 was injected i.p. in 100 μL saline. The same dose (25 μg in 100 μL) was again injected at 45 min and at 1 hr 45 min (treated group, n=8). Control animals (n=8) were injected with saline (3×100 μL). Untreated and treated animals were handled in an alternating mode.

Blood samples were immediately put on ice and plasma was prepared by centrifugation following each time point. Plasma was kept at −20° C. and free fatty acids (FFA) were determined within 24 hours using a standard test kit (Wako). Leptin and Insulin were determined by RIA (ML-82K and SRI-13K, LINCO Research, Inc., St. Charles, Mo.) following the manufacturer's protocol. However, only 20 μL plasma was used. Each determination was done in duplicate. Due to the limited amount of plasma available, leptin and insulin were determined in 4 pools of 2 animals each in both treatment groups.

Results

Figure 12B:
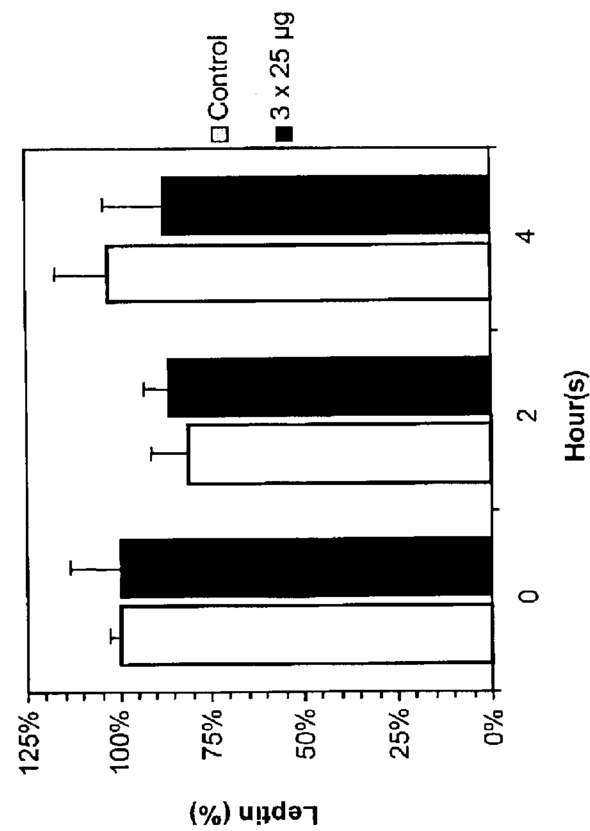
FIGS. 12A and 12B show graphical representations of the effect of gOBG3 (3×25 μg) on plasma leptin in C57BL6/J mice following a high fat meal.
Figure 12A:
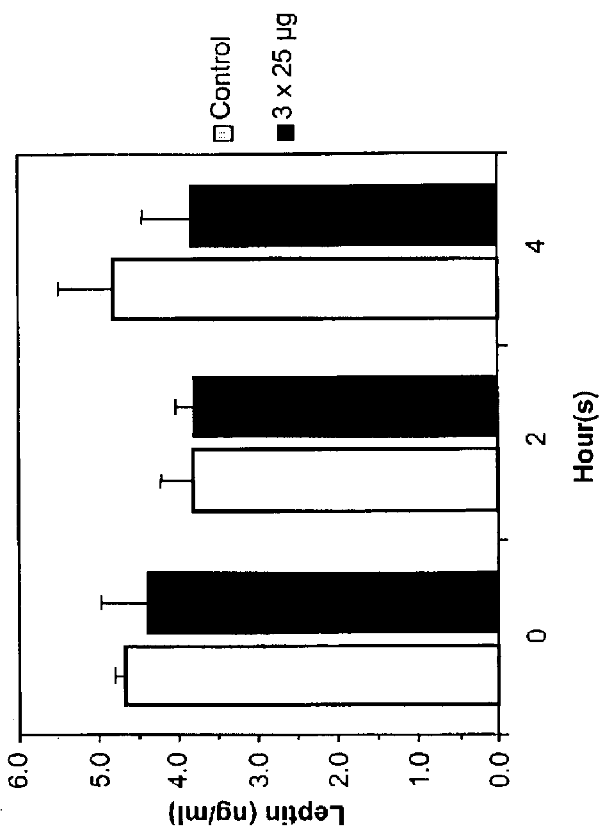
Figures 13A, 13B:
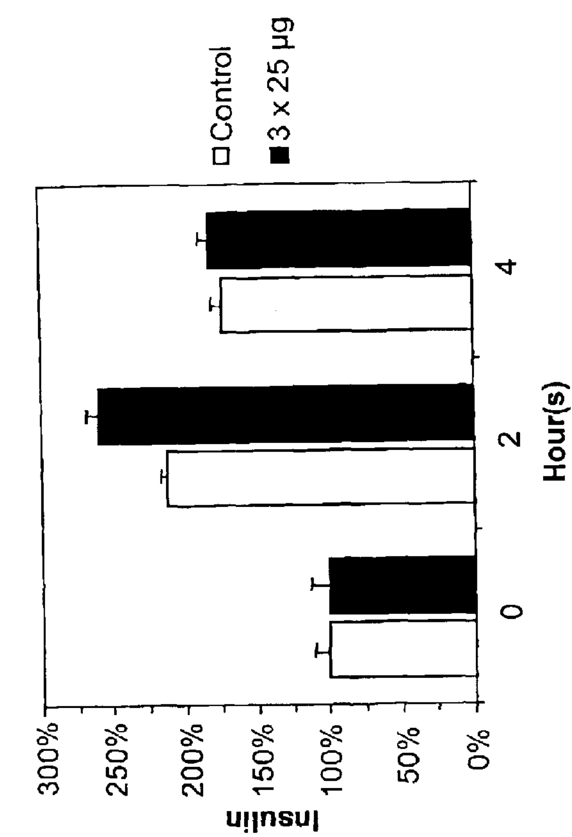
FIGS. 13A and 13B show graphical representations of the effect of gOBG3 (3×25 μg) on plasma Insulin in C57BL6/J mice following a high fat meal.

As shown previously (Example 8), treatment with gOBG3 significantly reduced the postprandial increase in plasma FFA caused by the high fat meal at 2 hours (FIG. 11). There was no significant change in plasma leptin levels at any time point; treatment with gOBG3 did not affect leptin levels (FIG. 12). Insulin levels (FIG. 13) indicate a marginal increase in insulin at 2 hours. However, when analyzed as percentage change from to, this increase (212% vs. 260%, control vs. treated) was statistically not significant (p=0.09).

These data reconfirm the previously shown acceleration of FFA metabolism by treatment with gOBG3. They also show that gOBG3 does not affect leptin and insulin plasma levels and that gOBG3 reduces hyperglycemia during postprandial lipemia and also induces weight loss during treatment over several days. Without being limited by any particular theory, the data suggests: a) that the reduction in weight is caused by a leptin independent increase in metabolism; and b) that gOBG3 leads to increased insulin sensitivity.

Example 10

Effect of OBG3 on Plasma FFA, TG and Glucose in C57 BL/6 Mice

The effect of the globular head of ACRP30 on plasma FFA, TG, glucose, leptin and insulin levels during postprandial lipemia (PPL) in normal C57BL6/J mice has been described. Weight loss resulting from gOBG3 (2.5 μg/day) given to normal C57BL6/J mice on a high fat diet has also been shown (Example 5). In comparison, a much higher dose of the complete form of ACRP30 (200 μg/day) was needed to induce a relatively smaller effect in mice. This example shows the effect of the ACRP30-complete form on plasma FFA, TG and glucose levels.

The experimental procedure was similar to that described in Example 8. Briefly, 14 mice were fasted for 2 hours prior to the experiment after which a baseline blood sample was taken. All blood samples were taken from the tail using EDTA coated capillary tubes (50 μL each time point). At time 0 (9:00 AM), a standard high fat meal (see Example 8) was given by gavage (vol.=1% of body weight) to all animals. Immediately following the high fat meal, 4 mice were injected 25 μg OBG3 i.p. in 10 μL saline. The same dose (25 μg in 100 μL) was again injected at 45 min and at 1 hr 45 min. A second treatment group (n=4) received 3 times 50 μg OBG3 at the same intervals. Control animals (n=6) were injected with saline (3×100 μL). Untreated and treated animals were handled in an alternating mode.

Blood samples were immediately put on ice. Plasma was prepared by centrifugation following each time point. Plasma was kept at −20° C. and free fatty acids (FFA), triglycerides (TG) and glucose were determined within 24 hours using standard test kits (Sigma and Wako).

Results

Figure 14B:
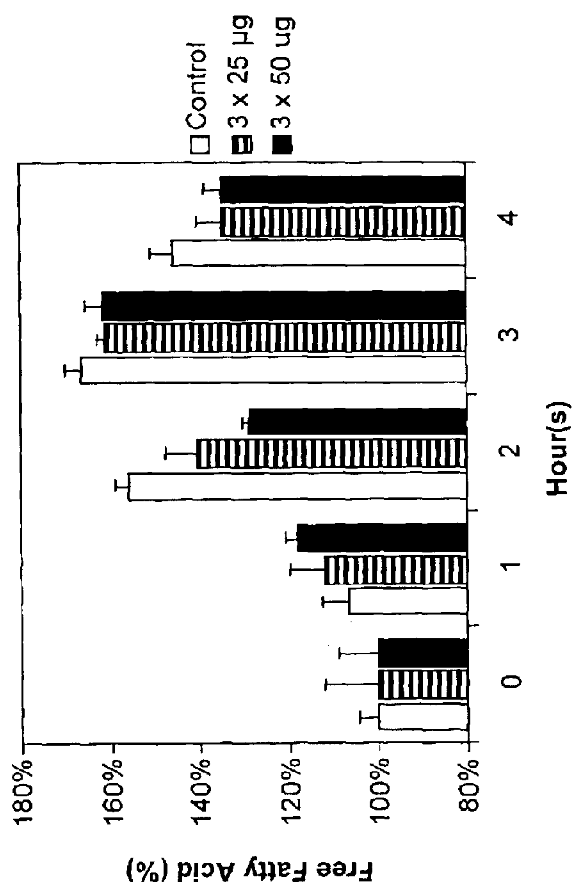
FIGS. 14A and 14B show graphical representations of the effect of OBG3 on plasma FFA in C57BL6/J mice following a high fat meal. At t=2 hours a significant reduction in FFA was seen for both treatment groups ($p<0.05$).
Figure 14A:
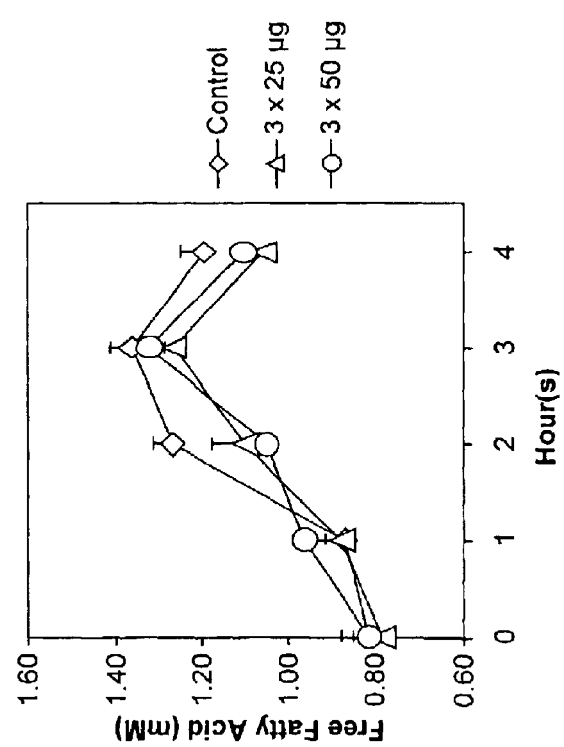
Figure 15B:
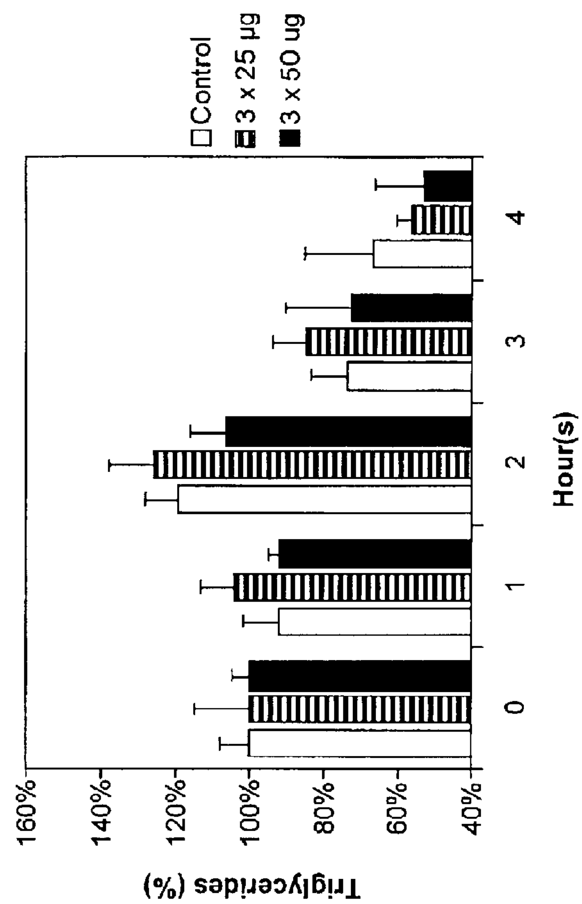
FIGS. 15A and 15B show graphical representations of the effect of OBG3 on plasma TG in C57BL6/J mice following a high fat meal.
Figure 15A:
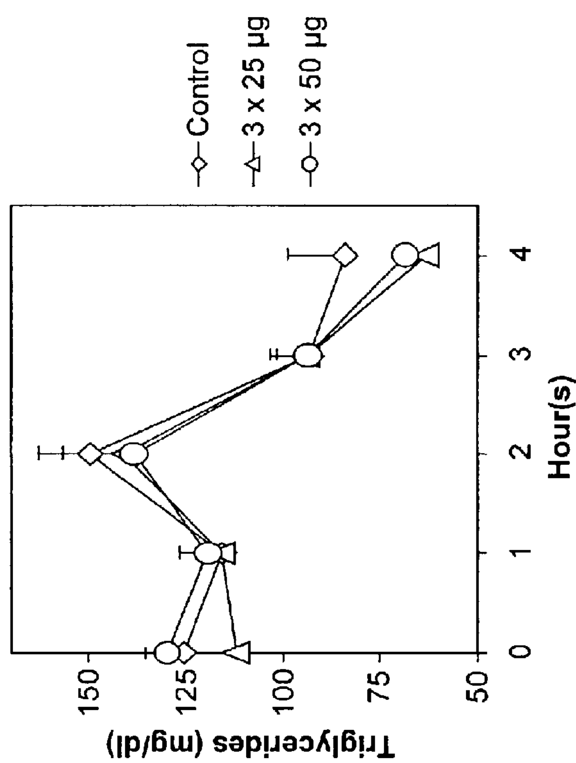
Figure 16B:
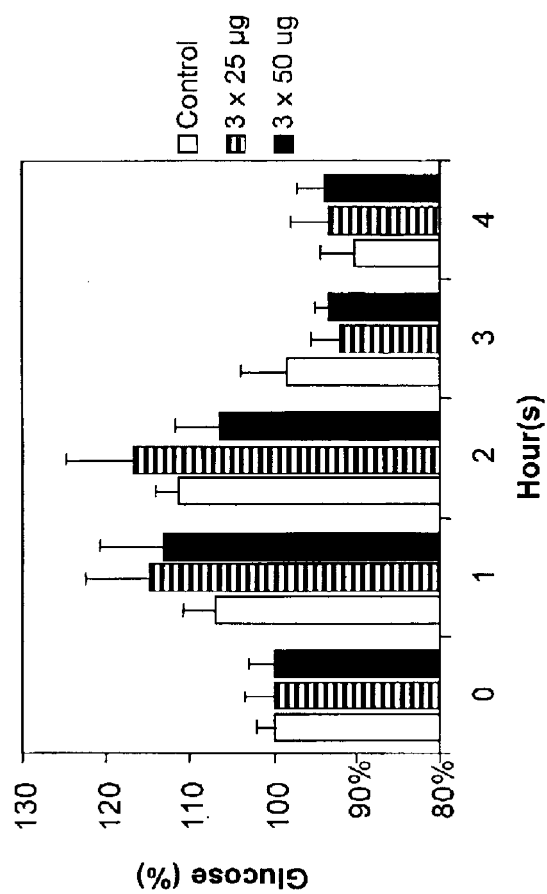
FIGS. 16A and 16B show graphical representations of the effect of OBG3 on plasma glucose in C57BL6/J mice following a high fat meal.
Figure 16A:
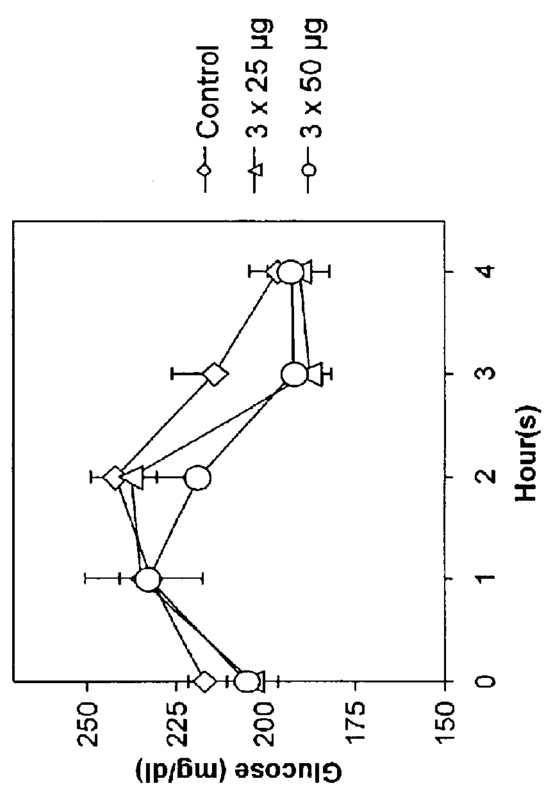

Treatment with full-length OBG3 had no effect on plasma FFA levels (FIG. 14) except for t=2 hours when a statistically significant reduction was shown (p<0.05). No significant change in postprandial TG (FIG. 15) and glucose levels (FIG. 16) was seen in treated animals. The data presented show that the complete form of OBG3 did not reduce FFA, TG and glucose levels in contrast to what was observed for the globular region (Examples 5, 8, 9). Only at 2 hours post-gavage, did treatment with OBG3 reduce FFA plasma concentrations significantly (p<0.05). These results demonstrate that gOBG3 is much more active in vivo than the full-length protein. A similar effect was seen for body weight reduction; the globular head was much more active than the full-length protein.

Example 11

Effect of gACRP30 on FFA Following Epinephrine Injection

In mice, plasma free fatty acids increase after intragastric administration of a high fat/sucrose test meal. These free fatty acids are mostly produced by the activity of lipolytic enzymes i.e. lipoprotein lipase (LPL) and hepatic lipase (HL). In this species, these enzymes are found in significant amounts both bound to endothelium and freely circulating in plasma. Another source of plasma free fatty acids is hormone sensitive lipase (HSL) that releases free fatty acids from adipose tissue after β-adrenergic stimulation. To test whether gACRP30 also regulates the metabolism of free fatty acid released by HSL, mice were injected with epinephrine.

Figure 18B:
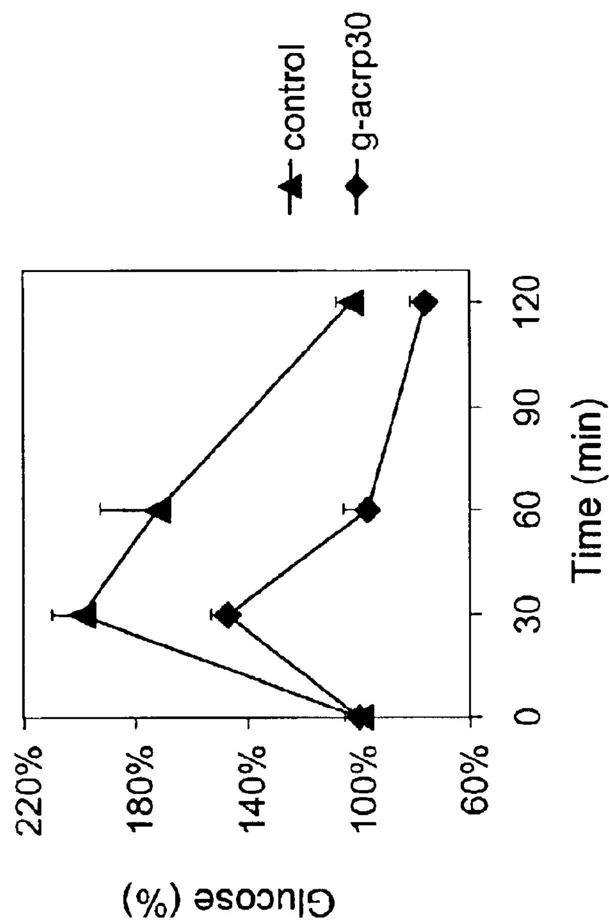
FIGS. 18A and 18B show graphical representations of the effect of gACRP30 injection in mice on the FFA (FIG. 18A) and glucose (FIG. 18B) increases resulting from epinephrine injection.
Figure 18A:
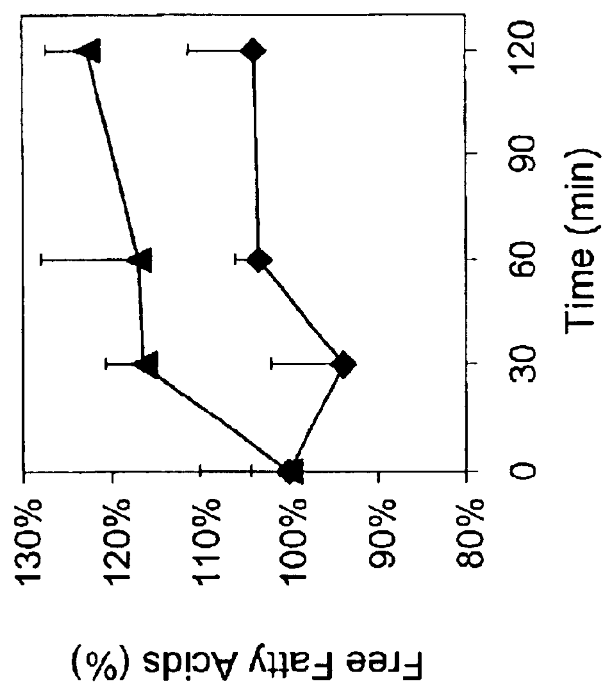

Two groups of mice (n=5 each) were given epinephrine (5 μg) by intraperitoneal injection. A treated group was injected with gACRP30 (25 μg) one hour before and again together with epinephrine, while control animals received saline. Plasma was isolated and free fatty acids and glucose were measured as described above (Example 10). As shown in FIG. 18, epinephrine injections (5 μg) caused an increase in plasma free fatty acids and glucose. Both effects were significantly reduced in gACRP30-treated mice.

This reduction in the increases of glucose and FFA levels was not due to blockage of the β-adrenergic effect of epinephrine, as shown by inducing the release of FFA from isolated adipose tissue in vitro. In these control studies, adipose tissue was removed from normal C57BL/6J mice and incubated in Krebs-Henseleit bicarbonate buffer. Epinephrine was added and the concentration of FFA in the medium following a 90 min incubation was determined. Epinephrine (10 uM) caused a 1.7-fold increase in free fatty acids in the media. Increasing concentrations of gACRP30 or ACRP30 up to 50 μg/ml did not inhibit this effect of epinephrine. The data presented thus far indicate that the globular region of ACRP30 exerts profound pharmacological effects on the metabolism of energy substrates with the most evident effect on plasma free fatty acids. Further, the reduction in plasma FFA concentration cannot be explained by inhibition of either LPL which would cause an increase in plasma triglycerides while a decrease of plasma triglycerides is actually observed, or by inhibition of HSL. Thus, the simplest explanation is that gACRP30 causes increased removal of free fatty acids from the circulation by promoting cellular uptake.

Example 12

Effect of gACRP30 on Muscle FFA Oxidation

To investigate the effect of gACRP30 on muscle free fatty acid oxidation, intact hind limb muscles from C57BL/6J mice were isolated and FFA oxidation was measured using oleate as substrate [Clee, et al., "Plasma and vessel wall lipoprotein lipase have different roles in atherosclerosis", J Lipid Res 41, 521–531 (2000); Muoio, et al., "Leptin opposes insulin's effects on fatty acid partitioning in muscles isolated from obese ob/ob mice", Am J Physiol 276, E913921 (1999). Oleate oxidation in isolated muscle was measured as previously described [Cuendet, et al., "Decreased basal, noninsulin-stimulated glucose uptake and metabolism by skeletal soleus muscle isolated from obese-hyperglycemic (ob/ob) mice", J Clin Invest 58, 1078–1088 (1976); Le Marchand-Brustel, et al., "Insulin binding and effects in isolated soleus muscle of lean and obese mice", Am J Physiol 234, E348-E358 (1978)]. Briefly, mice were sacrificed by cervical dislocation and soleus and EDL muscles were rapidly isolated from the hind limbs. The distal tendon of each muscle was tied to a piece of suture to facilitate transfer among different media. All incubations were carried out at 30° C. in 1.5 mL of Krebs-Henseleit bicarbonate buffer (118.6 mM NaCl, 4.76 mM KCl, 1.19 mM $KH_2PO_4$, 1.19 mM $MgSO_4$, 2.54 mM $CaCl_2$, 25 mM $NaHCO_3$, 10 mM Hepes, pH 7.4) supplemented with 4% FFA free bovine serum albumin (fraction V, RIA grade, Sigma) and 5 mM glucose (Sigma). The total concentration of oleate (Sigma) throughout the experiment was 0.25 mM. All media were oxygenated (95% $O_2$; 5% $CO_2$) prior to incubation. The gas mixture was hydrated throughout the experiment by bubbling through a gas washer (Kontes Inc., Vineland, N.J.).

Muscles were rinsed for 30 min in incubation media with oxygenation. The muscles were then transferred to fresh media (1.5 mL) and incubated at 30° C. in the presence of 1 μCi/mL [1-$^{14}$C] oleic acid (American Radiolabeled Chemicals). The incubation vials containing this media were sealed with a rubber septum from which a center well carrying a piece of Whatman paper (1.5 cm×11.5 cm) was suspended.

After an initial incubation period of 10 min with constant oxygenation, gas circulation was removed to close the system to the outside environment and the muscles were incubated for 90 min at 30° C. At the end of this period, 0.45 mL of Solvable (Packard Instruments, Meriden, Conn.) was injected onto the Whatman paper in the center well and oleate oxidation by the muscle was stopped by transferring the vial onto ice.

After 5 min, the muscle was removed from the medium, and an aliquot of 0.5 mL medium was also removed. The vials were closed again and 1 mL of 35% perchloric acid was injected with a syringe into the media by piercing through the rubber septum. The $CO_2$ released from the acidified media was collected by the Solvable in the center well. After a 90 min collection period at 30° C., the Whatman paper was removed from the center well and placed in scintillation vials containing 15 mL of scintillation fluid (HionicFlour, Packard Instruments, Meriden, Conn.). The amount of $^{14}$C radioactivity was quantitated by liquid scintillation counting. The rate of oleate oxidation was expressed as mmol oleate produced in 90 min/g muscle.

To test the effect of gACRP30 or ACRP30 on oleate oxidation, these proteins were added to the media at a final concentration of 2.5 μg/mL and maintained in the media throughout the procedure.

Figure 19:
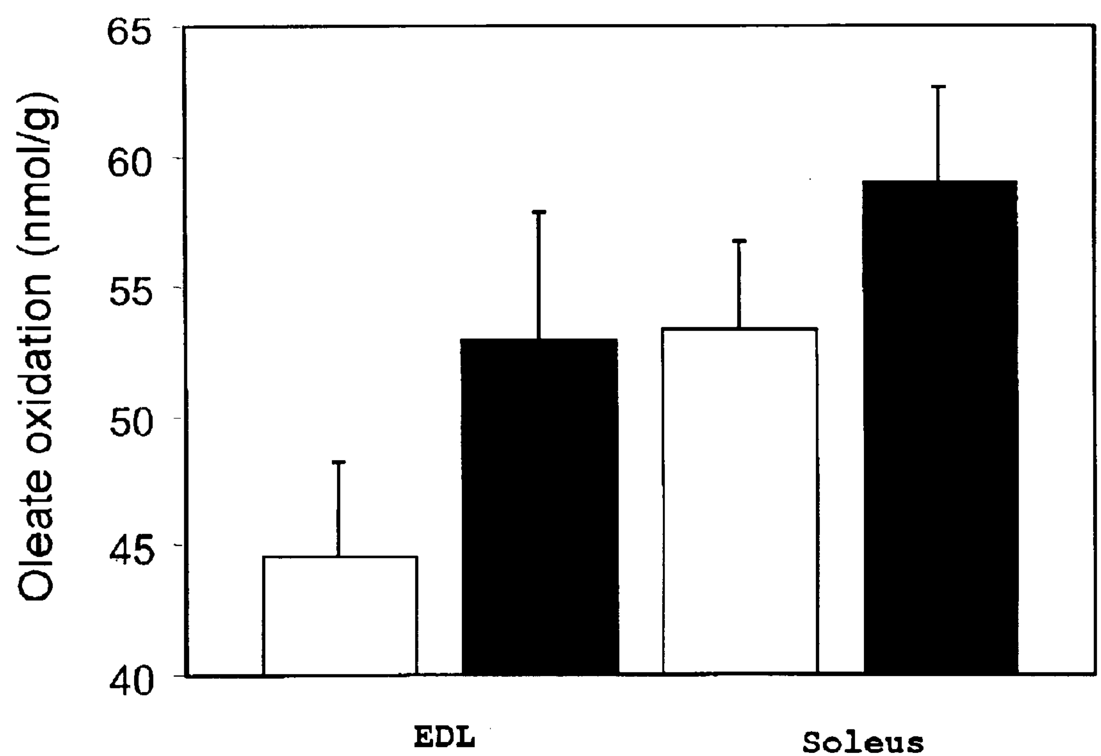
FIG. 19 shows a graphical representation of the effect of gACRP30 treatment on fatty acid metabolism in muscle isolated from mice. Treatments shown are control (yellow) and gACRP30 (red).

Two muscles of different oxidative capacity (soleus and extensor digitorum longus (EDL)) were tested (FIG. 19). EDL and Soleus muscles were isolated from both legs of normal C57BL/6J mice (n=18). One muscle of each pair was incubated in medium with 2.5 μg/mL gACRP30 (dark gray) and one in medium without gACRP30 (control—light gray). This experimental design allowed us to compare oleate oxidation in pairs of muscles isolated from the same animal. $^{14}$C-Oleate oxidation was determined over 90 minutes. Incubation of EDL and soleus muscles for 90 minutes in medium containing 2.5 μg/ml gACRP30 leads to a statistically significant increase in oleate oxidation ($p<0.05$, paired, one-tailed, t-Test) or ($p=0.0041$, Repeated Measures Analysis of Variance, Univariate Tests of Hypotheses for Within Subject Effects) in both muscle types.

Both muscle types showed a significant response to gACRP30. The relative increase in FFA oxidation was 17% ($p=0.03$) and 10% ($p=0.04$) for EDL and soleus, respectively. In humans, muscles represent approximately 25% of body weight. Therefore, even a moderate increase in free fatty acid oxidation can have quantitatively important consequences on overall energy utilization.

Example 13

Effect of gACRP30 on Triglyceride in Muscle & Liver Isolated from Mice

To determine whether the increased FFA oxidation induced by gACRP30 is also accompanied by increased FFA delivery into muscle or liver, the hindlimb muscle and liver triglyceride content was measured after gACRP30 treatment of mice. Hind limb muscles as well as liver samples were removed from treated and untreated animals and the triglyceride and free fatty acid concentration was determined following a standard lipid extraction method Shimabukuro, et al., "Direct antidiabetic effect of leptin through triglyceride depletion of tissues", Proc Natl Acad Sci USA 94, 4637–4641 (1997) followed by TG and FFA analysis using standard test kits.

Figures 20A, 20B:
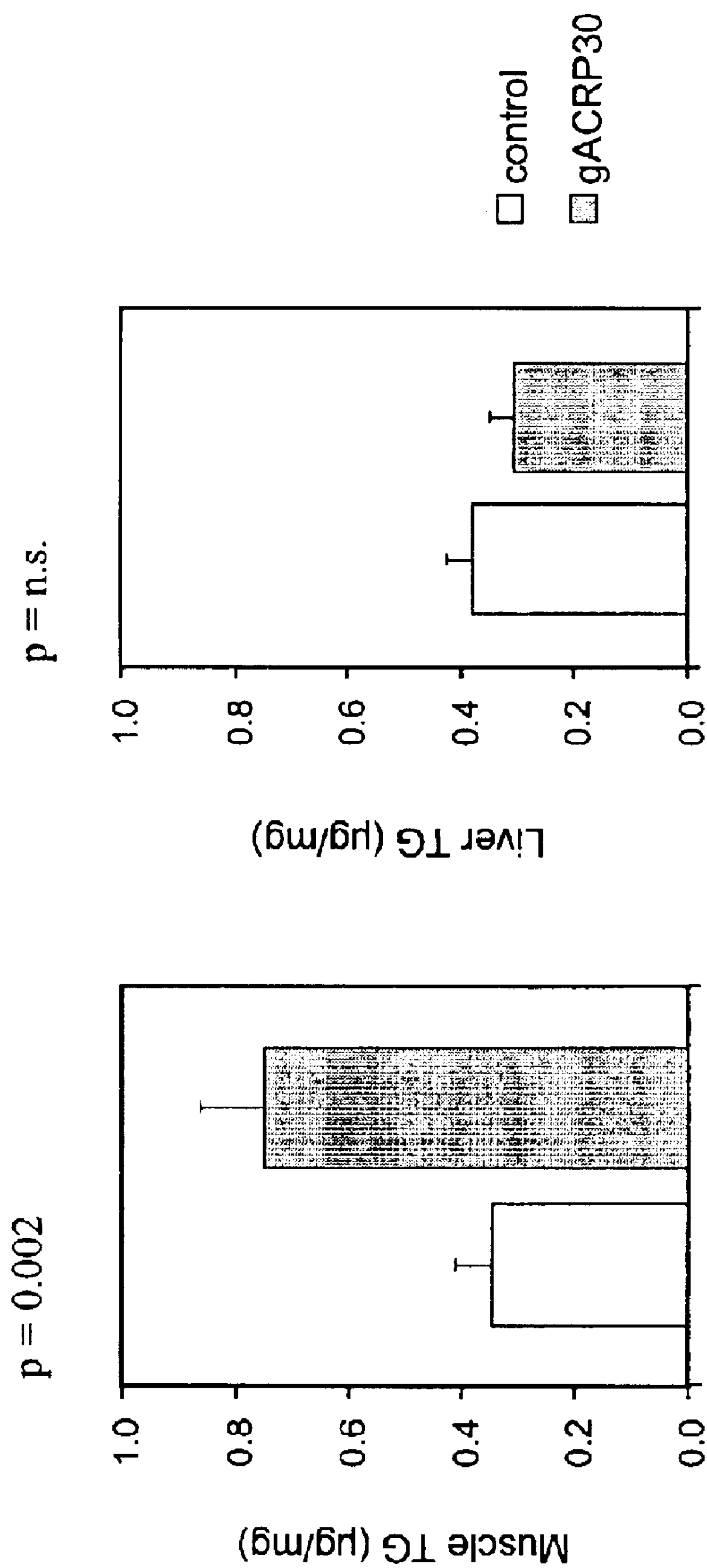
FIGS. 20A and 20B show a graphical representation of the effect of gACRP30 treatment on triglyceride content of muscle and liver isolated from mice.

Short-term treatment of animals with gACRP30 (2 injections of 25 μg each given within 3 hours before sacrifice) did not change the triglyceride content either of hind limb muscle or liver tissue (data not shown). However, after 3 days of treatment, during which period normal C57BL/6J mice consumed a regular rodent diet, mice that had received 25 μg of gACRP30 twice daily showed significantly higher (p=0.002) muscle triglyceride content (FIG. 20A) than those receiving saline (control: light gray; gACRP30: dark gray). This contrasted with a lack of increase in liver triglycerides (FIG. 20B). Furthermore, no detectable increase in muscle TG was observed after the 16-day treatment shown independently by directly measuring the muscle TG content and by oil red O staining of frozen microscope sections. In summary, the data indicate that the increase in TG content was transient.

These data are consistent with the notion that gACRP30 increases the rate of removal of free fatty acids from plasma at least partly by increasing their delivery to the muscle; much of the FFAs are immediately oxidized while some are stored as triglycerides and subsequently oxidized. Further support for this interpretation was obtained by measuring the concentration of ketone bodies in plasma of treated and untreated animals following a high fat/sucrose meal.

Ketone bodies (KB) are produced in the liver as a result of free fatty acid oxidation, but KB formation does not occur significantly in muscle. In mice receiving the high fat test meal and saline injection, the level of plasma KB increased significantly over the next 3 hours (183+12%, n=6). Animals treated with gACRP30, on the other hand, showed no increase in plasma KB concentrations. Thus, gACRP30 inhibits either directly KB formation or can decrease KB production by inhibiting liver FFA oxidation.

Example 14

Effect of 2ACRP30 on Weight Gain and Weight Loss of Mice

Two independent studies showed that gACRP30 also affects overall energy homeostasis. In the first, 10-week-old male C57BL/6J mice were put on a very high fat/sucrose purified diet for 19 days to promote weight gain (see Example 5); the average body weight at this time was 30 g. The mice were then surgically implanted with an osmotic pump (Alzet, Newark, Del.) delivering either 2.5 μg/day of gACRP30, 5 μg/day of ACRP30, or physiological saline. The mice were continued on the high fat diet and their body weight was recorded over the following 10-day period.

Figure 21B:
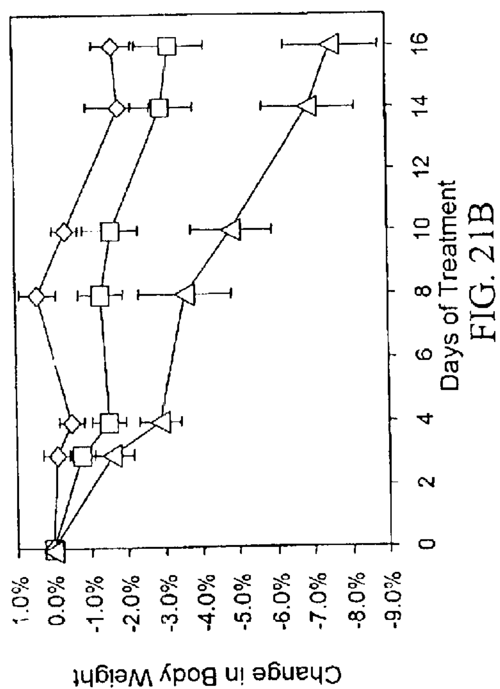
FIGS. 21A, 21B, 21C, & 21D show graphical representations of the effect of gACRP30 treatment on weight gain & loss in mice. Treatments shown are saline (diamond), ACRP30 (filled square), and gACRP30 (triangle).
Figure 21D:
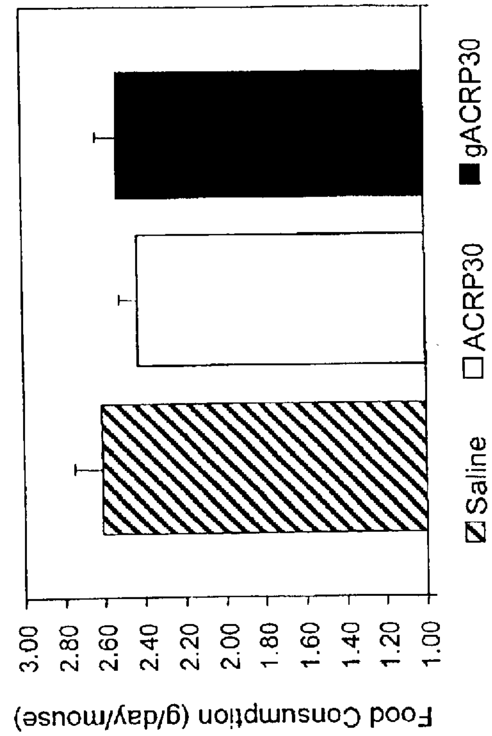
Figure 21A:
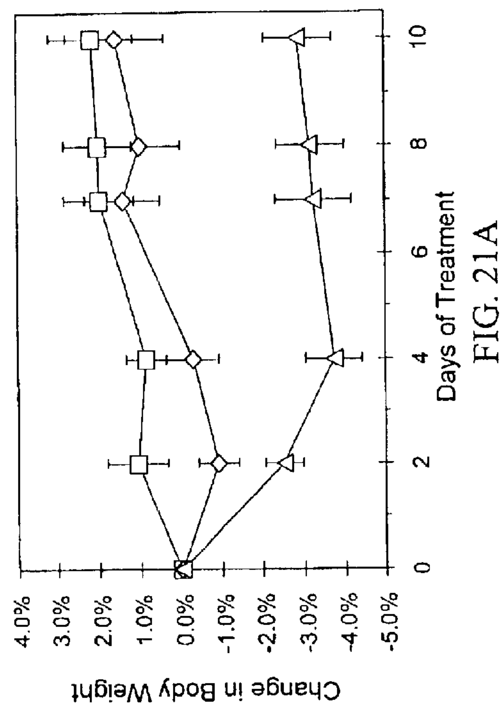

Mice treated with saline or 5 μg/day of full-length ACRP30 continued to gain weight at an average daily rate of 0.16% and 0.22%, respectively. In contrast, mice treated with gACRP30 experienced a significant weight reduction (−3.7%, p=0.002) during the first 4 days and then their weight remained constant (FIG. 21A). Thus, in this inbred strain of normal mice, a continuous infusion of a daily low dose of gACRP30 can prevent weight gain caused by high fat/sucrose feeding, in a sustainable way.

This result was confirmed and extended in a second study performed in mature 9 month old, male obese C57BL/6J mice that had been on the same high fat/sucrose diet for 6 months; the average body weight when the study began was 52.5+0.8 g. Three groups of 8 mice were treated with saline, ACRP30 or gACRP30 for 16 days. Animals in the treated group received twice daily 25 μg of protein subcutaneously. Body weights were recorded at the indicated time points.

Treatment with gACRP30 led to significant (p<0.05) weight loss at day 3. This effect became even more significant as the study continued. During the 16 day study period, the obese C57BL/6J mice that received gACRP30 lost about 8% (p=0.001) of their initial body weight despite the fact that they were maintained on a high fat/sucrose diet (FIG. 21B). Saline treated animals showed only marginal fluctuations in their body weight (p=n.s.). Animals treated with the full-length ACRP30, but at a 10-fold higher dose than that used in the first experiment, also lost significant weight (−3.2%, p=0.025). Interestingly, mice treated with gACRP30 continued to lose weight at a steady rate during the 16-day study period, while the rate of weight reduction in those treated with the full-length ACRP30 decreased during the later phase of the study. Food consumption in gACRP30 treated animals was not significantly different from saline or ACRP30 treated animals (FIG. 21D).

Figure 21C:
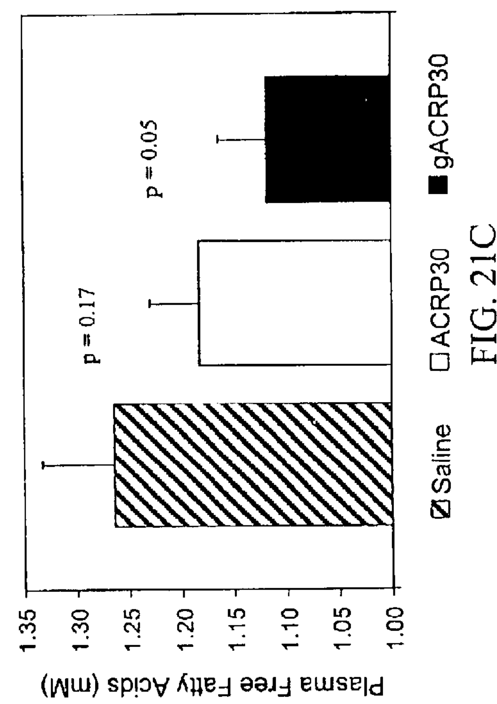

Treatment with gACRP30 caused a significant reduction in the concentration of plasma free fatty acids (FIG. 21C). This effect was significant after 3 days of treatment (p<0.05 vs. saline) and continued throughout the complete study period. Shown is the plasma FFA level at day 16 of the study. The initial FFA plasma concentration was the same in all three treatment groups. It should be noted, however, that despite this reduction the plasma free fatty acid concentration of these massively obese animals remains about 40–60% higher than that of normal mice. A blood chemistry analysis (including determination of SGPT, SGOT, urea, creatinine or bilirubin) performed on the terminal blood samples did not reveal any abnormal plasma parameters (FIG. 22).

Data are expressed throughout as mean±SEM; a p-value<0.05 was considered statistically significant. Statistical analysis was typically done using either the unpaired Student's t test or the paired Student's t test, as indicated in each study.

Example 15

Detection of APM1 (gOBG3) Fragment in Human Plasma After Immunoprecipitation

Figures 23A, 23B:
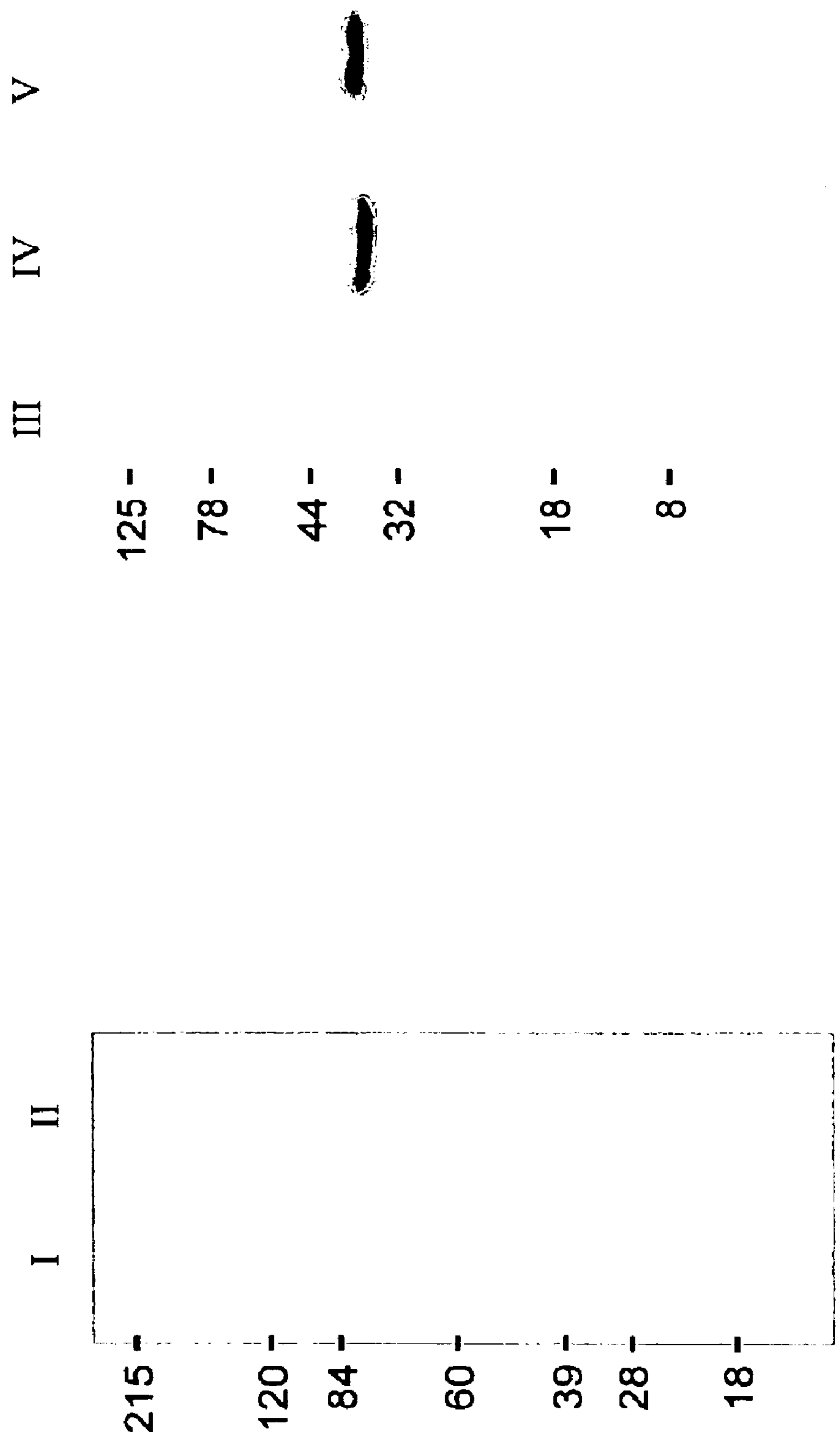
FIGS. 23A and 23B show a SDS-PAGE separation of the purification of ACRP30 and gACRP30 (23A) and a cleavage product of APM1 (23B).

The recombinant form of ACRP30 protein used has an apparent molecular weight of 37 kDa and forms a dimer of 74 kDa (FIG. 23A, Lane II). A proteolytic fragment that contains the entire globular head region (gACRP30) and that migrates with an apparent molecular weight of 18 kDa was generated using acetylated trypsin (FIG. 23A, lane I). Both protein preparations (ACRP30 and gACRP30) were essentially endotoxin free; ActiClean Etox affinity columns (Sterogene Bioseparations Inc., Carlsbad, Calif.) were used to remove potential endotoxin contaminations following the manufacturer's protocol. Endotoxin levels were determined by Endosafe, Charleston, S.C. As determined by N-terminal sequencing of purified gACRP30, the site of cleavage was just before amino acid 104 (just before amino acid 101 for human gOBG3 or APM1).

Immunoprecipitation of human plasma APM1 followed by Western blotting was used to detect a cleavage product of APM1, the human homolog of ACRP30, using a globular head specific anti-serum for the immunoprecipitation step as well as for the detection step. Preimmune serum or serum raised against the globular head domain or human non-homologous region (HDQETTTQGPGVLLPLPKGA) were cross-linked to protein A (Sigma Chemical CO, Saint Louis, Mo.) using dimethyl-pimelimidate-dihydrochloride (Sigma Chemical Co, Saint Louis, Mo.). After washing (0.2 M salt) proteins were eluted from protein A, separated by SDS-PAGE, transferred to Protran® pure nitrocellulose membrane (Schleicher and Schuell, Keene, N.H.) using standard procedures. APM1 products were visualized using globular head domain antibodies labeled with biotin; horseradish peroxidase conjugated to Streptavidin and CN/DAB substrate kit (Pierce, Rockford, Ill.) according to manufacturer's instructions.

The apparent molecular weight of this truncated form was 27 kDa, corresponding to about 70% of the complete form of APM1 (FIG. 23B, Lane IV). This truncated form was not detectable when immunoprecipitation was performed using a different antibody directed against the human non-homologous region (HDQETTTQGPGVLLPLPKGA) of APM1; this domain is located toward the $NH_2$ terminal end of the protein outside of the globular domain (FIG. 23, Lane V). Both anti-APM1 antibodies directed against either the globular or the non-globular domain identified the full-length form of the protein, as well as a low abundance dimer of apparent MW 74 kDa.

Example 16

Effect of gACRP30 on FFA Following Intralipid Injection

Two groups of mice (n=5 each) were intravenously (tail vein) injected with 30 μL bolus of Intralipid-20% (Clintec) to generate a sudden rise in plasma FFAs, thus by-passing intestinal absorption. (Intralipid is an intravenous fat emulsion used in nutritional therapy). A treated group (♦ gACRP30-treated) was injected with gACRP30 (25 μg) at 30 and 60 minutes before Intralipid was given, while control animals (▲ control) received saline. Plasma was isolated and FFAs were measured as described previously.

Figure 24:
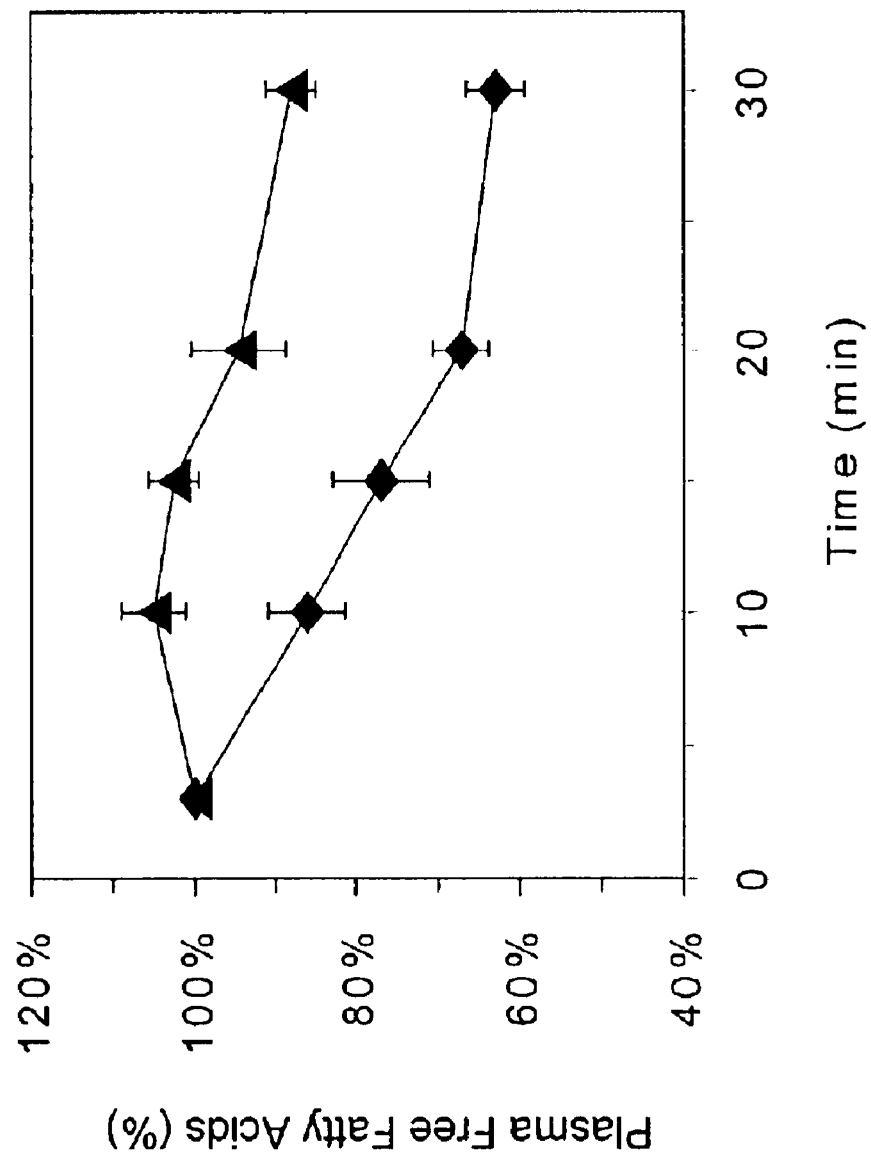
FIG. 24 shows a graph depicting the removal of plasma FFAs after Intralipid injection following treatment with gACRP30 (diamonds) or a saline control (triangles).

The effect of gACRP30 on the decay in plasma FFAs following the peak induced by Intralipid injection was then monitored. As shown in FIG. 24, gACRP30 accelerates the removal of FFAs from plasma after Intralipid injection. Thus, gACRP30 accelerates the clearance of FFAs without interfering with intestinal absorption. Although not wishing to be bound by any theory, because Intralipid does not elicit a significant insulin response, the results also indicate that gACRP30 regulation of FFA metabolism occurs independently of insulin.

Example 17

Solubilization of OBG3 and Fragments thereof

Vector construction: Polynucleotides encoding for polypeptides comprising amino acid residues 111–191, 191–244, 101–244, 105–244, or 110–244 of APM1 (SEQ ID NO:6) or amino acid residues 104–247 of ACRP30 (SEQ ID NO:4) were cloned into bacterial expression vector pTrcHis. Polynucleotides encoding for polypeptides comprising amino acid residues 111–191, 191–244, 101–244, 110–244 or 19–244 (full-length) of APM1 (SEQ ID NO:6) were cloned into a modified bacterial expression vector pET30a (containing His Tag at C-terminal of the APM1 polypeptides). Polynucleotides encoding for polypeptides comprising amino acid residues 111–191, 191–244, 101–244, 105–244, 110–244, or 19–244 of APM1 (SEQ ID NO:6) or amino acid residues 104–247 of ACRP30 (SEQ ID NO:4) were cloned into Baculoviral expression vector FastBacHT. Polynucleotides encoding for polypeptides comprising amino acid residues 111–191, 191–244, 101–244, 105–244, or 110–244 of APM1 (SEQ ID NO:6) were cloned into mammalian expression vector pcDNA4HisMax. Polynucleotides encoding for polypeptides comprising amino acid residues 1–244 or 1–19 and 101–244 of APM1 (SEQ ID NO:6) were cloned into mammalian expression vector pcDNA3.1Hygro. Alternatively, polynucleotides encoding for polypeptides comprising amino acid residues 1–244, 18–244, 85–244, 101–244, 102–244, 103–244, 111–191, 191–244, 144–199, or any fragment of APM1 (SEQ ID NO:6), or amino acid residues 88–247, 104–247, 105–247, 106–247 or any fragment of ACRP30 (SEQ ID NO:4) are cloned into any bacterial, mammalian, or baculoviral expression vector, preferably selected from pTrcHis, pET30a, FastBacHT, pcDNA4His, or pcDNA3.1Hygro. Alternately, polynucleotides encoding for polypeptides comprising amino acid residues 18–244, 85–244, 101–244, 102–244, 103–244, 111–191, 191–244, 144–199, or any fragment of APM1 (SEQ ID NO:6), or amino acid residues 88–247, 104–247, 105–247, 106–247 or any fragment of ACRP30 (SEQ ID NO:4) are cloned into *Pichia Pastoris* (yeast) expression vector, preferably PHIL-S1.

Cell growth and induction of OBG3 expression: DH5alpha *E. coli* host cells were transformed with a pTrcHis expression vector containing polynucleotides of SEQ ID NO:5 encoding for a polypeptide comprising amino acid residues 110–244 of APM1 (SEQ ID NO:6), also referred to as gAPM1 (110–244). Cells were grown overnight at room temperature (~22° C.) and induced at an approximate density of 0.45 $OD_{600}$. The cells were induced with 1 mM IPTG for 6 hours at room temperature. Cells were harvested and lysed by French Press and sonication in buffer comprising 50 mM Bis-Tris-Propane, pH 8.75, 1% Triton X-100, 5 mM $MgCl_2$ and 5 mM $CaCl_2$ and 50 mM NaCl. Extracts were centrifuged to obtain a soluble fraction. The soluble protein in the supernatant fraction was passed over a Ni-affinity column at 5° C. The column was then washed with 25 mM imidazole. Alternatively, several washes of increasing imidazole up to 25 mM is used. The gAPM1 (110–224) protein was eluted from the column with a concentration of 100 mM imidazole. The eluant comprising the gAPM1 (110–244) fraction was run over an ion exchange column using DEAE resin. Alternatively, a hydroxyapatite column is used. The gAPM1 (110–244) protein was eluted with high salt buffer and dialyzed to reduce the salt concentration. This material was used in Example 18 to assay affect on FFA oxidation.

Example 18

Effect of gAPM1 on Free Fatty Acid Oxidation

Bacterially expressed gAPM1-His tag (110–244), gACRP30-his tag (104–247) and gACRP30 (104–247)—N-term-His/C-term-Flag tagged proteins were compared for activity in a free fatty acid (FFA) oxidation assay. Briefly, C2C12 cells and SKMC cells were grown to ~95% confluency. Cells were differentiated for 7 days. Cells were starved overnight in serum free DME containing 0.5% Albumax I (fatty acid rich BSA). Cells were then preincubated in medium comprising Basal Medium Eagle (BME), 20 mM HEPES, pH 7.4, 4 mM L-Glutamine, 1% fatty acid free BSA (0.15 mM). (As a negative control, a flask with no cells was included with 2 ml of Preincubation media alone.) Cells were treated with either 5.0 ug/ml gACRP30 trypsin-cleaved (0.275 mg/ml), 5.0 ug/ml gACRP30 bacterially expressed (0.36 mg/ml), 5.0 ug/ml gACRP30 His-Flag tagged bacterially expressed (0.24 mg/ml), 5.0 ug/ml gAPM1 (110–244) (0.09 mg/ml) bacterially expressed (bacterial expression described in Example 17) for 2 hours at 37° C. As a positive control, 100 uM isoproteranol was added to the cells 15 minutes before addition of perchloric acid.

Treated cells were assayed as follows:

1. 100 ul of media with 4 mM palmitic acid and 4 uCi/ml 14C-palmitic acid was added to each of the flasks, and cells were incubated at 37° C. for 90 minutes.

2. Using a 1 ml Luer-lok syringe, Solvable was injected into the center well containing a filter paper approximately 15 min before adding the perchloric acid.
3. Using a 1 ml Luer-lok syringe, 1 ml perchloric acid was added and cells were incubated for 1 hour at 37° C.
4. After 1 hour, 15 ml Hionic Fluor was added and filter paper was transferred into appropriate scintillation vial and shaken for 30 min at 4° C., then counted.

The N-terminally His tagged gAPM1 (110–244), gACRP30 (104–247) and isoproterenol (positive control) significantly increased FFA oxidation above non-treated cells. The recombinant mouse protein containing both an N-term His tag and a C-term FLAG tag was not active in this assay.

Example 19

Assay for Dipeptidyl Peptidase Cleavage of OBG3 or gOBG3 Polypeptide Fragment

Dipeptidyl peptidase cleavage of gAPM1 (85–244) or gAPM1 (103–244) polypeptide fragment is determined by ELISA using a monoclonal antibody that specifically binds to intact gAPM1 polypeptide fragment but not to said gAPM1 polypeptide fragment from which the N-terminal dipeptide EP has been removed. That is, said antibody binds to gAPM1 (85–244) but not to gAPM1 (binding to 85–244) or said antibody binds to gAPM1 (103–244) but not to gAPM1 (105–244). Dipetidyl peptidase is selected from but not restricted to human plasma comprised of dipeptidyl peptidase, soluble human CD26, or soluble human Attractin.

Briefly, gAPM1 (5 $\mu$l, 100 fmol) is added to plasma samples (95 $\mu$l) and incubated for 1 h at 37° C., after which the amount of gAPM1 polypeptide fragment that remains undegraded is determined by enzyme-linked immunosorbent assay (ELISA) using a monoclonal antibody specific for intact gAPM1 polypeptide fragment. As a reference, gAPM1 polypeptide fragment (5 $\mu$l, 100 fmol) is added to heat-inactivated plasma (95 $\mu$l), which contains 0.01 mmol/l valine-pyrrolidide and 500 KIE/ml aprotinin. By defining the dipeptidyl peptidase activity in the reference as zero and comparing the amount of intact gAPM1 polypeptide fragment in the samples with the reference, the extent of dipeptidyl peptidase cleavage of gAPM1 polypeptide fragment is calculated relative to the reference and expressed as a percentage.

Example 20

In Vivo Evaluation of OBG3 of gOBG3 Polypeptide Fragments of the Invention

7-Day Evaluation: A study protocol was established to evaluate the effects on lipid or glucose metabolism of isolated and purified recombinant OBG3 or gOBG3 polypeptides of the invention, for example, amino acids 101–244, 105–244, 110–244, 19–244, 111–191, 191–244, and 144–199 of SEQ ID NO:6, and amino acids 104–247 of SEQ ID NO:4, and His-tagged analogues thereof. This protocol can be expanded to include the efficient screening of any polypeptide for potential use in methods to alter lipid or glucose metabolism. A feature of this protocol is the short-term experimental length as well as detection of intermediate-term experimental effects. Mice are treated for a total of 7 days. At the start of the treatment acute effects either on fat/glucose metabolism or on hepatic glucose output are measured by conducting a postprandial lipemia study (PPL) or an Insulin tolerance test (ITT), respectively. Short-term effects on blood chemistry are determined after 3–4 days of treatment and a complete analysis is performed at the end of the treatment period. This includes a second study, either PPL, ITT or OGTT (oral glucose tolerance test). In addition effects on body weight, body composition (% lean and fat tissue), fat storage in liver and muscle are measured and tissues are isolated to follow effects on gene expression or to determine histological changes according to routine methods known in the art.

I. Assay for Glucose Tolerance

A standard Glucose Tolerance Test (GTT) following injection of test polypeptides is performed on mice as follows:

1. Mice are fasted for 3–6 hours. The standard model uses C57B1/6 male mice kept on a high fat diet, this results in decreased insulin sensitivity.
2. A baseline blood sample is taken from the tail and the glucose level is measured using glucose test strips and the 'One Touch Ultra System' (Johnson & Johnson), as with all following blood draws.
3. Treatment with test polypeptide (5–150 ug/50 ul/mouse) is given by i.p. injection. Control animals are injected with equal volume of saline.
4. Immediately following treatment, glucose is injected i.p. (Dose: 1 g/kg body weight).
5. After all injections are done, the plasma glucose level is monitored at 30', 60', 90', and 120' post-treatment.
6. For the 7-day evaluation, mice are injected at the same time everyday for 7 consecutive days, and GTT assay is performed on each day according to step 5 above.

II. Assay for Insulin Tolerance

A standard Insulin Tolerance Test (ITT) following injection of test polypeptides is performed on mice as follows:

1. Mice are fasted for 3–6 hours. The standard protocol uses C57B1/6 male mice kept on a high fat diet, this results in decreased insulin sensitivity.
2. A baseline blood sample is taken from the tail and the glucose level is measured using glucose test strips and the 'One Touch Ultra System' (Johnson & Johnson), as with all following blood draws.
3. Treatment with test protein (5–150 ug/50 ul/mouse) is given by i.p. injection. Untreated animals are injected with equal volume of saline.
4. Immediately following treatment insulin is injected (Dose: 0.3IU/kg body weight).
5. The plasma glucose level is monitored at 15', 30', 60', 90', and 120' post-treatment.
6. For the 7-day evaluation, mice are injected at the same time everyday for 7 consecutive days, and ITT assay is performed on each day according to step 5 above.

III. Assay for Postprandial Lipemia

A standard Postprandial lipemia assay (PPL) following injection of test polypeptides is performed on mice as follows:

1. Mice are fasted for 3–6 hours. The standard protocol uses normal C57B1/6 male mice.
2. A baseline blood sample is taken from the tail.
3. A high fat/high sucrose test meal (6 g butter, 6 g sunflower oil, 10 g non fat dry milk, 10 g sucrose, 12 ml distilled water prepared fresh) is given by gavage (Dose: 1% of the animal total body weight in ml).
4. Following the test meal, animals are treated with test protein (5–150 ug/5 ul/mouse) given by i.p. injection. Untreated animals are injected with equal volume of saline. This treatment is repeated each day throughout a 7-day evaluation study.

5. Blood samples are taken at 1, 2, 3 and 4 hrs following treatment. Samples are immediately stored on ice until plasma separation.
6. Plasma samples are assayed for metabolic parameters including glucose, insulin, leptin, triglycerides, and FFAs.

Plasma glucose concentration is determined as described above in the GTT assay using the 'One Touch Ultra System'. Alternatively, a standard glucose test kit is used (Sigma). The concentration of triglycerides and free fatty acids (FFAs) are determined using calorimetric assays (Triglycerides, Sigma; FFA, Wako Biochemicals, Osaka). Insulin and Leptin are determined by RIA (Linco Research, St Charles, Mo.).

In addition to the 7-day evaluation study protocol, GTT, ITT, and PPL assays can be performed in any length study, including single day, short-term, and long-term periods following injection of the test polypeptides.

Example 21

Infant Formula Supplementation

The following example describes a method of administering OBG3 or gOBG3 polypeptides to newborns as supplemental nutritional support and further provides a method of promoting growth of an infant by administering OBG3 or gOBG3-fortified human breast milk, or OBG3 or gOBG3-fortified breast milk substitute formulation from a nonhuman source. Dehydrated or lyophilized OBG3 or gOBG3 polypeptide powder is directly added to pumped human breast milk (freshly pumped or prewarmed after storage) or any prewarmed breast milk substitute formulation from a nonhuman source, in a range of 5–1000 ng/ml, preferably 20–800 ng/ml, more preferably 65–650 ng/ml. Supplementation with polypeptides of the invention is provided to infants, particularly preterm infants, in bottle feedings of human breast milk or breast milk substitute at every feeding throughout the day, and is continued to be provided from birth to 6 months of age. Preterm infants may be of low birth weight or very low birth weight.

A primary objective of the study is to demonstrate that a polypeptide of the invention added to human milk (HM) or human milk substitute (HMS) supports acceptable growth in preterm infants. A second objective is to evaluate the serum biochemistries (ie, protein status, calcium, alkaline phosphatase), tolerance, clinical problems, and morbidity of premature infants consuming the nutritional module. Another secondary objective is to compare the supplemental composition of the instant invention to a commercial fortifier powder that has been in use for a number of years to promote growth in preterm infants. An intent-to-treat, prospective, randomized, double-blinded multicenter study is conducted to evaluate preterm infants receiving preterm milk supplemented with either a commercially available powdered human milk fortifier (Enfamil.RTM. Human Milk Fortifier, control) or the supplemental polypeptide (test) powder of the current invention (experimental) at every feeding. Subjects are enrolled and randomized to each fortifier powder prior to 21 days of life. Study Day 1 is when fortification of the test powder begins and the subject reaches an intake of at least 100 mL/kg/day. Anthropometric indices, serum biochemistries, intake, tolerance, and morbidity data are assessed. Each infant is studied until hospital discharge; only anthropometric variables (weight, length, and head circumference) are collected after Study Day 29. Premature infants are recruited from neonatal intensive care units that had agreed to collaborate with study investigators. Single, twin, or triplet infants born around 33 weeks gestational age, with appropriate weight for gestational age, and weighing around 1600 g are eligible to participate. One hundred and forty-four infants are randomized to either control or experimental; 70 preterm infants are randomized to the control group and 74 preterm infants are randomized to the experimental group. The randomization is proportional for birth weight and gender.

The independent variables (treatments) are the control fortifier powder and the experimental test powder which are added to HM or HMS. Both fortifiers (test and control) are provided in small packets in powdered form and are added to 25 mL HM or HMS. The primary outcome variable is weight gain (g/kg/day) from study day 1 to study day 29 or discharge, whichever comes first. Secondary outcome variables are length gain (mm/day) and serum biochemistries to evaluate protein status, electrolyte status, mineral homeostasis, and vitamin A and E status. Serum biochemistries also include unscheduled laboratory results to be recorded in the medical chart. Tertiary variables include head circumference gain (mm/day), clinical history, intake, tolerance, clinical problems/morbidity, respiratory status, antibiotic use, and the number of transfusions. Mean total energy intakes during the study period is not different between the groups, around 118 kcal/kg/day.

Incorporation of Related Applications

This application hereby incorporates each of the provisional applications, non-provisional applications, and applications filed under the Patent Cooperation Treaty, as listed on the Application Data Sheet that is associated with the subject application, by reference and in their entireties, including any figures, tables, nucleic acid sequences, amino acid sequences, and/or drawings.

Additional References

1. Shapiro, L. & Scherer, P. E., "The crystal structure of a complement-1q family protein suggests an evolutionary link to tumor necrosis factor", Curr Biol 8, 335–338 (1998).
2. Kishore, U. & Reid, K. B., "Modular organization of proteins containing C1q-like globular domain", Immunopharmacology 42, 15–21 (1999).
3. Kavety, B. & Morgan, J. I., "Characterization of transcript processing of the gene encoding precerebellin-1", Brain Res Mol Brain Res 63, 98–104 (1998).
4. Satoh, F. et al., "Cerebellin and cerebellin mRNA in the human brain, adrenal glands and the tumour tissues of adrenal tumour, ganglioneuroblastoma and neuroblastoma", J Endocrinol 154, 27–34 (1997).
5. Mazzocchi, G. et al., "Cerebellin enhances in vitro secretory activity of human adrenal gland", J Clin Endocrinol Metab 84, 632–635 (1999).
6. Kondo, N. & Kondo, J., "Identification of novel blood proteins specific for mammalian hibernation", J Biol Chem 267, 473–478 (1992).
7. Takamatsu, N., Ohba, K., Kondo, J., Kondo, N. & Shiba, T., "Hibernation-associated gene regulation of plasma proteins with a collagen-like domain in mammalian hibernators", Mol Cell Biol 13, 1516–1521 (1993).
8. Spiegelman, B. M. & Hotamisligil, G. S., "Through thick and thin: wasting, obesity, and TNF alpha", Cell 73, 625–627 (1993).

9. Saito, K. et al., "Regulation of gelatin-binding protein 28 (GBP28) gene expression by C/EBP", Biol Pharm Bull 22, 1158–1162 (1999).
10. Takamatsu, N. et al., "Expression of multiple alpha 1-antitrypsin-like genes in hibernating species of the squirrel family", Gene 204, 127–132 (1997).
11. Ross, S. R., Graves, R. A. & Spiegelman, B. M., "Targeted expression of a toxin gene to adipose tissue: transgenic mice resistant to obesity", Genes Dev 7, 1318–1324 (1993).
12. Moitra, J. et al., "Life without white fat: a transgenic mouse", Genes Dev 12, 3168–3181 (1998).
13. Peters, S. J., Dyck, D. J., Bonen, A. & Spriet, L. L., "Effects of epinephrine on lipid metabolism in resting skeletal muscle", Am J Physiol 275, E300–309 (1998).
14. Rigotti, A., Acton, S. L. & Krieger, M., "The class B scavenger receptors SR-BI and CD36 are receptors for anionic phospholipids", J Biol Chem 270, 16221–16224 (1995).
15. Hirsch, D., Stahl, A. & Lodish, H. F., "A family of fatty acid transporters conserved from mycobacterium to man", Proc Natl Acad Sci USA 95, 8625–8629 (1998).
16. Hotamisligil, G. S. et al., "IRS-1-mediated inhibition of insulin receptor tyrosine kinase activity in TNF-alpha- and obesity-induced insulin resistance", Science 271, 665–668 (1996).
17. Peraldi, P. & Spiegelman, B., "TNF-alpha and insulin resistance: summary and future prospects", Mol Cell Biochem 182, 169–175 (1998).
18. Kirchgessner, T. G., Uysal, K. T., Wiesbrock, S. M., Marino, M. W. & Hotamisligil, G. S., "Tumor necrosis factor-alpha contributes to obesity-related hyperleptinemia by regulating leptin release from adipocytes", J Clin Invest 100, 2777–2782 (1997).
19. Uysal, K. T., Wiesbrock, S. M., Marino, M. W. & Hotamisligil, G. S., "Protection from obesity-induced insulin resistance in mice lacking TNF-alpha function", Nature 389, 610–614 (1997).
20. Jensen, D. R. et al. "Prevention of diet-induced obesity in transgenic mice overexpressing skeletal muscle lipoprotein lipase", Am J Physiol 273, R683–689 (1997).
21. Levak-Frank, S. et al., "Muscle-specific overexpression of lipoprotein lipase causes a severe myopathy characterized by proliferation of mitochondria and peroxisomes in transgenic mice", J Clin Invest 96, 976–986 (1995).
22. Scheja, L. et al., "Altered insulin secretion associated with reduced lipolytic efficiency in aP2-/- mice", Diabetes 48, 1987–1994 (1999).
23. Griffin, M. E. et al., "Free fatty acid-induced insulin resistance is associated with activation of protein kinase C theta and alterations in the insulin signaling cascade", Diabetes 48, 1270–1274 (1999).
24. Dresner, A. et al., "Effects of free fatty acids on glucose transport and IRS-1-associated phosphatidylinositol 3-kinase activity", J Clin Invest 103, 253–259 (1999).
25. Kelley, D. E., Goodpaster, B., Wing, R. R. & Simoneau, J. A., "Skeletal muscle fatty acid metabolism in association with insulin resistance, obesity, and weight loss", Am J Physiol 277, E1130–1141 (1999).
26. Roden, M. et al., "Mechanism of free fatty acid-induced insulin resistance in humans", J Clin Invest 97, 2859–2865 (1996).
27. Deacon, C. F. et al., "Dipeptidyl peptidase IV inhibition reduces the degradation and clearance of GIP and potentiates its insulinotropic and antihyperglycemic effects in anesthetized pigs", Diabetes 50, 1588–1597 (2001).

What is claimed is:

1. An isolated polypeptide fragment of a full-length OBG3 polypeptide, wherein said polypeptide fragment consists of consecutive amino acids 84 to 244, 85 to 244, 110 to 244, 102 to 244, or 103 to 244 of SEQ ID NO:6.

2. The isolated polypeptide fragment of claim 1, wherein said polypeptide fragment consists of consecutive amino acids 84 to 244 of SEQ ID NO:6.

3. The isolated polypeptide fragment of claim 1, wherein said polypeptide fragment consists of consecutive amino acids 85 to 244 of SEQ ID NO:6.

4. The isolated polypeptide fragment of claim 1, wherein said polypeptide fragment consists of consecutive amino acids 110 to 244 of SEQ ID NO:6.

5. The isolated polypeptide fragment of claim 1, wherein said polypeptide fragment consists of consecutive amino acids 102 to 244 of SEQ ID NO:6.

6. The isolated polypeptide fragment of claim 1, wherein said polypeptide fragment consists of consecutive amino acids 103 to 244 of SEQ ID NO:6.

7. A composition comprising a carrier and a polypeptide fragment consisting of consecutive amino acids 84 to 244, 85 to 244, 110 to 244, 102 to 244 or 103 to 244 of SEQ ID NO:6.

8. The composition according to claim 7, wherein said polypeptide fragment consists of consecutive amino acids 84 to 244 of SEQ ID NO:6.

9. The composition according to claim 7, wherein said polypeptide fragment consists of consecutive amino acids 85 to 244 of SEQ ID NO:6.

10. The composition according to claim 7, wherein said polypeptide fragment consists of consecutive amino acids 110 to 244 of SEQ ID NO:6.

11. The composition according to claim 7, wherein said polypeptide fragment consists of consecutive amino acids 102 to 244 of SEQ ID NO:6.

12. The composition according to claim 7, wherein said polypeptide fragment consists of consecutive amino acids 103 to 244 of SEQ ID NO:6.

13. A method of lowering circulating free fatty acid levels in an individual comprising administering to said individual a composition comprising a carrier and a polypeptide consisting of consecutive amino acids 84 to 244, 85 to 244, 110 to 244, 102 to 244, 103 to 244, or 105 to 244 of SEQ ID NO:6.

14. The method according to claim 13, wherein said polypeptide consists of consecutive amino acids 84 to 244 of SEQ ID NO:6.

15. The method of claim 14, wherein said method further reduces body mass.

16. The method according to claim 13, wherein said polypeptide consists of consecutive amino acids 85 to 244 of SEQ ID NO:6.

17. The method of claim 16, wherein said method further reduces body mass.

18. The method according to claim 13, wherein said polypeptide consists of consecutive amino acids 110 to 244 of SEQ ID NO:6.

19. The method of claim 18, wherein said method further reduces body mass.

20. The method according to claim 13, wherein said polypeptide consists of consecutive amino acids 102 to 244 of SEQ ID NO:6.

21. The method of claim 20, wherein said method further reduces body mass.

22. The method according to claim 13, wherein said polypeptide consists of consecutive amino acids 103 to 244 of SEQ ID NO:6.

23. The method of claim 22, wherein said method further reduces body mass.

24. The method according to claim 13, wherein said polypeptide consists of consecutive amino acids 105 to 244 of SEQ ID NO:6.

25. The method or claim 24, wherein said method further reduces body mass.

26. The method of claim 13, wherein said method further reduces body mass.

* * * * *

UNITED STATES PATENT AND TRADEMARK OFFICE

CERTIFICATE OF CORRECTION

PATENT NO. : 6,989,367 B2

APPLICATION NO. : 10/285833

DATED : January 24, 2006

INVENTOR(S) : Joachim Fruebis et al.

It is certified that error appears in the above-identified patent and that said Letters Patent is hereby corrected as shown below:

Column 4,
Line 51, “axe” should read -- are --.

Column 9,
Lines 14-15, “hyper-uncemia” should read -- hyperuricemia --.

Column 13,
Line 59, “FIG 1A shows”should read -- FIG. 11A shows --.

Column 14,
Lines 28-29, “are control (yellow) and gACRP30 (red)” should read -- are control (white) and gACRP30 (black) --.

Column 15,
Line 62, “polyaciylamide” should read -- polyacrylamide --.

Column 18,
Line 9, “Kopehnan” should read -- Kopelman --.

Column 21,
Line 23, “25 kg/M$^2$” should read -- 25 kg/m$^2$ --.
Lines 24-25, “18.5 kg/M$^2$” should read -- 18.5 kg/m$^2$ --.

Column 40,
Line 5, “alpha-minoalkylphosphonic” should read -- alpha-aminoalkylphosphonic --.

Column 45,
Lines 55-56, “wherein “`x1-x2” and “y1-y2’”” should read -- wherein “x1-x2” and “y1-y2” --.

Column 54,
Line 53, “Pseudoimonas” should read -- Pseudomonas --.

Column 61,
Line 35, “bamer” should read -- barrier --.

Column 78,
Line 32, “FFFA” should read -- FFA --.

UNITED STATES PATENT AND TRADEMARK OFFICE

CERTIFICATE OF CORRECTION

PATENT NO. : 6,989,367 B2
APPLICATION NO. : 10/285833
DATED : January 24, 2006
INVENTOR(S) : Joachim Fruebis et al.

It is certified that error appears in the above-identified patent and that said Letters Patent is hereby corrected as shown below:

Column 82,
Line 23, "into a 5 ml column" should read -- into a 5 mL column --.

Column 83,
Lines 50-51, "Generation of gOBG3 by Recombinant Methodology Restriction Site Cloning" should read -- Generation of gOBG3 by Recombinant Methodology Restriction Site Cloning --.

Column 86,
Line 67, "mm at 4° C." should read -- min at 4° C. --.

Column 87,
Line 1, "cytometly" should read -- cytometry --.
Line 1, "done on FACsCalibur" should read -- done on a FACsCalibur --.
Line 43, "FAGs buffer" should read -- FACs buffer --.
Line 65, "Hepa 16 cells" should read -- Hepa 1-6 cells --.

Column 88,
Line 5, "anti-gc 1qr" should read -- anti-gClqr --.

Column 90,
Line 32, "for 20 mm at" should read -- for 20 min at --.

Column 93,
Line 35, "from 04 h post" should read -- from 0-4 h post --.
Line 60, "5 mL/kg/min" should read -- 5 mU/kg/min --.
Line 65, "5 mL/kg/min" should read -- 5 mU/kg/min.

Column 94,
Line 1, "25 mL/kg/min" should read -- 25 mU/kg/min --.
Line 8, "25 mL/kg/min" should read -- 25 mU/kg/min --.

Column 95,
Line 50, "from to" should read -- from $t_o$ --.

Column 97,
Line 37, "E913921" should read -- E913-921 --.

CERTIFICATE OF CORRECTION

PATENT NO. : 6,989,367 B2
APPLICATION NO. : 10/285833
DATED : January 24, 2006
INVENTOR(S) : Joachim Fruebis et al.

It is certified that error appears in the above-identified patent and that said Letters Patent is hereby corrected as shown below:

Column 99,
Line 27, "(183+12%, n=6)." should read -- (183±12%, n=6). --.
Line 35, "2ACRP30" should read -- gACRP30 --.
Line 61, "52.5+0.8 g" should read -- 52.5±0.8 g --.

Column 146,
Line 26, "method or claim" should read -- method of claim --.

Signed and Sealed this

Twenty-fifth Day of December, 2007

JON W. DUDAS
*Director of the United States Patent and Trademark Office*